(12) United States Patent
Galazka et al.

(10) Patent No.: US 12,084,705 B2
(45) Date of Patent: Sep. 10, 2024

(54) METHYLOTROPHIC MICROORGANISMS EXPRESSING SOLUBLE METHANE MONOOXYGENASE PROTEINS

(71) Applicant: United States of America as Represented by the Administrator of the NASA, Washington, DC (US)

(72) Inventors: Jonathan Matthew Galazka, Mountain View, CA (US); Asif Rahman, San Francisco, CA (US); Samantha Therese Fleury, Littleton, MA (US)

(73) Assignee: United States of America as Represented by the Administrator of NASA, Washington, DC (US)

( * ) Notice: Subject to any disclaimer, the term of this patent is extended or adjusted under 35 U.S.C. 154(b) by 567 days.

(21) Appl. No.: 16/375,824

(22) Filed: Apr. 4, 2019

(65) Prior Publication Data

US 2020/0095611 A1    Mar. 26, 2020

Related U.S. Application Data

(60) Provisional application No. 62/652,834, filed on Apr. 4, 2018.

(51) Int. Cl.
| | | |
|---|---|---|
| *C12N 9/04* | (2006.01) | |
| *C12N 1/16* | (2006.01) | |
| *C12N 9/02* | (2006.01) | |
| *C12N 15/70* | (2006.01) | |
| *C12P 7/00* | (2006.01) | |
| *C12P 7/04* | (2006.01) | |

(52) U.S. Cl.
CPC .................. *C12P 7/04* (2013.01); *C12N 1/16* (2013.01); *C12N 9/0071* (2013.01); *C12Y 114/13025* (2013.01)

(58) Field of Classification Search
CPC .... C12N 15/70; C12N 9/0028; C12N 9/1007; C12N 15/74; C12N 9/0073; C12N 9/0004; C12N 9/0008; C12N 9/0067; C12N 9/0071; C12N 9/10; C12P 7/24; C12P 5/00; C12P 7/00; C12P 7/04; C12Y 101/01244; C12Y 101/05006; C12Y 114/13025
USPC ........................... 435/189, 136, 252.3, 320.1
See application file for complete search history.

(56) References Cited

U.S. PATENT DOCUMENTS

2005/0176121 A1    8/2005    Takeshita et al.

FOREIGN PATENT DOCUMENTS

| CN | 101392233 A | 3/2009 |
|---|---|---|
| WO | 2015013295 A1 | 1/2015 |
| WO | 2015160848 A1 | 10/2015 |
| WO | 2017087731 A1 | 5/2017 |

OTHER PUBLICATIONS

Kisselev L., Structure, 2002, vol. 10: 8-9.*
Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
Elongo etal. Prot. Sci 1997, 6. pp. 556-5568.*
Camattari, A., Goh, A., Yip, L.Y., Tan, A.H.M., Ng, S.W., Tran, A., Liu, G., Liachko, I., Dunham, M.J., and Rancati, G. (Aug. 2016) "Characterization of a panARS-based episomal vector in the methylotrophic yeast Pichia pastoris for recombinant protein production and synthetic biology applications," Microbial Cell Factories, 15:139, 11 pages.
Chng, J. ,Wang, T., Nian, R., Lau, A., Hoi, K.M., Ho, S.CL, Gagnon, P., Bi., X. and Yand, Y. (2015) "Cleavage efficient 2A peptides for high level monoclonal antibody expression in CHO cells," mAbs, 7:2, 403-412 Bioprocessing Technology Institute.
Liachko, I. and Dunham, M.J. (Mar. 2014) "An Autonomously Replicating Sequence for use in a wide range of budding yeasts," FEMS Yeast Re. 14(2):364-367.
Liang, S., Wang, B., Pan, L., Ye, Y., He, M., Han, S., Zheng, S., Wang, X., and Lin, Y. (Dec. 2012) "Comprehensive structural annotation of Pichia pastoris transcriptome and the response to various carbon sources using deep paired-end RNA sequencing," BMC Genomics 13:738, BioMed Central.
Lloyd, J.S. , Finch, R., Dalton, H. and Murrell, J.C. (1999) "Homologous expression of soluble methane monooxygenase genes in Methylosinus trichosporium OB3b," Microbiology, 145, 461-470.
Rosmalen, M. van, Krom, M. and Merkx, M. (Nov. 2017) "Tuning the Flexibility of Glycine-Serine Linkers To Allow Rational Design of Multidomain Proteins," 56(50) pp. 6565-6574.
Chichili, V.P.R., Kumar, V. and Sivaraman, J. (2013) "Linkers in the structural biology of protein-protein interactions," 22(2):153-167, published Dec. 6, 2012.
Gietz, R.D. and Schiestl R.H. (2007) "High-efficiency yeast transformation using the LiAc/SS carrier DNA/PEG method," Nature Protocols 2, 31-34.

(Continued)

*Primary Examiner* — Tekchand Saidha
(74) *Attorney, Agent, or Firm* — Rhys W. Cheung; Robert M. Padilla; Trenton J. Roche

(57) ABSTRACT

Methylotrophic microorganisms, particularly methylotrophic yeasts and more particularly *Pichia pastoris*, which exhibit the ability to oxidize methane to methanol. Methods of making such microorganisms and DNA constructs for making such microorganisms. Such methylotrophic microorganisms are genetically transformed to exhibit the oxidizing activity of a soluble methane monooxygenase of a methanotrophic bacterium. Such transformed methylotrophic microorganisms contain at least three methane monooxygenase hydroxylase (MMOH) protein subunits of a methanotrophic bacterium: MMOH alpha, MMOH beta and MMOH gamma and a methane monooxygenase reductase (MMOR) of a methanotrophic bacterium.

19 Claims, 6 Drawing Sheets
(6 of 6 Drawing Sheet(s) Filed in Color)

Specification includes a Sequence Listing.

(56) References Cited

OTHER PUBLICATIONS

Gietz, R.D. and Schiestl, R.H. (2007) "Frozen competent yeast cells that can be transformed with high efficiency using the LiAc/SS carrier DNA/PEG method," Nature Protocols 2, 1-4.

Lee, M.E., DeLoache, W.C., Cervantes, B. and Dueber, J.E. (Apr. 2015) "A Highly Characterized Yeast Toolkit for Modular, Multipart Assembly," ACS Synth. Biol. 4(9): 975-986.

Engler, C., Kandzia, R. and Marillonnet, S. (2008) "A One Pot, One Step, Precision Cloning Method with High Throughput Capability," PloS One 3, e3647, 9 pages.

Engler, C., Gruetzner, R., Kandzia, R. and Marillonnet, S. (2009) "Golden Gate Shuffling: A One-Pot DNA Shuffling Method Based on Type IIs Restriction Enzymes," PloS One 3, e5553, 11 pages.

Hamilton, S.R., et al. (2006) "Humanization of Yeast to Produce Complex Terminally Sialylated Glycoproteins," Science 313 (5792): 1441-1443.

Waugh, D.S. (2011) "An overview of enzymatic reagents for the removal of affinity tags," Protein Expression and Purification, 80 (2):283-293.

Chen, X., Zaro, J. Shen, W-C. (2013) "Fusion Protein Linkers: Property, Design and Functionality," Adv. Drug Deliv Rev. 65(10):1357-1369.

Fleury, S.T., Neff, L.S., Galazka, J.M. (Aug. 2017) "Engineering of Methane Metabolism in Pichia pastoris through Methane Monooxygenase Expression," available from ntrs.nasa.gov/archive/nasa/casi.ntrs.nasa.gov/20180004670 poster.

Galazka, J.M. (Aug. 2017) "New Frontiers in Synthetic Biology for Spaceflight".

Rahman, A., Dougherty, M.J., Hogan, J.A., Galaska, J.M. (Apr. 4, 2017) "Methane metabolism by yeast for solar system exploration," presentation on Apr. 4, 2017 at the American Chemical Society Meeting in San Francisco CA.

Pena, David A. et al. "Metabolic engineering of Pichia pastoris"; Metab Eng. Nov. 2018 50:2-15, https://doi.org/10.1016/j.ymben.2018.04.017.

Rahman et al. (Apr. 4, 2017) "Methane Metabolism by Yeast for Space Exploration," presented at The Am. Chem. Soc. Meeting in San Francisco CA held Apr. 2-4, 2017, 28 pages.

Rahaman et al. (Apr. 2, 2017) "Methane Metabolism by Yeast for Space Exploration," Abstract of Presentation at Am. Chem. Soc. Meeting San Francisco CA Apr. 2-4, 2017, 1 page.

* cited by examiner

METHYLOTROPHIC MICROORGANISMS EXPRESSING SOLUBLE METHANE MONOOXYGENASE PROTEINS

CROSS-REFERENCE TO RELATED APPLICATIONS

This application claims the benefit of U.S. Provisional application 62/652,834, filed Apr. 4, 2018, which is incorporated by reference herein in its entirety.

ORIGIN OF THE INVENTION

The invention described herein was made in the performance of work under a NASA contract and by employees of the United States Government and is subject to the provisions 51 U.S.C. § 20135(b), Public Law 111-314, § (124 Stat. 3330, 51 U.S.C. Chapter 201), and may be manufactured and used by or for the Government for governmental purposes without the payment of any royalties thereon or therefor.

REFERENCE TO A SEQUENCE LISTING

A Sequence Listing is submitted as a text file (ARC-17910-1_amended_ST25.txt) herewith. The material in this text file is incorporated by reference herein in its entirety.

FIELD OF THE INVENTION

Present embodiments of the invention are in the field of genetic engineering of microorganisms and is more specifically related to generation of methylotrophic microorganisms which exhibit the ability to oxidize methane to methanol.

BACKGROUND

Methane is available in abundance from sources such as ruminant agriculture, landfill decomposition, and the extraction of fossil fuels. Therefore, there is an incentive to find ways to utilize methane, as it is an inexpensive, but underutilized, carbon source.

Methane is also a product of the oxygen-reclaiming Sabatier system on the International Space Station. The Sabatier system reacts $CO_2$ and $H_2$ to form $CH_4$ and $H_2O$. The $H_2O$ is recycled, while the $CH_4$ is vented into space and lost. The Sabatier system's main purpose is to recapture oxygen from the $CO_2$. As part of NASA's long term goal of moving humans into deep space, technologies are being developed to make crews more self-sufficient, including means to effectively use local resources. To this end, the Sabatier system may also be deployed to Mars. Because humans on Mars will not have the benefit of relatively frequent delivery of supplies from Earth currently enjoyed by humans on the International Space Station, it is desirable to have a means to convert $CH_4$ to one or more useful products.

One use for methane is as a carbon substrate for microorganisms. Microorganisms can be used to naturally convert a carbon source, such as methane, into numerous bioproducts. Such biological manufacturing systems have numerous benefits over mechanical means of production, including scalability and precision. In addition, in some contexts (e.g., protein therapeutics), biological systems are currently the only method of producing a desired substance. Finally, recent analyses suggest that methane is a less expensive source of carbon for biological systems than the sugars that are traditionally utilized.

Microorganisms have particular advantages for humans living in deep space. Microbes are highly scalable; in principle, a single bacteria can multiply to have the mass of the Earth in twenty-four hours. Additionally, microbes are self-organizing and are increasingly programmable; a single type of microbe can make numerous bioproducts. Finally, microbes are regenerable. Therefore, a population of microorganisms could replace multiple larger and heavier systems, allowing space of other vital equipment in the space vehicle.

There are ongoing efforts to utilize methane as a carbon substrate for methanotrophic bacteria that naturally consume methane. However, while methanotrophic bacteria naturally consume methane, they are relatively poor synthetic biology platforms. Methanotrophic bacteria are not widely used as microbial manufacturing platforms; therefore, although they can consume methane, their current utility for production of bioproducts from that methane is limited. In addition, there are disadvantages to using bacteria as synthetic biology platforms, such as such bacteria being susceptible to bacteriophage infection and unstable integration of target genes, if achieved. Therefore, it is desirable to develop a widely utilized microbial manufacturing platform that can consume methane.

U.S. published application 2005/0176121 relates to recombinant microorganisms that are said to acquire an ability to convert an alkane into an alcohol due to transformation with DNA encoding a methane oxygenase. The reference refers to the microorganisms *Escherichia* bacterium, coryneform bacterium and *Bacillus* bacterium.

Published PCT application WO02015/013295 relates to methods for producing chemicals using recombinant organisms that utilize methane or methanol as a carbon source. The reference refers to cells from the genera *Saccharomyces, Escherichia, Pichia, Issatchenkia, Aspergillus* and *Yarrowia*.

Published PCT application WO2015/160848 relates to synthetic methanotrophic and methylotrophic microorganisms. The reference refers to non-naturally occurring microbial organism comprising a methane-oxidizing pathway. The reference refers to non-methanotropic microorganisms with one or more genetic modification that allow the organism to oxidize methane. The reference refers to non-methanotrophic microorganisms *Hansenula, Pichia, Candida* and *Torulopsis* as well as to *Escherichia coli, Bacillus subtilis, Bacilus methanolicus, Pseudomonas putida, Salmonella enterica* and *Corynebacterium glutamicum*.

Published PCT application WO2017/087731 relates to methods and compositions for the oxidation of short alkanes by engineered microorganisms expressing recombinant enzymes. The reference refers to a monooxygenase synthetic polynucleotide for a soluble diiron monooxygenase enzyme. The reference refers among others to the microorganisms *Escherichia coli, Pichia pastoris, Bacillus methanolicus, Bacillus subtilis* and *Corynebacterium glutamicum*.

CN101392233 published Mar. 25, 2009 (in Chinese) relates to a method for expressing granular methane monooxygenase apparently in an engineered host bacterium. The engineered bacteria are said to be useful in the transformation of biogas to methanol and the oxidation of propylene into 1,2-propylene oxide and the like.

While some efforts have been made with respect to expression of methane monooxygenase in non-methanotrophic microorganisms, applicant is not aware of reports of successful expression of soluble methane monooxygenase functional for oxidation of methane to methanol in a methylotrophic yeast, including methylotrophic yeast of the genus *Pichia*. Thus, there remains a need in the art for methods, compositions of matter and transformed microorganism that enable a methylotrophic microorganism, which is non-methanotrophic, particularly a methylotrophic yeast, and more particularly a methylotropic yeast of the genus *Pichia*, to oxidize methane, consume methane to make desired products or grow on methane as a carbon source.

SUMMARY

The disclosed embodiments of the invention provide compositions, systems, and methods that enable a methylotrophic (methanol-consuming) microorganism, which is naturally non-methanotropic, including bacteria or yeast, to oxidize methane and consume methane. In embodiments, the compositions, systems and methods herein enable such methylotrophic microorganisms to oxidize methane to methanol. In embodiments, the compositions, systems and methods herein enable such methylotrophic microorganisms to oxidize methane to methanol, where methanol is thereafter converted into desired microbial products. Of particular interest are methylotrophic yeast which can be employed as microbial platforms for the production of desired microbial products, such as polypeptide or protein pharmaceuticals, enzymes, amino acids, nucleic acids, saccharides or polysaccharides and biomass. Microbial manufacturing platforms based on methylotropic yeast such as *Pichia pastoris* are of particular interest because they grow on and produce microbial products from methanol, can be and have been genetically manipulated using or adapting now well-known techniques of genetic engineering, can be or have been used for the industrial production of microbial products, and avoid the disadvantages of methanotropic bacteria.

In some embodiments of the invention, a methylotrophic microorganism is engineered to express soluble methane monooxygenase (sMMO) functional for oxidation of methane. In some embodiments of the invention, a methylotrophic microorganism is engineered to express all subunits (alpha, beta, and gamma) of the MMO hydroxylase (MMOH). In some embodiments of the invention, a methylotrophic microorganism is engineered to express all subunits of the MMO hydroylase (MMOH) as a single transcript. In some embodiments of the invention, a methylotrophic microorganism is engineered to express MMO reductase (MMOR) and all MMOH subunits. In some embodiments of the invention, a methylotrophic microorganism is engineered to express MMO reductase (MMOR), all MMOH subunits and MMO regulatory protein (MMOB). In some embodiments of the invention, a methylotrophic microorganism is engineered to express MMO reductase (MMOR), all MMOH subunits and MMO regulatory protein (MMOB). In some embodiments of the invention, a methylotrophic microorganism is engineered to express MMO reductase (MMOR), all MMOHs subunits, MMO regulatory protein (MMOB) and putative chaperone protein MMOG. In some embodiments, the methylotrophic microorganism is a methylotrophic yeast. In some embodiments, the methylotropic yeast is a strain of the genus *Candida, Ogataea* (*Hansensula*), *Pichia, Dekkera*, or *Pachysolen*. In some embodiments, the methylotrophic yeast is *Candida arabinofermentans, Ogataea (Hansensula) polymorpha, Ogataea methanolica, Pichia pastoris, Pichia membranifaciens, Dekkera bruxellensis*, or *Pachysolen tannophilus*, Yeasts of the genus *Pichia* and particularly *Pichia pastoris* provide a refined microbial factory that is used widely by industry because it efficiently secretes products. *Pichia* can be used to produce a variety of useful products which clearly would be useful in space. *Pichia* does not consume methane, but robustly consumes methanol, which is one enzymatic step removed from methane. In some embodiments of the invention, *Pichia* is engineered to consume methane, thereby creating a powerful methane-consuming microbial factory. In some embodiments of the invention, *Pichia* is engineered to oxidize methane. In some embodiments of the invention, *Pichia* is engineered to express soluble methane monooxygenase (sMMO) functional for oxidation of methane. In some embodiments of the invention, *Pichia* is engineered to express all subunits of the MMO hydroxylase (MMOH). In some embodiments of the invention, *Pichia* is engineered to express all subunits of the MMO hydroxylase (MMOH) as a single transcript. In some embodiments of the invention, *Pichia* is engineered to express MMO reductase (MMOR) and all MMOH subunits. In some embodiments of the invention, *Pichia* is engineered to express MMO reductase (MMOR), all MMOH subunits and MMO regulatory protein (MMOB). In some embodiments of the invention, *Pichia* is engineered to express MMO reductase (MMOR), all MMOH subunits and MMO regulatory protein (MMOB). In some embodiments of the invention, *Pichia* is engineered to express MMO reductase (MMOR), all MMOH subunits, MMO regulatory protein (MMOB) and putative chaperone protein MMOG. In some embodiments, the *Pichia* is *Pichia pastoris*. In some embodiments, the *Pichia* is *Pichia membranifaciens*.

Some embodiments of the invention include a methylotrophic yeast, particularly a strain of methylotrophic yeast of the genus *Pichia*, and more particularly a strain of *Pichia pastoris*, comprising the nucleic acid construct pPTK052 (SEQ ID NO: 42) or pPTK053 (SEQ ID NO: 43) or variants of such constructs that are at least 85%, at least 90%, at least 95%, at least 98% or at least 99% identical to pPTK052 and pPTK053, respectively. In some embodiments, coding sequences in pPTK052 or pPTK053 are expressed such that the methylotrophic yeast expresses all three of the MMOH subunits. In some embodiments, coding sequences in pPTK052 or pPTK053 are expressed such that the MMOH complex forms. In some embodiments, coding sequences in pPTK052 or pPTK053 are expressed such that an MMOH complex forms that is active for methane oxidation.

Some embodiments of the invention include a methylotrophic yeast, particularly a strain of methylotrophic yeast of the genus *Pichia*, and more particularly a strain of *Pichia pastoris*, comprising the nucleic acid constructs pPTK052 (SEQ ID NO: 42) or PTK053 (SEQ ID NO: 43) and construct pPTK101 (SEQ ID NO: 48) or variants of such constructs that are at least 90%, at least 95% or at least 99% identical to pPTK052 or pPTK053 and pPTK101, respectively. In some embodiments, coding sequences in pPTK052 or pPTK053 and pPTK101 are expressed such that the methylotrophic yeast expresses all three of the MMOH subunits. In some embodiments, coding sequences in pPTK052 or pPTK053 and pPTK101 are expressed such that the MMOH complex forms. In some embodiments, coding sequences in pPTK052 or pPTK053 and pPTK101 are expressed such that an MMOH complex forms that is active for methane oxidation. In some embodiments, coding sequences in pPTK052 or pPTK053 and pPTK101 are expressed such that the methylotrophic yeast exhibits the ability to convert methane to methanol, and wherein said ability is not present in the methylotrophic yeast not containing the listed constructs.

Some embodiments of the invention include a methylotrophic yeast, particularly a strain of methylotrophic yeast of the genus *Pichia*, and more particularly a strain of *Pichia pastoris*, comprising the nucleic acid constructs pPTK052 (SEQ ID NO: 42) or PTK053 (SEQ ID NO: 43) and construct pPTK100 (SEQ ID NO: 47) or variants of such constructs that are at least 90%, at least 95% or at least 99% identical to pPTK052 or pPTK053 and pPTK100, respectively. In some embodiments, coding sequences in pPTK052 or pPTK053 and pPTK100 are expressed such that the methylotrophic yeast expresses all three of the MMOH subunits. In some embodiments, coding sequences in pPTK052 or pPTK053 and pPTK100 are expressed such that the MMOH complex forms. In some embodiments, coding sequences in pPTK052 or pPTK053 and pPTK100 are expressed such that an MMOH complex forms that is active for methane oxidation. In some embodiments, coding sequences in pPTK052 or pPTK053 and pPTK100 are expressed such that the methylotrophic yeast exhibits the ability to convert methane to methanol, and wherein said ability is not present in the methylotrophic yeast not containing the listed constructs.

Some embodiments include a methylotrophic microorganism, particularly a methylotrophic yeast, more particularly a methylotrophic *Pichia* strain, and yet more particularly a methylotrophic *Pichia pastoris* strain including nucleotide sequences for at least the two proteins: methane monooxygenase hydrolase (MMOH) and methane monooxygenase reductase (MMOR) from a soluble methane monooxygenase sequence found in a natural methanotroph, wherein the at least two proteins are expressed such that the methylotrophic microorganism, yeast, *Pichia* strain, or *Pichia pastoris* strain exhibits the ability to convert methane to methanol, and wherein said ability is not present in the methylotrophic microorganism not containing the at least two proteins.

Some embodiments include a methylotrophic microorganism, particularly a methylotrophic yeast, more particularly a methylotrophic *Pichia* strain, and yet more particularly a methylotrophic *Pichia pastoris* strain genetically modified to enable oxidation of methane to methanol, methods of so modifying methylotrophic microorganisms, and nucleic acid constructs employed as part of said methods.

Some embodiments include a non-naturally-occurring or synthetic polynucleotide useful in the methods or microorganisms, and particularly in methylotrophic yeast, of this invention, which is selected from the nucleotide sequences set forth in SEQ ID NOs: 26-48 or a polynucleotide which is at least 60%, at least 70%, at least 80%, at least 85%, at least 90%, at least 95%, at least 95%, at least 97%, at least 98%, or at least 99% identical to a nucleotide sequence set forth in SEQ ID NOs: 26-48. Some embodiments include a non-naturally-occurring or synthetic polynucleotide useful in the methods or microorganisms, and particularly in methylotrophic yeast, of this invention, which is selected from the nucleotide sequences set forth in SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, or a polynucleotide which is at least 60%, at least 70%, at least 80%, at least 85%, at least 90%, at least 95%, at least 95%, at least 97%, at least 98%, or at least 99% identical to a nucleotide sequence set forth SEQ ID NOs 41-48. In some embodiments, the invention provides a non-naturally-occurring or synthetic polynucleotide selected from the nucleotides set forth in SEQ ID NO: 42, SEQ ID NO: 43, SEQ ID NO: 47 or SEQ ID NO: 48 or a polynucleotide which is at least 85%, at least 90%, at least 95%, at least 95%, at least 97%, at least 98%, at least 99% identical thereto.

Some embodiments of the invention include methods for modifying a methylotrophic microorganism, particularly a methylotrophic yeast, more particularly a methylotrophic *Pichia* strain, and yet more particularly a methylotrophic *Pichia pastoris* strain, by introduction into the microorganism of one or more polynucleotide sequences, which when expressed in the microorganism result in generation of all three of the MMOH α, β, and γ subunits. In some embodiments, the three MMOH subunits are expressed as a single transcript. In some embodiments, expression of the one or more polynucleotide sequences in such a microorganism results in formation of the MMOH complex. In some embodiments, expression of the one or more polynucleotide sequences in such a microorganism results in formation of an MMOH complex that is active for methane oxidation. In some embodiments, expression of the one or more polynucleotide sequences in such a microorganism result in a modified microorganism which exhibits the ability to convert methane to methanol, and wherein said ability is not present in the microorganism not containing the expressed one or more polynucleotides.

Some embodiments of the invention include methods for making microbial products with a genetically modified methylotrophic microorganism which exhibits the ability to oxidize methane. Some further embodiments include methods for making microbial products with a genetically modified methylotrophic microorganism which exhibits the ability to convert methane to methanol. Some further embodiments include methods for making microbial products with a genetically modified methylotrophic microorganism which exhibits the ability to, at least in part, employ methane as a carbon source. In some embodiments, the modified methylotrophic microorganism is a methylotrophic yeast. In some embodiments, the modified methylotrophic yeast is a strain of *Pichia*. In embodiments, the modified methylotropic yeast is a strain of *Pichia pastoris*.

Other embodiments of the invention will be apparent to one of skill in the art in view of the non-limiting drawings, detailed description and examples which follow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

To avoid the challenges associated with utilizing natural methanotrophs, embodiments of the invention modify methylotrophic microorganisms to enable oxidation of methane to methanol. This is achieved by introducing into a methylotrophic microorganism one or more nucleic acid constructs that encode a soluble methane monooxygenase (sMMO) enzyme complex found in a natural methanotroph. Methylotrophic organisms do not consume methane, but do naturally consume methanol, which is one enzymatic step removed from methane. Accordingly, once the methylotrophic microorganism is modified to enable the microorganism to oxidize methane to methanol, methanol is consumed by the natural methanol-utilizing pathway of the methylotrophic microorganism. Previously, sMMO has been studied in vitro for basic research purposes, but it is believed that sMMO has not been transferred successfully into a non-native microorganism and particularly not into a methylotrophic yeast, such as *Pichia*.

Figure 2:
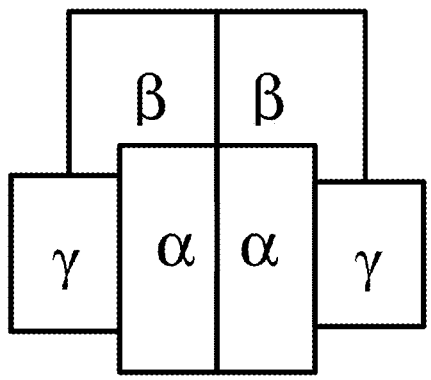
FIG. 2 illustrates the hexameric structure of the MMOH complex of soluble MMO contain two of each of subunits MMOH alpha, MMOH beta and MMOH gamma, according to some embodiments.

In methanotrophic bacteria, the first step in methane metabolism is to oxidize methane to methanol with methane monooxygenases (MMOs). To do this, methanotropic bacteria utilize two different types of MMO: soluble MMO (sMMO) and particulate MMO (pMMO). The requirements for pMMO function are less well characterized, but the mechanism of the sMMO methane oxidation is understood and includes a hydroxylase (MMOH), a reductase (MMOR) and a regulatory protein (MMOB). MMOH is a hexameric complex composed of two sets of three subunits ($\alpha$, $\beta$ and $\gamma$), as shown in FIG. 2. MMOR reduces MMOH by transferring electrons from NADH to the diiron center of MMOH. MMOB greatly increases the reaction rate between MMOH and $O_2$, and causes a conformational change in MMOH which is believed to increase access to its active site. A fourth protein MMOG, has been proposed as a putative chaperone protein that aids in the proper assembly of the sMMO system. MMOH and MMOR are strictly required to drive methane hydroxylation, while MMOB and MMOG may facilitate faster reaction rates. Methylotrophic microorganisms lack such a system to convert methane to methanol.

Figure 1:
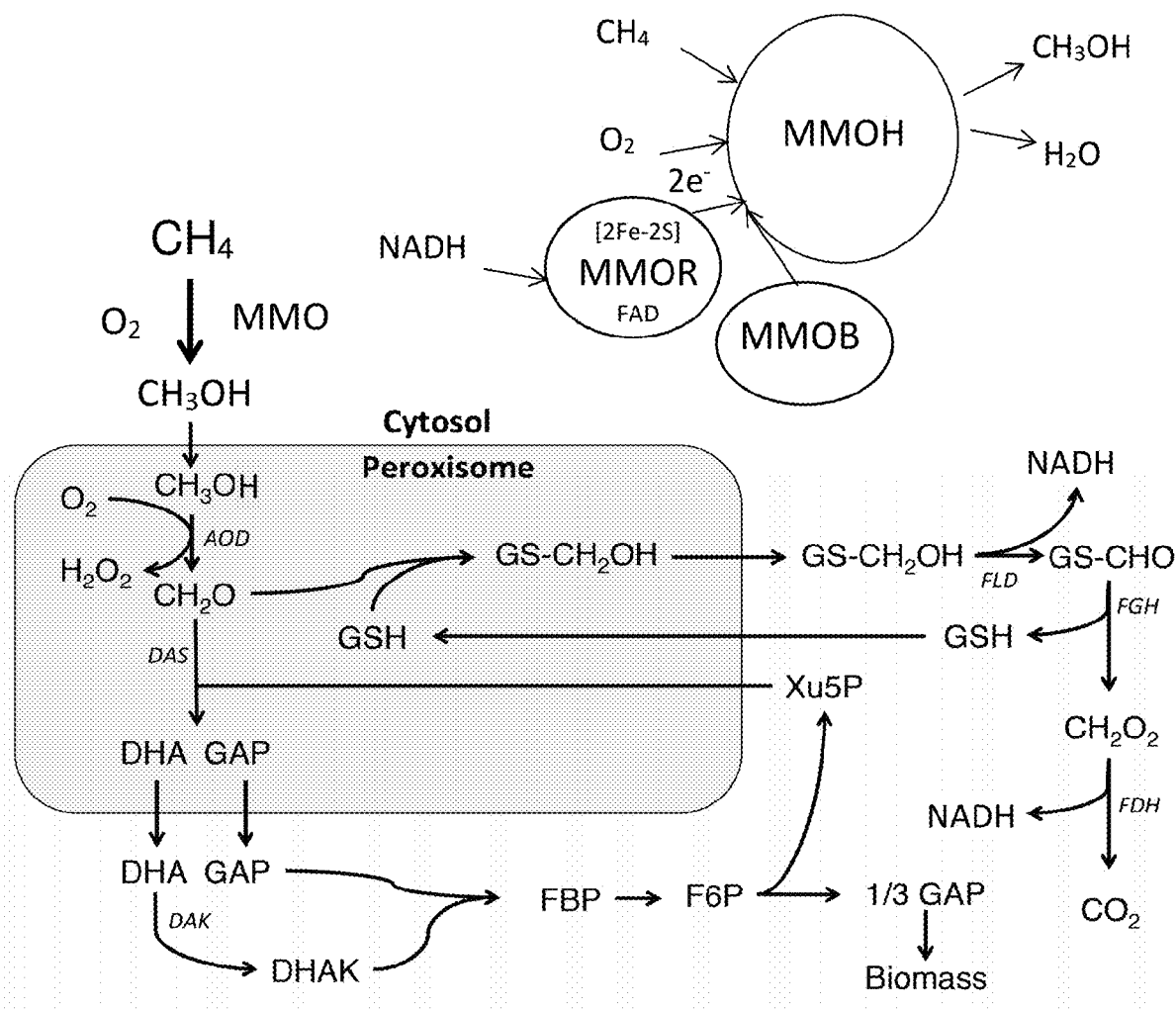
FIG. 1 schematically illustrates natural methanol metabolism by *Pichia pastoris* with the addition of methane metabolism via methane monooxygenase (MMO) to generate an exemplary synthetic (non-naturally occurring) methanotrophic yeast, according to some embodiments. In the figure, with respect to methanol metabolism, AOD is alcohol oxidase, FLD is formaldehyde dehydrogenase, FGH is S-formylglutathione hydrolase, FDH is formate dehydrogenase, DAS is dihydroxyacetone synthase and DAK is dihydroxyacetone kinase. Methane can be derived from any source, but for example, can be generated from $CO_2$ and hydrogen in a Sabatier reaction. With respect to methane metabolism, methane monooxygenase is MMO, and more specifically is soluble MMO (sMMO). MMO includes three components: methane monooxygenase hydroxylase (MMOH) composed of three subunits (MMOH alpha, MMOH beta, and MMOH gamma), methane monooxygenase reductase (MMOR) and a regulatory protein methane monooxygenase B (MMOB).

FIG. 1 illustrates natural methanol metabolism by *Pichia pastoris* with the addition of methane metabolism via methane monooxygenase (MMO), specifically soluble MMO, to generate an exemplary synthetic (non-naturally occurring) methanotrophic yeast. In *P. pastoris* methanol ($CH_3OH$) is oxidized to formaldehyde ($CH_2O$) by alcohol oxidase (AOD). Formaldehyde is then either oxidized to $CO_2$ through the successive action of formaldehyde dehydrogenase (FLD), S-formylglutathione hydrolase (FGH), and formate dehydrogenase (FDH), or appended to xylulose-5-phosphate and assimilated into biomass through a pathway involving dihydroxyacetone synthase (DAS) and dihydroxyacetone kinase (DAK). Methane can be derived from any source, but for example, can be generated from $CO_2$ and hydrogen in a Sabatier reaction. Methane is oxidized to methanol via MMO, specifically soluble MMO.

Figure 3A:
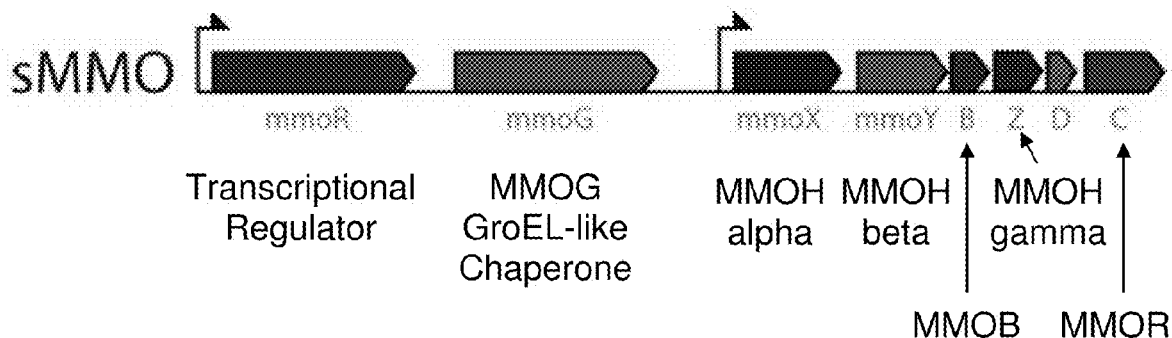
FIG. 3A schematically illustrates the MMO gene cluster of *Methosinus trichosporium*. The MMOH subunits, MMOG, MMOB and MMOR are described in the text.

FIG. 3A illustrates the MMO gene cluster from *Methylosinus trichosporim* indicating the location of coding sequences for the MMOH $\alpha$, MMOH $\beta$ and MMOH $\gamma$ subunits of MMOH. Additionally shown are the locations of coding sequences for MMOR, MMOB and MMOG.

To genetically modify a methyltrophic microorganism to exhibit the ability to convert methane to methanol, at least the three MMOH subunits are expressed in that microorganism. In addition, at least MMOR is also expressed in that microorganism in active form. The expressed MMOH subunits form the active hexamer MMOH complex as illustrated in FIG. 2. Optionally, additional expression of MMOB in active form in the methylotrophic microorganism facilitates methane oxidation. Optionally, additional expression of MMOG in active form in the methylotrophic microorganism facilitates the formation of MMO complex functional for methane oxidation.

In some embodiments, each MMOH subunit and MMOR are individually assembled for expression in the methylotrophic microorganism each coding sequence operably linked for expression with regulatory sequences, including at least a promoter and a terminator which function in the methylotrophic microorganism. Each such assembly with a coding sequence and associated promoter and terminator is introduced into the methylotrophic microorganism as is known in the art, for example on one or preferably more than one plasmid that can be transformed into, is replicated and maintained in, and from which the assembly is expressible in the methylotrophic microorganism. In some embodiments, the assemblies are introduced into the methylotrophic microorganism on two separate plasmid constructs. In some embodiments, the three assemblies each containing the coding sequence for an MMOH subunit are all contained on one first plasmid for introduction into the methylotrophic microorganism. In some embodiments, the assembly containing the coding sequence for MMOR is contained on a second plasmid for introduction into the methylotrophic microorganism. In some embodiments, the assembly containing the coding sequence for MMOR, that containing the coding sequence of MMOB, and optionally that containing the coding sequence of MMOG are contained on a second plasmid for introduction into the methylotrophic microorganism. In some embodiments, the three assemblies each containing the coding sequence for an MMOH subunit and the assembly containing the coding sequence for MMOR are all contained on one plasmid for introduction into the methylotrophic microorganism. In some embodiments, the assembly containing the coding sequence of MMOB and optionally that containing the coding sequence of MMOG are contained on a second plasmid.

Figure 3B:
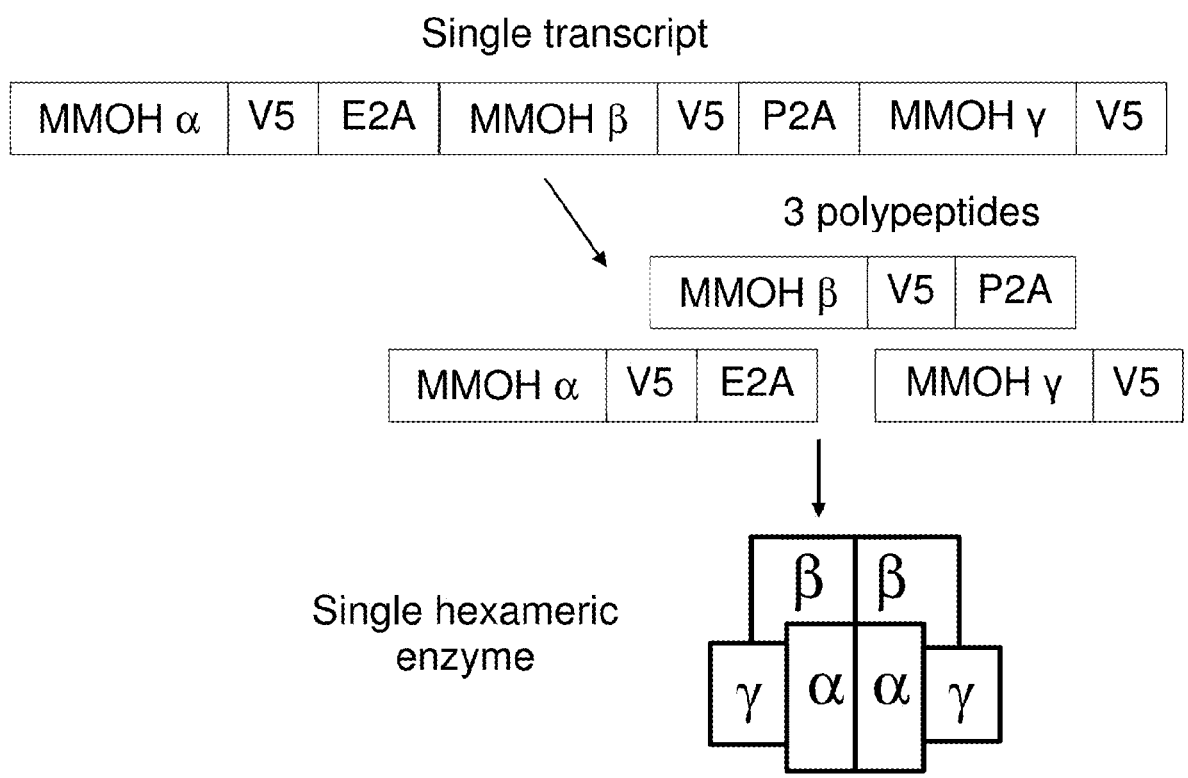
FIG. 3B illustrates a DNA construct in which the MMOH subunits are assembled in an exemplary single transcript in which each subunit is tagged with V5 for detection, and wherein the sequences encoding the MMOH subunits are separated by intervening polynucelotides, according to some embodiments. The intervening polynucleotides are exemplified as encoding certain self-cleaving peptide sequences. V5 tagging of the subunits is not necessary for generation of functional MMOH subunits. The use of self-cleaving peptides E2A and P2A are illustrated. After expression of the single transcript, the transcript is cleaved into component subunits by cleavage of the self-cleaving peptides. The single transcript approach is believed to represent a significant improvement over prior art approaches for expression of MMOH subunits. Using expression of the MMOH subunits in a single transcript is believed to better control the stoichiometry of the component subunits. Cleaved subunits form the hexameric MMOH enzyme complex. As described herein alternative intervening nucleotide sequences can be employed to facilitate formation of the hexameric MMOH enzyme complex. Additional intervening polynucleotides include those encoding sequence selective protease amino acid recognition sequences and those encoding flexible peptide linkers.

FIG. 3B illustrates assembly of the three MMOH subunits into a single transcript for expression from a single promoter and terminator pair. The three subunit coding sequences are positioned sequentially between the promoter and the terminator for expression as a single transcript in the methylotrophic microorganism. The order of positioning of the coding sequences in the single transcript is not critical. However, each of the coding sequences should be expressed in the single transcript. The coding sequences of the MMOH subunits are fused within the assembly and optionally separated by selected intervening nucleotide sequences which do not disrupt expression of the single transcript and optionally facilitate cleavage of the expressed subunits or allow for or facilitate formation of the hexamer MMOH.

In some embodiments, the intervening nucleotide sequences encode a self-cleaving peptide. FIG. 3B illustrates the use of coding sequences for two different self-cleaving peptides, E2A (SEQ ID NO: 9) and P2A (SEQ ID NO: 10).

In some embodiments, the intervening nucleotide sequence between each of the MMOH subunit coding sequences encodes a self-cleaving peptide selected from self-cleaving peptides E2A, F2A, P2A, T2A, GE2A, GF2A, GP2A or GT2A (SEQ ID NOs: 49 to 56, respectively).

In some embodiments, the intervening nucleotide sequences between each of the MMOH subunit coding sequences encodes a sequence-specific protease recognition site. In some embodiments, the intervening nucleotide sequence between each of the MMOH subunit coding sequences encodes a sequence-selective protease recognition site of a sequence-selective protease endogenous to the methylotrophic microorganism. In some embodiments, the intervening nucleotide sequence between each of the MMOH subunit coding sequences encodes a sequence-selective protease recognition site of a sequence-selective protease derived from a source exogenous to, or heterologous to, the methylotrophic microorganism. In some embodiments, the exogenously derived sequence-selective protease is derived from a virus. In some embodiments, the exogenously derived sequence-selective protease is derived from a mammal.

A variety of naturally-occurring and sequence-specific proteases that recognize and cleave specific amino acid sequences are known in the art. These proteases have been used for decades in biotechnology for a variety of purposes including the removal of expression tags. Waugh (2011) Protein Expression and Purification 80(2): 283-293 provides a review of enzymatic reagents including examples of sequence-selective proteases which can be employed in the methods and compositions of the invention. This reference is incorporated by reference herein in its entirety for descriptions of sequence-specific proteases including information on sources of the proteases and protease recognition sequences.

Sequence-selective proteases include among others, human rhinovirus (HRV) 3C protease which recognizes the amino acid sequence (LEVLFQ/GP), where the slash indicates cleavage, (SEQ ID NO: 57); enterokinase which recognizes the amino acid sequence (DDDDK/), where the slash indicates cleavage, (SEQ ID NO: 58); factor Xa protease which recognizes the amino acid sequence (IEGR/), where the slash indicates cleavage, (SEQ ID NO: 59); tobacco etch virus (TEV) protease which recognizes the amino acid sequence (ENLYFQ/G), where the slash indicates cleavage, (SEQ ID NO: 60); thrombin (EC 3.4.21.5) which recognizes the amino acid sequence (LVPR/GS), where the slash indicates cleavage, (SEQ ID NO: 61); tobacco vein mottling virus (TVMV) protease, which recognizes the amino acid sequence (ETVRFQG/S), where the slash indicates cleavage, (SEQ ID NO: 62); and plum pox potyvirus protease which recognizes the amino acid sequence (NVVVH/A)), where the slash indicates cleavage, (SEQ ID NO: 63).

In some embodiments, where the intervening sequences encode the amino acid recognition sequence of a given sequence-selective protease that is exogenous to the methylotrophic microorganism (i.e., not expressed in nature by the methylotrophic microorganism), the methylotrophic organism is further transformed to introduce a nucleotide coding sequence of the selected sequence-selective protease. It will be appreciated by one of ordinary skill in the art that a number of useful sequence-selective proteases have been cloned and introduced into and successfully expressed to produce active protease in cells other than those from which the given sequence-selective protease derives.

It will also be appreciated that genetically-modified versions of such proteases, for example, truncated proteases or mutated proteases, which still provide active proteases which retain sequence-selectivity may be used and introduced as the exogenous protease. For example, a modified TEV protease lacking the C-terminal 238-242 residues retains sequence-selective protease activity for cleavage at the protease recognition site.

One or more of these proteases can be used to generate equivalent amounts of MMOH alpha, beta and gamma from a single polypeptide (i.e., a single transcript) including the protease cleavage site between the subunits. In addition, the corresponding sequence-specific protease would be expressed within the selected methylotrophic organism, either from a plasmid or a site of genomic integration.

In some embodiments, the intervening nucleotide sequence between each of the MMOH subunit coding sequences encodes a sequence-selective protease recognition site of a sequence-selective protease selected from human rhinovirus (HRV) 3C protease, enterokinase, factor Xa protease, tobacco etch virus (TEV) protease, thrombin (EC 3.4.21.5), tobacco vein mottling virus (TVMV) protease, or plum pox potyvirus protease. In some embodiments, each of the intervening sequences between the MMOH subunit coding sequences encode the peptide recognition site of the same sequence-selective protease.

In some embodiments, the intervening nucleotide sequence encodes one or more flexible disordered linker amino acid sequences in order to fuse two or more of the MMOH polypeptides separated by a flexible amino acid sequence. Flexible linkers of various sizes, typically 2-31 amino acids, are designed, as is known in the art, by including various numbers and combinations of serine, threonine, or glycine residues or combinations thereof. Small non-polar (glycine) or polar (serine or theorine) amino acids confer flexibility. Lysine and glutamate residues can also be included to improve solubility, while alanine residues can be included to improve flexibility. Chen et al. (2013) Adv. Drug Deliv. Rev. 65(10): 1357-1369; Rosmalen et al. (2017) Biochemisty, 56, 50, 6565-6574; and Chichili et al. (2013) Protein Science 22(2), 153-167, for example, provide description of flexible amino acids linkers useful for preparation of fusion proteins. A commonly used linker is a stretch of one or more glycines and one or more serines, e.g., GGGGS, which are repeated. The number of repeats of such glycine/serine monomers is adjusted to obtain a desired separation between polypeptides. In some embodiments, the flexible linker ranges in length from 8 to 20 amino acids. In specific embodiments, the flexible linkers include among others:

(GS)n, where n is 3-15, (GGS)n, where n = 2-10, (GGSGG)n, where n = 1 to 6 (when n = 1, SEQ ID NO: 53)

(GGGGS)n, where n = 1 to 6 (when n = 1, SEQ ID NO: 54)

(GGGG)n, where n is 1 to 6 (when n = 2, SEQ ID NO: 55)

KESGSVSSEQLAQFRSLD (SEQ ID NO: 56)

GSAGSAAGSGEF (SEQ ID NO: 57)

In some embodiments, the soluble methane monooxygenase system (sMMO) from a methanotrophic bacterium, for example, a strain of *Methylosinus trichosporium* is employed in the methods, compositions, DNA constructs, and transformed microorganisms herein. In some embodiments, a soluble methane monooxygenase system (sMMO) from a methanotropic bacterium, for example, a strain of *Methylosinus trichosporium*, is transformed into a methylotrophic yeast, for example, a strain of *Pichia* and more particularly a stain of *Pichia pastoris*.

*Pichia pastoris* is a microbial manufacturing platform. *Pichia pastoris* is a desirable microbial manufacturing platform due to many factors including the existence of simple high density culturing conditions, strong regulated promoters, robust secretion of proteins, the ability to append appropriate post translational modifications to proteins, and its GRAS status (Generally Regarded As Safe). In contrast to bacteria, *P. pastoris* is not susceptible to bacteriophage infection, and genomic integrations of *P. pastoris* are more stable. In further advantage to the more commonly used yeast, *Saccharomyces cerevisiae*, *P. pastoris* is less likely to hyper-mannosylate proteins. As a result, *P. pastoris* exhibits improved activity and biocompatibility, and extensive engineering of *P. pastoris* has led to the generation of *P. pastoris* strains which exhibit full humanization of its glycosylation system (Hamilton et al. (2006) Science 313(5792):=1441-1443). In addition, the peroxisome of *P. pastoris* is used to compartmentalize engineered metabolic pathways that would otherwise interfere with the native metabolic networks. In addition to multiple protein products, *P. pastoris* has been used to produce over 30 small molecule metabolites.

Commercial products made in *Pichia* systems range from common proteins used in research such as trypsin, murine TNF-α and human stem cell factor to FDA approved drugs including ecallantide for hereditary angioedema and ocriplasmid for symptomatic vitreomacular adhesions. Work has also been done to develop host strains that produce more human-like glycosylation for proteins with clinical uses and strains that are deficient in proteases to prevent degradation of protein product.

Given the number of products produced in *Pichia* systems and the other benefits of using the *P. pastoris* as a microbial manufacturing platform, the utility of some embodiments of the invention that use a *P. pastoris* that is modified to consume an inexpensive waste product (such as methane) is high. Particularly in the context of deep space travel, it would be beneficial to have a methane-consuming microorganism that (unlike natural methanogens) could be used to produce numerous known bioproducts and to continue to develop additional strains of *P. pastoris* to produce other bioproducts as needed.

Previous approaches for production of a functional MMOH complex outside of the native host have proven to be challenging. One potential reason for this is that multi-subunit complexes may require precise control over subunit stoichiometry to ensure correct assembly and avoid aggregation of un-assembled subunits.

To alleviate this issue, some embodiments of the invention implement an innovative approach in which all three MMOH subunits are expressed as a single transcript (i.e., a single polypeptide). In some embodiments, this transcript contains type 2A ribosome skipping sequences between each subunit gene (alpha-2a-beta-2a-gamma). These short sequences cause the ribosome to skip a peptide bond during translation, see Chng et al. (2015) mAbs 7(2): 403-412. One purpose of this mechanism is to produce these three subunits at equivalent stoichiometry—a strategy that has been successfully implemented to differentiate stem cells. In some embodiments, the three polypeptides are encoded on a single gene assembled between a promoter and terminator, rather than in separate genes, and the entire sequence is transcribed as a single RNA, minimizing variables that may decrease the likelihood of equal expression of each polypeptide. Some embodiments of this invention therefore mimic the single transcript production of sMMO observed in natural methanogens.

Some embodiments employ other means of achieving the desired subunit stoichiometry. For example, in some embodiments, all MMOH subunits are expressed as a single protein, including protease cleavage sites that sever the protein into three subunits. Again, this would cause the proteins to be produced together and thus at equivalent stoichiometry. In some embodiments, one or more flexible disordered linker sequences are used to fuse two or more of the MMOH polypeptides. When assembled correctly, the end of one polypeptide in the complex is very close to the beginning of the next one. By producing one polypeptide, and eliminating the small gap, what are naturally separate polypeptides are connected by linker sequences. In this case, since the subunits are no longer separate, they are expressed at equivalent stoichiometry. The flexible linkers are selected to allow correct assembly of the MMOH subunits.

In some embodiments, once the sMMO components are successfully transformed into the methylotrophic microorganisms, successful assembly of MMOH subunits is optimized through directed evolution. In some embodiments, the transformed methylotrophic microorganisms are provided with methane as a sole carbon source. Methylotrophic microorganisms that survive are amplified and propagated, and any necessary changes to the sequences of their genome or the sMMO components identified.

In some embodiments, the assembly of the MMOH complex may be improved by modifying expression levels of the transcript by use of different promoter and terminator combinations. This approach may improve the assembly by titrating the amount of each MMOH subunit until their concentration is optimized for assembly. The promoters and terminators chosen include natural promoters from *Pichia pastoris* or other methylotrophic microorganisms, or engineered or synthetic promoters. Promoters may be selected from the methylotrophic microorganism based upon their expression levels in RNA sequencing datasets. Promoter/terminator pairs that drive high expression levels in these datasets presumably do the same when driving expression of MMOH subunits. Alternatively, in some embodiments, synthetic promoter sequences are developed by screening through semi-random sequences of DNA to find those giving optimal expression.

In some embodiments, the expression levels of the MMOH subunits may be modified by introducing additional copies of coding sequences of MMOH subunits into the methylotrophic microorganism. In some embodiments, additional MMOH subunit coding sequences may be introduced into the methylotrophic microorganism as a single transcript as described herein, where all subunit coding sequences are operably linked to a single selected promoter/terminator pair. In some embodiments, additional MMOH subunit coding sequences may be introduced into the methylotrophic microorganism as a second single transcription unit under the control of a single selected promoter/terminator pair.

In some embodiments, the invention provides methylotrophic microorganisms comprising three methane monooxygenase hydroxylase (MMOH) protein subunits of a methanotrophic bacterium: MMOH alpha, MMOH beta and MMOH gamma, and methane monooxygenase reductase (MMOR) of a methanotrophic bacterium, wherein the methane monooxygenase (MMO) is a soluble MMO and wherein the microorganism exhibits oxidation of methane to methanol. In some embodiments, the methylotrophic microorganism is a methylotropic yeast. In some embodiments, the methylotrophic microorganism is a methylotropic strain of the genus *Pichia*. In some embodiments, the methylotropic microorganism is *Pichia pastoris*. In some embodiments, the methanotrophic bacterium from which the MMOH subunits and MMOR are derived is a strain of *Methylosinus trichosporium* or *Methylococcus capsulatus*. In some embodiments, the methylotrophic microorganisms containing the MMOH and MMOR convert methane to microbial products. In some embodiments, the methylotrophic microorganisms containing the MMOH and MMOR at least in part employ methane as a carbon source.

In some embodiments, the nucleotide coding sequences of the three MMOH protein subunits are expressed in the microorganism as a single transcript. In some embodiments, in the single transcript the nucleotide coding sequences of MMOH protein subunits are separated by nucleotide sequences encoding one or more self-cleaving peptides, encoding one or more amino acid recognition sites of a sequence-selective protease, or encoding one or more flexible disordered linker amino acid sequences.

In some embodiments, the methylotrophic microorganisms comprising the three methane monooxygenase hydroxylase (MMOH) protein subunits of a methanotrophic bacterium: MMOH alpha, MMOH beta and MMOH gamma, and methane monooxygenase reductase (MMOR) of a methanotrophic bacterium, further comprises one or both of methane monooxygenase B (MMOB) or methane monooxygenase G (MMOG) both of a soluble MMO of a methanotrophic bacterium.

In some embodiments, the invention provides a strain of *Pichia pastoris* which is transformed to comprise pPTK052 (SEQ ID NO: 42), pPTK053 (SEQ ID NO: 43) or a DNA construct having at least 95% identity thereto. In some embodiments, the strain of *Pichia pastoris* is further transformed to comprise pPTK100 (SEQ ID NO: 47) or a DNA construct having at least 95% identity thereto or pPTK101 (SEQ ID NO: 48), or a DNA construct having at least 95% identity thereto or a combination thereof.

In some embodiments, the invention provides a non-naturally-occurring or synthetic polynucleotide useful in the methods or microorganisms of this invention which is selected from the nucleotide sequences set forth in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, and SEQ ID NO: 48, or a polynucleotide which is at least 60%, at least 70%, at least 80%, at least 85%, at least 90%, at least 95%, at least 95%, at least 97%, at least 98%, or at least 99% identical to a nucleotide sequence set forth in the listed SEQ ID NOs. In an embodiment, the invention provides a non-naturally-occurring or synthetic polynucleotide selected from the nucleotides set forth in SEQ ID NO: 28, SEQ ID NO: 32, SEQ ID NO: 41, SEQ ID NO: 43, SEQ ID NO: 44, SEQ ID NO: 45, SEQ ID NO: 46, SEQ ID NO: 47, and SEQ ID NO: 48 or a polynucleotide which is at least 60%, at least 70%, at least 80%, at least 85%, at least 90%, at least 95%, at least 95%, at least 97%, at least 98%, or at least 99% identical to a nucleotide sequence set forth in the listed SEQ ID NOs. In an embodiment, the invention provides a non-naturally-occurring or synthetic polynucleotide selected from the nucleotides set forth in SEQ ID NO: 42, SEQ ID NO: 43, SEQ ID NO: 47 and SEQ ID NO: 48 or a polynucleotide which is at least 85%, at least 90%, at least 95%, at least 95%, at least 97%, at least 98%, or at least 99% identical thereto. In an embodiment, the invention provides a non-naturally-occurring or synthetic polynucleotide selected from the nucleotides set forth in SEQ ID NO: 42, and SEQ ID NO: 43 or a polynucleotide which is at least 85%, at least 90%, at least 95%, at least 95%, at least 97%, at least 98%, or at least 99% identical thereto.

In some embodiments, the invention provides a non-naturally-occurring synthetic plasmid useful in the methods or selected microorganisms herein which comprises:

(1) a first origin for replication in a selected microorganism, preferably a methylotrophic microorganism, more preferably a methylotropic yeast, and yet more preferably a methylotrophic strain of *Pichia*;

(2) an expressible polynucleotide coding sequence for a selective marker for selection in the selected microorganism; and (3) at least one polypeptide coding assembly comprising at least one polynucleotide coding sequence encoding a selected polypeptide which is operably linked to a promoter sequence and a terminator sequence for expression in the selected microorganism on introduction of the plasmid into the selected microorganism, wherein the at least one coding sequence is selected from those encoding an MMOHα, an MMOHβ, an MMOHγ, an MMOB, an MMOR or an MMOG of a methanotroph. In some embodiments, the selected methylotropic yeast is a strain of *Pichia pastoris*.

In some further embodiments, the non-naturally-occurring synthetic plasmid further comprises a second origin of replication for replication and maintenance in an appropriate host organism, for example a strain of *E. coli* to allow replication and maintenance of the plasmid in the host organism and an expressible polynucleotide coding sequence for a selective marker for selection in the host organism.

In some further embodiments, the non-naturally-occurring synthetic plasmid further comprises at least one cloning site for introduction of one or more additional polynucleotide coding sequences.

In some more specific embodiments in the non-naturally-occurring synthetic plasmid, the at least one polypeptide coding assembly comprises at least one coding sequence of an MMOH alpha, at least one coding sequence of an MMOH beta, and at least one coding sequence of an MMOH gamma, all of which are of a methanotrophic bacterium, wherein the at least three coding sequences are assembled in a single transcript operably linked to a single promoter and a single terminator for expression as a single transcript in the selected microorganism. In some more specific embodiments in the non-naturally-occurring plasmid, the at least three coding sequences are assembled with an intervening polynucleotide positioned between each of the coding sequences of the MMOH alpha, MMOH beta and MMOH gamma subunits. In some specific embodiments, the intervening polynucleotide sequences encode a self-cleaving peptide. In specific embodiments, the self-cleaving peptides are selected from one or more of the E2A, F2A, P2A, T2A, GE2A, FG2A, GP2A, GT2A self-cleaving peptides (SEQ ID NOs: 49 to 56, respectively). In specific embodiments, the intervening polynucleotides are selected from a polynucleotide as set forth in SEQ ID NO: 9, SEQ ID NO:10, SEQ ID NO: 20, SEQ ID NO: 21, SEQ ID NO: 22, SEQ ID NO: 23, SEQ ID NO: 24 and SEQ ID NO: 25. Each intervening polynucleotide in the polypeptide coding assembly can be the same or can be different. In some specific embodiments, the MMOHα, MMOHβ and MMOHγ subunits are those of the same methanotroph. In some specific embodiments, the MMOHα, MMOHβ and MMOHγ subunits are those of the soluble MMO of a strain of *Methylosinus trichosporium* and more specifically those of *M. trichosporium* OB3b. In some specific embodiments, the MMOHα, MMOHβ and MMOHγ subunits are those of the soluble MMO of a strain of *Methylococcus capsulatus* and more specifically those of *M. capsulatus* (Bath). In some specific embodiments, the MMOHα, MMOHβ and MMOHγ subunits are those of the sequences set forth in SEQ ID NOs:1-3 or sequences having at least 90%, at least 95% or at least 99% identity thereto.

In some specific embodiments, the intervening polynucleotides positioned between the MMOH subunits encode a protease recognition site of a protease expressed in the selected microorganism. Preferably, the protease is a sequence-specific protease that recognizes and cleaves a specific amino acid sequence. The protease may be an endogenous protease of the selected microorganism or it may be an exogenous protease which is introduced and expressed in active form in the selected microorganism. In some specific embodiments, the exogenous protease is human rhinovirus (HRV) 3C protease which recognizes the amino acid sequence (LEVLFQ/GP, where the slash indicates cleavage, SEQ ID NO: 57). In some specific embodiments, the exogenous protease is enterokinase which recognizes the amino acid sequence (DDDDK/), where the slash indicates cleavage, (SEQ ID NO: 58). In some specific embodiments, the exogenous protease is factor Xa protease which recognizes the amino acid sequence (IEGR/), where the slash indicates cleavage, (SEQ ID NO: 59). In some specific embodiments, the exogenous protease is tobacco etch virus (TEV) protease which recognizes the amino acid sequence (ENLYFQ/G), where the slash indicates cleavage, (SEQ ID NO: 60). In specific embodiments, the exogenous protease is thrombin (EC 3.4.21.5) which recognizes the amino acid sequence (LVPR/GS), where the slash indicates cleavage, (SEQ ID NO: 61). In specific embodiments, the exogenous protease is tobacco vein mottling virus (TVMV) protease, which recognizes the amino acid sequence (ETVRFQG/S), where the slash indicates cleavage, (SEQ ID NO: 62). In specific embodiments, the exogenous protease is plum pox potyvirus protease which recognizes the amino acid sequence (NVVVH/A)), where the slash indicates cleavage, (SEQ ID NO: 63).

In some embodiments, the intervening polynucleotides positioned between the MMOH subunits encode a flexible peptide linker, particularly a flexible peptide linker rich in polar uncharged amino acids, and more particularly rich in glycine or rich in serine and glycine.

In some embodiments, the invention provides a DNA construct, particularly a plasmid, comprising;
(1) an origin for replication in a methylotrophic microorganism;
(2) a selective marker for selection in the methylotrophic microorganism; and
(3) nucleotide sequences encoding three methane monooxygenase hydroxylase (MMOH) protein subunits of a methanotrophic bacterium: MMOH alpha, MMOH beta and MMOH gamma,
wherein the three subunits are assembled in a single transcript operably linked to at least a promoter and a terminator which function for expression in the methylotrophic microorganism, and
wherein in the single transcript the nucleotide coding sequences of MMOH protein subunits are separated by nucleotide sequences encoding one or more self-cleaving peptides, encoding one or more amino acid recognition sites of a sequence-selective protease, or encoding one or more flexible disordered linker amino acid sequences. In some embodiments, the methanotrophic bacterium is a strain of *Methylosinus trichosporium* or *Methylococcus capsulatus*. In some embodiments, the methylotrophic microorganism is a methylotrophic yeast, particularly a strain of *Pichia* and more particularly a strain of *Pichia pastoris*.

In some embodiments, the DNA construct is a plasmid. In some embodiments, the plasmid is replicated and maintained in a methylotrophic yeast, particularly a strain of *Pichia* and more particularly a strain of *Pichia pastoris*.

In some embodiments the DNA construct is pPTK052 (SEQ ID NO: 42), pPTK053 (SEQ ID NO: 43) or a DNA construct having at least 85%, at least 90%, at least 95% identity or at least 99% identity thereto.

In some embodiments, the invention provides a method for modifying a methylotrophic microorganism to oxidize methane which comprises transforming the methylotrophic microorganism with a DNA construct, particularly a plasmid, comprising;
(1) an origin for replication in a methylotrophic microorganism;
(2) a selective marker for selection in the methylotrophic microorganism; and
(3) nucleotide sequences encoding three methane monooxygenase hydroxylase (MMOH) protein subunits of a methanotrophic bacterium: MMOH alpha, MMOH beta and MMOH gamma,
wherein the three subunits are assembled in a single transcript operably linked to at least a promoter and a terminator which function for expression in the methylotrophic microorganism, and
wherein in the single transcript the nucleotide coding sequences of MMOH protein subunits are separated by nucleotide sequences encoding one or more self-cleaving peptides, encoding one or more amino acid recognition sites of a sequence-selective protease, or encoding one or more flexible disordered linker amino acid sequences. In some embodiments, the methylotrophic microorganism is a methylotrophic yeast, a strain of *Pichia* or more specifically a strain of *Pichia pastoris*.

In some embodiments, the invention provides a method for modifying *Pichia pastoris* to oxidize methane which comprises transforming *Pichia pastoris* with pPTK052 (SEQ ID NO: 42), pPTK053 (SEQ ID NO: 43) or a DNA construct having at least 95% identity thereto.

In some embodiments, a single strain of a methylotrophic microorganism is used for all transformations.

In some embodiments, DNA fragments having the following nucleotide sequences, and functional variants thereof that are at least 80%, at least 85%, at least 90%, at least 95%, or at least 99% identical to the identified sequences, are transformed into a population of the methylotrophic microorganism:
MMOH α, β and γ subunits from a methanotrophic bacterium having SEQ ID NOs: 1, 2, and 3, respectively, and separated by 2A self-cleaving peptide sequences, and
MMOR from a methanotrophic bacterium having SEQ ID NO: 5.

In some embodiments, the DNA fragment may have more than one copy of the coding sequence for the MMOH α, β and γ subunits from a methanotrophic bacterium, e.g., more than one copy of SEQ ID NO: 1, 2 or 3. In some embodiments, the one or more copy of the coding sequence for the MMOH α, β and γ subunits from a methanotrophic bacterium may be assembled in a single transcription unit. In some embodiments, the DNA fragment may have two or more single transcription units each containing a copy of the coding sequence for the MMOH α, β and γ subunits from a methanotrophic bacterium.

In some embodiments, in addition to SEQ ID NOs: 1, 2, 3, and 5 (and variants thereof), MMOB from a methanotrophic bacteria having SEQ ID NO: 4, and variants thereof that are at least 80%, at least 85%, at least 90%, at least 95%, or at least 99% identical to SEQ ID NO: 4, are transformed into the population.

In some embodiments, in addition to SEQ ID NOs: 1, 2, 3, and 5 (and variants thereof), MMOG from a methanotrophic bacterium having SEQ ID NO: 6, and variants thereof that are at least 80%, at least 85%, at least 90%, at least 95%, or at least 99% identical to SEQ ID: NO 6, are transformed into the population.

In some embodiments, the MMOH expression is driven by a constitutive promoter.

In some embodiments, the MMOH expression is driven by an inducible promoter.

In some embodiments, the *Pichia pastoris* GS115 (his4) strain is used for all transformations. In some embodiments, plasmids are transformed into *Pichia* using a modification of the standard *S. cerevisiae* protocols described by Gietz and Schiestl (2007) Nature Protocols 2, 1-4(a); Gietz and Schiestl (2007) Nature Protocols 2, 31-34(b).

To allow rapid and flexible engineering of *Pichia pastoris*, a *Saccharomyces cerevisiae* toolkit for *P. pastoris* as developed and described in the Examples was used in some embodiments. The *S. cerevisiae* origins of replication in this kit (CEN6/ARS4, 2 micron) are not functional in *P. pastoris*. Therefore, in some embodiments, the panARS origin of replication was ported into this toolkit to make the toolkit functional in *P. pastoris*.

In some embodiments, to introduce the MMOH subunit sequences, a set of two DNA fragments is synthesized containing the genes for the α, β and γ subunits, marked with V5 epitope tags, separated by E2A and P2A self-cleaving peptide sequences, and flanked by appropriate restriction enzyme sites for assembly.

In some embodiments, three DNA fragments containing the sequences for MMOB, MMOR, and MMOG flanked by appropriate restriction sites were synthesized and cloned into the pYTK001 of the toolkit (Lee et al., 2015).

In some embodiments, nucleotide sequences for the PAS_chr1-4_0412, PAS_chr2-1_0481, PAS_chr2-1_0783 and PAS_FragB_0052 promoters and PAS_chr1-4_0412, PAS_chr2-1_0701, PAS_chr4_0210 and PAS_FragB_0052 terminators are amplified from *Pichia* genomic DNA using appropriate primers containing extra BsaI, BsmBI cut sites, and the appropriate overhangs based on part type to prepare these regulatory sequences for use in the toolkit and methods herein.

In some embodiments, an assembly cassette pPTK051 (SEQ ID NO: 41) with an *E. coli* ColE1 origin, a Kanamycin resistance marker, a panARS yeast origin and a Zeocin resistance marker is employed in methods herein.

In some embodiments, a second cassette for multigene assembly pPichiaTK049 (SEQ ID NO: 40) is made as described with *E. coli* ColE1 origin, a Kanamycin resistance marker, a panARS yeast origin and a hygromycin resistance marker is employed in methods herein.

In some embodiments, a plasmid for MMOH introduction into *Pichia* is created by assembling the AOX1 promoter, MMOH gene (with three subunits) and the PAS_FragB_0052 terminator in the pPichiaTK051 (SEQ ID NO: 41) assembly cassette using an appropriate restriction enzyme to give pPTK053 (SEQ ID No: 43).

Figure 5:
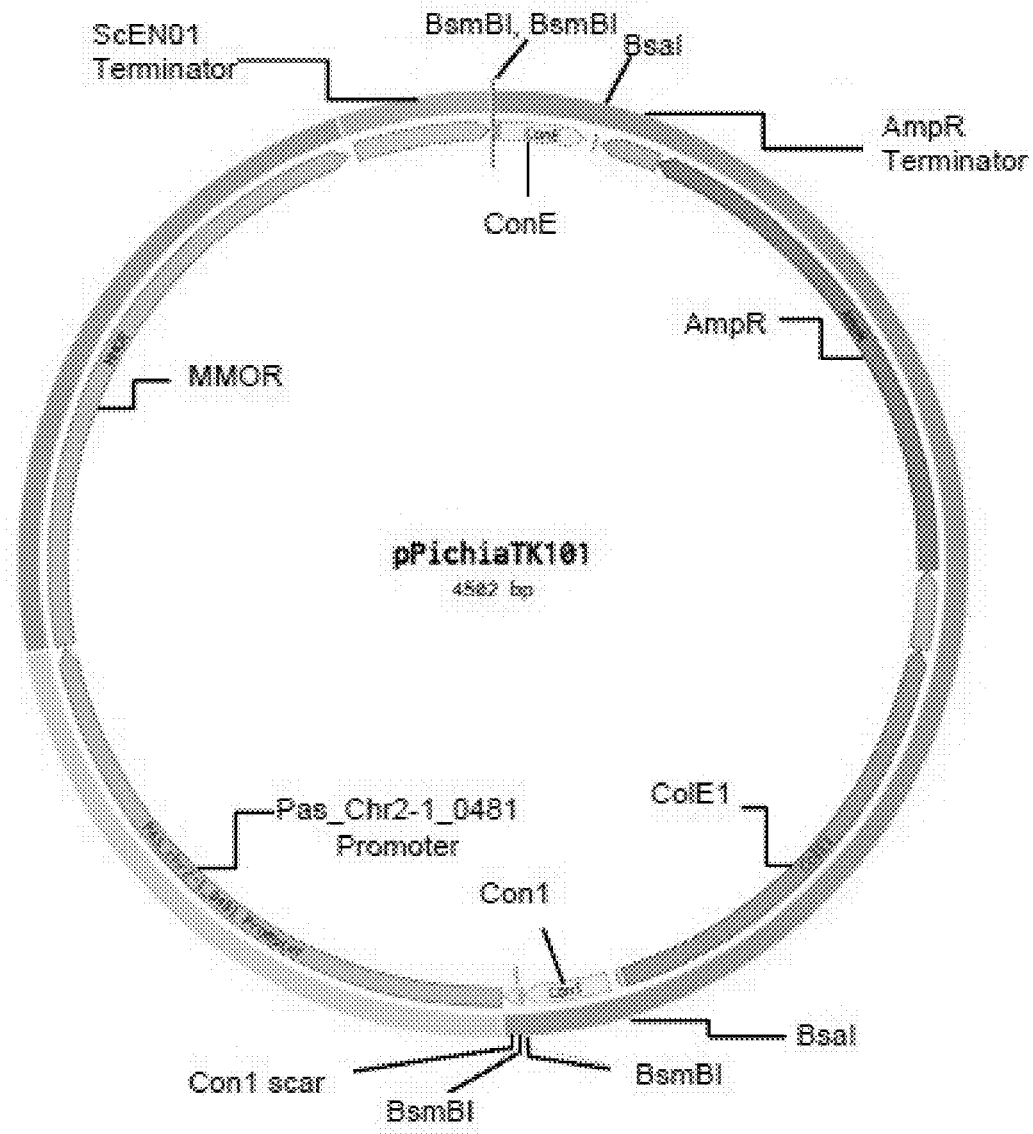
FIG. 5 is a plasmid map of pPTK101 (SEQ ID NO: 48), according to some embodiments.

In some embodiments, a second plasmid for MMOH introduction into *Pichia* is created by assembling the PAS_FragB_0052 promoter, MMOH gene and the PAS_FragB_0052 terminator in the pPichiaTK051 assembly cassette using an appropriate restriction enzyme to give pPTK052 (SEQ ID NO: 42). In some embodiments, MMOR is assembled with the PAS_chr2-1_0481 promoter and ScENO1 terminator to give pPichiaTK101 (SEQ ID NO: 48), see FIG. 5. In some embodiments, MMOB, MMOR and MMOG are assembled with promoters PAS_chr1-4_0412, PAS_chr2-1_0481 and PAS_hr2-1_0783, respectively and terminators PAS_chr1-4_0412, scENO1 and PAS_chr4_0210, respectively to give plasmid pPTK100 (SEQ ID NO: 47), see FIG. 6.

In some embodiments of methods herein, plasmids pPTK100 and pPTK052 are transformed into a population of the *Pichia pastoris* GS115 (his4) strain, and expression of MMOH subunits is measured by Western blot for the V5 epitope on each subunit.

In some embodiments of methods herein, the modified *P. pastoris* population is grown on media with methane as the sole carbon source. In addition, the catabolism of methane may be measured, for example, by monitoring the incorporation of $^{13}C$-labeled methane into *P. pastoris* metabolites, for example, glyceraldehyde-3-phosphate and dihydroxyacetone phosphate.

In some embodiments of the methods herein, plasmids pPTK101 (SEQ ID NO: 48) and pPTK052 (SEQ ID NO: 42) are transformed into a population of the *Pichia pastoris* GS115 (his4) strain. In some embodiments of the methods herein, plasmids pPTK100 (SEQ ID NO: 47) and pPTK052 (SEQ ID NO: 42) are transformed into a population of the *Pichia pastoris* GS115 (his4) strain. In some embodiments of methods herein, plasmids pPTK100 (SEQ ID NO: 47) and pPTK053 (SEQ ID NO: 43) are transformed into a population of the *Pichia pastoris* GS115 (his4) strain. In some embodiments, plasmids pPichiaTK101 (SEQ ID NO: 48) and pPTK053 (SEQ ID NO: 43) are transformed into a population of the *Pichia pastoris* GS115 (his4) strain. In some embodiments, plasmids pPTK100 (SEQ ID NO: 47), pPTK052 (SEQ ID NO: 42), and pPTK053 (SEQ ID NO: 43) are transformed into a population of the *Pichia pastoris* GS115 (his4) strain. In some embodiments, plasmids pPTK101 (SEQ ID NO: 48), pPTK052 (SEQ ID NO: 42), and pPTK053 (SEQ ID NO: 43) are transformed into a population of the *Pichia pastoris* GS115 (his4) strain. In some embodiments of the methods herein, plasmids pPTK101 (SEQ ID NO: 48), pPTK100 (SEQ ID NO: 47), and pPTK052 (SEQ ID NO: 42) or pPTK053 (SEQ ID NO: 43) are transformed into a population of the *Pichia pastoris* GS115 (his4) strain. In some embodiments, a strain of *Pichia pastoris* other than the GS115 (his4) strain is used.

In some embodiments in methods herein, coding sequences MMOB and MMOG, and associated promoters and terminators, are not transformed into the methylotrophic microorganism.

In some embodiments, the nucleotide sequences encoding self-cleaving peptide sequences used in methods herein comprise any combination, including multiple identical sequences, of those sequences of the group encoding 2A self-cleaving peptides consisting of E2A, P2A, T2A, F2A, GE2A, GP2A, GT2A, and GF2A peptides (SEQ ID NOs: 49-56, respectively).

In some embodiments of the methods herein, the nucleotides encoding self-cleaving peptide sequences are replaced in full or in part with one or more nucleotides which encode a sequence-selective protease recognition site, such as the 3C protease recognition site (SEQ ID NO: 57), the enterokinase recognition site (SEQ ID NO: 58), the Factor Xa recognition site (SEQ ID NO: 59), the tobacco etch virus (TEV) protease recognition site (SEQ ID NO: 60), the thrombin recognition site (SEQ ID NO: 61), the TVMV protease recognition site (SEQ ID No: 62) or the plum pox virus protease recognition site (SEQ ID NO: 63).

In some embodiments of the methods herein, two or three of the MMOH subunits are fused to each other via a flexible disorder linker peptide. In some embodiments of the method, the flexible linkers vary in length from 2-31 amino acids. In some embodiments, the flexible linkers are designed, as is known in the art, by including various numbers and combinations of serine, threonine, or glycine residues or combinations thereof. In some embodiments, one or more lysine and glutamate residues are included with serine, threonine, or glycine residue combination to improve solubility. In some embodiments, one or more alanine residues are included to improve flexibility. In some embodiments, the flexible linkers are selected from:

```
(GS)n, where n is 3-15, (GGS)n, where n = 2-10, (GGSGG)n, where n = 1 to 6 (when n = 1, SEQ ID
NO: 64)
or (GGGGS)n, where n = 1 to 6 (when n = 1, SEQ ID
NO: 65)

(GGGG)n, where n is 1 to 6 (when n = 2, SEQ ID
NO: 66)

(SEQ ID NO: 67)
KESGSVSSEQLAQFRSLD (SEQ ID NO: 68)
GSAGSAAGSGEF
```

In some embodiments herein, nucleotide sequences are designed to encode certain peptide and polypeptide sequences. One of ordinary skill in the art will understand that codon choice in such design can affect expression of such coding sequences in a given methylotrophic microorganism. Methods for designing coding sequences for expression in a given methylotrophic microorganism are known in the art and one of ordinary skill in the art can design coding sequences for use in a given methylotrophic microorganism based on known principles of codon bias and the like.

Tables 1-9 provide amino acid sequences of exemplary MMOH sub units, MMOR, MMOB and MMOG polypeptides. Any one of the named amino acid sequences provided in these Tables can be used as the basis for nucleotides encoding that amino acid for use in the methods, transformed microorganism and DNA constructs herein. The tables provide GenBank® Sequence Identifiers for the given amino acid sequence. The amino acid sequence associated with each given GenBank® Sequence Identifier is incorporated by reference herein in its entirety. One of ordinary skill in the art can derive coding sequences for any one or more of the amino acid sequences in Tables 1-9 and can apply known methods for optimization of codon usage for a selected methylotrophic microorganism.

In some embodiments, the MMOH alpha subunit nucleotide sequence used in methods and DNA constructs herein is a nucleotide sequence which encodes any one of the group identified in Tables 1 or 2.

In some embodiments, the MMOH beta subunit nucleotide sequence used in methods and DNA constructs herein is a nucleotide sequence which encodes any one of the group identified in Tables 3 or 4.

In some embodiments, the MMOH gamma subunit nucleotide sequence used in methods and DNA constructs herein is a nucleotide sequence which encodes any one of the group identified in Tables 5 or 6.

In some embodiments, the MMOR nucleotide sequence used in methods and DNA constructs herein is a nucleotide sequence which encodes any one of the group identified in Table 7.

In some embodiments, the MMOB nucleotide sequence used in methods and DNA constructs herein is a nucleotide sequence which encodes any one of the group identified in Table 8.

In some embodiments, the MMOG nucleotide sequence used in methods and DNA constructs herein is a nucleotide sequence which encodes any one of the group identified in Table 9.

In some embodiments, the promoters and terminators utilized are naturally occurring in the subject methylotrophic microorganism. These promoters and terminators are heterologous to the MMO coding sequences derived from methanotrophic bacteria employed herein and are functional in the subject methylotrophic microorganism that is to be genetically modified. In some embodiments, promoters are selected from the microorganism based upon their expression levels in RNA sequencing datasets. In some embodiments, promoter/terminator pairs that drive high expression levels in these datasets are chosen based on the assumption that a given promoter/terminator pair will drive high expression levels of the MMO coding sequences.

In some embodiments, the promoters utilized are engineered or synthetic promoters. Synthetic promoters can be developed by screening through semi-random sequences of DNA to identify those giving optimal expression of MMOH. In some embodiments, the terminators utilized are engineered or synthetic terminators. Synthetic terminators can be developed by screening through semi random sequences of DNA to identify those giving optimal expression of MMOH.

In some embodiments of the methods, materials and transformed organisms herein, the methylotrophic microorganism is one of the group of methylotrophic yeast, including *Candida arabinofermentans, Ogataea polymorpha, Pichia membranifaciens, Dekkera bruxellensis, Pachysolen tannophilus*, or an art-recognized relative of one of this group.

In some embodiments of the methods, materials and transformed organisms herein, the methylotrophic microorganism is a one of the group of methylotrophic bacteria, including *Methylosinus trichosporium, Methylococcus capsulatus, Methylobacteria extorquens* and *Ralstonia eutropha*.

All references throughout this application, for example patent documents including issued or granted patents or equivalents, patent application publications, and non-patent literature documents or other source material, are each incorporated by reference herein in its entirety, as though individually incorporated by reference.

References cited herein may be incorporated by reference herein in their entirety to indicate the state of the art, in some cases as of their filing date, and it is intended that this information can be employed herein, if needed, to exclude (for example, to disclaim) specific embodiments that are in the prior art.

When a group or range is disclosed herein, it is understood that each individual member of that group or range and all subgroups and subranges of the group or range members are disclosed separately herein. When a Markush group or other grouping is used herein, all individual members of the group and all combinations and subcombinations possible of the group are intended to be individually disclosed herein.

Every combination of components described or exemplified herein can be used to practice the invention, unless otherwise stated.

One of ordinary skill in the art will appreciate that methods, starting materials, growth conditions, transformation methods and conditions, strains, cloning methods and DNA assembly methods other than those specifically exemplified can be employed in the practice of the invention without resort to undue experimentation. All art-known functional equivalents, of any such methods, starting materials, growth conditions, transformation methods and conditions, strains, cloning methods and DNA assembly methods are intended to be included in this invention.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

TABLE 1

Exemplary MMOH Alpha Subunit Amino Acid Sequences (Identified by GenBank ® Sequence Identifiers)

WP_003609337.1, AAZ81968.1, 1MHZ_D, WP_036296721.1, ABD46892.1,
WP_018264225.1, WP_024878825.1, AAC45289.1, WP_085772150.1, ABD46898.1,
AAF01268.1, WP_012590301.1, WP_102845001.1, WP_020174569.1,
WP_069436906.1, PKO92487.1, BAO51828.1, WP_044435962.1, WP_017840379.1,
BAE86875.1, WP_010960482.1, 1FZ4_A, WP_064028395.1, WP_085215943.1,
WP_104425267.1, 1MMO_D, WP_087143657.1, PPD43331.1, WP_019865958.1,
OTE97883.1, BAJ17645.1, WP_026602865.1, WP_033157495.1, WP_064006727.1,
WP_020483901.1, WP_066985391.1, WP_013818321.1, AAY83388.1, BAM37167.1,
AAG31817.1, AAG31821.1, AAG31816.1, AAG31818.1, CAD30344.1, AAZ06201.1,
ABU89756.1, AAZ06198.1, CAD30355.1, CAD30349.1, ABG56535.1, CAD30350.1,
AAZ06199.1, AAZ06158.1, CAD30352.1, AAZ06164.1, CAD30345.1, AAZ06159.1,
CAD30361.1, AAZ06163.1, AAZ06200.1, AAV52905.1, AAV52906.1, CAD30351.1,
CAD30358.1, ABU89758.1, CAD30359.1, CAD30356.1, CAD30362.1, CAD30342.1,
CAD30343.1, CAD30347.1, AAZ06157.1, CAD30348.1, CAD30357.1, CAD30353.1,
CAD30346.1, CAK95255.1, CAI30810.1, CAZ65765.1, CAI30809.1, CAD30365.1,
CAD30363.1, AAZ06165.1, CAD30360.1, WP_104955546.1, AAZ06160.1,
CAD30364.1, EAA20247.1, CAD37188.1, CCH10602.1, CAD30366.1, CAD88243.1,
WP_093285538.1, PKO83176.1, AAR98534.1, WP_068635403.1, AAG31820.1,
ABD13903.1, AAG31819.1, BAJ07233.1

TABLE 2

Additional Exemplary MMOH Alpha Amino Acid Sequences (Identified by GenBank ® Sequence Identifier)

WP_010960482.1, 1FZ4_A, 1MMO_D, WP_085215943.1, BAO51828.1, WP_104425267.1, WP_064028395.1, BAE86875.1, WP_017840379.1, WP_033157495.1, WP_020483901.1, WP_026602865.1, WP_064006727.1, WP_013818321.1, WP_066985391.1, PPD43331.1, WP_019865958.1, BAJ17645.1, OTE97883.1, WP_087143657.1, WP_069436906.1, WP_020174569.1, WP_102845001.1, WP_012590301.1, WP_024878825.1, WP_085772150.1, ABD46892.1, WP_018264225.1, PKO92487.1, AAC45289.1, WP_036296721.1, AAZ81968.1, WP_003609337.1, WP_044435962.1, ABD46898.1, 1MHZ_D, AAF01268.1, EAA20247.1, ABD13903.1, AAG31819.1, AAG31820.1, BAJ07233.1, AAZ06161.1, ABG56535.1, ABU89756.1, AAG31816.1, AAZ06198.1, AAG31817.1, AAZ06201.1, WP_104955546.1, AAG31818.1, BAM37167.1, AAZ06158.1, AAY83388.1, AAG32821.1, AAZ06199.1, AAZ06160.1, AAZ06164.1, AAZ06159.1, AAV52906.1, AAV52905.1, AAZ06163.1, CAD30366.1, AAZ06200.1, WP_068635403.1, AAR98534.1, CAD88243.1, CAD37188.1, PKO83176.1, WP_093285538.1, ABU89758.1, AAZ06157.1, CAK95255.1, CAD30342.1, CAD30343.1, CAD30359.1, CAZ65765.1, CAD30347.1, CAD30358.1, CAD30346.1, CAD30357.1, CAD30351.1, CAD30356.1, CAD30348.1, CAD30353.1, CAD30344.1, CAI30810.1, CAD30362.1, CAD30355.1, CAD30349.1, CAD30345.1, CAD30350.1, CAD30352.1, CAD30361.1, CAD30360.1, CAD30363.1, AAZ06165.1, CAD30365.1, CAI30809.1, CBW47543.1

TABLE 3

MMOH beta amino acid sequences (Identified by GenBank ® Sequence Identifier)

P27354.3, 1MHZ_B, WP_003609340.1, AAZ81969.1, AAC45290.1, ABD46893.1, WP_024878824.1, AAF01269.1, WP_018264224.1, WP_085773729.1, WP_012590302.1, WP_102845000.1, WP_020174570.1, WP_069436907.1, WP_044435964.1, PKO92486.1, WP_064028393.1, WP_104425268.1, WP_017840378.1, BAE86876.1, OTE97882.1, WP_033157496.1, WP_064006728.1, WP_020483902.1, WP_013818322.1, WP_066985394.1, BBA32734.1, WP_085215942.1, WP_010960483.1, 1MTY_B, AAB62393.2, 1XMF_C, WP_019865959.1, BAJ17646.1, PPD43330.1, EAA20248.1, WP_087143656.1, 1MMO_B, WP_104955387.1, AAR98535.1, WP_093285533.1, WP_068635402.1, PKO83143.1, PCJ58203.1, WP_014805751.1, AEV73590.1, WP_102810291.1, WP_064893104.1, KKW63019.1, WP_052761628.1, WP_069407586.1, AEV73506.1, WP_015305850.1, WP_064080264.1, WP_005572958.1, WP_006947302.1, WP_006247400.1, WP_005148468.1, WP_014805365.1, WP_014805822.1, WP_087083745.1, WP_064914593.1, WP_102810203.1, BAF34295.1, AMK59199.1, WP_094361683.1, WP_102810305.1, WP_020785372.1, WP_096369472.1, WP_012392132.1, AAV52082.1, WP_011751518.1, WP_036451535.1, WP_015353966.1, KWW99075.1, WP_079046376.1, WP_020731273.1, AAS19482.1, OLB40646.1, OLB58087.1, WP_065133220.1, WP_090609800.1, BAA07112.1, WP_014805424.1, ACZ56344.1, WP_050594565.1, ETZ44710.1, WP_088234097.1, WP_074646606.1, WP_092632756.1, WP_031322145.1, WP_092911549.1, SDR32203.1, SED22440.1, WP_028075704.1, WP_084353651.1, OGB00404.1, WP_028080723.1, WP_028060363.1, WP_091295918.1

TABLE 4

Additional Exemplary Mmoh Beta Amino Acid Sequences (Identified by GenBank ® Sequence Identifier)

WP_010960483.1, AAB62393.2, 1XMF_C, EAA20248.1, 1MTY_B, 1MMO_B, WP_085215942.1, BBA32734.1, WP_064028393.1, WP_044435964.1, WP_017840378.1, BAE86876.1, WP_102845000.1, WP_012590302.1, WP_104425268.1, WP_020174570.1, WP_085773729.1, OTE97882.1, AAC45290.1, WP_087143656.1, ABD46893.1, PKO92486.1, AAZ81969.1, WP_033157496.1, AAF01269.1, WP_003609340.1, WP_064006728.1, WP_020483902.1, WP_069436907.1, WP_066985394.1, PPD43330.1, WP_013818322.1, 1MHZ_B, WP_019865959.1, BAJ17646.1, WP_024878824.1, WP_018264224.1, P27354.3, WP_104955387.1, WP_068635402.1, AAR98535.1, PKO83143.1, WP_093285533.1, PCJ58203.1, WP_102810291.1, WP_064893104.1, WP_014805751.1, WP_052761628.1, KKW63019.1, WP_069407586.1, AEV73590.1, WP_005572958.1, AEV73506.1, WP_015305850.1, WP_064080264.1, WP_014805365.1, WP_006947302.1, WP_006247400.1, WP_005148468.1, AAS19482.1, WP_087083745.1, WP_102810305.1, AMK59199.1, WP_014805822.1,

TABLE 4-continued

Additional Exemplary Mmoh Beta Amino Acid Sequences (Identified by GenBank ® Sequence Identifier)

WP_014805424.1, WP_064914593.1, BAF34295.1, WP_102810203.1, KWW99075.1, WP_020785372.1, WP_096369472.1, WP_079046376.1, WP_012392132.1, WP_094361683.1, WP_015353966.1, WP_090609800.1, WP_020731273.1, WP_103684342.1, BAA07112.1, WP_050594565.1, ETZ44710.1, WP_036451535.1, WP_065133220.1, WP_011751518.1, AAV52082.1, ACZ56344.1, WP_028080723.1, WP_030931318.1, WP_093784099.1, WP_090475937.1, WP_086725206.1, WP_084895192.1, WP_090004296.1, WP_028075704.1, WP_098510179.1, WP_047865163.1, WP_073252872.1, WP_088348744.1, OLB40646.1, OLB58087.1

TABLE 5

Exemplary MMOH Gamma Amino Acid Sequences (Identified by GenBank ® Sequence Identifier)

P27355.3, 1MHZ_G, WP_003609345.1, AAZ81977.1, WP_018264222.1, WP_024878822.1, AAC45292.1, AAZ81971.1, ABD46895.1, AAF01271.1, WP_085772148.1, WP_020174572.1, WP_012590304.1, WP_102844998.1, PKO92484.1, WP_069436909.1, BBA32732.1, WP_044435966.1, WP_017364983.1, WP_010960485.1, 1XMF_E, 1MMO_G, WP_017840376.1, WP_033157498.1, WP_026602864.1, WP_013818324.1, BAE86878.1, WP_064006729.1, WP_020483904.1, WP_064038541.1, WP_066985400.1, WP_085215940.1, WP_104425270.1, WP_064028389.1, OTE97880.1, WP_019865961.1, PPD43328.1, WP_087143654.1, WP_068635400.1, WP_014805748.1, AEV73594.1, WP_102810295.1, WP_093285528.1, AAR98537.1, PCJ58770.1, WP_104955389.1, WP_084223705.1, ODQ85225.1, WP_064893110.1, WP_046753694.1, EGK73271.1

TABLE 6

Additional Exemplary MMOH Gamma Amino Acid Sequences (Identified by GenBank ® Sequence Identifier)

WP_010960485.1, WP_017364983.1, 1XMF_E, 1MMO_G, WP_085215940.1, BBA32732.1, WP_064028389.1, WP_017840376.1, WP_026602864.1, BAE86878.1, WP_020483904.1, OTE97880.1, WP_064006729.1, WP_064038541.1, WP_013818324.1, WP_033157498.1, WP_087143654.1, AAZ81977.1, WP_024878822.1, WP_018264222.1, WP_066985400.1, WP_104425270.1, WP_003609345.1, AAC45292.1, 1MHZ_G, PKO92484.1, ABD46895.1, WP_102844998.1, AAF01271.1, WP_085772148.1, PPD43328.1, WP_012590304.1, WP_019865961.1, WP_020174572.1, P27355.3, WP_069436909.1, WP_044435966.1, AAZ81971.1, WP_068635400.1, WP_014805748.1, PKO83145.1, WP_102810295.1, WP_093285528.1, AEV73594.1, AAR98537.1, WP_104955389.1, PCJ58770.1, WP_046753694.1, WP_064893110.1, ODQ85225.1, WP_084223705.1

TABLE 7

Exemplary MMOR Amino Acid Sequences (Identified by GenBank ® Sequence Identifier)

CAB45257.1, WP_003609349.1, Q53563.1, WP_026597832.1, WP_018264220.1, WP_024878820.1, WP_036296712.1, ABD46897.1, AAZ81973.1, AAC45294.1, AAF01273.1, WP_085772147.1, WP_012590306.1, WP_102844996.1, PKO92482.1, WP_044435970.1, WP_020174574.1, WP_069436911.1, BAE86880.1, WP_017840374.1, WP_064028426.1, PPD43326.1, WP_019865963.1, BBA32729.1, WP_104425272.1, WP_066985406.1, WP_064038540.1, AEG00073.1, WP_064006730.1, WP_081470798.1, OTE97879.1, WP_026602862.1, WP_033157500.1, WP_087143660.1, WP_020483906.1, WP_085215938.1, WP_010960487.1, BAA84756.1, BBA33730.1, WP_077732208.1, WP_026609863.1, WP_028487665.1, WP_054774095.1, WP_022954315.1, WP_027158754.1, WP_036247552.1, WP_020158638.1, WP_036296409.1, WP_104955391.1, WP_031437292.1, WP_006891195.1, WP_074003507.1, WP_072659879.1, WP_104427609.1, WP_013130406.1, WP_100278485.1, 1TVC_A, WP_049654378.1, WP_027148518.1, WP_002708680.1, WP_069186500.1, WP_053567264.1, WP_028366457.1, WP_034180357.1, WP_105392110.1, WP_098552923.1, WP_080322534.1, WP_045450137.1, WP_089452532.1, WP_096501509.1,

TABLE 7-continued

Exemplary MMOR Amino Acid Sequences (Identified by GenBank® Sequence Identifier)

WP_077156181.1, WP_043177308.1, WP_012850789.1, WP_105131618.1,
WP_027780942.1, WP_089502384.1, WP_076482149.1, WP_077189356.1,
WP_031399094.1, WP_059731129.1, WP_060286721.1, WP_060251709.1,
KVZ35989.1, WP_059912909.1, WP_071751005.1, WP_060026289.1,
WP_059464617.1, WP_060231773.1, WP_042588597

TABLE 8

Exemplary MMOB Amino Acid Sequences (Identified by GenBank® Sequence Identifier)

WP_003609343.1, AAZ81970.1, WP_064032849.1, ABD46894.1, AAC45291.1,
WP_018264223.1, WP_036296718.1, WP_024878823.1, AAF01270.1,
WP_085772149.1, PKO92485.1, WP_020174571.1, WP_069436908.1, OTE97881.1,
WP_066985397.1, WP_033157497.1, WP_020483903.1, WP_013818323.1,
WP_064028391.1, WP_101053821.1, WP_019865960.1, WP_017840377.1,
KJB91174.1, WP_044436004.1, BAE86877.1, BBA32733.1, WP_087143655.1,
WP_012590303.1, WP_104425269.1, WP_102844999.1, WP_010960484.1,
WP_085215941.1, AAR98536.1, WP_068635401.1, WP_104955388.1,
WP_093285530.1, PKO83144.1, WP_069407585.1, WP_046753693.1,
WP_064893106.1, PCJ58202.1, WP_014805750.1, WP_102810292.1, AEV73591.1,
WP_096369471.1, WP_012392131.1, WP_038578224.1, WP_020731272.1,
WP_020785373.1, WP_015353965.1, GAQ35497.1, ACM61845.1, AEV73507.1,
WP_006247401.1, EHB46394.1, WP_015305851.1, WP_036424922.1,
WP_014805823.1, WP_011751517.1, SEJ42672.1, WP_027332034.1,
WP_090311220.1, PPR21099.1, OHC28673.1, GBD41183.1, KJS30201.1,
WP_028080263.1, WP_041066002.1, WP_100161632.1, XP_021975192.1,
SOC82628.1, WP_035648135.1

TABLE 9

MMOG Amino Acid Sequences (Identified By GenBank® Sequence Identifier)

CAD61956.1, WP_081735704.1, WP_024749729.1, WP_036296724.1,
WP_026597833.1, WP_024878827.1, WP_018264226.1, WP_064032850.1,
ABD46891.1, WP_085772146.1, PKO92481.1, WP_012590309.1, WP_102844994.1,
WP_020174577.1, WP_069436914.1, WP_087143652.1, WP_059671991.1,
WP_058506165.1, WP_058524787.1, WP_059879885.1, WP_060040773.1,
WP_060285580.1, KVZ52404.1, WP_017364985.1, WP_060066814.1,
WP_059705108.1, WP_010960489.1, WP_058529011.1, WP_071754430.1,
WP_060236022.1, WP_059812731.1, WP_060093464.1, WP_042587085.1,
WP_059885022.1, WP_060033700.1, WP_060055041.1, WP_059860295.1,
WP_059553621.1, WP_060153052.1, WP_059917877.1, WP_059935057.1,
WP_060021200.1, WP_059958427.1, WP_060139080.1, WP_059950166.1,
WP_060162672.1, WP_059853897.1, WP_060080748.1, WP_060230363.1,
WP_060228400.1, WP_059806490.1, WP_059961816.1, KVX12606.1,
WP_059910909.1, WP_059867196.1, WP_060130199.1, WP_025385339.1,
WP_060214311.1, WP_060318915.1, WP_059867815.1, WP_059633894.1,
WP_059619907.1, WP_010098915.1, WP_084907710.1, WP_060087971.1,
WP_059616897.1, WP_060095135.1, WP_069270884.1, WP_095411297.1,
WP_069237483.1, WP_058470388.1, WP_059821032.1, WP_060289198.1,
WP_060322058.1, WP_060133996.1, WP_059564136.1, WP_059717053.1,
WP_060363250.1, WP_060028802.1, WP_059661076.1, WP_059886331.1,
WP_064025510.1, WP_078482679.1, WP_033157501.1, WP_059989829.1,
WP_059931219.1, WP_017330537.1, WP_059959985.1, WP_060235603.1,
WP_060222984.1, WP_059763604.1, WP_060307161.1, WP_059967450.1,
WP_060001375.1, WP_059803523.1, WP_058451787.1, WP_045106550.1,
WP_060070017.1, WP_059904529.1, WP_095402731.1

TABLE 10

Selected Amino Acid Sequences from
Tables 1, 3, 5, 7, 8 and 9

Exemplary Table 1 Sequences (MMOH alpha):
>AAZ81968.1 protein A alpha subunit of soluble
methane monooxygenase [Methylosinus trichosporium]
(SEQ ID NO: 69)
MAISLATKAATDALKVNRAPVGVEPQEVHKWLQSFNWDFKENRTKYPTK
YHMANETKEQFKVIAKEYARMEAAKDERQFGTLLDGLTRLGAGNKVHPR
WGETMKVISNFLEVGEYNAIAASAMLWDSATAAEQKNGYLAQVLDEIRH
THQCAFINHYYSKHYHDPAGHNDARRTRAIGPLWKGMKRVFADGFISGD
AVECSVNLQLVGEACFTNPLIVAVTEWASANGDEITPTVFLSVETDELR
HMANGYQTVVSIANDPASAKFLNTDLNNAFWTQQKYFTPVLGYLFEYGS
KFKVEPWVKTWNRWVYEDWGGIWIGRLGKYGVESPASLRDAKRDAYWAH
HDLALAAYAMWPLGFARLALPDEEDQAWFEANYPGWADHYGKIFNEWKK
LGYEDPKSGFIPYKWLLENGHDVYIDRVSQVPFIPSLAKGSGSLRVHEF
NGKKHSLTDDWGERQWLIEPERYECHNVFEQYEGRELSEVIAEGHGVRS
DGKTLIAQPHTRGDNLWTLEDIKRAGCVFPDPLAKF >WP_010960482.1 methane monooxygenase component A
alpha chain [Methylococcus capsulatus]
(SEQ ID NO: 70)
MALSTATKAATDALAANRAPTSVNAQEVHRWLQSFNWDFKNNRTKYATK
YKMANETKEQFKLIAKEYARMEAVKDERQFGSLQDALTRLNAGVRVHPK
WNETMKVVSNFLEVGEYNAIAATGMLWDSAQAAEQKNGYLAQVLDEIRH
THQCAYVNYYFAKNGQDPAGHNDARRTRTIGPLWKGMKRVFSDGFISGD
AVECSLNLQLVGEACFTNPLIVAVTEWAAANGDEITPTVFLSIETDELR
HMANGYQTVVSIANDPASAKYLNTDLNNAFWTQQKYFTPVLGMLFEYGS
KFKVEPWVKTWNRWVYEDWGGIWIGRLGKYGVESPRSLKDAKQDAYWAH
HDLYLLAYRALWPTGFFRLALPDQEEMEWFEANYPGWYDHYGKIYEEWRA
RGCEDPSSGFIPLMWFIENNHPIYIDRVSQVPFCPSLAKGASTLRVHEY
NGQMHTFSDQWGERMWLAEPERYECQNIFEQYEGRELSEVIAELHGLRS
DGKTLIAQPHVRGDKLWTLDDIKRLNCVFKNPVKAFN Exemplary Table 3 Sequences (MMOH beta):
>AAZ81969.1 protein A beta subunit of soluble
methane monooxygenase [Methylosinus trichosporium]
(SEQ ID NO: 71)
MSQPQSSQVTKRGLTDPERAAIIAAAVPDHALDTQRKYHYFIQPRWKRL
SEYEQLSCYAQPNPDWIAGGLDWGDWTQKFHGGRPSWGNESTELRTTDW
FRHRDPARRWHHPYVKDKSEEARYTQRFLAGYASEGSIRTIDPYWRDEI
LNKYYGALIYSEYGLFNSHSSVGRDCLSDTIRQSAVPAALLDKVDNAQMI
QMERLFIAKLVPGFDASTDVPKKVWTTDPIYAGARGTVQAIWQGIQDWN
EILWAGHAVYDATFGQFARREFFQRLATVYGDTLTPFFTAQSQTYFQTT
RGAIDDLFVYCLANDSEFGAHNRTFLNAWTEHYLASSVAALKDFVGLYA
KVEKVAGATDRAGVSEALQRVFGDWKVDYADKIGFKVDVDQKVDAVLAG
YKN >WP_010960483.1 methane monooxygenase component A
subunit beta [Methylococcus capsulatus]
(SEQ ID NO: 72)
MSMLGERRRGLTDPEMAAVILKALPEAPLDGNNKMGYFVTPRWKRLTEY
EALTVYAQPNADWIAGGLDWGDWTQKFHGGRPSWGNETTELRTVDWFKH
RDPLRRWHAPYVKDKAEEWRYTDRFLQGYSADGQIRAMNPTWRDEFINR
YWGAFLFNEYGLFNAHSQGAREALSDVTRVSLAFWGFDKIDIAQMIQLE
RGFLAKIVPGFDESTAVPKAEWTNGEVYKSARLAVEGLWQKPFDWNESA
FSVHAVYDALFGQFVRREFFQRLAPRFGDNLTPFFINQAQTYFQIAKQG
VQDLYYNCLGDDPEFSDYNRTVMRNWTGKWLEPTIAALRDFMGLFAKLP
AGTTDKEEITASLYRVVDDWIEDYASRIDFKADRDQIVKAVLAGLK Exemplary Table 5 Sequences (MMOH gamma):
>AAZ81971.1 protein A gamma subunit of soluble
methane monooxygenase [Methylosinus trichosporium]
(SEQ ID NO: 73)
MAKREPIHDNSTRTEWEAKIAKLTSVDQATKFIQDFRVAYTSPFRKSYD
IDVDYQYIERKIEEKLSVLKTEKLPVADLITKASTGEDAAAVEAAWIAK
IKAAKTKYEAERVHIEFRQLYKPPVLPVNVFLRTDAALGTVLMEIRNTD
YYATPLEGLRKERGVKVLHLQA >WP_010960485.1 methane monooxygenase component A
subunit gamma [Methylococcus capsulatus]
(SEQ ID NO: 74)
MAKLGIHSNDTRDAWVNKIAQLNTLEKAAEMLKQFRMDHTTPFRNSYEL
DNDYLWIEAKLEEKVAVLKARAFNEVDFRHKTAFGEDAKSVLDGTVAKM
NAAKDKWEAEKIHIGFRQAYKPPIMPVNYFLDGERQLGTRLMELRNLNY
YDTPLEELRKQRGVRVVHLQSPH Exemplary Table 7 Sequences (MMOR):
(SEQ ID NO: 75)
>AAZ81973.1 protein C of soluble methane
monooxygenase [Methylosinus trichosporium]
MYQIVIETEDGETCSFECGPSEDVISAGLRQSVILLASCRAGGCATCKG
DCTDGDYELIDVKVQALPPDEEENGKVLLCRTFPRSDLHILVPYTFDRI
SFQAIQTNWLAEIVACDKVSSNVARLVLQCLTADGSTPIALDFVPGQFV
DIEIPGTHTRRSYSMASVAEDGRLEFFIRLLPDGAFSNYLQTGAKVGQR
VALRGPAGSFSLHKSERARFFVAGGTGLSPVLSMIRQLKKESASQPATL
FFGVTNHEELFYVDELKALQEAMPSLDVRVAVVNAAEGNGVAKGTVIDL
MRAELAKSGEKPDIYLCGPPGMIEAAFAAAATAGVPKEQVYLEKFLASG >WP_010960487.1 2Fe-2S iron-sulfur cluster binding
domain-containing protein [Methylococcus capsulatus]
(SEQ ID NO: 76)
MQRVHTITAVTEDGESLRFECRSDEDVITAALRQNIFLMSSCREGGCAT
CKALCSEGDYDLKGCSVQALPPEEEEEGLVLLCRTYPKTDLEIELPYTH
CRISFGEVGSFEAEVVGLNWVSSNTVQFLLQKRPDECGNRGVKFPEGQF
MDLTIPGTDVSRSYSPANLPNPEGRLEFLIRVLPEGRFSDYLRNDARVG
QVLSVKGPLGVFGLKERGMAPRYFVAGGTGLAPVVSMVRQMQEWTAPNE
TRIYFGVNTEPELFYIDELKSLERSMRNLTVKACVWHPSGDWEGEQGSP
IDALREDLESSDANPDIYLCGPPGMIDAACELVRSRGIPGEQVFFEKFL
PSGAA Exemplary Table 8 Sequences (MMOB)
>AAZ81970.1 protein B of soluble methane
monooxygenase [Methylosinus trichosporium]
(SEQ ID NO: 77)
MTSAHNAYNAGIMQKTGKAFADEFFAEENQVVHESNAVVLVLMKSDEID
AIIEDIVLKGGKAKNPSIVVEDKAGFWWIKADGAIEIDAAEEAGELLGKP
FSVYDLLINVSSTVGRAYTLGTKFTITSELMGLDRALTDI >WP_010960484.1 methane monooxygenase regulatory
protein B [Methylococcus capsulatus]
(SEQ ID NO: 78)
MSVNSNAYDAGIMGLKGKDFADQFFADENQVVHESDTVVLVLKKSDEIN
TFIEEILLTDYKKNVNPTVNVEDRAGYWWIKANGKIEVDCDEISELLGR
QFNVYDFLVDVSSTIGRAYTLGNKFTITSELMGLDRKLEDYHA Exemplary Table 9 Sequences (MMOG):
>CAD61956.1 GroEL homologue [Methylosinus
trichosporium OB3b]
(SEQ ID NO: 79)
MTNPRKRERRRPAFDVTREKFVARNIRFGDVVRRDLLAGVDALADAVAV
TLGPRGRNVVIEHRAAGLPPVATKDGVTVAQAVELAGRTQSVGVSLVRQ
MATAVAKEAGDGTTTSVVLARRLAAETRKALAAGMNPRDIVLGMEKAAR
IVDRDLAARARRCDDTRALAHVATLAAGGDESIGAIVADALTRAGEGGV
VDVELGAALCDEMDIVEGMRWEQGYRSPYFMTDSARKIAELENPYILIY
DRVINQFSELVPALELVRRQRGSLLIVAENIVEEALPGLLLNHIRKNLC
SIAVKGPGYGDSRYEFLHDLAALTGGRAIMEACGEELSNVTMAHLGRAK
RVVVREDDTVVIGGEGDGAAITERLAAARQQADWITDGDPSKGSPSGKR
HDLENLQTRIKALSGKVVTIKAGGLSDILIKERMQRIENALASARAARS
DGVVAGGGVGLYRARAALTEATGDTLDQTYGIAIVRAALDEPIRRIAAN
AGRDAHEFLFELKRSNDDFWGMDMRSGECGDLYAAGVIDPARVTRLALR
NAVATASSLMTVECAVTHIPPSDPTYGFDPHLAAATREDPRS >WP_010960489.1 molecular chaperone GroEL
[Methylococcus capsulatus]
(SEQ ID NO: 80)
MAKEVVYRGSARQRMMQGIEILARAAIPTLGATGPSVMIQHRADGLPPI
STRDGVTVANSIVLKDRVANLGARLLRDVAGTMSREAGDGTTTAIVLAR
HIAREMFKSLAVGADPIALKRGIDRAVARVSEDIGARAWRGDKESVILG
VAAVATKGEPGVGRLLLEALDAVGVHGAVSIELGQRREDLLDVVDGYRW
EKGYLSPYFVTDRARELAELEDVYLLMTDREVVDFIDLVPLLEAVTEAG
GSLLIAADRVHEKALAGLLLNHVRGVFKAVAVTAPGFGDKRPNRLLDLA
ALTGGRAVLEAQGDRLDRVTLADLGRVRRAVVSADDTALLGIPGTEASR
ARLEGLRLEAEQYRALKPGQGSATGRLHELEEIEARIVGLSGKSAVYRV
GGVTDVEMKERMVRIENAYRSVVSALEEGVLPGGGVGFLGSMPVAELE
ARDADEARGIGIVRSALTEPLRIIGENSGLSGEAVVAKVMDHANPGWGY
DQESGSFCDLHARGIWDAAKVLRLALEKAASVAGTFLTTEAVVLEIPDT
DAFAGFSAEWAAATREDPRV

THE EXAMPLES

Strains

The *Pichia pastoris* GS115 (his4) strain was used for all transformations. Routine cloning and plasmid amplification was performed in *E. coli* DH5alpha.

Pichia Transformation

Plasmids were transformed into *Pichia* using a modification of the standard *Saccharomyces cerevisiae* protocol (Gietz and Schiestl (2007) Nature Protocols 2, 1-4(a); Gietz and Schiestl (2007) Nature Protocols 2, 31-34(b)). Frozen competent *Pichia* cells were first generated according to a protocol used with *S. cerevisiae* (Gietz and Schiest, 2007a). To transform these cells, an aliquot was removed and thawed in a 37° C. water bath for 30 s and centrifuged at 13,000 g for 2 min. Poly(ethylene glycol) (50% weight/vol, PEG3350) 260 µL, 1 M lithium acetate 36 µL, boiled salmon sperm DNA 50 µL, and plasmid 14 µL (concentration ~200-600 ng/uL) were added to 25 uL of competent GS115 cells. The cells were fully resuspended. Cells were incubated at 42° C. for 20-60 min. Cells were then pelleted and resuspended in 1 mL of yeast extract-peptone-dextrose (YPD) medium and incubated at 30° C. for 2-3 h before being plated onto YPD plates with appropriate antibiotic. Plates were incubated at 30 C for 3-4 days until colonies appeared.

Pichia Pastoris Plasmid Construction

To allow rapid and flexible engineering of *Pichia pastoris*, a *Saccharomyces cerevisiae* toolkit (Lee et al. (2015) ACS Synt. Biol., 4(9), 975-986) was used. As described for this toolkit, well-known Golden Gate reaction assembly methods, more specifically BsaI Golden Gate reactions, were used for assembly of DNA fragments. See also: Engler (2008) PLoS One 3, e3647, Engler (2009) PLoS One 4, e5553, as well as Lee et al., 2015.

The *S. cerevisiae* origin of replications in this kit (CEN6/ARS4, 2 micron) are not functional in *P. pastoris*. Therefore, a recently identified and validated origin of replication, panARS (Liachko and Dunham (2014) FEMS Yeast Res. 14(2), 364-367; Camattari et al. (2016) Microb Cell Fact 15, 139) was introduced into this toolkit. The 452 bp panARS sequence (SEQ ID NO: 8), flanked by BsmBI and BsaI sites as required for use in the toolkit, was obtained as a Gblock from Integrated DNA Technologies (Coralville, IA) and cloned into the pYTK001 vector from the *S. cerevisiae* toolkit, creating plasmid pPTK001 (pPTK001, SEQ ID No: 26). The *P. pastoris* AOX1 promoter was similarly cloned into the pYTK001 vector, creating plasmid pPTK002 (pPTK002, SEQ ID NO: 27).

A set of two DNA fragments was obtained containing the genes for the MMOH α, β and γ subunits of the methanotroph *Methylosinus trichosporium* Ob3b (see: SEQ ID NOs: 1, 2 and 3, respectively), marked with V5 epitope tags, separated by selected nucleotides encoding E2A and P2A self-cleaving peptide sequences (see: SEQ ID NO: 9 and SEQ ID NO: 10, respectively), and flanked by BsmBI and BsaI sites for assembly. This MMOH gene set was cloned into the pYTK001 vector to create plasmid pPTK033 (SEQ ID NO: 32) to introduce the MMOH gene. The coding sequences for the MMOH subunits were codon optimized for expression in *Pichia*.

Three DNA fragments containing the sequences for MMOB, MMOR, and MMOG also of *M. trichosporium* Ob3b (see: SEQ ID NOs: 4, 5 and 6, respectively) flanked by BsmBI and BsaI sites were obtained and cloned individually into the pYTK001 vector to create plasmids pPTK020 (SEQ ID NO: 29), pPTK021 (SEQ ID NO: 30) and pPTK022 (SEQ ID NO: 31), respectively. The coding sequences for MMOB, MMOR and MMOG were codon optimized for expression in *Pichia*.

Sequences for the PAS_chr1-4_0412 promoter (SEQ ID NO: 11), PAS_chr2-1_0481 promoter (SEQ ID NO: 12), PAS_chr2-1_0783 promoter (SEQ ID NO: 13) and PAS-FragB_0052 promoter (SEQ ID NO: 14) and the PAS_chr1-4_0412 terminator (SEQ ID NO; 15), PAS_chr2-1_0701 terminator (SEQ ID NO: 16), PAS_chr4_0210 terminator (SEQ ID NO: 17) and PAS_FragB_0052 terminator (SEQ ID NO: 18) were amplified from *Pichia* genomic DNA using primers containing extra BsaI, BsmBI cut sites and the appropriate overhangs based on part type. These sequences were then cloned into the pYTK001 vector.

An assembly cassette pPTK051 (SEQ ID NO: 41) was made with an *E. coli* ColE1 origin for maintenance in *E. coli*, a Kanamycin resistance marker for selection in *E. coli*, a panARS yeast origin for maintenance in *Pichia* and a Zeocin resistance marker for selection in *Pichia* (Lee et al., 2015).

A second cassette for multigene assembly pPTK049 (SEQ ID NO: 40) was made with an *E. coli* ColE1 origin, a Kanamycin resistance marker, a panARS yeast origin and a hygromycin resistance marker for selection in *Pichia* (Lee et al., 2015).

Figure 3C:
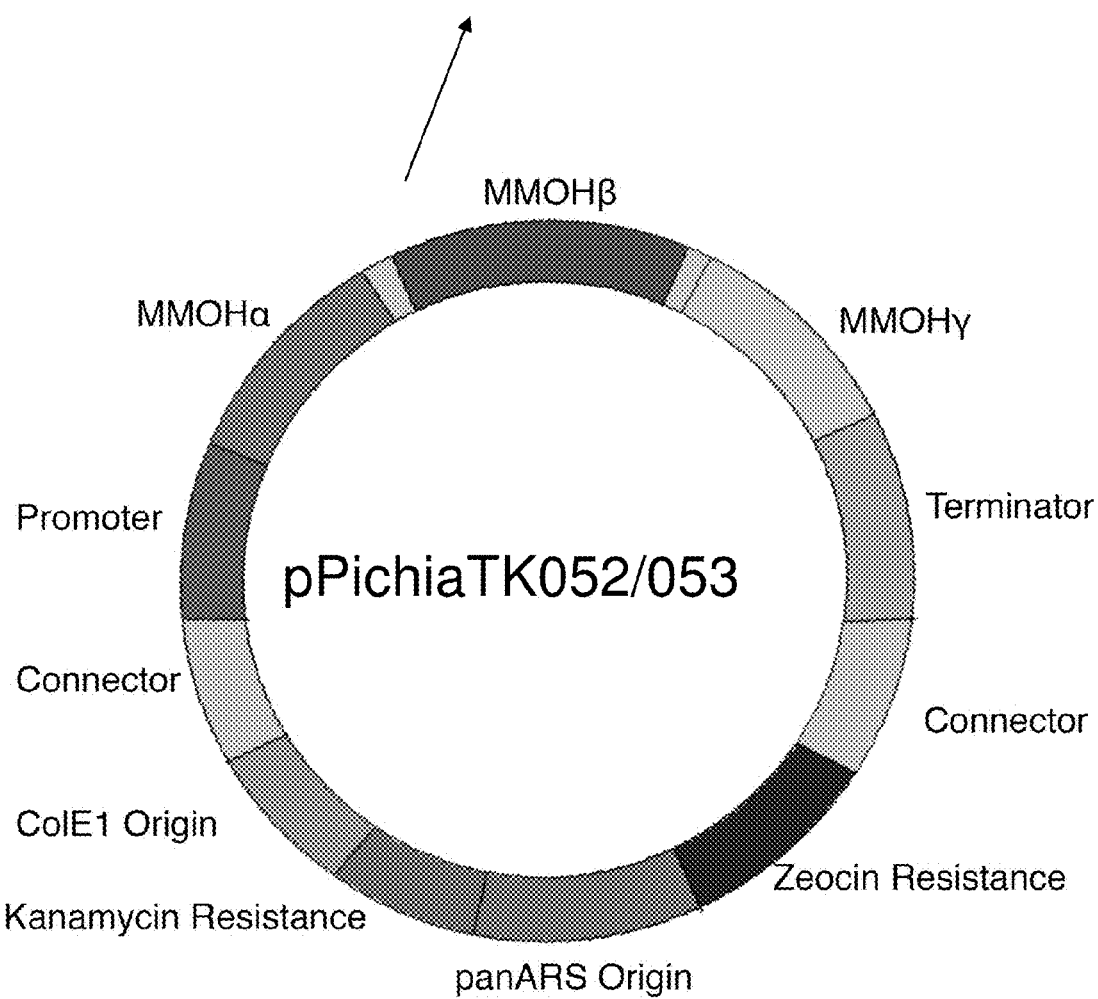
FIG. 3C is an illustration of a plasmid containing the coding sequences of the three MMOH subunits (MMOH alpha, MMOH beta and MMOH gamma) fused into a single transcript operably linked to a promoter and a terminator, according to some embodiments. The coding sequences of the MMOH subunits are separated by intervening nucleotide sequences which can encode one or more (1) self-cleaving peptide, (2) one or more selected sequence-specific protease recognition site (for cleavage by a selected sequence-specific protease), (3) one or more flexible peptide linker, or any combination of 1-3. Exemplary plasmids for use in transforming methylotrophic yeast such as *Pichia* include pPTK052 (SEQ ID NO: 42) and pPTK053 (SEQ ID NO: 43), the preparation of which is described in the Examples.

A plasmid for MMOH introduction into *Pichia* was created by assembling the AOX1 promoter (SEQ ID NO: 7), MMOH gene (pPTK033) and PAS_FragB-0052 terminator (SEQ ID NO: 18) in the pPTK051 (SEQ ID NO: 41) assembly cassette using BsaI (Lee et al., 2015) to give pPTK053 (SEQ ID NO: 43 and FIG. 3C).

A second plasmid for MMOH introduction into *Pichia* was created by assembling the PAS-FragB_0052 promoter (SEQ ID NO: 14), the MMOH gene subunits (pPichiaK033) and PAS-FragB-0052 terminator (SEQ ID NO: 18) in the pPTK051 (SEQ ID NO: 41) assembly cassette using BsaI (Lee et al., 2015) to give pPTK052 (SEQ ID NO: 42 and FIG. 3C).

MMOR was assembled with the PAS_chr2-1_0481 promoter (SEQ ID NO: 12) and ScENO1 terminator (SEQ ID NO:19) to give pPTK101 (SEQ ID NO: 48 and FIG. 5) (Lee et al., 2015).

Figure 6:
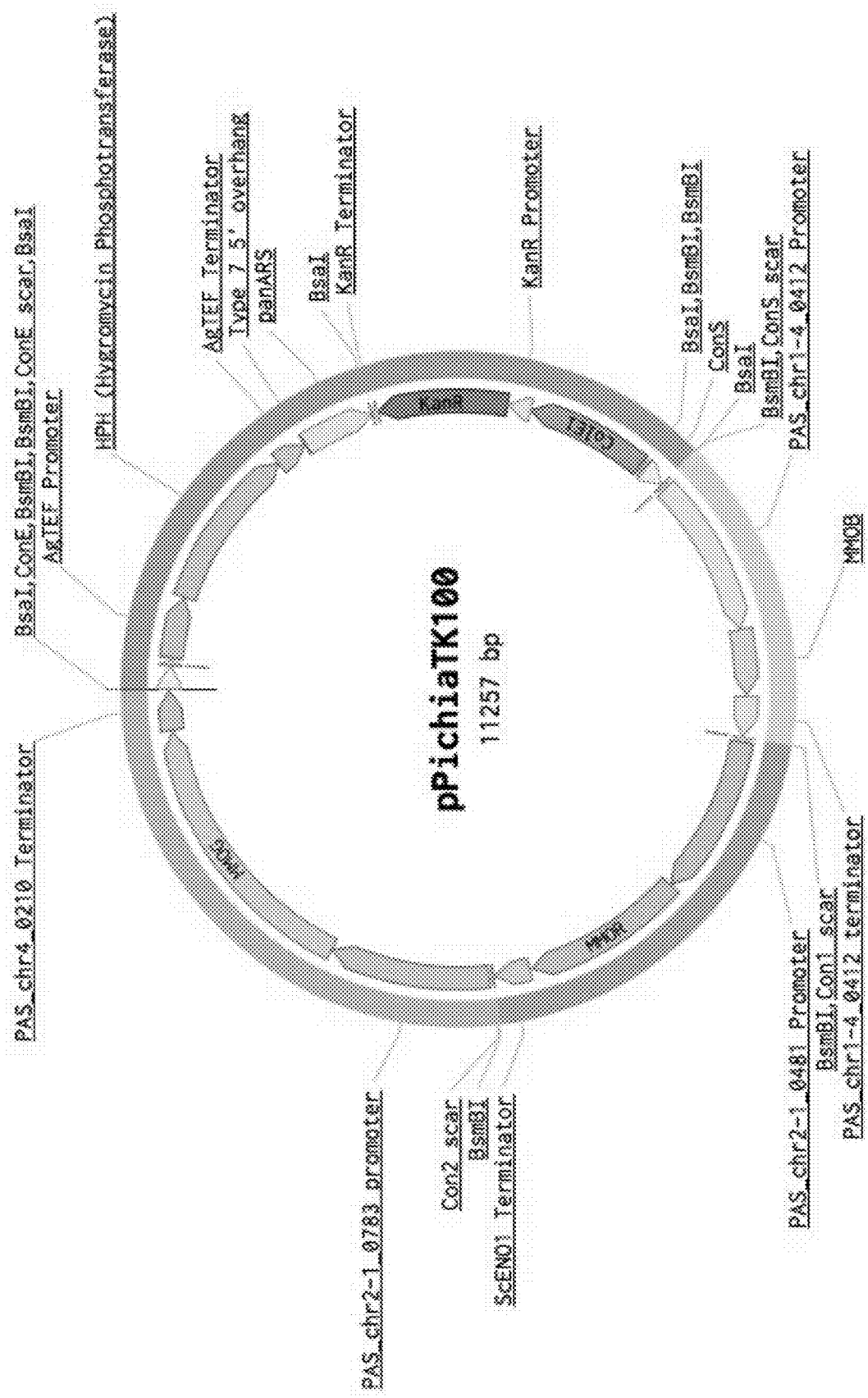
FIG. 6 is a plasmid map of pPTK100 (SEQ ID NO: 47), according to some embodiments.

The coding sequences of MMOB, MMOR and MMOG were assembled with promoters PAS_chr1-4_0412 (SEQ ID NO:11), PAS_chr2-1_0481 (SEQ ID NO: 12) and PAS_chr2-1_0783 (SEQ ID NO: 13), respectively and terminators PAS_chr1-4_0412 (SEQ ID NO:15), scENO1(SEQ ID NO: 19) and PAS_chr4_0210 (SEQ ID NO:17), respectively, to give plasmid pPTK100 (SEQ ID NO: 47, and FIG. 6).

*Pichia* promoter containing plasmids were constructed by inserting the PCR amplified promoter into pYTK001. For example, pPTK042 (SEQ ID NO: 35) (PAS_chr1-4_0412_promoter part plasmid), pPTK043 (SEQ ID NO: 36) (PAS_chr2-1_0481_promoter part plasmid), pPTK044 (SEQ ID NO: 37) (PAS_chr2-1_0783_promoter part plasmid) pPTK037 (SEQ ID NO: 33) (PAS_FragB_0052 promoter part plasmid) were constructed using a BsmBI Golden Gate reaction to insert the PCR amplified promoters into pYTK001 (Lee et al., 2015).

*Pichia* terminator containing plasmids were constructed by inserting the PCR amplified promoter into pYTK001. For example, pPTK045 (SEQ ID NO: 38) (PAS_chr1-4_0412_terminator part plasmid), pPTK047 (SEQ ID NO: 39) (PAS_chr4_0210_terminator part plasmid) and pPTK041 (SEQ ID NO: 34) (PAS_FragB_0052 promoter part plasmid) were constructed using a BsmBI Golden Gate reaction to insert the PCR amplified terminators into pYTK001 (Lee et al., 2015)

The plasmid pPTK100 (SEQ ID NO: 47) contains MMOB coding sequence (with the PAS_chr1-4_0412 promoter, and PAS_chr1-4_0412_terminator), MMOR coding sequence (with the PAS_chr2-1_0481 promoter, and ScENO1 terminator) and MMOG coding sequence (with the PAS_chr2-1_0783 promoter, and PAS_chr4_0210 terminator). pPTK100 additionally contains the panARS for maintenance in *Pichia*, the hygromycin phosphotransferase gene for selection in *Pichia*, the ColE1 origin for maintenance in *E. coli*, and a kanamycin resistance marker for selection in *E. coli*.

Intermediate plasmid pPTK097 (SEQ ID NO: 44) was created in a BsaI Golden Gate reaction with PAS-chr2-1_0481_Promoter (pPTK043), MMOR (pPTK021), ScENO1 terminator (pPTK051, SEQ ID NO: 41), the ConL1 part (pYK003), and ConR2 part (pYTK068) and pYTK083 part (containing an ampicillin resistance marker and the ColE1 origin of replication). pYK003, pYTK068 and pYTK083 are all from the toolkit of Lee et al., 2015.

Intermediate plasmid pPTK098 (SEQ ID NO: 45) was created in a BsaI Golden Gate reaction with the PAS-chr1-4_0412_Promoter (pPTK042), MMOB (pPTK020), the PAS_chr1-4_0412_terminator (pPTK045), the ConLS part (pYK002), and ConR1 part (pYTK067) and pYTK083 part. pYK002, pYTKo67 and pYTK083 are all from the toolkit of Lee et al., 2015.

Intermediate plasmid pPTK099 (SEQ ID NO: 46) was created in a BsaI Golden Gate reaction with the PAS-chr2-1_0783_Promoter (pPTK044), MMOG (pPTK022), the PAS_chr4_0210_terminator (pPTK047), the ConL2 part (pYK004), the ConRE part (pYTK072) and the pYTK083 part. pYK004, pYTK072 and pYTK083 are all from the toolkit of Lee et al., 2015.

Plasmid pPTK101 (SEQ ID NO: 47) was created in a BsaI Golden Gate reaction with PAS-chr2-1_0481_Promoter (pPTK043), MMOR (pPTK021), ScENO1 terminator (pPTK051), the ConL1 part (pYK001), and ConRE part (pYTK0721) and the pYTK083 part. pYK001, pYTK0721 and pYTK083 are all from the toolkit of Lee et al., 2015.

For example, to generate pPTK100, four parts were assembled in a BsmBI Golden Gate reaction: 1) the MMOB operon (BsmBI fragment of pPTK098); 2) the MMOR operon (BsmBI fragment of pPTK101); 3) the MMOG operon (BsmBI fragment of pPTK099); 4) the BsmBI fragment of pPTK013 (SEQ ID NO: 28, containing panARS, hygromycin resistance, ColE1 origin, Kanamycin resistance).

Gene Expression

In general, to express a desired gene on a plasmid in *Pichia*, the plasmid is transformed into a desired strain of *Pichia* as described above. The strain is grown in appropriate growth medium with a selected carbon source, e.g., methanol or glucose. At a selected culture OD, a sample of culture is collected, washed and the cells are lysed. Protein concentrations are measured using standard methods and protein samples are assessed for expressed protein. For example, the molecular weights of expressed proteins can be assessed using standard methods. Biological activities of expressed proteins can be assayed by known methods.

For example, to express MMOH, plasmid pPTK052 (or pPTK053) was transformed into *Pichia pastoris* strain GS115. This strain was grown on Yeast Nitrogen Base medium plus biotin and histidine with either methanol (M) or glucose (G) as a carbon source. Once cultures reached an OD of 1.6, 1 mL of culture was removed, washed 1× with phosphate-buffered saline (PBS), and lysed with glass beads. Protein concentrations in these extracts were measured by BCA (bicinchoninic acid assay), and equivalent amounts of protein loaded onto an SDS-PAGE gel. Protein extracts were centrifuged at 10,000 g for 10 m to create a soluble (supernatant) and insoluble (pellet) fraction. These were loaded separately onto the SDS-PAGE gel.

Proteins on this gel were transferred onto an PVDF (polyvinylidene difluoride) membrane. The transferred proteins were probed with an anti-V5 primary antibody, followed by an anti-mouse secondary antibody that was conjugated to horse radish peroxidase. Blots were developed using with the West Pico Plus chemiluminescent substrate (ThermoFisher). Strains expressing untagged mCherry (red fluorescent protein, RFP) were included as negative controls. V5-tagged GFP was used as a blotting control.

Figure 4:
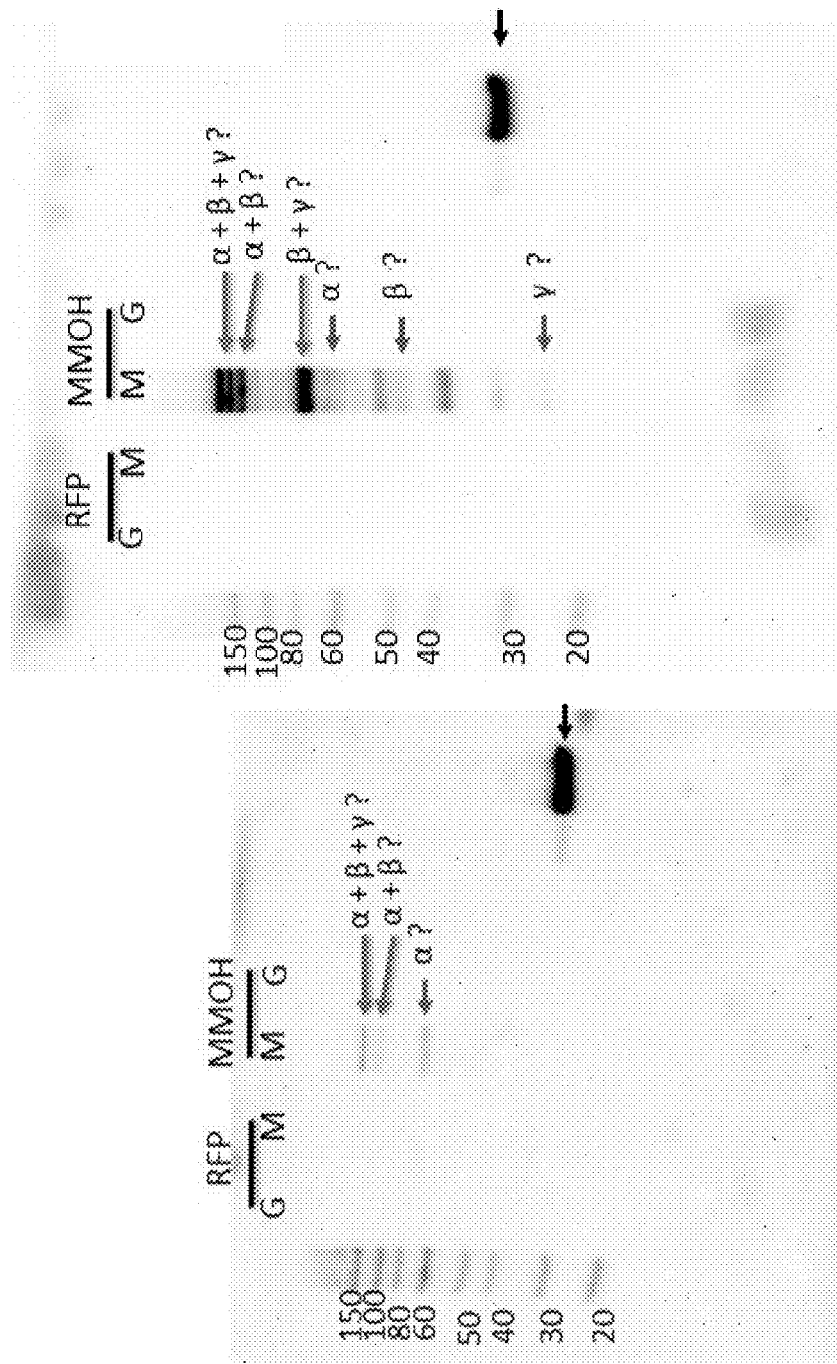
FIG. 4 illustrates protein blots showing expression of the MMOH subunits in *Pichia pastoris* transformed with pPTK052, according to some embodiments.

FIG. 4 illustrates Western blots of proteins expressed in *Pichia pastoris* strain GS115 transformed with plasmid pPTK052. The blot on the left is the soluble protein fraction (supernatant) and the blot on the right is the insoluble protein fraction (pellet). The arrow in the blots is the GFP-V5 (V5-tagged green fluorescent protein) marker. Columns labelled G are from transformed *Pichia* grown with glucose as the carbon source. Columns labelled M are from transformed *Pichia* grown with methanol as the carbon source. Negative controls are labelled RFP. The blots show expression of the single transcript containing all three MMOH subunits when transformed *Pichia* is grown on methanol as well as the cleavage products of the single transcript.

The invention claimed is:

1. An engineered methylotrophic yeast, which is a strain of *Pichia pastoris*, transformed to comprise:

three methane monooxygenase hydroxylase (MMOH) protein subunits of a soluble methane monooxygenase (MMO) of a methanotrophic bacterium, the three MMOH protein subunits comprising MMOH alpha, MMOH beta and MMOH gamma, and a methane monooxygenase reductase (MMOR) of the methanotrophic bacterium, wherein the methylotrophic yeast exhibits oxidation of methane to methanol, and wherein the three MMOH protein subunits are expressed from a DNA construct of SEQ ID NO:42, SEQ ID NO:43, or from a DNA construct having at least 95% sequence identity to either SEQ ID NO:42, or SEQ ID NO:43.

2. The engineered methylotrophic yeast of claim 1, wherein the MMOR is expressed from a DNA construct of SEQ ID NO:47, SEQ ID NO:48, or a DNA construct having at least 95% sequence identity to either SEQ ID NO:47 or SEQ ID NO:48.

3. The engineered methylotrophic yeast of claim 1, which is transformed to comprise a DNA construct of SEQ ID NO:42, or a DNA construct of SEQ ID NO:43.

4. The engineered methylotrophic yeast of claim 3, which is transformed to further comprise a DNA construct of SEQ ID NO:47, or a DNA construct of SEQ ID NO:48.

5. The engineered methylotrophic yeast of claim 1, which converts methane to microbial products.

6. The engineered methylotrophic yeast of claim 1, which at least in part employs methane as a carbon source.

7. A DNA construct comprising SEQ ID NO:42, SEQ ID NO:43, or a nucleotide sequence having at least 95% sequence identity to either SEQ ID NO:42 or SEQ ID NO:43, wherein
the nucleotide sequence comprises:
  (1) an origin for replication in a methylotrophic microorganism;
  (2) a selective marker for selection in the methylotrophic microorganism; and
  (3) nucleotide sequence encoding three methane monooxygenase hydroxylase (MMOH) protein subunits of a methanotrophic bacterium, the three MMOH protein subunits comprising MMOH alpha, MMOH beta and MMOH gamma.

8. The DNA construct of claim 7, wherein the three MMOH protein subunits are assembled in a single transcript operably linked to at least a promoter and a terminator which function for expression in the methylotrophic microorganism.

9. The DNA construct of claim 8, wherein in the single transcript, the nucleotide sequences encoding MMOH alpha, MMOH beta and MMOH gamma are separated from each other by nucleotide sequences that: encode one or more self-cleaving peptides, encode one or more amino acid recognition sites of a sequence-selective protease, or encode one or more flexible disordered linker amino acid sequences.

10. The DNA construct of claim 7 comprising SEQ ID NO:42 or SEQ ID NO:43.

11. The DNA construct of claim 10 further comprising SEQ ID NO:47 or SEQ ID NO:48.

12. A DNA construct comprising a nucleic acid sequence selected from the group consisting of SEQ ID NO:42, SEQ ID NO:43, SEQ ID NO:47 and SEQ ID NO:48.

13. The DNA construct of claim 10 which is selected from any one of the group consisting of SEQ ID NO:42, SEQ ID NO:43, SEQ ID NO:47 and SEQ ID NO:48.

14. A method for modifying a methylotrophic yeast to oxidize methane which comprises transforming the methylotrophic yeast with the DNA construct of claim 7.

15. A method for modifying a methylotrophic yeast to oxidize methane which comprises transforming the methylotrophic yeast with the DNA construct of claim 8.

16. A method for modifying a methylotrophic yeast to oxidize methane which comprises transforming the methylotrophic yeast with the DNA construct of claim 9.

17. A method for modifying a methylotrophic yeast to oxidize methane which comprises transforming the methylotrophic yeast with the DNA construct of claim 10.

18. A method for modifying a methylotrophic yeast to oxidize methane which comprises transforming the methylotrophic yeast with the DNA construct of claim 11.

19. A method for converting methane to microbial products which comprises growing the engineered methylotrophic yeast of claim 1 employing methane as a carbon source.

* * * * *

SEQUENCE LISTING

```
<160> NUMBER OF SEQ ID NOS: 80

<210> SEQ ID NO 1
<211> LENGTH: 1581
<212> TYPE: DNA
<213> ORGANISM: Methylosinus trichosporium

<400> SEQUENCE: 1
gcaatcagtc ttgctaccaa agcagcaacg gatgccttga aggtcaacag agctcccgtc      60
ggagtagagc cacaggaggt tcacaaatgg ctgcagtcct tcaactggga tttcaaggag     120
aatcgtacga aatatccaac aaaataccac atggccaacg aaacgaaaga gcagttcaaa     180
gtcattgcta aagaatatgc tcgtatggag gctgctaaag acgaaagaca atttggaaca     240
ctattagatg gcctgactag attaggcgct ggcaacaagg tacaccccag atggggagag     300
```

```
actatgaaag tcatcagtaa tttcctggag gtaggagaat acaatgcaat agccgcttct    360
gccatgcttt gggacagtgc tacggctgcc gaacaaaaaa acggctatct ggctcaagtg    420
ttagacgaga ttagacacac gcatcagtgc gcttttataa accattacta ttctaaacac    480
tatcacgatc cagccggcca caacgatgct agacgtaccc gtgcaattgg tccactttgg    540
aagggtatga agcgtgtgtt tgccgacgga ttcatctccg agatgctgt cgaatgctcc     600 gtaaatctgc agcttgtcgg cgaagcctgt ttcacaaatc ctttaatcgt tgcagtaacg    660
gagtgggctt cagccaatgg agatgagatc acgcccaccg ttttctttc agttgaaacg     720 gacgagctac gtcacatggc taatggttac caaaccgtgg tatcaatcgc caatgatccc    780
gcttctgcaa agttcttgaa cacagatcta acaatgcat tctggacgca acagaagtat     840
ttcacacctg ttttgggata cctttttgag tatggaagta agttcaaagt tgagccctgg    900
gtgaagacct ggaaccgttg ggtgtatgag gactggggcg gaatttggat cggcaggtta    960
ggcaaatacg gagtagaaag tcctgcttca ctgaggacg ccaagagaga tgcttattgg    1020
gcacaccacg atctagctct ggccgcttac gctatgtggc ctcttggatt tgcacgtcta   1080
gccttgcctg atgaagaaga tcaagcctgg tttgaagcta actatccagg atgggccgac   1140
cactacggta aaatctttaa tgaatggaag aaattaggct atgaagaccc aaagtccgga   1200
ttcatcccct accaatggtt gctggctaac ggtcacgatg tgtacattga cagggtaagt   1260
caagttccat ttattccctc cctggctaag ggcactggaa gtctacgtgt gcatgaattt   1320
aacggtaaaa acattctct aactgatgat tggggagaac gtcaatggtt aatagaaccc     1380
gagcgttatg agtgtcataa cgtgttcgag cagtatgagg gacgtgaatt gtccgaggta   1440
atagctgaag gtcatggagt gaggtcagac ggtaaaactc ttatagcaca gccccatact   1500
agaggagata atctttggac actagaagat atcaaaaggg ctggctgtgt tttccctgac   1560
cctttagcaa aattcggatc c                                             1581
```

<210> SEQ ID NO 2
<211> LENGTH: 1185
<212> TYPE: DNA
<213> ORGANISM: Methylosinus trichosporium

<400> SEQUENCE: 2

```
tcccaaccac aatcaagtca agtgactaag cgtggactta cagaccccga aagagcagca     60
atcatcgccg cagccgtccc tgaccatgcc cttgacactc agagaaaata ccactatttt    120
atccagccac gttggaaacc tttatctgag tacgagcagt tatcctgcta tgcccagcca    180
aatcctgatt ggatagcagg aggcttagat tggggcgatt ggactcagaa gtttcacggc    240
ggcagacctt cctgggcaa tgagtctacc gagctacgta caacggattg gtatcgtcac     300
agagatcccg ctcgtcgttg gcaccatcct tatgtaaaag ataagtccga ggaagccaga    360
tatacacaga gattccttgc tgcctatagt tccgagggat ctatacgtac catcgacccc    420
tactggcgtg acgagatatt gaacaagtac tttggtgcat tactttacag tgagtatggc    480
ttgttcaatg cccattcttc cgtgggaagg gattgcttat cagacacgat tagacagacg    540
gccgtatttg ctgccttgga caaggtggat aacgcccaga tgatacaaat ggaacgtctt    600
tttatcgcta agttagtgcc aggttttgac gctagtactg acgtgccaaa aaaaatatgg    660
accactgatc ccatctattc aggtgctcgt gccactgtgc aagaaatatg gcagggcgta    720
caggattgga atgaaatcct ttgggccgga catgcagtca tgatagctac atttggccag    780
```

-continued

```
ttcgcaagaa gggaattctt tcaaagactg gccactgtgt atggtgatac tttaacacca     840
tttttcacgg cccaaagtca gacctacttt caaacaacga gaggcgctat tgatgattta     900
tttgtctact gcttggccaa tgattctgag tttggtgccc acaatcgtac tttccttaat     960
gcttggacgg agcactattt agccagttct gtagcagcat taaaagactt cgttggactg    1020
tatgccaagg tcgaaaaatc tagggccgac agatcccgta ggagacttcg tggtgctgct    1080
gcttcatcag ctattggtcg ttctattacg cccgacaaga taggcttccg tgtggacgtg    1140
gaccaaaaag ttgacgccgt cctagctggt tacaagaacg gatcc                    1185
```

<210> SEQ ID NO 3
<211> LENGTH: 510
<212> TYPE: DNA
<213> ORGANISM: Methylosinus trichosporium

<400> SEQUENCE: 3

```
gcaaaacgtg agcctataca cgataactca atcaggaccg agtgggaagc caagatagct      60
aaactgacat cagttgacca agcaaccaaa ttcatccaag actttagact tgcatatacc     120
tctcctttca gaaagtctta tgacatagac gttgattatc agtacattga aaggaagatc     180
gaggagaaac tgtctgtact aaagacagag aaactgcctg tcgctgatct aattaccaaa     240
gctacaactg gagaggaccg tgccgcagtt gaggccacct ggatagctaa aattaaggct     300
gctaagtcta agtacgaagc cgacggaata catattgaat tccgtcagct atataagcct     360
ccagtcctgc ctgtgaacgt cttccttagg acagacgctg ctctgggtac agtattgatg     420
gaaattagga atacggacta ctatggaact ccactagagg gattgaggaa ggaacctggt     480
gtaaaagttc tgcatttaca ggctggatcc                                      510
```

<210> SEQ ID NO 4
<211> LENGTH: 423
<212> TYPE: DNA
<213> ORGANISM: Methylosinus trichosporium

<400> SEQUENCE: 4

```
atgtcatctg cccataatgc atataatgcc ggtatcatgc agaaaacagg caaggctttt      60
gcagatgagt tttttgcaga agaaaaccag gtcgtccatg aaagtaatgc cgttgttctg     120
gtattaatga agagtgacga gattgatgct ataattgagg acatagttct aaaaggcgga     180
aaagcaaaaa acccatcaat tgtggtagag gataaagctg gattttggtg gataaaggcc     240
gatggcgcaa ttgaaataga tgccgccgag gctggagaac ttttgggtaa gcccttctct     300
gtgtacgatt tactaataaa cgtgtcctct acagtaggaa gagcctatac gctaggcact     360
aagttcacta ttacgtcaga gcttatgggt ttagacaggg ctctaacgga catcggatcc     420
tga                                                                   423
```

<210> SEQ ID NO 5
<211> LENGTH: 1029
<212> TYPE: DNA
<213> ORGANISM: Methylosinus trichosporium

<400> SEQUENCE: 5

```
atgtatcaaa tagtgataga gactgaagat ggcgagactt gcaggaggat gaggccatct      60
gaagattgga tctcaagagc tgaggctgaa agaaacttgt tggcctcctg tcgtgctggt     120
tgtgccacct gcaaagcaga ctgcacggac ggcgactacg aacttattga cgtgaaggtc     180
caagctgtgc caccagacga ggaagaagat ggaaaagtgt tgttgtgcag gaccttcccc     240
```

-continued

```
agatcagact tacatcttct agtaccttac acctacgata ggatcagttt tgaagccatt    300
caaacaaatt ggttagctga aattttagca tgcgacagag tttctagtaa cgtcgtacgt    360
ttggtactac agagatctcg tcccatggct gcccgtatat cactaaattt cgttcccggc    420
caattcgtgg acatcgagat cccaggaacg cacacacgta aagttactc aatggcctct     480 gtagctgagg atggacaact agaatttatc atacgtttac taccagatgg tgctttttct    540
aaatttcttc agacagaggc aaaagtggga atgagagtgg acttgagagg cccagctggt    600 tcttttttt tgcacgatca tggaggccgt tctcgtgtgt tgtcgcagg cggtacagga      660 ttatccccg tgttaagtat gatcaggcag ctgggcaagg catctgaccc atctcccgcc     720
acacttctgt ttggagtaac aaaccgtgaa gaactttct atgtagacga attaaaaacg     780
cttgcacaga gtatgccaac cctgggagtg aggatcgccg ttgtaaatga cgacggtgga    840
aacggagttg ataaaggtac tgtcatagat cttctgagag cagagctaga gaaatccgat    900
gccaaacccg acatctatct atgcggccca ccaggaatga tcgaggctgc ctttgccgcc    960
gcagctacag ctggtgtacc aaaagaacaa gtatacttag agaagttttt agccagtggc   1020
ggatcctga                                                          1029
```

<210> SEQ ID NO 6
<211> LENGTH: 1752
<212> TYPE: DNA
<213> ORGANISM: Methylosinus trichosporium

<400> SEQUENCE: 6

```
atgaccaacc cacgtaaaag ggagcgtagg cgtcccgcct tcgacgtcac gagagaaaag     60
ttcgtggcac gtaatatccg tttcggtgat gtagttagaa gggatctact agccggagtg    120
gacgccttgg ctgacgcagt cgctgtaaca cttggccctc gtggtcgtaa cgtggttata    180
gaacataggg ccgctggact gcctcctgtt gccactaaag acggcgtgac agtggcccag    240
gctgtcgagt tagcaggccg tacccagtcc gtcggtgtct ccttagtccg tcagatggcc    300
accgcagtgg caaggaaagc tggtgacgga actacaactt ccgtagttct ggccaggaga    360
ctagctgcag aaacacgtaa agccttagct gctggcatga accctagaga catagttta    420 ggcatggaaa aggctgcaag gattgtggat agggacctag cagccagagc tcgtcgttgc    480
gacgacacga gggccttggc tcacgtggcc accttggccg ccgagggtga cgaaagtata    540
ggagcaatag ttgccgatgc tctgacacgt gctggagaag gaggcgttgt agacgttgaa    600
ctgggtgccg ctctatgcga cgaaatggat attgtagagg gaatgaggtg ggagcaaggt    660
taccgttccc catacttcat gactgactcc gccagaaaga tcgctgaatt agagaaccc    720 tatatcttaa tttacgatag ggtgataaat caattttcag agttggttcc tgctctggag    780
ctagtcagga ggcagagagg cagtctttg atcgtggccg aaaacatcgt tgaagaggct    840
ttgccaggtc tgttgcttaa tcatatcagg aaaaacttat gtagtattgc agtcaaggga    900
cctggctacg gcgacagtcg ttacgaattc ttgcatgacc tggcagcatt aactggcgga    960
cgtgcaatta tggaagcttg tggtgaagaa ctgagtaatg tcacaatggc acatttgggt   1020
agggccaaaa gagtagtcgt gcgtgaagat gacacagtgg taataggcgg agaaggagat   1080
ggagctgcaa ttacggaaag gttagctgca gcaagacaac aggccgattg gattacggat   1140
ggcgacccct ccaagggttc tccctccggc aaacgtcacg acctagagaa tcttcaaaca   1200
cgtattaaag cctttgagtgg aaaggtcgta acgatcaaag ccggaggatt atccgacatc   1260
```

| | |
|---|---|
| ttgataaaag aaagaatgca aagaatcgag aacgccctag cttccgccag agctgctcgt | 1320 |
| tcagatggag tggttgctgg cggaggtgtc ggattgtatc gtgcccgtgc tgctcttaca | 1380 |
| gaggctacag gagataccct tgatcagact tacggcattg ctattgttcg tgccgctcta | 1440 |
| gacgagccaa ttcgtagaat agctgcaaat gctggcaggg acgcacatga gttttgttc | 1500 |
| gagcttaaaa gatctaacga tgacttctgg ggtatggata tgaggagtgg tgaatgcggt | 1560 |
| gacttgtatg ctgcaggagt tatcgatcct gcccgtgtca ccagattagc tctaagaaac | 1620 |
| gctgttgcaa ccgcctccag tttgatgacg gtcgaatgtg cagttacaca cattcctccc | 1680 |
| tctgatccta cttatggatt tgaccctcac ctagctgctg caacgcgtga agatcctcgt | 1740 |
| tcaggatcct ga | 1752 |

<210> SEQ ID NO 7
<211> LENGTH: 928
<212> TYPE: DNA
<213> ORGANISM: Pichia pastoris

<400> SEQUENCE: 7

| | |
|---|---|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcggca taccgtttgt | 540 |
| cttgtttggt attgattgac gaatgctcaa aaataatctc attaatgctt agcgcagtct | 600 |
| ctctatcgct tctgaacccc ggtgcacctg tgccgaaacg caaatgggga acacccgct | 660 |
| ttttggatga ttatgcattg tctccacatt gtatgcttcc aagattctgg tgggaatact | 720 |
| gctgatagcc taacgttcat gatcaaaatt taactgttct aaccctact tgacagcaat | 780 |
| atataaacag aaggaagctg ccctgtctta aacctttttt tttatcatca ttattagctt | 840 |
| actttcataa ttgcgactgg ttccaattga caagcttttg atttttaacga cttttaacga | 900 |
| caacttgaga agatcaaaaa acaactaa | 928 |

<210> SEQ ID NO 8
<211> LENGTH: 452
<212> TYPE: DNA
<213> ORGANISM: Kluyveromyces lactis

<400> SEQUENCE: 8

| | |
|---|---|
| tcaacatctt tggataatat cagaatgaga aagaacagat acgcagtacg tttttggtg | 60 |
| agctctttgc acttctttag ttctttccat caatatcagt tgcttatgca cttatgacta | 120 |
| atattgatgt ttaacttcaa tatctttaaa cttttgttct tcccgacgtt cattaagaat | 180 |
| actaatacac tttaataatt agtttaatat ttgtttctat ataatgacat ttaattaaaa | 240 |
| aagataaaat ataaaaacat cataataact caccagaggt taagaacaaa aaaacaaatt | 300 |
| agatatctgc taatccaata tagttaaatc aatctttcct tggtataatg ggtatattac | 360 |
| atatatttca aggaccgaca ctcctaccaa atatctaaaa tttaccatat taacataaca | 420 |

```
tgtatataaa cgtcaaatca taatcagcac ta                              452
```

<210> SEQ ID NO 9
<211> LENGTH: 60
<212> TYPE: DNA
<213> ORGANISM: Artificial sequence
<220> FEATURE:
<223> OTHER INFORMATION: Exemplary nucleotide sequence encoding the E2A
      self-cleaving peptide sequence

<400> SEQUENCE: 9

```
caatgtacca attacgcctt gctaaagctg gccggtgacg tagagtcaaa tccaggtcca    60
```

<210> SEQ ID NO 10
<211> LENGTH: 57
<212> TYPE: DNA
<213> ORGANISM: Artificial sequence
<220> FEATURE:
<223> OTHER INFORMATION: Exemplary nucleotide sequence encoding the P2A
      self-cleaving peptide sequence

<400> SEQUENCE: 10

```
gctacgaatt tttccctact taaacaggcc ggagatgtcg aggagaatcc tggacct       57
```

<210> SEQ ID NO 11
<211> LENGTH: 1000
<212> TYPE: DNA
<213> ORGANISM: pichia pastoris

<400> SEQUENCE: 11

```
acacgacatc aatgcaatca atagtcaacg caatgcaatt actaaacttt attactttca    60
ttattatgta tcttagccag aaattgggac aacttctttg ctggtaaagc aactcctaaa   120
gtgtctctgc cacatataat acaatttggt tttcttcttg accgttgcag gaaacattgt   180
tcgcaaaaat aatgattgca agaagttttc acgggtgatt tgtaatctcc tttgcatata   240
atgcatttaa acgggatatc tttgagctca tcttcattaa acatttggat ctccttaacc   300
ccttttgagag tattatgctt cttcttttgg acatttttccc actccctatc taatttccat   360
ccctgtttga aatcatccct caggtgcaaa aacttacaag tgtcaccata tccgcagtaa   420
cctgtctgtt tgtagtcctt gcaaacatct ggttgaaaat cgatagttgt tgtactatta   480
atgttagtag ccgactttga cattggctta ttagcgcttg gggttatgaa tttggcaaag   540
ttgttcactg aatgctcttc tcgtggtgca tcccctccta tttctgttac tgtgtttctc   600
tgtggcaatg taattggagc tttatcatca gcctcaacag gtgctctttt cttgtgcact   660
ttaactaccg ctattgatcc ttcattatct tgtatgctag ctaactctcc ctcgcctata   720
tgccttttct ttcctttcac tacccttttc ttgaacatat agaatgatgc ctacggagca   780
agaaagatga cctaatcgct ttgatagtag tgcagcggat aatatgaata ccttatcaac   840
tgtggtcctt gccctcgct gaaacgatca cgtggttgtt tttagggcta ctgccgctcc   900
tacctcctac tttcctccat gaaccttctt cctcgcgagg agattaccga ttttttttca   960
gtctgaccaa attaattttg cacaccaaca cacacaccaa                        1000
```

<210> SEQ ID NO 12
<211> LENGTH: 1000
<212> TYPE: DNA
<213> ORGANISM: Pichia pastoris

<400> SEQUENCE: 12

```
atcattttc   aaaagtatcc   aggaaccagg   tgaaagacca   tcgacagaac   agattattcg     60
tatcgcccgt   cgtttcaaga   atgaccaagt   gctagacaat   cttcccgac   cacaattgat    120 ggcaatggcc   cgttacatga   atttacgtcc   gtttggaact   gacgagattt   tacgttatca   180
gatcagatat   aagttattgc   aaatcatcaa   ggatgatcga   gccattgatt   acgaaggagt   240
tgaatctctg   tcaattcagg   agctccagag   tgcttgtgct   tcacgtggta   tcaaaaccgt   300
tggtgcttct   cctgcaagac   tgagggatga   tttgaagatt   tggctggact   tgaggttgcg   360
tcagaagatt   ccttcgacac   ttttgatttt   gagtagcacg   ttcacttatg   gagatcacgc   420
tgatgacctg   gacaattact   acgatgccct   gttggcagta   cttcttcga   ttcctgatga   480 ggtttacaat   gttgctaagt   tagagctggc   cgaccaggac   aataagttga   agctgaatgt   540
cttgaaggaa   caagatgagc   tgataaagga   agagagacaa   cagagtaaat   cacaacgccg   600
ttccactcca   atcaaagacg   atatcaaact   agacgaatac   gaggaggtga   agaagatga   660 agtgaaggat   gacgttacta   aagacaccgt   ggaggagaag   agggaagata   cgaacgaaca   720
tgtcaaagaa   gaaccaaagg   ttgatgcaag   cgaggaggtc   aaagacgaaa   ctccagcgca   780
atctgaagag   gaggtgaaag   aacccagtaa   ggatggcacc   gtaatcgagt   ccaaggacca   840
acctcaaacc   accgacaaaa   aggagtagga   aaataccagc   aaataaaaca   gctcagcgtc   900
tgtttcaatt   aaatatctac   aatcaattta   tcacgccgaa   attaaattca   atcccacgac   960
tagtgtatat   agtatatgaa   tatagtaaaa   agagatccgt                             1000

<210> SEQ ID NO 13
<211> LENGTH: 1000
<212> TYPE: DNA
<213> ORGANISM: Pichia pastoris

<400> SEQUENCE: 13
ccgttcgttt   ccttctttag   aacctcacac   tgtattgcct   atatcaacag   aatttttgaa    60
cagtccactt   aggagggatt   tgctatggaa   agcagtagtg   atggaatttg   acaacatacg   120
tgtaggtgct   tcgaatccac   ctggtagggg   tgaacataag   ttctccagga   gaaaattacg   180 ccccaaaaa    gggtctggaa   gggctcgtgt   aggagatgcc   aactctccga   cgagacacaa   240
tggagctaga   gcgctagcta   gaaatgcgcc   taatgatttc   tctactgatt   taccgtttaa   300
agtttatgct   agggcttaca   gaatagcttt   aagcagtttt   tacatcaagg   ggcatttaca   360
tatcattgga   ggttgttcat   cactcatccc   tttcaatcga   ggtgatcaaa   atatactcga   420
gctctctacc   gacaaaaaag   aggccctgga   aattttccag   gcaattcaca   atctaaaagg   480
actgaatatt   ctgttcatct   ctgatagctt   aaataactca   cagaatctga   acaaagccat   540
tcaggcttta   aacgatgacc   agatcagcct   gttggataaa   gaaaatgttg   aggttaggca   600
tttattgaaa   gctaatagag   tgttcattga   tcaggcatca   ctgcagtttt   tcgcgaagga   660
gtttgctggc   tgatgcattt   ttgtatatag   ttacgctatg   taaatagtca   aaatagattc   720
gctccactgt   ttaagggtca   aaaattacct   ctccaaatag   aaggaggcta   gaattaaac    780 taccgataac   catgttcgaa   gaaacgttgg   aaggctcagc   cagattcttg   acaagctcga   840
caaattgttt   cttaagacta   aaaactcact   catacattct   agggctcaac   cctaatgtac   900
aataattgca   cgtgcacaga   gaatttacac   cctcacataa   tctcactgtt   tttcgaatac   960
gaaaaaaatt   cgttttctaa   cttctcttca   ctacagcaac                             1000

<210> SEQ ID NO 14
<211> LENGTH: 1000
```

<212> TYPE: DNA
<213> ORGANISM: Pichia pastoris

<400> SEQUENCE: 14

```
ggtatttgac aggttgggga gcaaataagt gatgatgtcc catgaaagta gaaaatggct      60
agtagaaggc aaaaatttga aattcttaga gtcaaatagt tagactccaa gttctaatcc     120
acatttggtc agtttcatag catccagagc ttttgccact ggtgaacata tctacccatt     180
gcgatgcaac aagtcactga aagcctaaaa cggagattcc cctatcttac agcctcgttc     240
aaaaaaactg ctaccgttta tctgctatgg ccgatgtgag gatgcgctca tgcccaagag     300
tccaaccttta tcaaaaactt gacccgtcat acaggctcta gatcaagaag caaacttaat     360
ctcagcatct ggttacgtaa ctctggcaac cagtaacacg cttaaggttt ggaacaacac     420
taaactacct tgcggtacta ccattgacac tacacatcct taattccaat cctgtctggc     480
ctccttcacc ttttaaccat cttgcccatt ccaactcgtg tcagattgcg tatcaagtga     540
aaaaaaaaaa ttttaaaatc tttaacccaa tcaggtaata actgtcgcct ctttttatctg     600
ccgcactgca tgaggtgtcc ccttagtggg aaagagtact gagccaaccc tggaggacag     660
caagggaaaa atacctacaa cttgcttcat aatggtcgta aaaacaatcc ttgtcggata     720
taagtgttgt agactgtccc ttatcctctg cgatgttctt cctctcaaag tttgcgattt     780
ctctctatca gaattgccat caagagactc aggactaatt tcgcagtccc acacgcactc     840
gtacatgatt ggctgaaatt tccctaaaga atttcttttt cacgaaaatt ttttttttaca     900
caagattttc agcagatata aaatggagag caggacctcc gctgtgactc ttctttttt     960
tcttttattc tcactacata catttttagtt attcgccaac                          1000
```

<210> SEQ ID NO 15
<211> LENGTH: 250
<212> TYPE: DNA
<213> ORGANISM: Pichia pastoris

<400> SEQUENCE: 15

```
attcggatag tgtaatttaa tcaataactt gaaaaaaata tcatttaatt tactatacac      60
acggacataa actgaaaggg caaggaaggg gaaaatggga aaaataatga ggatatgcaa     120
gatgagagat gagagatgag agatgtccac tttagtcagt tttggcttta cttttatctt     180
tttctatggc atctttcgtt tcttcaacgt ttacctgctc cttttcttgc tctggttcta     240
tatcgatctc                                                            250
```

<210> SEQ ID NO 16
<211> LENGTH: 250
<212> TYPE: DNA
<213> ORGANISM: Pichia pastoris

<400> SEQUENCE: 16

```
ttgaagacgt tgaacgatga gtaaagaaga agaacaaaat cgtaatctca ggaaatctgc      60
agctatttaa actcatcgct tggcacaata agtcgctccc ataagactca tctggtgtag     120
gggttttta aaatagacag cattatacgc ttgtcagtgc gctattggtt gaaactgagg     180
ggtccaagcg catgaaaaga tctattgata cttttcggga cgaacatgag gggaccaaga     240
tgcgtagtta                                                            250
```

<210> SEQ ID NO 17
<211> LENGTH: 250
<212> TYPE: DNA

<213> ORGANISM: Pichia pastoris

<400> SEQUENCE: 17

```
gccaattagt ttgaagtgag attttatttc attcctgtta atattatata ctagagtata    60
ttttaaatta attgttcatg aacttgccaa attatgttag ttttgtgtaa acaatcttag   120
gctatccaat ttagttctac ttttggtaga tttcctgttt tggtaaatta caaacaacaa   180
tgatttgact tatattctat tcggaatttt acttatcacc ttgtacagtt tgtggggatt   240
tccggacatg                                                          250
```

<210> SEQ ID NO 18
<211> LENGTH: 250
<212> TYPE: DNA
<213> ORGANISM: Pichia pastoris

<400> SEQUENCE: 18

```
gattgcttga agctttaatt tattttatta acataataat aatacaagca tgatatattt    60
gtattttgtt cgttaacatt gatgttttct tcatttactg ttattgtttg taactttgat   120
cgatttatct tttctacttt actgtaatat ggctggcggg tgagccttga actccctgta   180
ttactttacc ttgctattac ttaatctatt gactagcagc gacctcttca accgaagggc   240
aagtacacag                                                          250
```

<210> SEQ ID NO 19
<211> LENGTH: 225
<212> TYPE: DNA
<213> ORGANISM: Saccharomyces cerevisiae

<400> SEQUENCE: 19

```
agcttttgat taagccttct agtccaaaaa acacgttttt ttgtcattta tttcattttc    60
ttagaatagt ttagtttatt cattttatag tcacgaatgt tttatgattc tatataggt   120
tgcaaacaag catttttcat tttatgttaa aacaatttca ggtttacctt ttattctgct   180
tgtggtgacg cgtgtatccg cccgctcttt tggtcaccca tgtat                   225
```

<210> SEQ ID NO 20
<211> LENGTH: 54
<212> TYPE: DNA
<213> ORGANISM: Artificial sequence
<220> FEATURE:
<223> OTHER INFORMATION: Exemplary nucleotide sequence encoding the T2A
      self-cleaving peptide sequence

<400> SEQUENCE: 20

```
gaaggcagag gatcattatt gacttgcgga gatgtggagg aaaatcctgg tcca          54
```

<210> SEQ ID NO 21
<211> LENGTH: 66
<212> TYPE: DNA
<213> ORGANISM: Artificial sequence
<220> FEATURE:
<223> OTHER INFORMATION: Exemplary nucleotide sequence encoding the F2A
      self-cleaving peptide sequence

<400> SEQUENCE: 21

```
gtaaaacaga cgcttaactt tgatttattg aaactagcag gcgacgtaga gagtaatcct    60
ggtcca                                                               66
```

<210> SEQ ID NO 22
<211> LENGTH: 69

```
<212> TYPE: DNA
<213> ORGANISM: Artificial sequence
<220> FEATURE:
<223> OTHER INFORMATION: Exemplary nucleotide sequence encoding the E2A
      self-cleaving peptide sequence

<400> SEQUENCE: 22
ggcagtggac aatgtaccaa ttacgccttg ctaaagctgg ccggtgacgt agagtcaaat    60
ccaggtcca                                                            69

<210> SEQ ID NO 23
<211> LENGTH: 66
<212> TYPE: DNA
<213> ORGANISM: Artificial sequence
<220> FEATURE:
<223> OTHER INFORMATION: Exemplary nucleotide sequence encoding the P2A
      self-cleaving peptide sequence

<400> SEQUENCE: 23
ggcagtggag ctacgaattt ttccctactt aaacaggccg agatgtcga ggagaatcct    60 ggacct                                                               66

<210> SEQ ID NO 24
<211> LENGTH: 63
<212> TYPE: DNA
<213> ORGANISM: Artificial sequence
<220> FEATURE:
<223> OTHER INFORMATION: Exemplary nucleotide sequence encoding the T2A
      self-cleaving peptide sequence

<400> SEQUENCE: 24
ggcagtggag aaggcagagg atcattattg acttgcggag atgtggagga aaatcctggt    60
cca                                                                  63

<210> SEQ ID NO 25
<211> LENGTH: 75
<212> TYPE: DNA
<213> ORGANISM: Artificial sequence
<220> FEATURE:
<223> OTHER INFORMATION: Exemplary nucleotide sequence encoding the F2A
      self-cleaving peptide sequence

<400> SEQUENCE: 25
ggcagtggag taaaacagac gcttaacttt gatttattga aactagcagg cgacgtagag    60
agtaatcctg gtcca                                                     75

<210> SEQ ID NO 26
<211> LENGTH: 2118
<212> TYPE: DNA
<213> ORGANISM: Artificial sequence
<220> FEATURE:
<223> OTHER INFORMATION: plasmid

<400> SEQUENCE: 26
tcggtctcag agttcaacat ctttggataa tatcagaatg agaaagaaca gatacgcagt    60
acgttttttg gtgagctctt tgcacttctt tagttctttc catcaatatc agttgcttat   120
gcacttatga ctaatattga tgtttaactt caatatcttt aaactttgt tcttcccgac    180 gttcattaag aatactaata cactttaata attagtttaa tatttgtttc tatataatga   240
catttaatta aaaagataa aatataaaaa catcataata actcaccaga ggttaagaac   300
aaaaaaacaa attagatatc tgctaatcca atatagttaa atcaatcttt ccttggtata   360
```

| | |
|---|---|
| atgggtatat tacatatatt tcaaggaccg acactcctac caaatatcta aaatttacca | 420 |
| tattaacata acatgtatat aaacgtcaaa tcataatcag cactaccgat gagaccagac | 480 |
| caataaaaaa cgcccggcgg caaccgagcg ttctgaacaa atccagatgg agttctgagg | 540 |
| tcattactgg atctatcaac aggagtccaa gcgagctcga tatcaaatta cgccccgccc | 600 |
| tgccactcat cgcagtactg ttgtaattca ttaagcattc tgccgacatg aagccatca | 660 |
| caaacggcat gatgaacctg aatcgccagc ggcatcagca ccttgtcgcc ttgcgtataa | 720 |
| tatttgccca tggtgaaaac gggggcgaag aagttgtcca tattggccac gtttaaatca | 780 |
| aaactggtga aactcaccca gggattggct gaaacgaaaa acatattctc aataaaccct | 840 |
| ttagggaaat aggccaggtt ttcaccgtaa cacgccacat cttgcgaata tatgtgtaga | 900 |
| aactgccgga atcgtcgtg gtattcactc cagagcgatg aaaacgtttc agtttgctca | 960 |
| tggaaaacgg tgtaacaagg gtgaacacta tcccatatca ccagctcacc gtctttcatt | 1020 |
| gccatacgaa attccggatg agcattcatc aggcgggcaa gaatgtgaat aaaggccgga | 1080 |
| taaaacttgt gcttattttt ctttacggtc tttaaaaagg ccgtaatatc cagctgaacg | 1140 |
| gtctggttat aggtacattg agcaactgac tgaaatgcct caaaatgttc tttacgatgc | 1200 |
| cattgggata tatcaacggt ggtatatcca gtgattttt tctccatttt agcttcctta | 1260 |
| gctcctgaaa atctcgataa ctcaaaaaat acgcccggta gtgatcttat ttcattatgg | 1320 |
| tgaaagttgg aacctcttac gtgcccgatc aatcatgacc aaaatccctt aacgtgagtt | 1380 |
| ttcgttccac tgagcgtcag accccgtaga aaagatcaaa ggatcttctt gagatccttt | 1440 |
| ttttctgcgc gtaatctgct gcttgcaaac aaaaaaacca ccgctaccag cggtggtttg | 1500 |
| tttgccggat caagagctac caactctttt tccgaaggta actggcttca gcagagcgca | 1560 |
| gataccaaat actgttcttc tagtgtagcc gtagttaggc caccacttca agaactctgt | 1620 |
| agcaccgcct acatacctcg ctctgctaat cctgttacca gtggctgctg ccagtggcga | 1680 |
| taagtcgtgt cttaccgggt tggactcaag acgatagtta ccggataagg cgcagcggtc | 1740 |
| gggctgaacg gggggttcgt gcacacagcc cagcttggag cgaacgacct acaccgaact | 1800 |
| gagataccta cagcgtgagc tatgagaaag cgccacgctt cccgaaggga gaaaggcgga | 1860 |
| caggtatccg gtaagcggca gggtcggaac aggagagcgc acgagggagc ttccaggggg | 1920 |
| aaacgcctgg tatctttata gtcctgtcgg gtttcgccac ctctgacttg agcgtcgatt | 1980 |
| tttgtgatgc tcgtcagggg ggcggagcct atggaaaaac gccagcaacg cggcctttt | 2040 |
| acggttcctg gccttttgct ggccttttgc tcacatgttc tttcctgcgt tatcccctga | 2100 |
| ttctgtggat aaccgtag | 2118 |

<210> SEQ ID NO 27
<211> LENGTH: 2599
<212> TYPE: DNA
<213> ORGANISM: Artificial sequence
<220> FEATURE:
<223> OTHER INFORMATION: Plasmid

<400> SEQUENCE: 27

| | |
|---|---|
| tcggtctcaa acgagatcta acatccaaag acgaaaggtt gaatgaaacc tttttgccat | 60 |
| ccgacatcca caggtccatt ctcacacata agtgccaaac gcaacaggag gggatacact | 120 |
| agcagcagac cgttgcaaac gcaggacctc cactcctctt ctcctcaaca cccacttttg | 180 |
| ccatcgaaaa accagcccag ttattgggct tgattggagc tcgctcattc caattccttc | 240 |
| tattaggcta ctaacaccat gactttatta gcctgtctat cctggccccc ctggcgaggt | 300 |

```
tcatgtttgt ttatttccga atgcaacaag ctccgcatta cacccgaaca tcactccaga    360
tgagggcttt ctgagtgtgg ggtcaaatag tttcatgttc cccaaatggc ccaaaactga    420
cagtttaaac gctgtcttgg aacctaatat gacaaaagcg tgatctcatc caagatgaac    480
taagtttggt tcgttgaaat gctaacggcc agttggtcaa aaagaaactt ccaaaagtcg    540
gcataccgtt tgtcttgttt ggtattgatt gacgaatgct caaaaataat ctcattaatg    600
cttagcgcag tctctctatc gcttctgaac cccggtgcac ctgtgccgaa acgcaaatgg    660
ggaaacaccc gcttttggga tgattatgca ttgtctccac attgtatgct tccaagattc    720
tggtgggaat actgctgata gcctaacgtt catgatcaaa atttaactgt tctaacccct    780
acttgacagc aatatataaa cagaaggaag ctgccctgtc ttaaaccttt ttttttatca    840
tcattattag cttactttca taattgcgac tggttccaat tgacaagctt ttgattttaa    900
cgacttttaa cgacaacttg agaagatcaa aaaacaacta agatctatg tgagaccaga    960 ccaataaaaa acgcccggcg gcaaccgagc gttctgaaca atccagatg gagttctgag    1020 gtcattactg gatctatcaa caggagtcca agcgagctcg atatcaaatt acgccccgcc    1080
ctgccactca tcgcagtact gttgtaattc attaagcatt ctgccgacat ggaagccatc    1140
acaaacggca tgatgaacct gaatcgccag cggcatcagc accttgtcgc cttgcgtata    1200
atatttgccc atggtgaaaa cggggcgaa gaagttgtcc atattggcca cgtttaaatc    1260
aaaactggtg aaactcaccc agggattggc tgaaacgaaa aacatattct caataaaccc    1320 tttaggaaa taggccaggt tttcaccgta acacgccaca tcttgcgaat atatgtgtag    1380
aaactgccgg aaatcgtcgt ggtattcact ccagagcgat gaaaacgttt cagtttgctc    1440
atggaaaacg gtgtaacaag ggtgaacact atcccatatc accagctcac cgtcttttcat    1500 tgccatacga aattccggat gagcattcat caggcgggca agaatgtgaa taaaggccgg    1560
ataaaacttg tgcttatttt tctttacggt ctttaaaaag gccgtaatat ccagctgaac    1620
ggtctggtta taggtacatt gagcaactga ctgaaatgcc tcaaaatgtt ctttacgatg    1680
ccattgggat atatcaacgg tggtatatcc agtgattttt ttctccattt tagcttcctt    1740
agctcctgaa aatctcgata actcaaaaaa tacgcccggt agtgatctta tttcattatg    1800
gtgaaagttg gaacctctta cgtgcccgat caatcatgac caaaatccct taacgtgagt    1860
tttcgttcca ctgagcgtca gaccccgtag aaaagatcaa aggatcttct tgagatcctt    1920 ttttttctgcg cgtaatctgc tgcttgcaaa caaaaaaacc accgctacca gcggtggttt    1980
gtttgccgga tcaagagcta ccaactcttt ttccgaaggt aactggcttc agcagagcgc    2040
agataccaaa tactgttctt ctagtgtagc cgtagttagg ccaccacttc aagaactctg    2100
tagcaccgcc tacatacctc gctctgctaa tcctgttacc agtggctgct gccagtggcg    2160
ataagtcgtg tcttaccggg ttggactcaa gacgatagtt accggataag gcgcagcggt    2220
cgggctgaac ggggggttcg tgcacacagc ccagcttgga gcgaacgacc tacaccgaac    2280
tgagatacct acagcgtgag ctatgagaaa gcgccacgct tcccgaaggg agaaaggcgg    2340
acaggtatcc ggtaagcggc agggtcggaa caggagagcg cacgagggag cttccagggg    2400
gaaacgcctg gtatctttat agtcctgtcg ggtttcgcca cctctgactt gagcgtcgat    2460
ttttgtgatg ctcgtcaggg gggcggagcc tatggaaaaa cgccagcaac gcggcctttt    2520
tacggttcct ggccttttgc tggccttttg ctcacatgtt ctttcctgcg ttatcccctg    2580
attctgtgga taaccgtag                                                  2599
```

<210> SEQ ID NO 28
<211> LENGTH: 5122
<212> TYPE: DNA
<213> ORGANISM: Artificial sequence
<220> FEATURE:
<223> OTHER INFORMATION: Synthetic plasmid pPTK013

<400> SEQUENCE: 28

```
tatgggtata aatgggctcg cgataatgtc gggcaatcag gtgcgacaat ctatcgattg      60
tatgggaagc ccgatgcgcc agagttgttt ctgaaacatg gcaaaggtag cgttgccaat     120
gatgttacag atgagatggt cagactaaac tggctgacgg aatttatgcc tcttccgacc     180
atcaagcatt ttatccgtac tcctgatgat gcatggttac tcaccactgc gatccccggc     240
aaaacagcat tccaggtatt agaagaatat cctgattcag gtgaaaatat tgttgatgcg     300
ctggcagtgt tcctgcgccg gttgcattcg attcctgttt gtaattgtcc ttttaacagc     360
gatcgcgtat ttcgtctggc tcaggcgcaa tcacgaatga ataacggttt ggttgatgcg     420
agtgattttg atgacgagcg taatggctgg cctgttgaac aagtctggaa agaaatgcat     480
aagcttttgc cattctcacc ggattcagtc gtcactcatg gtgatttctc acttgataac     540
cttatttttg acgaggggaa attaataggt tgtattgatg ttggacgagt cggaatcgca     600
gaccgatacc aggatcttgc catcctatgg aactgcctcg gtgagttttc tccttcatta     660
cagaaacggc ttttttcaaaa atatggtatt gataatcctg atatgaataa attgcagttt     720
catttgatgc tcgatgagtt tttctaaagt aactgacaat aaaaagattc ttgttttcaa     780
gaacttgtca tttgtatagt tttttttatat tgtagttgtt ctattttaat caaatgttag     840
cgtgatttat attttttttc gcctcgacat catctgccca gatgcgaagt taagtgcgca     900
gaaagtaata tcatgcgtca atcgtatgtg aatgctggtc gctatactgg agttcaacat     960
ctttggataa tatcagaatg agaaagaaca gatacgcagt acgttttttg gtgagctctt    1020
tgcacttctt tagttctttc catcaatatc agttgcttat gcacttatga ctaatattga    1080
tgtttaactt caatatcttt aaacttttgt tcttcccgac gttcattaag aatactaata    1140
cactttaata attagtttaa tatttgtttc tatataatga catttaatta aaaaagataa    1200
aatataaaaa catcataata actcaccaga ggttaagaac aaaaaaacaa attagatatc    1260
tgctaatcca atatagttaa atcaatcttt ccttggtata atgggtatat tacatatatt    1320
tcaaggaccg acactcctac caaatatcta aaatttacca tattaacata acatgtatat    1380
aaacgtcaaa tcataatcag cactaccgag cggccgcgat tatcaaaaag gatcttcacc    1440
tagatccttt taaattaaaa atgaagtttt aaatcaatct aaagtatata tgagtaaact    1500
tggtctgaca gttaccaatg cttaatcagt gaggcaccta tctcagcgat ctgtctattt    1560
cgttcatcca tagttgcctg actccccgtc gtgtagataa ctacgatacg ggagggctta    1620
ccatctggcc ccagtgctgc aatgataccg cgggacccac gctcaccggc tccagattta    1680
tcagcaataa accagccagc cggaagggcc gagcgcagaa gtggtcctgc aactttatcc    1740
gcctccatcc agtctattaa ttgttgccgg gaagctagag taagtagttc gccagttaat    1800
agtttgcgca acgttgttgc cattgctaca ggcatcgtgg tgtcacgctc gtcgtttggt    1860
atggcttcat tcagctccgg ttcccaacga tcaaggcgag ttacatgatc ccccatgttg    1920
tgcaaaaaag cggttagctc cttcggtcct ccgatcgttg tcagaagtaa gttggccgca    1980
gtgttatcac tcatggttat ggcagcactg cataattctc ttactgtcat gccatccgta    2040
agatgctttt ctgtgactgg tgagtactca accaagtcat tctgagaata gtgtatgcgg    2100
```

```
cgaccgagtt gctcttgccc ggcgtcaata cgggataata ccgcgccaca tagcagaact    2160
ttaaaagtgc tcatcattgg aaaacgttct tcggggcgaa aactctcaag gatcttaccg    2220
ctgttgagat ccagttcgat gtaacccact cgtgcaccca actgatcttc agcatctttt    2280
actttcacca gcgtttctgg gtgagcaaaa acaggaaggc aaaatgccgc aaaaaaggga    2340
ataagggcga cacggaaatg ttgaatactc atactcttcc ttttcaata ttattgaagc    2400 atttatcagg gttattgtct catgagcgga tacatatttg aatgtattta gaaaaataaa    2460
caaatagggg ttccgcgcac atttccccga aaagtgccac ctgtcatgac caaaatccct    2520
taacgtgagt tttcgttcca ctgagcgtca gaccccgtag aaaagatcaa aggatcttct    2580
tgagatcctt ttttctgcg cgtaatctgc tgcttgcaaa caaaaaaacc accgctacca    2640
gcggtggttt gtttgccgga tcaagagcta ccaactcttt ttccgaaggt aactggcttc    2700
agcagagcgc agataccaaa tactgttctt ctagtgtagc cgtagttagg ccaccacttc    2760
aagaactctg tagcaccgcc tacatacctc gctctgctaa tcctgttacc agtggctgct    2820
gccagtggcg ataagtcgtg tcttaccggg ttggactcaa gacgatagtt accggataag    2880
gcgcagcggt cgggctgaac ggggggttcg tgcacacagc ccagcttgga gcgaacgacc    2940
tacaccgaac tgagatacct acagcgtgag ctatgagaaa gcgccacgct cccgaaggg    3000 agaaaggcgg acaggtatcc ggtaagcggc agggtcggaa caggagagcg cacgagggag    3060
cttccagggg gaaacgcctg gtatctttat agtcctgtcg ggtttcgcca cctctgactt    3120
gagcgtcgat ttttgtgatg ctcgtcaggg gggcggagcc tatggaaaaa cgccagcaac    3180
gcggcctttt tacggttcct ggccttttgc tggccttttg ctcacatgtt ctttcctgcg    3240 ttatccctg attctgtgga taaccgtgcg gccgcccctg aattcgcatc tagatggtag    3300
agccacaaac agccggtaca agcaacgatc tccaggacca tctgaatcat gcgcggatga    3360
cacgaactca cgacggcgat cacagacatt aacccacagt acagacactg cgacaacgtg    3420
gcaattcgtc gcaataccgt ctcactgaac tggccgataa ttgcagacga acgtgagacc    3480
gaaagtgaaa cgtgatttca tgcgtcattt tgaacatttt gtaaatctta tttataatg    3540 tgtgcggcaa ttcacattta atttatgaat gttttcttaa catcgcggca actcaagaaa    3600
cggcaggttc ggatcttagc tactagagaa agaggagaaa tactagatgc gtaaaggcga    3660
agagctgttc actggtgtcg tccctattct ggtggaactg gatggtgatg tcaacggtca    3720
taagttttcc gtgcgtggcg agggtgaagg tgacgcaact aatggtaaac tgacgctgaa    3780
gttcatctgt actactggta aactgccggt tccttggccg actctggtaa cgacgctgac    3840
ttatggtgtt cagtgctttg ctcgttatcc ggaccatatg aagcagcatg acttcttcaa    3900
gtccgccatg ccgaaggct atgtgcagga acgcacgatt tcctttaagg atgacggcac    3960
gtacaaaacg cgtgcggaag tgaaatttga aggcgatacc ctggtaaacc gcattgagct    4020
gaaaggcatt gactttaaag aggacggcaa tatcctgggc cataagctgg aatacaattt    4080
taacagccac aatgtttaca tcaccgccga taaacaaaa aatggcatta aagcgaattt    4140
taaaattcgc cacaacgtgg aggatggcag cgtgcagctg gctgatcact accagcaaaa    4200
cactccaatc ggtgatggtc ctgttctgct gccagacaat cactatctga gcacgcaaag    4260
cgttctgtct aaagatccga acgagaaacg cgatcatatg gttctgctgg agttcgtaac    4320
cgcagcgggc atcacgcatg gtatggatga actgtacaaa tgaccaggca tcaaataaaa    4380
cgaaaggctc agtcgaaaga ctgggccttt cgttttatct gttgtttgtc ggtgaacgct    4440
```

```
ctctactaga gtcacactgg ctcaccttcg ggtgggcctt tctgcgttta taggtctcag    4500
ctgccaatga gacgacgggg tcatcacggc tcatcatgcg ccaaacaaat gtgtgcaata    4560
cacgctcgga tgactgcatg atgaccgcac tgactgggga cagcagatcc acctaagcct    4620
gtgagagaag cagacacccg acagatcaag gcagttaact agtgcactgc agtacagttt    4680
agcttgcctc gtccccgccg ggtcacccgg ccagcgacat ggaggcccag aatacccctcc   4740 ttgacagtct tgacgtgcgc agctcagggg catgatgtga ctgtcgcccg tacatttagc    4800
ccatacatcc ccatgtataa tcatttgcat ccatacattt tgatggccgc acggcgcgaa    4860
gcaaaaatta cggctcctcg ctccagacct gcgagcaggg aaacgctccc ctcacagacg    4920
cgttgaattg tccccacgcc gcgcccctgt agagaaatat aaaaggttag gatttgccac    4980
tgaggttctt ctttcatata cttccttta aatcttgct aggatacagt tctcacatca      5040
catccgaaca taaacaaaaa tgggtaagga aaagactcac gtttcgaggc cgcgattaaa    5100
ttccaacatg gatgctgatt ta                                              5122
```

<210> SEQ ID NO 29
<211> LENGTH: 2079
<212> TYPE: DNA
<213> ORGANISM: Artificial sequence
<220> FEATURE:
<223> OTHER INFORMATION: plasmid

<400> SEQUENCE: 29

```
actcaaaaaa tacgcccggt agtgatctta tttcattatg gtgaaagttg gaacctctta      60
cgtgcccgat caatcatgac caaaatccct taacgtgagt tttcgttcca ctgagcgtca    120 gacccccgtag aaaagatcaa aggatcttct tgagatcctt ttttctgcg cgtaatctgc    180 tgcttgcaaa caaaaaaacc accgctacca gcggtggttt gtttgccgga tcaagagcta    240
ccaactcttt ttccgaaggt aactggcttc agcagagcgc agataccaaa tactgttctt    300
ctagtgtagc cgtagttagg ccaccacttc aagaactctg tagcaccgcc tacatacctc    360
gctctgctaa tcctgttacc agtggctgct gccagtggcg ataagtcgtg tcttaccggg    420
ttggactcaa gacgatagtt accggataag gcgcagcggt cgggctgaac ggggggttcg    480
tgcacacagc ccagcttgga gcgaacgacc tacaccgaac tgagatacct acagcgtgag    540
ctatgagaaa gcgccacgct tcccgaaggg agaaaggcgg acaggtatcc ggtaagcggc    600
agggtcggaa caggagagcg cacgagggag cttccagggg gaaacgcctg gtatctttat    660
agtcctgtcg ggtttcgcca cctctgactt gagcgtcgat ttttgtgatg ctcgtcaggg    720
gggcggagcc tatggaaaaa cgccagcaac gcggcctttt tacggttcct ggccttttgc    780
tggccttttg ctcacatgtt ctttcctgcg ttatccctg attctgtgga taaccgtagt    840
cggtctcata tgtcatctgc ccataatgca tataatgccg gtatcatgca gaaaacaggc    900
aaggcttttg cagatgagtt ttttgcagaa gaaaaccagg tcgtccatga agtaatgcc    960 gttgttctgg tattaatgaa gagtgacgag attgatgcta taattgagga catagttcta   1020
aaaggcggaa aagcaaaaaa cccatcaatt gtggtagagg ataaagctgg attttggtgg   1080
ataaaggccg atggcgcaat tgaaatagat gccgccgagg ctgagaact tttgggtaag   1140 cccttctctg tgtacgattt actaataaac gtgtcctcta cagtaggaag agcctatacg   1200
ctaggcacta agtcactat tacgtcagag cttatgggtt tagacagggc tctaacggac    1260
atcggatcct gagaccagac caataaaaaa cgcccggcgg caaccgagcg ttctgaacaa    1320
atccagatgg agttctgagg tcattactgg atctatcaac aggagtccaa gcgagctcga    1380
```

```
tatcaaatta cgccccgccc tgccactcat cgcagtactg ttgtaattca ttaagcattc   1440
tgccgacatg gaagccatca caaacggcat gatgaacctg aatcgccagc ggcatcagca   1500
ccttgtcgcc ttgcgtataa tatttgccca tggtgaaaac gggggcgaag aagttgtcca   1560
tattggccac gtttaaatca aaactggtga aactcaccca gggattggct gaaacgaaaa   1620
acatattctc aataaaccct ttagggaaat aggccaggtt ttcaccgtaa cacgccacat   1680
cttgcgaata tatgtgtaga aactgccgga atcgtcgtg gtattcactc cagagcgatg    1740
aaaacgtttc agtttgctca tggaaaacgg tgtaacaagg gtgaacacta tcccatatca   1800
ccagctcacc gtctttcatt gccatacgaa attccggatg agcattcatc aggcgggcaa   1860
gaatgtgaat aaaggccgga taaaacttgt gcttattttt ctttacggtc tttaaaaagg   1920
ccgtaatatc cagctgaacg gtctggttat aggtacattg agcaactgac tgaaatgcct   1980
caaaatgttc tttacgatgc cattgggata tatcaacggt ggtatatcca gtgattttt    2040 tctccatttt agcttcctta gctcctgaaa atctcgata                          2079

<210> SEQ ID NO 30
<211> LENGTH: 2685
<212> TYPE: DNA
<213> ORGANISM: Artificial sequence
<220> FEATURE:
<223> OTHER INFORMATION: plasmid

<400> SEQUENCE: 30
tcaaaaaata cgcccggtag tgatcttatt tcattatggt gaaagttgga acctcttacg     60
tgcccgatca atcatgacca aaatcccctta acgtgagttt tcgttccact gagcgtcaga   120
ccccgtagaa aagatcaaag gatcttcttg agatcctttt tttctgcgcg taatctgctg    180
cttgcaaaca aaaaaaccac cgctaccagc ggtggtttgt ttgccggatc aagagctacc    240
aactcttttt ccgaaggtaa ctggcttcag cagagcgcag ataccaaata ctgttcttct    300
agtgtagccg tagttaggcc accacttcaa gaactctgta gcaccgccta catacctcgc    360
tctgctaatc ctgttaccag tggctgctgc cagtggcgat aagtcgtgtc ttaccgggtt    420
ggactcaaga cgatagttac cggataaggc gcagcggtcg ggctgaacgg ggggttcgtg    480
cacacagccc agcttggagc gaacgaccta caccgaactg agatacctac agcgtgagct    540
atgagaaagc gccacgcttc ccgaagggag aaaggcggac aggtatccgg taagcggcag    600
ggtcggaaca ggagagcgca cgagggagct tccaggggga aacgcctggt atctttatag    660
tcctgtcggg tttcgccacc tctgacttga gcgtcgattt ttgtgatgct cgtcaggggg    720
gcggagccta tggaaaaacg ccagcaacgc ggccttttta cggttcctgg ccttttgctg    780
gccttttgct cacatgttct ttcctgcgtt atcccctgat tctgtggata accgtagtcg    840
gtctcatatg tatcaaatag tgatagagac tgaagatggc gagacttgca ggaggatgag    900
gccatctgaa gattggatct caagagctga ggctgaaaga aacttgttgg cctcctgtcg    960
tgctggttgt gccacctgca aagcagactg cacggacggc gactacgaac ttattgacgt   1020
gaaggtccaa gctgtgccac cagacgagga agaagatgga aaagtgttgt tgtgcaggac   1080
cttccccaga tcagacttac atcttctagt accttacacc tacgatagga tcagttttga   1140
agccattcaa acaaattggt tagctgaaat tttagcatgc gacagagttt ctagtaacgt   1200
cgtacgtttg gtactacaga gatctcgtcc catggctgcc cgtatatcac taaatttcgt   1260
tcccggccaa ttcgtggaca tcgagatccc aggaacgcac acacgtagaa gttactcaat   1320
```

```
ggcctctgta gctgaggatg acaactagaa atttatcata cgtttactac cagatggtgc      1380
tttttctaaa tttcttcaga cagaggcaaa agtgggaatg agagtggact tgagaggccc      1440
agctggttct ttttttttgc acgatcatgg aggccgttct cgtgtgtttg tcgcaggcgg      1500
tacaggatta tcccccgtgt taagtatgat caggcagctg ggcaaggcat ctgacccatc      1560
tcccgccaca cttctgtttg gagtaacaaa ccgtgaagaa cttttctatg tagacgaatt      1620
aaaaacgctt gcacagagta tgccaaccct gggagtgagg atcgccgttg taaatgacga      1680
cggtggaaac ggagttgata aaggtactgt catagatctt ctgagagcag agctagagaa      1740
atccgatgcc aaacccgaca tctatctatg cggcccacca ggaatgatcg aggctgcctt      1800
tgccgccgca gctacagctg gtgtaccaaa agaacaagta tacttagaga agtttttagc      1860
cagtggcgga tcctgagacc agaccaataa aaaacgcccg gcggcaaccg agcgttctga      1920
acaaatccag atggagttct gaggtcatta ctggatctat caacaggagt ccaagcgagc      1980
tcgatatcaa attacgcccc gccctgccac tcatcgcagt actgttgtaa ttcattaagc      2040
attctgccga catggaagcc atcacaaacg gcatgatgaa cctgaatcgc cagcggcatc      2100
agcaccttgt cgccttgcgt ataatatttg cccatggtga aaacggggc gaagaagttg      2160 tccatattgg ccacgtttaa atcaaaactg gtgaaactca cccagggatt ggctgaaacg      2220
aaaaacatat tctcaataaa cccttaggg aaataggcca ggttttcacc gtaacacgcc      2280
acatcttgcg aatatatgtg tagaaactgc cggaaatcgt cgtggtattc actccagagc      2340
gatgaaaacg tttcagtttg ctcatggaaa acggtgtaac aagggtgaac actatcccat      2400
atcaccagct caccgtcttt cattgccata cgaaattccg gatgagcatt catcaggcgg      2460
gcaagaatgt gaataaaggc cggataaaac ttgtgcttat ttttctttac ggtctttaaa      2520
aaggccgtaa tatccagctg aacggtctgg ttataggtac attgagcaac tgactgaaat      2580
gcctcaaaat gttctttacg atgccattgg gatatatcaa cggtggtata ccagtgatt       2640 tttttctcca tttagcttc cttagctcct gaaaatctcg ataac                       2685

<210> SEQ ID NO 31
<211> LENGTH: 3408
<212> TYPE: DNA
<213> ORGANISM: Artificial sequence
<220> FEATURE:
<223> OTHER INFORMATION: plasmid

<400> SEQUENCE: 31
tcaaaaaata cgcccggtag tgatcttatt tcattatggt gaaagttgga acctcttacg        60
tgcccgatca atcatgacca aaatccctta acgtgagttt tcgttccact gagcgtcaga      120
ccccgtagaa aagatcaaag gatcttcttg agatcctttt tttctgcgcg taatctgctg      180
cttgcaaaca aaaaaaccac cgctaccagc ggtggtttgt ttgccggatc aagagctacc      240
aactcttttt ccgaaggtaa ctggcttcag cagagcgcag ataccaaata ctgttcttct      300
agtgtagccg tagttaggcc accacttcaa gaactctgta gcaccgccta catacctcgc      360
tctgctaatc ctgttaccag tggctgctgc cagtggcgat aagtcgtgtc ttaccgggtt      420
ggactcaaga cgatagttac cggataaggc gcagcggtcg ggctgaacgg ggggttcgtg      480
cacacagccc agcttggagc gaacgaccta ccgaactg agatacctac agcgtgagct      540
atgagaaagc gccacgcttc ccgaaggag aaaggcggac aggtatccgg taagcggcag      600
ggtcggaaca ggagagcgca cgagggagct tccagggga acgcctggt atctttatag       660 tcctgtcggg tttcgccacc tctgacttga gcgtcgattt ttgtgatgct cgtcaggggg      720
```

```
gcggagccta tggaaaaacg ccagcaacgc ggccttttta cggttcctgg ccttttgctg    780
gccttttgct cacatgttct ttcctgcgtt atccctgat tctgtggata accgtagtcg    840
gtctcatatg accaacccac gtaaaaggga gcgtaggcgt cccgccttcg acgtcacgag    900
agaaaagttc gtggcacgta atatccgttt cggtgatgta gttagaaggg atctactagc    960
cggagtggac gccttggctg acgcagtcgc tgtaacactt ggccctcgtg gtcgtaacgt   1020
ggttatagaa catagggccg ctggactgcc tcctgttgcc actaaagacg gcgtgacagt   1080
ggcccaggct gtcgagttag caggccgtac ccagtccgtc ggtgtctcct tagtccgtca   1140
gatggccacc gcagtggcaa aggaagctgg tgacggaact acaacttccg tagttctggc   1200
caggagacta gctgcagaaa cacgtaaagc cttagctgct ggcatgaacc ctagagacat   1260
agttttaggc atggaaaagg ctgcaaggat tgtggatagg acctagcag ccagagctcg   1320 tcgttgcgac gacacgaggg ccttggctca cgtggccacc ttggccgccg gaggtgacga   1380
aagtatagga gcaatagttg ccgatgctct gacacgtgct ggagaaggag gcgttgtaga   1440
cgttgaactg ggtgccgctc tatgcgacga aatggatatt gtagagggaa tgaggtggga   1500
gcaaggttac cgttcccat acttcatgac tgactccgcc agaaagatcg ctgaattaga   1560
gaacccctat atcttaattt acgatagggt gataaatcaa ttttcagagt tggttcctgc   1620
tctggagcta gtcaggaggc agagaggcag tcttttgatc gtggccgaaa acatcgttga   1680
agaggctttg ccaggtctgt tgcttaatca tatcaggaaa aacttatgta gtattgcagt   1740
caagggacct ggctacggcg acagtcgtta cgaattcttg catgacctgg cagcattaac   1800
tggcggacgt gcaattatgg aagcttgtgg tgaagaactg agtaatgtca caatggcaca   1860
tttgggtagg gccaaaagag tagtcgtgcg tgaagatgac acagtggtaa taggcggaga   1920
aggagatgga gctgcaatta cggaaaggtt agctgcagca agacaacagg ccgattggat   1980
tacggatggc gacccctcca agggttctcc ctccggcaaa cgtcacgacc tagagaatct   2040
tcaaacacgt attaaagcct tgagtggaaa ggtcgtaacg atcaaagccg gaggattatc   2100
cgacatcttg ataaaagaaa gaatgcaaag aatcgagaac gccctagctt ccgccagagc   2160
tgctcgttca gatggagtgg ttgctggcgg aggtgtcgga ttgtatcgtg cccgtgctgc   2220
tcttacagag gctacaggag ataccttga tcagacttac ggcattgcta ttgttcgtgc   2280
cgctctagac gagccaattc gtagaatagc tgcaaatgct ggcagggacg cacatgagtt   2340
tttgttcgag cttaaaagat ctaacgatga cttctggggt atggatatga ggagtggtga   2400
atgcggtgac ttgtatgctg caggagttat cgatcctgcc cgtgtcacca gattagctct   2460
aagaaacgct gttgcaaccg cctccagttt gatgacggtc gaatgtgcag ttacacacat   2520
tcctccctct gatcctactt atggatttga ccctcaccta gctgctgcaa gcgcgtgaaga   2580 tcctcgttca ggatcctgag accagaccaa taaaaaacgc ccggcggcaa ccgagcgttc   2640
tgaacaaatc cagatggagt tctgaggtca ttactggatc tatcaacagg agtccaagcg   2700
agctcgatat caaattacgc cccgccctgc cactcatcgc agtactgttg taattcatta   2760
agcattctgc cgacatggaa gccatcacaa acggcatgat gaacctgaat cgccagcggc   2820
atcagcacct tgtcgccttg cgtataatat ttgcccatgg tgaaacggg ggcgaagaag   2880 ttgtccatat tggccacgtt taaatcaaaa ctggtgaaac tcacccaggg attggctgaa   2940
acgaaaaaca tattctcaat aaacccttta gggaaatagg ccaggttttc accgtaacac   3000
gccacatctt gcgaatatat gtgtagaaac tgccggaaat cgtcgtggta ttcactccag   3060
```

-continued

| | |
|---|---|
| agcgatgaaa acgtttcagt tgctcatgg aaaacggtgt aacaagggtg aacactatcc | 3120 |
| catatcacca gctcaccgtc tttcattgcc atacgaaatt ccggatgagc attcatcagg | 3180 |
| cgggcaagaa tgtgaataaa ggccggataa aacttgtgct tattttttctt tacggtcttt | 3240 |
| aaaaaggccg taatatccag ctgaacggtc tggttatagg tacattgagc aactgactga | 3300 |
| aatgcctcaa aatgttcttt acgatgccat tgggatatat caacggtggt atatccagtg | 3360 |
| atttttttct ccatttagc ttccttagct cctgaaaatc tcgataac | 3408 |

<210> SEQ ID NO 32
<211> LENGTH: 5187
<212> TYPE: DNA
<213> ORGANISM: Artificial sequence
<220> FEATURE:
<223> OTHER INFORMATION: plasmid

<400> SEQUENCE: 32

| | |
|---|---|
| agcgcagata ccaaatactg ttcttctagt gtagccgtag ttaggccacc acttcaagaa | 60 |
| ctctgtagca ccgcctacat acctcgctct gctaatcctg ttaccagtgg ctgctgccag | 120 |
| tggcgataag tcgtgtctta ccgggttgga ctcaagacga tagttaccgg ataaggcgca | 180 |
| gcggtcgggc tgaacggggg gttcgtgcac acagcccagc ttggagcgaa cgacctacac | 240 |
| cgaactgaga tacctacagc gtgagctatg agaaagcgcc acgcttcccg aagggagaaa | 300 |
| ggcggacagg tatccggtaa gcggcagggt cggaacagga gagcgcacga gggagcttcc | 360 |
| agggggaaac gcctggtatc tttatagtcc tgtcgggttt cgccacctct gacttgagcg | 420 |
| tcgatttttg tgatgctcgt caggggggcg gagcctatgg aaaaacgcca gcaacgcggc | 480 |
| cttttacgg ttcctggcct tttgctggcc ttttgctcac atgttctttc ctgcgttatc | 540 |
| ccctgattct gtggataacc gtagtcggtc tcatatggca atcagtcttg ctaccaaagc | 600 |
| agcaacggat gccttgaagg tcaacagagc tcccgtcgga gtagagccac aggaggttca | 660 |
| caaatggctg cagtccttca actgggattt caaggagaat cgtacgaaat atccaacaaa | 720 |
| ataccacatg gccaacgaaa cgaaagagca gttcaaagtc attgctaaag aatatgctcg | 780 |
| tatggaggct gctaaagacg aaagacaatt tggaacacta ttagatggcc tgactagatt | 840 |
| aggcgctggc aacaaggtac accccagatg gggagagact atgaaagtca tcagtaattt | 900 |
| cctggaggta ggagaataca atgcaatagc cgcttctgcc atgctttggg acagtgctac | 960 |
| ggctgccgaa caaaaaaacg gctatctggc tcaagtgtta gacgagatta gacacacgca | 1020 |
| tcagtgcgct tttataaacc attactattc taaacactat cacgatccag ccggccacaa | 1080 |
| cgatgctaga cgtacccgtg caattggtcc actttggaag ggtatgaagc gtgtgtttgc | 1140 |
| cgacggattc atctccggag atgctgtcga atgctccgta aatctgcagc ttgtcggcga | 1200 |
| agcctgtttc acaaatcctt taatcgttgc agtaacggag tgggcttcag ccaatggaga | 1260 |
| tgagatcacg cccaccgttt ttctttcagt tgaaacggac gagctacgtc acatggctaa | 1320 |
| tggttaccaa accgtggtat caatcgccaa tgatcccgct tctgcaaagt tcttgaacac | 1380 |
| agatctaaac aatgcattct ggacgcaaca gaagtatttc acacctgttt tgggatacct | 1440 |
| ttttgagtat ggaagtaagt tcaaagttga gccctgggtg aagacctgga accgttgggt | 1500 |
| gtatgaggac tggggcggaa tttggatcgg caggttaggc aaatacggag tagaaagtcc | 1560 |
| tgcttcactg agggacgcca agagagatgc ttattgggca caccacgatc tagctctggc | 1620 |
| cgcttacgct atgtggcctc ttggatttgc acgtctagcc ttgcctgatg aagaagatca | 1680 |
| agcctggttt gaagctaact atccaggatg ggccgaccac tacggtaaaa tctttaatga | 1740 |

```
atggaagaaa ttaggctatg aagacccaaa gtccggattc atccctacc aatggttgct      1800 ggctaacggt cacgatgtgt acattgacag ggtaagtcaa gttccattta ttccctccct      1860
ggctaagggc actggaagtc tacgtgtgca tgaatttaac ggtaaaaaac attctctaac      1920
tgatgattgg ggagaacgtc aatggttaat agaacccgag cgttatgagt gtcataacgt      1980
gttcgagcag tatgagggac gtgaattgtc cgaggtaata gctgaaggtc atggagtgag      2040
gtcagacggt aaaactctta tagcacagcc ccatactaga ggagataatc tttgacact       2100 agaagatatc aaaagggctg gctgtgtttt ccctgaccct ttagcaaaat tcggatccgg      2160
caagcctatc ccaaacccct tgttaggtct ggactccacc caatgtacca attacgcctt      2220
gctaaagctg gccggtgacg tagagtcaaa tccaggtcca tcccaaccac aatcaagtca      2280
agtgactaag cgtggactta cagaccccga aagagcagca atcatcgccg cagccgtccc      2340
tgaccatgcc cttgacactc agagaaaata ccactatttt atccagccac gttggaaacc      2400
tttatctgag tacgagcagt tatcctgcta tgcccagcca aatcctgatt ggatagcagg      2460
aggcttagat tggggcgatt ggactcagaa gtttcacggc ggcagacctt cctggggcaa      2520
tgagtctacc gagctacgta caacggattg gtatcgtcac agagatcccg ctcgtcgttg      2580
gcaccatcct tatgtaaaag ataagtccga ggaagccaga tatacacaga gattccttgc      2640
tgcctatagt tccgagggat ctatacgtac catcgacccc tactggcgtg acgagatatt      2700
gaacaagtac tttggtgcat tactttacag tgagtatggc ttgttcaatg cccattcttc      2760
cgtgggaagg gattgcttat cagacacgat tagacagacg gccgtatttg ctgccttgga      2820
caaggtggat aacgcccaga tgatacaaat ggaacgtctt tttatcgcta agttagtgcc      2880
aggttttgac gctagtactg acgtgccaaa aaaaatatgg accactgatc ccatctattc      2940
aggtgctcgt gccactgtgc aagaaatatg gcagggcgta caggattgga atgaaatcct      3000
ttgggccgga catgcagtca tgatagctac atttggccag ttcgcaagaa gggaattctt      3060
tcaaagactg gccactgtgt atggtgatac tttaacacca ttttttcacgg cccaaagtca      3120 gacctacttt caaacaacga gaggcgctat tgatgattta tttgtctact gcttggccaa      3180
tgattctgag tttggtgccc acaatcgtac tttccttaat gcttggacgg agcactattt      3240
agccagttct gtagcagcat taaaagactt cgttggactg tatgccaagg tcgaaaaatc      3300
tagggccgac agatcccgta ggagacttcg tggtgctgct gcttcatcag ctattggtcg      3360
ttctattacg cccgacaaga taggcttccg tgtggacgtg gaccaaaaag ttgacgccgt      3420
cctagctggt tacaagaacg gatccggcaa gcctatccca aacccttgt taggtctgga      3480 ctccaccgct acgaattttt ccctacttaa acaggccgga gatgtcgagg agaatcctgg      3540
acctgcaaaa cgtgagccta tacacgataa ctcaatcagg accgagtggg aagccaagat      3600
agctaaactg acatcagttg accaagcaac caaattcatc caagacttta gacttgcata      3660
tacctctcct ttcagaaagt cttatgacat agacgttgat tatcagtaca ttgaaaggaa      3720
gatcgaggag aaactgtctg tactaaagac agagaaactg cctgtcgctg atctaattac      3780
caaagctaca actggagagg accgtgccgc agttgaggcc acctggatag ctaaaattaa      3840
ggctgctaag tctaagtacg aagccgacgg aatacatatt gaattccgtc agctatataa      3900
gcctccagtc ctgcctgtga acgtcttcct taggacagac gctgctctgg gtacagtatt      3960
gatggaaatt aggaatacgg actactatgg aactccacta gagggattga ggaaggaacc      4020
tggtgtaaaa gttctgcatt tacaggctgg atccggcaag ccaatcccta accccttatt      4080
```

-continued

```
gggtctggat tccaccggat cctgagacca gaccaataaa aaacgcccgg cggcaaccga    4140
gcgttctgaa caaatccaga tggagttctg aggtcattac tggatctatc aacaggagtc    4200
caagcgagct cgatatcaaa ttacgccccg ccctgccact catcgcagta ctgttgtaat    4260
tcattaagca ttctgccgac atggaagcca tcacaaacgg catgatgaac ctgaatcgcc    4320
agcggcatca gcaccttgtc gccttgcgta taatatttgc ccatggtgaa acgggggcg    4380 aagaagttgt ccatattggc cacgtttaaa tcaaaactgg tgaaactcac ccagggattg    4440
gctgaaacga aaacatatt ctcaataaac cctttaggga ataggccag gttttcaccg     4500 taacacgcca catcttgcga atatatgtgt agaaactgcc ggaaatcgtc gtggtattca    4560
ctccagagcg atgaaaacgt ttcagtttgc tcatggaaaa cggtgtaaca agggtgaaca    4620
ctatcccata tcaccagctc accgtctttc attgccatac gaaattccgg atgagcattc    4680
atcaggcggg caagaatgtg aataaaggcc ggataaaact tgtgcttatt tttctttacg    4740
gtctttaaaa aggccgtaat atccagctga acggtctggt tataggtaca ttgagcaact    4800
gactgaaatg cctcaaaatg ttctttacga tgccattggg atatatcaac ggtggtatat    4860
ccagtgattt ttttctccat tttagcttcc ttagctcctg aaaatctcga taactcaaaa    4920
aatacgcccg gtagtgatct tatttcatta tggtgaaagt tggaacctct tacgtgcccg    4980
atcaatcatg accaaaatcc cttaacgtga gttttcgttc cactgagcgt cagacccgt     5040 agaaaagatc aaaggatctt cttgagatcc ttttttttctg cgcgtaatct gctgcttgca    5100
aacaaaaaaa ccaccgctac cagcggtggt ttgtttgccg atcaagagc taccaactct     5160 ttttccgaag gtaactggct tcagcag                                        5187
```

<210> SEQ ID NO 33
<211> LENGTH: 2666
<212> TYPE: DNA
<213> ORGANISM: Artificial sequence
<220> FEATURE:
<223> OTHER INFORMATION: Synthetic plasmid pPTK037

<400> SEQUENCE: 33

```
tcaaaaaata cgcccggtag tgatcttatt tcattatggt gaaagttgga acctcttacg      60
tgcccgatca atcatgacca aaatccctta acgtgagttt tcgttccact gagcgtcaga    120
ccccgtagaa aagatcaaag gatcttcttg agatcctttt tttctgcgcg taatctgctg    180
cttgcaaaca aaaaaaccac cgctaccagc ggtggtttgt ttgccggatc aagagctacc    240
aactcttttt ccgaaggtaa ctggcttcag cagagcgcag ataccaaata ctgttcttct    300
agtgtagccg tagttaggcc accacttcaa gaactctgta gcaccgccta catacctcgc    360
tctgctaatc ctgttaccag tggctgctgc cagtggcgat aagtcgtgtc ttaccgggtt    420
ggactcaaga cgatagttac cggataaggc gcagcggtcg gctgaacgg ggggttcgtg     480 cacacagccc agcttggagc gaacgaccta caccgaactg agatacctac agcgtgagct    540
atgagaaagc gccacgcttc ccgaagggag aaaggcggac aggtatccgg taagcggcag    600
ggtcggaaca ggagagcgca cgagggagct tccaggggga aacgcctggt atctttatag    660
tcctgtcggg tttcgccacc tctgacttga gcgtcgattt tgtgatgct cgtcaggggg     720 gcggagccta tggaaaaacg ccagcaacgc ggcctttta cggttcctgg ccttttgctg     780
gccttttgct cacatgttct ttcctgcgtt atcccctgat tctgtggata accgtagtcg    840
gtctcaaacg ggtatttgac aggttgggga gcaaataagt gatgatgtcc catgaaagta    900
gaaaatggct agtagaaggc aaaaatttga aattcttaga gtcaaatagt tagactccaa    960
```

```
gttctaatcc acatttggtc agtttcatag catccagagc ttttgccact ggtgaacata    1020
tctacccatt gcgatgcaac aagtcactga aagcctaaaa cggagattcc cctatcttac    1080
agcctcgttc aaaaaaactg ctaccgttta tctgctatgg ccgatgtgag gatgcgctca    1140
tgcccaagag tccaacttta tcaaaaactt gacccgtcat acaggctcta gatcaagaag    1200
caaacttaat ctcagcatct ggttacgtaa ctctggcaac cagtaacacg cttaaggttt    1260 ggaacaaacac taaactacct tgcggtacta ccattgacac tacacatcct taattccaat    1320
cctgtctggc ctccttcacc ttttaaccat cttgcccatt ccaactcgtg tcagattgcg    1380
tatcaagtga aaaaaaaaaa ttttaaaatc tttaacccaa tcaggtaata actgtcgcct    1440
cttttatctg ccgcactgca tgaggtgtcc ccttagtggg aaagagtact gagccaaccc    1500
tggaggacag caagggaaaa atacctacaa cttgcttcat aatggtcgta aaacaatcc     1560 ttgtcggata taagtgttgt agactgtccc ttatcctctg cgatgttctt cctctcaaag    1620
tttgcgattt ctctctatca gaattgccat caagagactc aggactaatt tcgcagtccc    1680
acacgcactc gtacatgatt ggctgaaatt tccctaaaga atttcttttt cacgaaaatt    1740 ttttttttaca caagattttc agcagatata aaatggagag caggacctcc gctgtgactc    1800 ttctttttttt tcttttattc tcactacata catttagtt attcgccaac tatgtgagac     1860
cagaccaata aaaacgcccc ggcggcaacc gagcgttctg aacaaatcca gatggagttc    1920
tgaggtcatt actggatcta tcaacaggag tccaagcgag ctcgatatca aattacgccc    1980
cgccctgcca ctcatcgcag tactgttgta attcattaag cattctgccg acatggaagc    2040
catcacaaac ggcatgatga acctgaatcg ccagcggcat cagcaccttg tcgccttgcg    2100
tataatattt gcccatggtg aaaacggggg cgaagaagtt gtccatattg ccacgtttta    2160
aatcaaaact ggtgaaactc acccagggat tggctgaaac gaaaaacata ttctcaataa    2220 acccttagg gaaataggcc aggttttcac cgtaacacgc cacatcttgc gaatatatgt      2280
gtagaaactg ccggaaatcg tcgtggtatt cactccagag cgatgaaaac gtttcagttt    2340
gctcatggaa aacggtgtaa caagggtgaa cactatccca tatcaccagc tcaccgtctt    2400
tcattgccat acgaaattcc ggatgagcat tcatcaggcg ggcaagaatg tgaataaagg    2460
ccggataaaa cttgtgctta ttttttcttta cggtctttaa aaaggccgta atatccagct    2520
gaacggtctg gttataggta cattgagcaa ctgactgaaa tgcctcaaaa tgttctttac    2580
gatgccattg ggatatatca acggtggtat atccagtgat tttttctcc attttagctt    2640 ccttagctcc tgaaaatctc gataac                                         2666
```

<210> SEQ ID NO 34
<211> LENGTH: 1919
<212> TYPE: DNA
<213> ORGANISM: Artificial sequence
<220> FEATURE:
<223> OTHER INFORMATION: Synthetic plasmid pPTK041

<400> SEQUENCE: 34

```
cctgaaaatc tcgataactc aaaaaatacg cccggtagtg atcttatttc attatggtga     60
aagttggaac tcttacgtg cccgatcaat catgaccaaa atcccttaac gtgagttttc     120
gttccactga gcgtcagacc ccgtagaaaa gatcaaagga tcttcttgag atccttttt     180 tctgcgcgta atctgctgct tgcaaacaaa aaaaccaccg ctaccagcgg tggtttgttt    240
gccggatcaa gagctaccaa ctctttttcc gaaggtaact ggcttcagca gagcgcagat    300
```

```
accaaatact gttcttctag tgtagccgta gttaggccac cacttcaaga actctgtagc    360
accgcctaca tacctcgctc tgctaatcct gttaccagtg gctgctgcca gtggcgataa    420
gtcgtgtctt accgggttgg actcaagacg atagttaccg gataaggcgc agcggtcggg    480
ctgaacgggg ggttcgtgca cacagcccag cttggagcga acgacctaca ccgaactgag    540
atacctacag cgtgagctat gagaaagcgc cacgcttccc gaagggagaa aggcggacag    600
gtatccggta agcggcaggg tcggaacagg agagcgcacg agggagcttc caggggaaa    660 cgcctggtat ctttatagtc ctgtcgggtt tcgccacctc tgacttgagc gtcgattttt    720
gtgatgctcg tcaggggggc ggagcctatg gaaaaacgcc agcaacgcgg cctttttacg    780
gttcctggcc ttttgctggc cttttgctca catgttcttt cctgcgttat cccctgattc    840
tgtggataac cgtagtcggt ctcaatccta agattgcttg aagctttaat ttatttatt    900 aacataataa taatacaagc atgatatatt tgtatttgt tcgttaacat tgatgttttc    960
ttcatttact gttattgttt gtaactttga tcgatttatc ttttctactt tactgtaata   1020
tggctggcgg gtgagccttg aactccctgt attactttac cttgctatta cttaatctat   1080
tgactagcag cgacctcttc aaccgaaggg caagtacaca ggctgtgaga ccagaccaat   1140
aaaaaacgcc cggcggcaac cgagcgttct gaacaaatcc agatggagtt ctgaggtcat   1200
tactggatct atcaacagga gtccaagcga gctcgatatc aaattacgcc ccgccctgcc   1260
actcatcgca gtactgttgt aattcattaa gcattctgcc gacatggaag ccatcacaaa   1320
cggcatgatg aacctgaatc gccagcggca tcagcacctt gtcgccttgc gtataatatt   1380
tgcccatggt gaaaacgggg gcgaagaagt tgtccatatt ggccacgttt aaatcaaaac   1440
tggtgaaact cacccaggga ttggctgaaa cgaaaaacat attctcaata aaccctttag   1500
ggaaataggc caggttttca ccgtaacacg ccacatcttg cgaatatatg tgtagaaact   1560
gccggaaatc gtcgtggtat tcactccaga gcgatgaaaa cgtttcagtt tgctcatgga   1620
aaacggtgta acaagggtga acactatccc atatccaccag ctcaccgtct ttcattgcca   1680
tacgaaattc cggatgagca ttcatcaggc gggcaagaat gtgaataaag gccggataaa   1740
acttgtgctt atttttcttt acggtcttta aaaaggccgt aatatccagc tgaacggtct   1800
ggttataggt acattgagca actgactgaa atgcctcaaa atgttcttta cgatgccatt   1860
gggatatatc aacggtggta tatccagtga ttttttttctc catttagct tccttagct   1919
```

<210> SEQ ID NO 35
<211> LENGTH: 3915
<212> TYPE: DNA
<213> ORGANISM: Artificial sequence
<220> FEATURE:
<223> OTHER INFORMATION: Synthetic plasmid pPTK042

<400> SEQUENCE: 35

```
gcggccgcga ttatcaaaaa ggatcttcac ctagatcctt ttaaattaaa aatgaagttt     60
taaatcaatc taaagtatat atgagtaaac ttggtctgac agttaccaat gcttaatcag    120
tgaggcacct atctcagcga tctgtctatt tcgttcatcc atagttgcct gactccccgt    180
cgtgtagata actacgatac gggagggctt accatctggc cccagtgctg caatgatacc    240
gcgggaccca cgctcaccgg ctccagattt atcagcaata aaccagccag ccggaagggc    300
cgagcgcaga agtggtcctg caactttatc cgcctccatc cagtctatta attgttgccg    360
ggaagctaga gtaagtagtt cgccagttaa tagtttcgcc aacgttgttg ccattgctac    420
aggcatcgtg gtgtcacgct cgtcgtttgg tatggcttca ttcagctccg gttcccaacg    480
```

```
atcaaggcga gttacatgat cccccatgtt gtgcaaaaaa gcggttagct ccttcggtcc    540
tccgatcgtt gtcagaagta agttggccgc agtgttatca ctcatggtta tggcagcact    600
gcataattct cttactgtca tgccatccgt aagatgcttt tctgtgactg gtgagtactc    660
aaccaagtca ttctgagaat agtgtatgcg gcgaccgagt tgctcttgcc cggcgtcaat    720
acgggataat accgcgccac atagcagaac tttaaaagtg ctcatcattg gaaaacgttc    780
ttcggggcga aaactctcaa ggatcttacc gctgttgaga tccagttcga tgtaacccac    840
tcgtgcaccc aactgatctt cagcatcttt tactttcacc agcgtttctg ggtgagcaaa    900
aacaggaagg caaaatgccg caaaaaaggg aataagggcg acacggaaat gttgaatact    960
catactcttc cttttcaat  attattgaag catttatcag ggttattgtc tcatgagcgg   1020
atacatattt gaatgtattt agaaaaataa acaaatagg  gttccgcgca catttccccg   1080
aaaagtgcca cctgtcatga ccaaaatccc ttaacgtgag ttttcgttcc actgagcgtc   1140 agacccgta  gaaagatca  aaggatcttc ttgagatcct ttttttctgc gcgtaatctg   1200
ctgcttgcaa acaaaaaaac caccgctacc agcggtggtt tgtttgccgg atcaagagct   1260
accaactctt tttccgaagg taactggctt cagcagagcg cagataccaa atactgttct   1320
tctagtgtag ccgtagttag gccaccactt caagaactct gtagcaccgc ctacatacct   1380
cgctctgcta atcctgttac cagtggctgc tgccagtggc gataagtcgt gtcttaccgg   1440
gttggactca agacgatagt taccggataa ggcgcagcgg tcgggctgaa cggggggttc   1500
gtgcacacag cccagcttgg agcgaacgac ctacaccgaa ctgagatacc tacagcgtga   1560
gctatgagaa agcgccacgc ttcccgaagg agaaaggcg  gacaggtatc cggtaagcgg   1620
cagggtcgga acaggagagc gcacgaggga gcttccaggg ggaaacgcct ggtatcttta   1680
tagtcctgtc gggtttcgcc acctctgact tgagcgtcga ttttttgtgat gctcgtcagg   1740 ggggcggagc ctatgaaaaa acgccagcaa cgcggccttt ttacggttcc tggccttttg   1800
ctggcctttt gctcacatgt tctttcctgc gttatcccct gattctgtgg ataaccgtgc   1860
ggccgcccct gaattcgcat ctagatggta gagccacaaa cagccggtac aagcaacgat   1920
ctccaggacc atctgaatca tgcgcggatg acacgaactc acgacggcga tcacagacat   1980
taacccacag tacagacact gcgacaacgt ggcaattcgt cgcaataccg tctcactgaa   2040
ctggccgata attgcagacg aacgacacga catcaatgca atcaatagtc aacgcaatgc   2100
aattactaaa ctttattact ttcattatta tgtatcttag ccagaaattg ggacaacttc   2160
tttgctggta aagcaactcc taaagtgtct ctgccacata taatcaatt tggttttctt    2220 cttgaccgtt gcaggaaaca ttgttcgcaa aaataatgat tgcaagaagt tttcacgggt   2280
gatttgtaat ctcctttgca tataatgcat ttaaacggga tatctttgag ctcatcttca   2340
ttaaacattt ggatctcctt aaccccttg  agagtattat gcttcttctt ttggacattt   2400
tcccactccc tatctaattt ccatcccgt  ttgaaatcat ccctcaggtg caaaaactta   2460
caagtgtcac catatccgca gtaacctgtc tgtttgtagt ccttgcaaac atctggttga   2520
aaatcgatag ttgttgtact attaatgtta gtagccgact ttgacattgg cttattagcg   2580
cttggggtta tgaatttggc aaagttgttc actgaatgct cttctcgtgg tgcatcccct   2640
cctatttctg ttactgtgtt tctctgtggc aatgtaattg gagctttatc atcagcctca   2700
acaggtgctc ttttcttgtg cactttaact accgctattg atccttcatt atcttgtatg   2760
ctagctaact ctccctcgcc tatatgcctt ttctttcctt tcactaccct tttcttgaac   2820
```

| | |
|---|---:|
| atatagaatg atgcctacgg agcaagaaag atgacctaat cgctttgata gtagtgcagc | 2880 |
| ggataatatg aataccttat caactgtggt ccttgcccct cgctgaaacg atcacgtggt | 2940 |
| tgtttttagg gctactgccg ctcctacctc ctactttcct ccatgaacct tcttcctcgc | 3000 |
| gaggagatta ccgattttttt ttcagtctga ccaaattaat tttgcacacc aacacacaca | 3060 |
| ccaatatgtc atctgcccat aatgcatata atgccggtat catgcagaaa acaggcaagg | 3120 |
| cttttgcaga tgagtttttt gcagaagaaa accaggtcgt ccatgaaagt aatgccgttg | 3180 |
| ttctggtatt aatgaagagt gacgagattg atgctataat tgaggacata gttctaaaag | 3240 |
| gcggaaaagc aaaaaaccca tcaattgtgg tagaggataa agctggatttt tggtggataa | 3300 |
| aggccgatgg cgcaattgaa atagatgccg ccgaggctgg agaactttttg ggtaagccct | 3360 |
| tctctgtgta cgatttacta ataaacgtgt cctctacagt aggaagagcc tatacgctag | 3420 |
| gcactaagtt cactattacg tcagagctta tgggtttaga cagggctcta acggacatcg | 3480 |
| gatcctaaat tcggatagtg taatttaatc aataacttga aaaaaatatc atttaattta | 3540 |
| ctatacacac ggacataaac tgaaagggca aggaagggga aaatgggaaa ataatgagg | 3600 |
| atatgcaaga tgagagatga gagatgagag atgtccactt tagtcagttt tggctttact | 3660 |
| tttatctttt tctatggcat ctttcgtttc ttcaacgttt acctgctcct tttcttgctc | 3720 |
| tggttctata tcgatctcgc tgccaatgag acgacggggt catcacggct catcatgcgc | 3780 |
| caaacaaatg tgtgcaatac acgctcggat gactgcatga tgaccgcact gactggggac | 3840 |
| agcagatcca cctaagcctg tgagagaagc agacacccga cagatcaagg cagttaacta | 3900 |
| gtgcactgca gtaca | 3915 |

<210> SEQ ID NO 36
<211> LENGTH: 4521
<212> TYPE: DNA
<213> ORGANISM: Artificial Sequence
<220> FEATURE:
<223> OTHER INFORMATION: Synthetic plasmid pPTK043

<400> SEQUENCE: 36

| | |
|---|---:|
| tccaaggacc aacctcaaac caccgacaaa aaggagtagg aaaataccag caaataaaac | 60 |
| agctcagcgt ctgtttcaat taaatatcta caatcaatttt atcacgccga aattaaattc | 120 |
| aatcccacga ctagtgtata tagtatatga atatagtaaa aagagatccg ttatgtatca | 180 |
| aatagtgata gagactgaag atggcgagac ttgcaggagg atgaggccat ctgaagattg | 240 |
| gatctcaaga gctgaggctg aaagaaactt gttggcctcc tgtcgtgctg gttgtgccac | 300 |
| ctgcaaagca gactgcacgg acggcgacta cgaacttatt gacgtgaagg tccaagctgt | 360 |
| gccaccagac gaggaagaag atggaaaagt gttgttgtgc aggaccttcc ccagatcaga | 420 |
| cttacatctt ctagtacctt acacctacga taggatcagt ttttgaagcca ttcaaacaaa | 480 |
| ttggttagct gaaattttag catgcgacag agtttctagt aacgtcgtac gtttggtact | 540 |
| acagagatct cgtcccatgg ctgcccgtat atcactaaat ttcgttcccg gccaattcgt | 600 |
| ggacatcgag atcccaggaa cgcacacacg tagaagttac tcaatggcct ctgtagctga | 660 |
| ggatggacaa ctagaattta tcatacgttt actaccagat ggtgcttttt ctaaatttct | 720 |
| tcagacagag gcaaaagtgg gaatgagagt ggacttgaga ggcccagctg gttctttttt | 780 |
| tttgcacgat catggaggcc gttctcgtgt gtttgtcgca ggcggtacag gattatcccc | 840 |
| cgtgttaagt atgatcaggc agctgggcaa ggcatctgac ccatctcccg ccacacttct | 900 |
| gtttggagta acaaaccgtg aagaactttt ctatgtagac gaattaaaaa cgcttgcaca | 960 |

```
gagtatgcca accctgggag tgaggatcgc cgttgtaaat gacgacggtg gaaacggagt    1020
tgataaaggt actgtcatag atcttctgag agcagagcta gagaaatccg atgccaaacc    1080
cgacatctat ctatgcggcc caccaggaat gatcgaggct gcctttgccg ccgcagctac    1140
agctggtgta ccaaaagaac aagtatactt agagaagttt ttagccagtg gcggatccta    1200
attgaagacg ttgaacgatg agtaaagaag aagaacaaaa tcgtaatctc aggaaatctg    1260
cagctattta aactcatcgc ttggcacaat aagtcgctcc cataagactc atctggtgta    1320
ggggtttttt aaaatagaca gcattatacg cttgtcagtg cgctattggt tgaaactgag    1380
gggtccaagc gcatgaaaag atctattgat acttttcggg acgaacatga ggggaccaag    1440
atgcgtagtt agctggatgt gagacgataa atcgcagcca agtgagtgaa tagatgacgc    1500
accacggtca gacacggcca catcgtatct cacaggagca agcgcgatag gagcactcac    1560
acatagtacg gtgatccgct gactcctttg cccaaataag acgtgagcca ctagtgcact    1620
gcagtacagc ggccgcgatt atcaaaaagg atcttcacct agatcctttt aaattaaaaa    1680
tgaagtttta aatcaatcta agtatatat gagtaaactt ggtctgacag ttaccaatgc    1740
ttaatcagtg aggcacctat ctcagcgatc tgtctatttc gttcatccat agttgcctga    1800
ctccccgtcg tgtagataac tacgatacgg gagggcttac catctggccc cagtgctgca    1860
atgataccgc gggacccacg ctcaccggct ccagatttat cagcaataaa ccagccagcc    1920
ggaagggccg agcgcagaag tggtcctgca actttatccg cctccatcca gtctattaat    1980
tgttgccggg aagctagagt aagtagttcg ccagttaata gtttgcgcaa cgttgttgcc    2040
attgctacag gcatcgtggt gtcacgctcg tcgtttggta tggcttcatt cagctccggt    2100
tcccaacgat caaggcgagt tacatgatcc cccatgttgt gcaaaaaagc ggttagctcc    2160
ttcggtcctc cgatcgttgt cagaagtaag ttggccgcag tgttatcact catggttatg    2220
gcagcactgc ataattctct tactgtcatg ccatccgtaa gatgcttttc tgtgactggt    2280
gagtactcaa ccaagtcatt ctgagaatag tgtatgcggc gaccgagttg ctcttgcccg    2340
gcgtcaatac gggataatac cgcgccacat agcagaactt taaaagtgct catcattgga    2400
aaacgttctt cggggcgaaa actctcaagg atcttaccgc tgttgagatc cagttcgatg    2460
taacccactc gtgcacccaa ctgatcttca gcatctttta ctttcaccag cgtttctggg    2520
tgagcaaaaa caggaaggca aaatgccgca aaaagggaa taagggcgac acggaaatgt    2580
tgaatactca tactcttcct ttttcaatat tattgaagca tttatcaggg ttattgtctc    2640
atgagcggat acatatttga atgtatttag aaaaataaac aaataggggt tccgcgcaca    2700
tttccccgaa aagtgccacc tgtcatgacc aaaatccctt aacgtgagtt tcgttccac    2760 tgagcgtcag accccgtaga aaagatcaaa ggatcttctt gagatccttt ttttctgcgc    2820
gtaatctgct gcttgcaaac aaaaaaacca ccgctaccag cggtggtttg tttgccggat    2880
caagagctac caactctttt tccgaaggta actggcttca gcagagcgca gataccaaat    2940
actgttcttc tagtgtagcc gtagttaggc caccacttca agaactctgt agcaccgcct    3000
acatacctcg ctctgctaat cctgttacca gtggctgctg ccagtggcga taagtcgtgt    3060
cttaccgggt tggactcaag acgatagtta ccggataagg cgcagcggtc gggctgaacg    3120
gggggttcgt gcacacagcc cagcttggag cgaacgacct acaccgaact gagataccta    3180
cagcgtgagc tatgagaaag cgccacgctt cccgaaggga gaaaggcgga caggtatccg    3240
gtaagcggca gggtcggaac aggagagcgc acgagggagc ttccaggggg aaacgcctgg    3300
```

```
tatctttata gtcctgtcgg gtttcgccac ctctgacttg agcgtcgatt tttgtgatgc    3360
tcgtcagggg ggcggagcct atggaaaaac gccagcaacg cggcctttt acggttcctg     3420 gccttttgct ggccttttgc tcacatgttc tttcctgcgt tatcccctga ttctgtggat    3480
aaccgtgcgg ccgcccctga attcgcatct agaacgggt catcacggct catcatgcgc     3540
caaacaaatg tgtgcaatac acgctcggat gactgcatga tgaccgcact gactggggac    3600
agcagatcca cctaagcctg tgagagaagc agacacccga cagatcaagg cagttacgtc    3660
tcaccaaacc agatgtcaac acagctacaa cgatcatttt tcaaaagtat ccaggaacca    3720
ggtgaaagac catcgacaga acagattatt cgtatcgccc gtcgtttcaa gaatgaccaa    3780
gtgctagaca atctttcccg accacaattg atggcaatgg cccgttacat gaatttacgt    3840
ccgtttggaa ctgacgagat tttacgttat cagatcagat ataagttatt gcaaatcatc    3900
aaggatgatc gagccattga ttacgaagga gttgaatctc tgtcaattca ggagctccag    3960
agtgcttgtg cttcacgtgg tatcaaaacc gttggtgctt ctcctgcaag actgagggat    4020
gatttgaaga tttggctgga cttgaggttg cgtcagaaga ttccttcgac acttttgatt    4080
ttgagtagca cgttcactta tggagatcac gctgatgacc tggacaatta ctacgatgcc    4140
ctgttggcag tactttcttc gattcctgat gaggtttaca atgttgctaa gttagagctg    4200
gccgaccagg acaataagtt gaagctgaat gtcttgaagg aacaagatga gctgataaag    4260
gaagagagac aacagagtaa atcacaacgc cgttccactc caatcaaaga cgatatcaaa    4320
ctagacgaat acgaggaggt gaaagaagat gaagtgaagg atgacgttac taaagacacc    4380
gtggaggaga gagggaaga tacgaacgaa catgtcaaag aagaaccaaa ggttgatgca     4440
agcgaggagg tcaaagacga aactccagcg caatctgaag aggaggtgaa agaacccagt    4500
aaggatggca ccgtaatcga g                                              4521
```

<210> SEQ ID NO 37
<211> LENGTH: 5244
<212> TYPE: DNA
<213> ORGANISM: Artificial sequence
<220> FEATURE:
<223> OTHER INFORMATION: Synthetic plasmid pPTK044

<400> SEQUENCE: 37

```
gacaagctcg acaaattgtt tcttaagact aaaaactcac tcatacattc tagggctcaa      60
ccctaatgta caataattgc acgtgcacag agaatttaca ccctcacata atctcactgt     120
ttttcgaata cgaaaaaaat tcgttttcta acttctcttc actacagcaa ctatgaccaa     180
cccacgtaaa agggagcgta ggcgtcccgc cttcgacgtc acgagagaaa agttcgtggc     240
acgtaatatc cgtttcggtg atgtagttag aagggatcta ctagccggag tggacgcctt     300
ggctgacgca gtcgctgtaa cacttggccc tcgtggtcgt aacgtggtta tagaacatag     360
ggccgctgga ctgcctcctg ttgccactaa agacggcgtg acagtgggcc aggctgtcga    420
gttagcaggc cgtacccagt ccgtcggtgt ctccttagtc cgtcagatgg ccaccgcagt    480
ggcaaaggaa gctggtgacg gaactacaac ttccgtagtt ctggccagga gactagctgc    540
agaaacacgt aaagccttag ctgctggcat gaacccataga gacatagttt taggcatgga   600
aaaggctgca aggattgtgg atagggacct agcagccaga gctcgtcgtt gcgacgacac    660
gagggccttg gctcacgtgg ccaccttggc cgccggaggt gacgaaagta taggagcaat    720
agttgccgat gctctgacac gtgctggaga aggaggcgtt gtagacgttg aactgggtgc    780
cgctctatgc gacgaaatgg atattgtaga gggaatgagg tgggagcaag gttaccgttc    840
```

| | | | | |
|---|---|---|---|---|
| cccatacttc | atgactgact | ccgccagaaa | gatcgctgaa | ttagagaacc cctatatctt | 900 |
| aatttacgat | agggtgataa | atcaatttc | agagttggtt | cctgctctgg agctagtcag | 960 |
| gaggcagaga | ggcagtcttt | tgatcgtggc | cgaaaacatc | gttgaagagg ctttgccagg | 1020 |
| tctgttgctt | aatcatatca | ggaaaaactt | atgtagtatt | gcagtcaagg gacctggcta | 1080 |
| cggcgacagt | cgttacgaat | tcttgcatga | cctggcagca | ttaactggcg gacgtgcaat | 1140 |
| tatggaagct | tgtggtgaag | aactgagtaa | tgtcacaatg | gcacatttgg gtagggccaa | 1200 |
| aagagtagtc | gtgcgtgaag | atgacacagt | ggtaataggc | ggagaaggag atggagctgc | 1260 |
| aattacggaa | aggttagctg | cagcaagaca | acaggccgat | tggattacgg atggcgaccc | 1320 |
| ctccaagggt | tctccctccg | gcaaacgtca | cgacctagag | aatcttcaaa cacgtattaa | 1380 |
| agccttgagt | ggaaaggtcg | taacgatcaa | agccggagga | ttatccgaca tcttgataaa | 1440 |
| agaaagaatg | caaagaatcg | agaacgccct | agcttccgcc | agagctgctc gttcagatgg | 1500 |
| agtggttgct | ggcggaggtg | tcggattgta | tcgtgcccgt | gctgctctta cagaggctac | 1560 |
| aggagatacc | cttgatcaga | cttacggcat | tgctattgtt | cgtgccgctc tagacgagcc | 1620 |
| aattcgtaga | atagctgcaa | atgctggcag | ggacgcacat | gagttttgt tcgagcttaa | 1680 |
| aagatctaac | gatgacttct | ggggtatgga | tatgaggagt | ggtgaatgcg gtgacttgta | 1740 |
| tgctgcagga | gttatcgatc | ctgcccgtgt | caccagatta | gctctaagaa acgctgttgc | 1800 |
| aaccgcctcc | agtttgatga | cggtcgaatg | tgcagttaca | cacattcctc cctctgatcc | 1860 |
| tacttatgga | tttgaccctc | acctagctgc | tgcaacgcgt | gaagatcctc gttcaggatc | 1920 |
| ctaagccaat | tagtttgaag | tgagattta | tttcattcct | gttaatatta tatactagag | 1980 |
| tatatttaa | attaattgtt | catgaacttg | ccaaattatg | ttagttttgt gtaaacaatc | 2040 |
| ttaggctatc | caatttagtt | ctacttttgg | tagatttcct | gttttggtaa attacaaaca | 2100 |
| acaatgattt | gacttatatt | ctattcggaa | ttttacttat | caccttgtac agtttgtggg | 2160 |
| gatttccgga | catggctgag | catgagacgg | aaatctgctc | gtcagtggtg ctcacactga | 2220 |
| cgaatcatgt | acagatcata | ccgatgactg | cctggcgact | cacaactaag caagacagcc | 2280 |
| ggaaccagcg | ccggcgaaca | ccactgcata | tatggcatat | cacaacagtc caactagtgc | 2340 |
| actgcagtac | agcggccgcg | attatcaaaa | aggatcttca | cctagatcct tttaaattaa | 2400 |
| aaatgaagtt | ttaaatcaat | ctaaagtata | tatgagtaaa | cttggtctga cagttaccaa | 2460 |
| tgcttaatca | gtgaggcacc | tatctcagcg | atctgtctat | ttcgttcatc catagttgcc | 2520 |
| tgactccccg | tcgtgtagat | aactacgata | cgggagggct | taccatctgg ccccagtgct | 2580 |
| gcaatgatac | cgcgggaccc | acgctcaccg | gctccagatt | tatcagcaat aaaccagcca | 2640 |
| gccggaaggg | ccgagcgcag | aagtggtcct | gcaactttat | ccgcctccat ccagtctatt | 2700 |
| aattgttgcc | gggaagctag | agtaagtagt | tcgccagtta | atagtttgcg caacgttgtt | 2760 |
| gccattgcta | caggcatcgt | ggtgtcacgc | tcgtcgtttg | gtatggcttc attcagctcc | 2820 |
| ggttcccaac | gatcaaggcg | agttacatga | tcccccatgt | tgtgcaaaaa agcggttagc | 2880 |
| tccttcggtc | ctccgatcgt | tgtcagaagt | aagttggccg | cagtgttatc actcatggtt | 2940 |
| atggcagcac | tgcataattc | tcttactgtc | atgccatccg | taagatgctt ttctgtgact | 3000 |
| ggtgagtact | caaccaagtc | attctgagaa | tagtgtatgc | ggcgaccgag ttgctcttgc | 3060 |
| ccggcgtcaa | tacgggataa | taccgcgcca | catagcagaa | cttaaaagt gctcatcatt | 3120 |
| ggaaaacgtt | cttcggggcg | aaaactctca | aggatcttac | cgctgttgag atccagttcg | 3180 |

```
atgtaaccca ctcgtgcacc caactgatct tcagcatctt ttactttcac cagcgtttct    3240
gggtgagcaa aaacaggaag gcaaaatgcc gcaaaaaagg gaataagggc gacacggaaa    3300
tgttgaatac tcatactctt cctttttcaa tattattgaa gcatttatca gggttattgt    3360
ctcatgagcg gatacatatt tgaatgtatt tagaaaaata aacaaatagg ggttccgcgc    3420
acatttcccc gaaaagtgcc acctgtcatg accaaaatcc cttaacgtga gttttcgttc    3480
cactgagcgt cagaccccgt agaaaagatc aaaggatctt cttgagatcc ttttttttctg    3540 cgcgtaatct gctgcttgca acaaaaaaa ccaccgctac cagcggtggt ttgtttgccg    3600
gatcaagagc taccaactct ttttccgaag gtaactggct tcagcagagc gcagatacca    3660
aatactgttc ttctagtgta gccgtagtta ggccaccact tcaagaactc tgtagcaccg    3720
cctacatacc tcgctctgct aatcctgtta ccagtggctg ctgccagtgg cgataagtcg    3780
tgtcttaccg ggttggactc aagacgatag ttaccggata aggcgcagcg gtcgggctga    3840
acggggggtt cgtgcacaca gcccagcttg gagcgaacga cctacaccga actgagatac    3900
ctacagcgtg agctatgaga aagcgccacg cttcccgaag ggagaaaggc ggacaggtat    3960
ccggtaagcg gcagggtcgg aacaggagag cgcacgaggg agcttccagg gggaaacgcc    4020
tggtatcttt atagtcctgt cgggtttcgc cacctctgac ttgagcgtcg atttttgtga    4080
tgctcgtcag gggggcggag cctatggaaa aacgccagca acgcggcctt tttacggttc    4140
ctggcctttt gctggccttt tgctcacatg ttctttcctg cgttatcccc tgattctgtg    4200
gataaccgtg cggccgcccc tgaattcgca tctagaataa atcgcagcca agtgagtgaa    4260
tagatgacgc accacggtca gacacggcca catcgtatct cacaggagca agcgcgatag    4320
gagcactcac acatagtacg gtgatccgct gactcctttg cccaaataag acgtgagccc    4380
gtctcagatg cacacactgg cttaagatga caacgccgtt cgtttccttc tttagaacct    4440
cacactgtat tgcctatatc aacagaattt ttgaacagtc cacttaggag ggatttgcta    4500
tggaaagcag tagtgatgga atttgacaac atacgtgtag gtgcttcgaa tccacctggt    4560
aggggtgaac ataagttctc caggagaaaa ttacgccccc aaaaagggtc tggaagggct    4620
cgtgtaggag atgccaactc tccgacgaga cacaatggag ctagagcgct agctagaaat    4680
gcgcctaatg atttctctac tgatttaccg tttaaagttt atgctagggc ttacagaata    4740
gctttaagca gtttttacat caaggggcat ttacatatca ttggaggttg ttcatcactc    4800 atcccttttca atcgaggtga tcaaaatata ctcgagctct ctaccgacaa aaagaggcc    4860 ctggaaattt tccaggcaat tcacaatcta aaaggactga atattctgtt catctctgat    4920
agcttaaata actcacagaa tctgaacaaa gccattcagg ctttaaacga tgaccagatc    4980
agcctgttgg ataaagaaaa tgttgaggtt aggcatttat tgaaagctaa tagagtgttc    5040
attgatcagg catcactgca gttttttcgcg aaggagtttg ctggctgatg cattttttgta    5100 tatagttacg ctatgtaaat agtcaaaata gattcgctcc actgtttaag ggtcaaaaat    5160
tacctctcca aatagaagga ggctagaatt taaaactaccg ataaccatgt tcgaagaaac    5220
gttggaaggc tcagccagat tctt                                          5244
```

<210> SEQ ID NO 38
<211> LENGTH: 1916
<212> TYPE: DNA
<213> ORGANISM: Artificial sequence
<220> FEATURE:
<223> OTHER INFORMATION: Synthetic plasmid pPTK045

<400> SEQUENCE: 38

```
tcggtctcat ggcattcgga tagtgtaatt taatcaataa cttgaaaaaa atatcattta      60
atttactata cacacggaca taaactgaaa gggcaaggaa ggggaaaatg ggaaaaataa     120
tgaggatatg caagatgaga gatgagagat gagagatgtc cactttagtc agttttggct     180
ttacttttat cttttctat ggcatctttc gtttcttcaa cgtttacctg ctccttttct      240
tgctctggtt ctatatcgat ctcgctgtga gaccagacca ataaaaaacg cccggcggca     300
accgagcgtt ctgaacaaat ccagatggag ttctgaggtc attactggat ctatcaacag     360
gagtccaagc gagctcgata tcaaattacg ccccgccctg ccactcatcg cagtactgtt     420
gtaattcatt aagcattctg ccgacatgga agccatcaca acggcatga tgaacctgaa      480 tcgccagcgg catcagcacc ttgtcgcctt gcgtataata tttgcccatg gtgaaaacgg     540
gggcgaagaa gttgtccata ttggccacgt ttaaatcaaa actggtgaaa ctcacccagg     600
gattggctga aacgaaaaac atattctcaa taaacccttt agggaaatag gccaggtttt     660
caccgtaaca cgccacatct tgcgaatata tgtgtagaaa ctgccggaaa tcgtcgtggt     720
attcactcca gagcgatgaa acgtttcag tttgctcatg gaaaacggtg taacaagggt      780
gaacactatc ccatatcacc agctcaccgt ctttcattgc catacgaaat tccgatgag     840 cattcatcag gcgggcaaga atgtgaataa aggccggata aaacttgtgc ttatttttct     900
ttacggtctt taaaaggcc gtaatatcca gctgaacggt ctggttatag gtacattgag      960
caactgactg aaatgcctca aaatgttctt tacgatgcca ttgggatata tcaacggtgg    1020
tatatccagt gatttttttc tccatttag cttcttagc tcctgaaaat ctcgataact      1080 caaaaatac gcccggtagt gatcttattt cattatggtg aaagttggaa cctcttacgt      1140
gcccgatcaa tcatgaccaa aatcccttaa cgtgagtttt cgttccactg agcgtcagac    1200
cccgtagaaa agatcaaagg atcttcttga gatccttttt ttctgcgcgt aatctgctgc    1260
ttgcaaacaa aaaaccacc gctaccagcg gtggtttgtt tgccggatca agagctacca     1320
actctttttc cgaaggtaac tggcttcagc agagcgcaga taccaaatac tgttcttcta    1380
gtgtagccgt agttaggcca ccacttcaag aactctgtag caccgcctac atacctcgct    1440
ctgctaatcc tgttaccagt ggctgctgcc agtggcgata gtcgtgtct taccgggttg     1500 gactcaagac gatagttacc ggataaggcg cagcggtcgg gctgaacggg gggttcgtgc    1560
acacagccca gcttggagcg aacgacctac accgaactga gatacctaca gcgtgagcta    1620
tgagaaagcg ccacgcttcc cgaagggaga aggcggaca ggtatccggt aagcggcagg     1680
gtcggaacag gagagcgcac gagggagctt ccaggggaa acgcctggta tctttatagt     1740
cctgtcgggt ttcgccacct ctgacttgag cgtcgatttt tgtgatgctc gtcaggggg     1800 cggagcctat ggaaaaacgc cagcaacgcg gccttttac ggttcctggc cttttgctgg     1860
ccttttgctc acatgttctt tcctgcgtta tcccctgatt ctgtggataa ccgtag        1916
```

<210> SEQ ID NO 39
<211> LENGTH: 1916
<212> TYPE: DNA
<213> ORGANISM: Artificial sequence
<220> FEATURE:
<223> OTHER INFORMATION: Synthetic plasmid

<400> SEQUENCE: 39

```
tcggtctcat ggcgccaatt agtttgaagt gagattttat ttcattcctg ttaatattat      60
atactagagt atattttaaa ttaattgttc atgaacttgc caaattatgt tagttttgtg     120
```

```
taaacaatct taggctatcc aatttagttc tacttttggt agatttcctg tttggtaaa      180
ttacaaacaa caatgatttg acttatattc tattcggaat tttacttatc accttgtaca     240
gtttgtgggg atttccggac atggctgtga gaccagacca ataaaaaacg cccggcggca     300
accgagcgtt ctgaacaaat ccagatggag ttctgaggtc attactggat ctatcaacag    360
gagtccaagc gagctcgata tcaaattacg ccccgccctg ccactcatcg cagtactgtt    420
gtaattcatt aagcattctg ccgacatgga agccatcaca acggcatga tgaacctgaa     480
tcgccagcgg catcagcacc ttgtcgcctt gcgtataata tttgcccatg gtgaaaacgg    540
gggcgaagaa gttgtccata ttggccacgt ttaaatcaaa actggtgaaa ctcacccagg    600
gattggctga acgaaaaac atattctcaa taaacccttt agggaaatag gccaggtttt      660
caccgtaaca cgccacatct tgcgaatata tgtgtagaaa ctgccggaaa tcgtcgtggt    720
attcactcca gagcgatgaa aacgtttcag tttgctcatg gaaaacggtg taacaagggt    780
gaacactatc ccatatcacc agctcaccgt ctttcattgc catacgaaat tccggatgag    840
cattcatcag gcgggcaaga atgtgaataa aggccggata aaacttgtgc ttatttttct    900
ttacggtctt taaaaaggcc gtaatatcca gctgaacggt ctggttatag gtacattgag    960
caactgactg aaatgcctca aatgttctt acgatgcca ttgggatata tcaacggtgg     1020
tatatccagt gattttttc tccatttag cttccttagc tcctgaaaat ctcgataact      1080
caaaaatac gcccggtagt gatcttattt cattatggtg aaagttggaa cctcttacgt      1140
gcccgatcaa tcatgaccaa aatcccttaa cgtgagtttt cgttccactg agcgtcagac    1200
cccgtagaaa agatcaaagg atcttcttga gatccttttt ttctgcgcgt aatctgctgc    1260
ttgcaaacaa aaaaccacc gctaccagcg gtggtttgtt tgccggatca agagctacca     1320
actctttttc cgaaggtaac tggcttcagc agagcgcaga taccaaatac tgttcttcta    1380
gtgtagccgt agttaggcca ccacttcaag aactctgtag caccgcctac atacctcgct   1440
ctgctaatcc tgttaccagt ggctgctgcc agtggcgata gtcgtgtct taccgggttg    1500
gactcaagac gatagttacc ggataaggcg cagcggtcgg gctgaacggg gggttcgtgc    1560
acacagccca gcttggagcg aacgacctac accgaactga gatacctaca gcgtgagcta   1620
tgagaaagcg ccacgcttcc cgaagggaga aaggcggaca ggtatccggt aagcggcagg    1680
gtcggaacag gagagcgcac gagggagctt ccagggggaa acgcctggta tctttatagt    1740
cctgtcgggt ttcgccacct ctgacttgag cgtcgatttt tgtgatgctc gtcagggggg    1800
cggagcctat ggaaaaacgc cagcaacgcg gcctttttac ggttcctggc cttttgctgg   1860
ccttttgctc acatgttctt tcctgcgtta tcccctgatt ctgtggataa ccgtag       1916
```

<210> SEQ ID NO 40
<211> LENGTH: 5246
<212> TYPE: DNA
<213> ORGANISM: Artificial sequence
<220> FEATURE:
<223> OTHER INFORMATION: plasmid

<400> SEQUENCE: 40

```
gcggccgcgt gttacaacca attaaccaat tctgattaga aaaactcatc gagcatcaaa      60
tgaaactgca atttattcat atcaggatta tcaataccat attttgaaa aagccgtttc      120
tgtaatgaag gagaaaactc accgaggcag ttccatagga tggcaagatc ctggtatcgg    180
tctgcgattc cgactcgtcc aacatcaata caacctatta atttcccctc gtcaaaaata    240
aggttatcaa gtgagaaatc accatgagtg acgactgaat ccggtgagaa tggcaaaagc    300
```

```
ttatgcattt ctttccagac ttgttcaaca ggccagccat tacgctcgtc atcaaaatca    360
ctcgcatcaa ccaaaccgtt attcattcgt gattgcgcct gagcgaggcg aaatacgcga    420
tcgctgttaa aaggacaatt acaaacagga atcgaatgca accggcgcag gaacactgcc    480
agcgcatcaa caatattttc acctgaatca ggatattctt ctaatacctg gaatgctgtt    540
ttcccgggga tcgcagtggt gagtaaccat gcatcatcag gagtacggat aaaatgcttg    600
atggtcggaa gaggcataaa ttccgtcagc cagtttagtc tgaccatctc atctgtaaca    660
tcattggcaa cgctaccttt gccatgtttc agaaacaact ctggcgcatc gggcttccca    720
tacaatcgat agattgtcgc acctgattgc ccgacattat cgcgagccca tttataccca    780
tataaatcag catccatgtt ggaatttaat cgcggcctgg agcaagacgt tcccgttga     840 atatggctca taaccccct tgtattactg tttatgtaag cagacagttt tattgttcat     900
gatgatatat ttttatcttg tgcaatgtaa catcagagat tttgagacac aacgtggctt    960
tgttgaataa atcgaacttt tgctgagttg aaggatcagt catgaccaaa atcccttaac   1020
gtgagttttc gttccactga gcgtcagacc ccgtagaaaa gatcaaagga tcttcttgag   1080 atccttttt tctgcgcgta atctgctgct tgcaaacaaa aaaaccaccg ctaccagcgg   1140
tggtttgttt gccggatcaa gagctaccaa ctcttttcc gaaggtaact ggcttcagca   1200
gagcgcagat accaaatact gttcttctag tgtagccgta gttaggccac cacttcaaga   1260
actctgtagc accgcctaca tacctcgctc tgctaatcct gttaccagtg gctgctgcca   1320
gtggcgataa gtcgtgtctt accgggttgg actcaagacg atagttaccg gataaggcgc   1380
agcggtcggg ctgaacgggg ggttcgtgca cacagcccag cttggagcga acgacctaca   1440
ccgaactgag atacctacag cgtgagctat gagaaagcgc cacgcttccc gaagggagaa   1500
aggcggacag gtatccggta agcggcaggg tcggaacagg agagcgcacg agggagcttc   1560 caggggggaaa cgcctggtat ctttatagtc ctgtcgggtt tcgccacctc tgacttgagc   1620 gtcgatttt gtgatgctcg tcagggggc ggagcctatg gaaaaacgcc agcaacgcgg   1680 ccttttacg gttcctggcc ttttgctggc cttttgctca catgttcttt cctgcgttat   1740
cccctgattc tgtggataac cgtgcggccg ccctgaatt cgcatctaga ctgatgagac   1800
gtggtagagc cacaaacagc cggtacaagc aacgatctcc aggaccatct gaatcatgcg   1860
cggatgacac gaactcacga cggcgatcac agacattaac ccacagtaca gacactgcga   1920
caacgtggca attcgtcgca atacaacgtg agaccgaaag tgaaacgtga tttcatgcgt   1980
cattttgaac attttgtaaa tcttatttaa taatgtgtgc ggcaattcac atttaattta   2040
tgaatgtttt cttaacatcg cggcaactca agaaacggca ggttcggatc ttagctacta   2100
gagaaagagg agaaatacta gatgcgtaaa ggcgaagagc tgttcactgg tgtcgtccct   2160
attctggtgg aactggatgg tgatgtcaac ggtcataagt tttccgtgcg tggcgagggt   2220
gaaggtgacg caactaatgg taaactgacg ctgaagttca tctgtactac tggtaaactg   2280
ccggttcctt ggccgactct ggtaacgacg ctgacttatg gtgttcagtg ctttgctcgt   2340
tatccggacc atatgaagca gcatgacttc ttcaagtccg ccatgccgga aggctatgtg   2400
caggaacgca cgatttcctt taaggatgac ggcacgtaca aaacgcgtgc ggaagtgaaa   2460
tttgaaggcg ataccctggt aaaccgcatt gagctgaaag gcattgactt taaagaggac   2520
ggcaatatcc tgggccataa gctggaatac aattttaaca gccacaatgt ttacatcacc   2580
gccgataaac aaaaaaatgg cattaaagcg aattttaaaa ttcgccacaa cgtggaggat   2640
```

```
ggcagcgtgc agctggctga tcactaccag caaaacactc caatcggtga tggtcctgtt    2700
ctgctgccag acaatcacta tctgagcacg caaagcgttc tgtctaaaga tccgaacgag    2760
aaacgcgatc atatggttct gctggagttc gtaaccgcag cgggcatcac gcatggtatg    2820
gatgaactgt acaaatgacc aggcatcaaa taaaacgaaa ggctcagtcg aaagactggg    2880
cctttcgttt tatctgttgt ttgtcggtga acgctctcta ctagagtcac actggctcac    2940
cttcgggtgg cctttctgcg tttataggt ctcagctgga atctgctcg tcagtggtgc      3000 tcacactgac gaatcatgta cagatcatac cgatgactgc ctggcgactc acaactaagc    3060
aagacagccg gaaccagcgc cggcgaacac cactgcatat atggcatatc acaacagtcc    3120
acgtctcaag cagttacaga gatgttacga accactagtg cactgcagta cagtttagct    3180
tgcctcgtcc ccgccgggtc acccggccag cgacatggag gcccagaata ccctccttga    3240
cagtcttgac gtgcgcagct caggggcatg atgtgactgt cgcccgtaca tttagcccat    3300
acatccccat gtataatcat ttgcatccat acattttgat ggccgcacgg cgcgaagcaa    3360
aaattacggc tcctcgctcc agacctgcga gcagggaaac gctcccctca cagacgcgtt    3420
gaattgtccc cacgccgcgc ccctgtagag aaatataaaa ggttaggatt tgccactgag    3480
gttcttcttt catatacttc cttttaaaat cttgctagga tacagttctc acatcacatc    3540
cgaacataaa caaaaatggg taaaaagcct gaactcaccg cgacgtctgt cgagaagttt    3600
ctgatcgaaa agttcgacag cgtgtccgac ctgatgcagc tctcggaggg cgaagaatct    3660
cgtgctttca gcttcgatgt aggagggcgt ggatatgtcc tgcgggtaaa tagctgcgcc    3720
gatggtttct acaaagatcg ttatgtttat cggcactttg catcggccgc gctcccgatt    3780
ccggaagtgc ttgacattgg ggaatttagc gagagcctga cctattgcat ctcccgccgt    3840
gcacagggtg tcacgttgca agacctgcct gaaaccgaac tgcccgctgt tctgcaaccg    3900
gtcgcggagg ccatggatgc gatcgctgcg gccgatctta gccagacgag cgggttcggc    3960
ccattcggac cgcaaggaat cggtcaatac actacatggc gtgatttcat atgcgcgatt    4020
gctgatcccc atgtgtatca ctggcaaact gtgatggacg acaccgtcag tgcgtccgtc    4080
gcgcaggctc tcgatgagct gatgctttgg gccgaggact gccccgaagt ccggcacctc    4140
gtgcacgcgg atttcggctc caacaatgtc ctgacggaca atggccgcat aacagcggtc    4200
attgactgga gcgaggcgat gttcggggat tcccaatacg aggtcgccaa catcttcttc    4260
tggaggccgt ggttggcttg tatggagcag cagacgcgct acttcgagcg gaggcatccg    4320
gagcttgcag atcgccgcg gctccggcg tatatgctcc gcattggtct tgaccaactc      4380
tatcagagct tggttgacgg caatttcgat gatgcagctt gggcgcaggg tcgatgcgac    4440
gcaatcgtcc gatccggagc cgggactgtc gggcgtacac aaatcgcccg cagaagcgcg    4500
gccgtctgga ccgatggctg tgtagaagta ctcgccgata gtggaaaccg acgccccagc    4560
actcgtccga gggcaaagga ataaagtaac tgacaataaa aagattcttg ttttcaagaa    4620
cttgtcattt gtatagtttt tttatattgt agttgttcta ttttaatcaa atgttagcgt    4680
gatttatatt ttttttcgcc tcgacatcat ctgcccagat gcgaagttaa gtgcgcagaa    4740
agtaatatca tgcgtcaatc gtatgtgaat gctggtcgct atactggagt tcaacatctt    4800
tggataatat cagaatgaga aagaacagat acgcagtacg ttttttggtg agctctttgc    4860
acttctttag ttcttccat caatatcagt tgcttatgca cttatgacta atattgatgt      4920
ttaacttcaa tatcttaaaa cttttgttct tcccgacgtt cattaagaat actaatacac    4980
tttaataatt agtttaatat ttgtttctat ataatgacat ttaattaaaa aagataaaat    5040
```

```
ataaaaacat cataataact caccagaggt taagaacaaa aaaacaaatt agatatctgc    5100
taatccaata tagttaaatc aatcttctcct tggtataatg ggtatattac atatatttca    5160
aggaccgaca ctcctaccaa atatctaaaa tttaccatat taacataaca tgtatataaa    5220
cgtcaaatca taatcagcac taccga                                         5246

<210> SEQ ID NO 41
<211> LENGTH: 4592
<212> TYPE: DNA
<213> ORGANISM: Artificial sequence
<220> FEATURE:
<223> OTHER INFORMATION: plasmid

<400> SEQUENCE: 41
gcggccgcgt gttacaacca attaaccaat tctgattaga aaaactcatc gagcatcaaa      60
tgaaactgca atttattcat atcaggatta tcaataccat attttgaaa aagccgtttc     120 tgtaatgaag gagaaaactc accgaggcag ttccatagga tggcaagatc ctggtatcgg    180
tctgcgattc cgactcgtcc aacatcaata caacctatta atttcccctc gtcaaaaata    240
aggttatcaa gtgagaaatc accatgagtg acgactgaat ccggtgagaa tggcaaaagc    300
ttatgcattt ctttccagac ttgttcaaca ggccagccat tacgctcgtc atcaaaatca    360
ctcgcatcaa ccaaaccgtt attcattcgt gattgcgcct gagcgaggcg aaatacgcga    420
tcgctgttaa aaggacaatt acaaacagga atcgaatgca accggcgcag gaacactgcc    480
agcgcatcaa caatattttc acctgaatca ggatattctt ctaatacctg gaatgctgtt    540
ttcccgggga tcgcagtggt gagtaaccat gcatcatcag gagtacggat aaaatgcttg    600
atggtcggaa gaggcataaa ttccgtcagc cagtttagtc tgaccatctc atctgtaaca    660
tcattggcaa cgctaccttt gccatgtttc agaaacaact ctggcgcatc gggcttccca    720
tacaatcgat agattgtcgc acctgattgc ccgacattat cgcgagccca tttatcccca    780
tataaatcag catccatgtt ggaatttaat cgcggcctgg agcaagacgt ttcccgttga    840
atatggctca taacacccct tgtattactg tttatgtaag cagacagttt tattgttcat    900
gatgatatat ttttatcttg tgcaatgtaa catcagagat tttgagacac aacgtggctt    960
tgttgaataa atcgaacttt tgctgagttg aaggatcagt catgaccaaa atcccttaac   1020
gtgagttttc gttccactga gcgtcagacc ccgtagaaaa gatcaaagga tcttcttgag   1080 atccttttt tctgcgcgta atctgctgct tgcaaacaaa aaaaccaccg ctaccagcgg   1140
tggtttgttt gccggatcaa gagctaccaa ctcttttttcc gaaggtaact ggcttcagca   1200
gagcgcagat accaaatact gttcttctag tgtagccgta gttaggccac cacttcaaga   1260
actctgtagc accgcctaca tacctcgctc tgctaatcct gttaccagtg ctgctgcca   1320 gtggcgataa gtcgtgtctt accgggttgg actcaagacg atagttaccg gataaggcgc   1380
agcggtcggg ctgaacgggg ggttcgtgca cacagcccag cttggagcga acgacctaca   1440
ccgaactgag atacctacag cgtgagctat gagaaagcgc cacgcttccc gaagggagaa   1500
aggcggacag gtatccggta agcggcaggg tcggaacagg agagcgcacg agggagcttc   1560 caggggaaa cgcctggtat ctttatagtc ctgtcgggtt tcgccacctc tgacttgagc   1620 gtcgatttt gtgatgctcg tcagggggc ggagcctatg gaaaaacgcc agcaacgcgg   1680
cctttttacg gttcctggcc ttttgctggc cttttgctca catgttcttt cctgcgttat   1740
cccctgattc tgtggataac cgtgcggccg ccctgaatt cgcatctaga tggtagagcc   1800
```

-continued

```
acaaacagcc ggtacaagca acgatctcca ggaccatctg aatcatgcgc ggatgacacg    1860
aactcacgac ggcgatcaca gacattaacc cacagtacag acactgcgac aacgtggcaa    1920
ttcgtcgcaa taccgtctca ctgaactggc cgataattgc agacgaacgt gagaccgaaa    1980
gtgaaacgtg atttcatgcg tcattttgaa cattttgtaa atcttattta ataatgtgtg    2040
cggcaattca catttaattt atgaatgttt tcttaacatc gcggcaactc aagaaacggc    2100
aggttcggat cttagctact agagaaagag gagaaatact agatgcgtaa aggcgaagag    2160
ctgttcactg gtgtcgtccc tattctggtg aactggatg tgatgtcaa cggtcataag     2220 ttttccgtgc gtggcgaggg tgaaggtgac gcaactaatg gtaaactgac gctgaagttc    2280
atctgtacta ctggtaaact gccggttcct tggccgactc tggtaacgac gctgacttat    2340
ggtgttcagt gctttgctcg ttatccggac catatgaagc agcatgactt cttcaagtcc    2400
gccatgccgg aaggctatgt gcaggaacgc acgatttcct ttaaggatga cggcacgtac    2460
aaaacgcgtg cggaagtgaa atttgaaggc gatacctgg taaaccgcat tgagctgaaa    2520
ggcattgact ttaaagagga cggcaatatc ctgggccata agctggaata caattttaac    2580
agccacaatg tttacatcac cgccgataaa caaaaaaatg gcattaaagc gaattttaaa    2640
attcgccaca acgtggagga tggcagcgtg cagctggctg atcactacca gcaaaacact    2700
ccaatcggtg atggtcctgt tctgctgcca gacaatcact atctgagcac gcaaagcgtt    2760
ctgtctaaag atccgaacga gaaacgcgat catatggttc tgctggagtt cgtaaccgca    2820
gcgggcatca cgcatggtat ggatgaactg tacaaatgac caggcatcaa ataaaacgaa    2880
aggctcagtc gaaagactgg gccttttcgtt ttatctgttg tttgtcggtg aacgctctct   2940
actagagtca cactggctca ccttcgggtg ggcctttctg cgtttatagg tctcagctgc    3000
caatgagacg acggggtcat cacggctcat catgcgccaa acaaatgtgt gcaatacacg    3060
ctcggatgac tgcatgatga ccgcactgac tggggacagc agatccacct aagcctgtga    3120
gagaagcaga cacccgacag atcaaggcag ttaactagtg cactgcagta cagtttagct    3180
tgcctcgtcc ccgccgggtc acccggccag cgacatggag gcccagaata ccctccttga    3240
cagtcttgac gtgcgcagct caggggcatg atgtgactgt cgcccgtaca tttagcccat    3300
acatccccat gtataatcat ttgcatccat acattttgat ggccgcacgg cgcgaagcaa    3360
aaattacggg tcctcgctcc agacctgcga gcagggaaac gctcccctca cagacgcgtt    3420
gaattgtccc cacgccgcgc ccctgtagag aaatataaaa ggttaggatt tgccactgag    3480
gttcttcttt catatacttc ctttttaaaat cttgctagga tacagttctc acatcacatc    3540
cgaacataaa caaaaatggc taaattaaca tctgccgttc ctgttttaac agctagggat    3600
gttgcaggtg ctgtagagtt ttggacagat aggttaggat tctcaagaga ctttgttgag    3660
gacgattttg ctggtgttgt cagggatgac gttactttat ttatctcagc agtccaagat    3720
caagttgtcc ctgataatac attggcttgg gtctgggtca ggggtttaga tgaattatat    3780
gctgaatggt cagaagttgt atctacaaac ttcagagatg cttctggtcc agctatgacc    3840
gagattggtg aacagccatg gggtagagaa tttgctttga gagatccagc tggaaattgt    3900
gttcattttg ttgctgaaga acaagattaa agtaactgac aataaaaaga ttcttgttt     3960 caagaacttg tcatttgtat agttttttta tattgtagtt gttctatttt aatcaaatgt    4020
tagcgtgatt tatattttt ttcgcctcga catcatctgc ccagatgcga agttaagtgc     4080
gcagaaagta atatcatgcg tcaatcgtat gtgaatgctg tcgctatac tggagttcaa     4140 catctttgga taatatcaga atgagaaaga acagatacgc agtacgtttt ttggtgagct    4200
```

-continued

| | |
|---|---|
| ctttgcactt ctttagttct ttccatcaat atcagttgct tatgcactta tgactaatat | 4260 |
| tgatgtttaa cttcaatatc tttaaacttt tgttcttccc gacgttcatt aagaatacta | 4320 |
| atacacttta ataattagtt taatatttgt ttctatataa tgacatttaa ttaaaaaga | 4380 |
| taaaatataa aaacatcata ataactcacc agaggttaag aacaaaaaaa caaattagat | 4440 |
| atctgctaat ccaatatagt taaatcaatc tttccttggt ataatgggta tattacatat | 4500 |
| atttcaagga ccgacactcc taccaaatat ctaaaattta ccatattaac ataacatgta | 4560 |
| tataaacgtc aaatcataat cagcactacc ga | 4592 |

<210> SEQ ID NO 42
<211> LENGTH: 8348
<212> TYPE: DNA
<213> ORGANISM: Artificial sequence
<220> FEATURE:
<223> OTHER INFORMATION: plasmid

<400> SEQUENCE: 42

| | |
|---|---|
| ccaatgagac gacggggtca tcacggctca tcatgcgcca aacaaatgtg tgcaatacac | 60 |
| gctcggatga ctgcatgatg accgcactga ctggggacag cagatccacc taagcctgtg | 120 |
| agagaagcag acacccgaca gatcaaggca gttaactagt gcactgcagt acagtttagc | 180 |
| ttgcctcgtc cccgccgggt cacccggcca gcgacatgga ggcccagaat accctccttg | 240 |
| acagtcttga cgtgcgcagc tcaggggcat gatgtgactg tcgcccgtac atttagccca | 300 |
| tacatcccca tgtataatca tttgcatcca tacattttga tggccgcacg gcgcgaagca | 360 |
| aaaattacgg ctcctcgctc cagacctgcg agcagggaaa cgctcccctc acagacgcgt | 420 |
| tgaattgtcc ccacgccgcg cccctgtaga gaaatataaa aggttaggat ttgccactga | 480 |
| ggttcttctt tcatatactt ccttttaaaa tcttgctagg atacagttct cacatcacat | 540 |
| ccgaacataa acaaaaatgg ctaaattaac atctgccgtt cctgttttaa cagctaggga | 600 |
| tgttgcaggt gctgtagagt tttggacaga taggttagga ttctcaagag actttgttga | 660 |
| ggacgatttt gctggtgttg tcagggatga cgttacttta tttatctcag cagtccaaga | 720 |
| tcaagttgtc cctgataata cattggcttg ggtctgggtc aggggtttag atgaattata | 780 |
| tgctgaatgg tcagaagttg tatctacaaa cttcagagat gcttctggtc cagctatgac | 840 |
| cgagattggt gaacagccat ggggtagaga atttgctttg agagatccag ctggaaattg | 900 |
| tgttcatttt gttgctgaag aacaagatta agtaactga caataaaaag attcttgttt | 960 |
| tcaagaactt gtcatttgta tagtttttttt atattgtagt tgttctattt taatcaaatg | 1020 |
| ttagcgtgat ttatattttt tttcgcctcg acatcatctg cccagatgcg aagttaagtg | 1080 |
| cgcagaaagt aatatcatgc gtcaatcgta tgtgaatgct ggtcgctata ctggagttca | 1140 |
| acatctttgg ataatatcag aatgagaaag aacagatacg cagtacgttt tttggtgagc | 1200 |
| tctttgcact tctttagttc tttccatcaa tatcagttgc ttatgcactt atgactaata | 1260 |
| ttgatgttta acttcaatat ctttaaactt ttgttcttcc cgacgttcat taagaatact | 1320 |
| aatacacttt aataattagt ttaatatttg tttctatata atgacattta attaaaaaag | 1380 |
| ataaaatata aaacatcat aataactcac cagaggttaa gaacaaaaaa acaaattaga | 1440 |
| tatctgctaa tccaatatag ttaaatcaat cttttccttgg tataatgggt atattacata | 1500 |
| tatttcaagg accgacactc ctaccaaata tctaaaattt accatattaa cataacatgt | 1560 |
| atataaacgt caaatcataa tcagcactac cgagcggccg cgtgttacaa ccaattaacc | 1620 |

-continued

```
aattctgatt agaaaaactc atcgagcatc aaatgaaact gcaatttatt catatcagga    1680
ttatcaatac catattttg aaaaagccgt ttctgtaatg aaggagaaaa ctcaccgagg     1740
cagttccata ggatggcaag atcctggtat cggtctgcga ttccgactcg tccaacatca    1800
atacaaccta ttaatttccc ctcgtcaaaa ataaggttat caagtgagaa atcaccatga    1860
gtgacgactg aatccggtga aatggcaaa agcttatgca ttcttttcca gacttgttca    1920
acaggccagc cattacgctc gtcatcaaaa tcactcgcat caaccaaacc gttattcatt    1980
cgtgattgcg cctgagcgag gcgaaatacg cgatcgctgt taaaaggaca attacaaaca    2040
ggaatcgaat gcaaccggcg caggaacact gccagcgcat caacaatatt ttcacctgaa    2100
tcaggatatt cttctaatac ctggaatgct gttttcccgg ggatcgcagt ggtgagtaac    2160
catgcatcat caggagtacg gataaaatgc ttgatggtcg aagaggcat aaattccgtc     2220
agccagttta gtctgaccat ctcatctgta acatcattgg caacgctacc tttgccatgt    2280
ttcagaaaca actctggcgc atcgggcttc ccatacaatc gatagattgt cgcacctgat    2340
tgcccgacat tatcgcgagc ccatttatac ccatataaat cagcatccat gttggaattt    2400
aatcgcggcc tggagcaaga cgtttcccgt tgaatatggc tcataacacc ccttgtatta    2460
ctgtttatgt aagcagacag ttttattgtt catgatgata tatttttatc ttgtgcaatg    2520
taacatcaga gattttgaga cacaacgtgg ctttgttgaa taaatcgaac ttttgctgag    2580
ttgaaggatc agtcatgacc aaaatccctt aacgtgagtt ttcgttccac tgagcgtcag    2640
accccgtaga aaagatcaaa ggatcttctt gagatccttt ttttctgcgc gtaatctgct    2700
gcttgcaaac aaaaaaacca ccgctaccag cggtggtttg tttgccggat caagagctac    2760
caactctttt tccgaaggta actggcttca gcagagcgca gataccaaat actgttcttc    2820
tagtgtagcc gtagttaggc caccacttca agaactctgt agcaccgcct acatacctcg    2880
ctctgctaat cctgttacca gtggctgctg ccagtggcga taagtcgtgt cttaccgggt    2940
tggactcaag acgatagtta ccggataagg cgcagcggtc gggctgaacg ggggttcgt     3000
gcacacagcc cagcttggag cgaacgacct acaccgaact gagatacta cagcgtgagc     3060
tatgagaaag cgccacgctt cccgaaggga gaaaggcgga caggtatccg gtaagcggca    3120
gggtcggaac aggagagcgc acgagggagc ttccaggggg aaacgcctgg tatctttata    3180
gtcctgtcgg gtttcgccac ctctgacttg agcgtcgatt tttgtgatgc tcgtcagggg    3240
ggcggagcct atggaaaaac gccagcaacg cggcctttt acggttcctg gccttttgct     3300
ggccttttgc tcacatgttc tttcctgcgt tatcccctga ttctgtggat aaccgtgcgg    3360
ccgcccctga attcgcatct agatggtaga gccacaaaca gccggtacaa gcaacgatct    3420
ccaggaccat ctgaatcatg cgcggatgac acgaactcac gacggcgatc acagacatta    3480
acccacagta cagacactgc gacaacgtgg caattcgtcg caataccgtc tcactgaact    3540
ggccgataat tgcagacgaa cgggtatttg acaggttggg gagcaaataa gtgatgatgt    3600
cccatgaaag tagaaaatgg ctagtagaag gcaaaaattt gaaattctta gagtcaaata    3660
gttagactcc aagttctaat ccacatttgg tcagtttcat agcatccaga gcttttgcca    3720
ctggtgaaca tatctaccca ttgcgatgca acaagtcact gaaagcctaa aacgagatt    3780
ccctatcttt acagcctcgt tcaaaaaaac tgctaccgtt tatctgctat ggccgatgtg    3840
aggatgcgct catgcccaag agtccaactt tatcaaaaac ttgacccgtc atacaggctc    3900
tagatcaaga agcaaactta atctcagcat ctggttacgt aactctggca accagtaaca    3960
cgcttaaggt ttggaacaac actaaactac cttgcggtac taccattgac actacacatc    4020
```

```
cttaattcca atcctgtctg gcctccttca ccttttaacc atcttgccca ttccaactcg   4080
tgtcagattg cgtatcaagt gaaaaaaaaa aattttaaaa tctttaaccc aatcaggtaa   4140
taactgtcgc ctcttttatc tgccgcactg catgaggtgt cccccttagtg ggaaagagta  4200
ctgagccaac cctggaggac agcaagggaa aaatacctac aacttgcttc ataatggtcg   4260
taaaaacaat ccttgtcgga tataagtgtt gtagactgtc ccttatcctc tgcgatgttc   4320
ttcctctcaa agtttgcgat ttctctctat cagaattgcc atcaagagac tcaggactaa   4380
tttcgcagtc ccacacgcac tcgtacatga ttggctgaaa tttccctaaa gaatttcttt   4440
ttcacgaaaa tttttttta cacaagattt tcagcagata taaaatggag agcaggacct    4500
ccgctgtgac tcttcttttt tttcttttat tctcactaca tacattttag ttattcgcca   4560
actatggcaa tcagtcttgc taccaaagca gcaacggatg ccttgaaggt caacagagct   4620
cccgtcggag tagagccaca ggaggttcac aaatggctgc agtccttcaa ctgggatttc   4680
aaggagaatc gtacgaaata tccaacaaaa taccacatgg ccaacgaaac gaaagagcag   4740
ttcaaagtca ttgctaaaga atatgctcgt atggaggctg ctaaagacga aagacaattt   4800
ggaacactat tagatggcct gactagatta ggcgctggca acaaggtaca ccccagatgg   4860
ggagagacta tgaaagtcat cagtaatttc ctggaggtag gagaatacaa tgcaatagcc   4920
gcttctgcca tgctttggga cagtgctacg gctgccgaac aaaaaaacgg ctatctggct   4980
caagtgttag acgagattag acacacgcat cagtgcgctt ttataaacca ttactattct   5040
aaacactatc acgatccagc cggccacaac gatgctagac gtacccgtgc aattggtcca   5100
ctttggaagg gtatgaagcg tgtgtttgcc gacggattca tctccggaga tgctgtcgaa   5160
tgctccgtaa atctgcagct tgtcggcgaa gcctgtttca caaatccttt aatcgttgca   5220
gtaacggagt gggcttcagc caatggagat gagatcacgc ccaccgtttt tctttcagtt   5280
gaaacggacg agctacgtca catggctaat ggttaccaaa ccgtggtatc aatcgccaat   5340
gatcccgctt ctgcaaagtt cttgaacaca gatctaaaca atgcattctg gacgcaacag   5400
aagtatttca cacctgtttt gggataccct tttgagtatg gaagtaagtt caaagttgag   5460
ccctgggtga agacctggaa ccgttgggtg tatgaggact ggggcggaat ttggatcggc   5520
aggttaggca aatacggagt agaaagtcct gcttcactga gggacgccaa gagagatgct   5580
tattgggcac accacgatct agctctggcc gcttacgcta tgtggcctct tggatttgca   5640
cgtctagcct tgcctgatga agaagatcaa gcctggtttg aagctaacta tccaggatgg   5700
gccgaccact acggtaaaat ctttaatgaa tggaagaaat taggctatga agacccaaag   5760
tccggattca tccccctacca atggttgctg gctaacggtc acgatgtgta cattgacagg   5820
gtaagtcaag ttccatttat tccctccctg gctaagggca ctggaagtct acgtgtgcat   5880
gaatttaacg gtaaaaaaca ttctctaact gatgattggg gagaacgtca atggttaata   5940
gaacccgagc gttatgagtg tcataacgtg ttcgagcagt atgagggacg tgaattgtcc   6000
gaggtaatag ctgaaggtca tggagtgagg tcagacggta aaactcttat agcacagccc   6060
catactagag gagataatct ttggacacta gaagatatca aaagggctgg ctgtgttttc   6120
cctgacccctt tagcaaaatt cggatccggc aagcctatcc caaccccctt gttaggtctg   6180
gactccaccc aatgtaccaa ttacgccttg ctaaagctgg ccggtgacgt agagtcaaat   6240
ccaggtccat cccaaccaca atcaagtcaa gtgactaagc gtggacttac agaccccgaa   6300
agagcagcaa tcatcgccgc agccgtccct gaccatgccc ttgacactca gagaaaatac   6360
```

```
cactattta tccagccacg ttggaaacct ttatctgagt acgagcagtt atcctgctat    6420
gcccagccaa atcctgattg gatagcagga ggcttagatt ggggcgattg gactcagaag    6480
tttcacggcg gcagaccttc ctggggcaat gagtctaccg agctacgtac aacggattgg    6540
tatcgtcaca gagatcccgc tcgtcgttgg caccatcctt atgtaaaaga taagtccgag    6600
gaagccagat atacacagag attccttgct gcctatagtt ccgagggatc tatacgtacc    6660
atcgacccct actggcgtga cgagatattg aacaagtact ttggtgcatt actttacagt    6720
gagtatggct tgttcaatgc ccattcttcc gtgggaaggg attgcttatc agacacgatt    6780
agacagacgg ccgtatttgc tgccttggac aaggtggata acgcccagat gatacaaatg    6840
gaacgtcttt ttatcgctaa gttagtgcca ggttttgacg ctagtactga cgtgccaaaa    6900
aaaatatgga ccactgatcc catctattca ggtgctcgtg ccactgtgca agaaatatgg    6960
cagggcgtac aggattggaa tgaaatcctt tgggccggac atgcagtcat gatagctaca    7020
tttggccagt tcgcaagaag ggaattcttt caaagactgg ccactgtgta tggtgatact    7080
ttaacaccat ttttcacggc ccaaagtcag acctactttc aaacaacgag aggcgctatt    7140
gatgatttat ttgtctactg cttggccaat gattctgagt ttggtgccca caatcgtact    7200
ttccttaatg cttggacgga gcactattta gccagtctg tagcagcatt aaaagacttc    7260
gttggactgt atgccaaggt cgaaaaatct agggccgaca gatcccgtag gagacttcgt    7320
ggtgctgctg cttcatcagc tattggtcgt tctattacgc ccgacaagat aggcttccgt    7380
gtggacgtgg accaaaaagt tgacgccgtc ctagctggtt acaagaacgg atccggcaag    7440
cctatcccaa accccttgtt aggtctggac tccaccgcta cgaattttc cctacttaaa    7500 caggccggag atgtcgagga gaatcctgga cctgcaaaac gtgagcctat acacgataac    7560
tcaatcagga ccgagtggga agccaagata gctaaactga catcagttga ccaagcaacc    7620
aaattcatcc aagactttag acttgcatat acctctcctt tcagaaagtc ttatgacata    7680
gacgttgatt atcagtacat tgaaaggaag atcgaggaga aactgtctgt actaaagaca    7740
gagaaactgc ctgtcgctga tctaattacc aaagctacaa ctggagagga ccgtgccgca    7800
gttgaggcca cctggatagc taaaattaag gctgctaagt ctaagtacga agccgacgga    7860
atacatattg aattccgtca gctatataag cctccagtcc tgcctgtgaa cgtcttcctt    7920
aggacagacg ctgctctggg tacagtattg atggaaatta ggaatacgga ctactatgga    7980
actccactag agggattgag gaaggaacct ggtgtaaaag ttctgcattt acaggctgga    8040
tccggcaagc caatccctaa ccccttattg ggtctggatt ccaccggatc ctaagattgc    8100
ttgaagcttt aatttatttt attaacataa taataataca agcatgatat atttgtattt    8160
tgttcgttaa cattgatgtt ttcttcattt actgttattg tttgtaactt tgatcgattt    8220
atcttttcta ctttactgta atatggctgg cgggtgagcc ttgaactccc tgtattactt    8280
taccttgcta ttacttaatc tattgactag cagcgacctc ttcaaccgaa gggcaagtac    8340
acaggctg                                                              8348
```

<210> SEQ ID NO 43
<211> LENGTH: 8357
<212> TYPE: DNA
<213> ORGANISM: Artificial sequence
<220> FEATURE:
<223> OTHER INFORMATION: plasmid

<400> SEQUENCE: 43

```
ccaatgagac gacggggtca tcacggctca tcatgcgcca aacaaatgtg tgcaatacac      60
```

-continued

```
gctcggatga ctgcatgatg accgcactga ctggggacag cagatccacc taagcctgtg    120
agagaagcag acacccgaca gatcaaggca gttaactagt gcactgcagt acagtttagc    180
ttgcctcgtc cccgccgggt cacccggcca gcgacatgga ggcccagaat accctccttg    240
acagtcttga cgtgcgcagc tcaggggcat gatgtgactg tcgcccgtac atttagccca    300
tacatcccca tgtataatca tttgcatcca tacattttga tggccgcacg gcgcgaagca    360
aaaattacgg ctcctcgctc cagacctgcg agcaggaaa cgctcccctc acagacgcgt     420
tgaattgtcc ccacgccgcg cccctgtaga gaaatataaa aggttaggat tgccactga    480 ggttcttctt tcatatactt cctttaaaa tcttgctagg atacagttct cacatcacat     540
ccgaacataa acaaaaatgg ctaaattaac atctgccgtt cctgttttaa cagctaggga    600
tgttgcaggt gctgtagagt tttggacaga taggttagga ttctcaagag actttgttga    660
ggacgatttt gctggtgttg tcagggatga cgttacttta tttatctcag cagtccaaga    720
tcaagttgtc cctgataata cattggcttg ggtctgggtc aggggtttag atgaattata    780
tgctgaatgg tcagaagttg tatctacaaa cttcagagat gcttctggtc cagctatgac    840
cgagattggt gaacagccat ggggtagaga atttgctttg agagatccag ctggaaattg    900
tgttcatttt gttgctgaag aacaagatta aagtaactga caataaaaag attcttgttt    960
tcaagaactt gtcatttgta tagttttttt atattgtagt tgttctattt taatcaaatg    1020
ttagcgtgat ttatattttt tttcgcctcg acatcatctg cccagatgcg aagttaagtg    1080
cgcagaaagt aatatcatgc gtcaatcgta tgtgaatgct ggtcgctata ctggagttca    1140
acatctttgg ataatatcag aatgagaaag aacagatacg cagtacgttt tttggtgagc    1200
tctttgcact tctttagttc tttccatcaa tatcagttgc ttatgcactt atgactaata    1260
ttgatgttta acttcaatat cttaaactt ttgttcttcc cgacgttcat taagaatact    1320
aatacacttt aataattagt ttaatatttg tttctatata atgacattta attaaaaaag    1380
ataaaatata aaaacatcat aataactcac cagaggttaa gaacaaaaaa acaaattaga    1440
tatctgctaa tccaatatag ttaaatcaat cttttccttgg tataatgggt atattacata    1500
tatttcaagg accgacactc ctaccaaata tctaaaattt accatattaa cataacatgt    1560
atataaacgt caaatcataa tcagcactac cgagcggccg cgattatcaa aaaggatctt    1620
cacctagatc cttttaaatt aaaaatgaag ttttaaatca atctaaagta tatatgagta    1680
aacttggtct gacagttacc aatgcttaat cagtgaggca cctatctcag cgatctgtct    1740
atttcgttca tccatagttg cctgactccc cgtcgtgtag ataactacga tacgggaggg    1800
cttaccatct ggccccagtg ctgcaatgat accgcgggac ccacgctcac cggctccaga    1860
tttatcagca ataaaccagc cagccggaag ggccgagcgc agaagtggtc ctgcaacttt    1920
atccgcctcc atccagtcta ttaattgttg ccgggaagct agagtaagta gttcgccagt    1980
taatagtttg cgcaacgttg ttgccattgc tacaggcatc gtggtgtcac gctcgtcgtt    2040
tggtatggct tcattcagct ccggttccca acgatcaagg cgagttacat gatcccccat    2100
gttgtgcaaa aaagcggtta gctccttcgg tcctccgatc gttgtcagaa gtaagttggc    2160
cgcagtgtta tcactcatgg ttatggcagc actgcataat tctcttactg tcatgccatc    2220
cgtaagatgc ttttctgtga ctggtgagta ctcaaccaag tcattctgag aatagtgtat    2280
gcggcgaccg agttgctctt gcccggcgtc aatacgggat aataccgcgc cacatagcag    2340
aactttaaaa gtgctcatca ttggaaaacg ttcttcgggg cgaaaactct caaggatctt    2400
```

```
accgctgttg agatccagtt cgatgtaacc cactcgtgca cccaactgat cttcagcatc    2460
ttttactttc accagcgttt ctgggtgagc aaaaacagga aggcaaaatg ccgcaaaaaa    2520
gggaataagg gcgacacgga aatgttgaat actcatactc ttccttttc  aatattattg    2580 aagcatttat cagggttatt gtctcatgag cggatacata tttgaatgta tttagaaaaa    2640
taaacaaata ggggttccgc gcacatttcc ccgaaaagtg ccacctgtca tgaccaaaat    2700
cccttaacgt gagttttcgt tccactgagc gtcagacccc gtagaaaaga tcaaaggatc    2760
ttcttgagat cctttttttc tgcgcgtaat ctgctgcttg caaacaaaaa aaccaccgct    2820
accagcggtg gtttgtttgc cggatcaaga gctaccaact ctttttccga aggtaactgg    2880
cttcagcaga gcgcagatac caaatactgt tcttctagtg tagccgtagt taggccacca    2940
cttcaagaac tctgtagcac cgcctacata cctcgctctg ctaatcctgt taccagtggc    3000
tgctgccagt ggcgataagt cgtgtcttac cgggttggac tcaagacgat agttaccgga    3060
taaggcgcag cggtcgggct gaacggggg  ttcgtgcaca cagcccagct tggagcgaac    3120
gacctacacc gaactgagat acctacagcg tgagctatga gaaagcgcca cgcttcccga    3180
agggagaaag gcggacaggt atccggtaag cggcagggtc ggaacaggag agcgcacgag    3240
ggagcttcca gggggaaacg cctggtatct ttatagtcct gtcgggtttc gccacctctg    3300
acttgagcgt cgatttttgt gatgctcgtc aggggggcgg agcctatgga aaaacgccag    3360
caacgcggcc ttttacggtt cctggccctt tgctggcct  tttgctcaca tgttctttcc    3420
tgcgttatcc cctgattctg tggataaccg tgcgccgcc  cctgaattcg catctagatg    3480
gtagagccac aaacagccgg tacaagcaac gatctccagg accatctgaa tcatgcgcgg    3540
atgacacgaa ctcacgacgg cgatcacaga cattaaccca cagtacagac actgcgacaa    3600
cgtggcaatt cgtcgcaata ccgtctcact gaactggccg ataattgcag acgaacgaga    3660
tctaacatcc aaagacgaaa ggttgaatga aaccttttg ccatccgaca tccacaggtc    3720
cattctcaca cataagtgcc aaacgcaaca ggaggggata cactagcagc agaccgttgc    3780
aaacgcagga cctccactcc tcttctcctc aacacccact tttgccatcg aaaaaccagc    3840
ccagttattg ggcttgattg gagctcgctc attccaattc cttctattag gctactaaca    3900
ccatgacttt attagcctgt ctatcctggc ccccctggcg aggttcatgt tgtttatttt    3960
ccgaatgcaa caagctccgc attacacccg aacatcactc cagatgaggg ctttctgagt    4020
gtggggtcaa atagtttcat gttccccaaa tggcccaaaa ctgacagttt aaacgctgtc    4080
ttggaaccta atatgacaaa agcgtgatct catccaagat gaactaagtt tggttcgttg    4140
aaatgctaac ggccagttgg tcaaaaagaa acttccaaaa gtcggcatac cgtttgtctt    4200
gtttggtatt gattgacgaa tgctcaaaaa taatctcatt aatgcttagc gcagtctctc    4260
tatcgcttct gaacccggt  gcacctgtgc cgaaacgcaa atggggaaac cccgcttttt    4320
tggatgatta tgcattgtct ccacattgta tgcttccaag attctggtgg gaatactgct    4380
gatagcctaa cgttcatgat caaaatttaa ctgttctaac ccctacttga cagcaatata    4440
taaacagaag gaagctgccc tgtcttaaac cttttttttt atcatcatta ttagcttact    4500
ttcataattg cgactggttc caattgacaa gcttttgatt ttaacgactt ttaacgacaa    4560
cttgagaaga tcaaaaaaca actaaagatc tatggcaatc agtcttgcta ccaaagcagc    4620
aacggatgcc ttgaaggtca acagagctcc cgtcggagta gagccacagg aggttcacaa    4680
atggctgcag tccttcaact gggatttcaa ggagaatcgt acgaaatatc caacaaaata    4740
ccacatggcc aacgaaacga aagagcagtt caaagtcatt gctaaagaat atgctcgtat    4800
```

```
ggaggctgct aaagacgaaa gacaatttgg aacactatta gatggcctga ctagattagg    4860
cgctggcaac aaggtacacc ccagatgggg agagactatg aaagtcatca gtaatttcct    4920
ggaggtagga gaatacaatg caatagccgc ttctgccatg ctttgggaca gtgctacggc    4980
tgccgaacaa aaaaacggct atctggctca agtgttagac gagattagac acacgcatca    5040
gtgcgctttt ataaaccatt actattctaa acactatcac gatccagccg gccacaacga    5100
tgctagacgt acccgtgcaa ttggtccact ttggaagggt atgaagcgtg tgtttgccga    5160
cggattcatc tccggagatg ctgtcgaatg ctccgtaaat ctgcagcttg tcggcgaagc    5220
ctgtttcaca aatcctttaa tcgttgcagt aacggagtgg gcttcagcca atggagatga    5280
gatcacgccc accgttttc tttcagttga aacggacgag ctacgtcaca tggctaatgg    5340
ttaccaaacc gtggtatcaa tcgccaatga tcccgcttct gcaaagttct tgaacacaga    5400
tctaaacaat gcattctgga cgcaacagaa gtatttcaca cctgttttgg gataccttt    5460
tgagtatgga agtaagttca agttgagcc ctgggtgaag acctggaacc gttgggtgta    5520
tgaggactgg ggcggaattt ggatcggcag gttaggcaaa tacggagtag aaagtcctgc    5580
ttcactgagg gacgccaaga gagatgctta ttgggcacac cacgatctag ctctggccgc    5640
ttacgctatg tggcctcttg gatttgcacg tctagccttg cctgatgaag aagatcaagc    5700
ctggtttgaa gctaactatc caggatgggc cgaccactac ggtaaaatct ttaatgaatg    5760
gaagaaatta ggctatgaag acccaaagtc cggattcatc ccctaccaat ggttgctggc    5820
taacggtcac gatgtgtaca ttgacagggt aagtcaagtt ccatttattc cctccctggc    5880
taagggcact ggaagtctac gtgtgcatga atttaacggt aaaaaacatt ctctaactga    5940
tgattgggga gaacgtcaat ggttaataga acccgagcgt tatgagtgtc ataacgtgtt    6000
cgagcagtat gagggacgtg aattgtccga ggtaatagct gaaggtcatg gagtgaggtc    6060
agacggtaaa actcttatag cacagcccca tactagagga gataatcttt ggacactaga    6120
agatatcaaa agggctggct gtgttttccc tgacccttta gcaaaattcg gatccggcaa    6180
gcctatccca aacccttgt taggtctgga ctccacccaa tgtaccaatt acgccttgct    6240
aaagctggcc ggtgacgtag agtcaaatcc aggtccatcc caaccacaat caagtcaagt    6300
gactaagcgt ggacttacag accccgaaag agcagcaatc atcgccgcag ccgtccctga    6360
ccatgccctt gacactcaga gaaaatacca ctattttatc cagccacgtt ggaaaccttt    6420
atctgagtac gagcagttat cctgctatgc ccagccaaat cctgattgga tagcaggagg    6480
cttagattgg ggcgattgga ctcagaagtt tcacggcggc agaccttcct ggggcaatga    6540
gtctaccgag ctacgtacaa cggattggta tcgtcacaga gatcccgctc gtcgttggca    6600
ccatccttat gtaaaagata agtccgagga agccagatat acacagagat tccttgctgc    6660
ctatagttcc gagggatcta acgtaccat cgaccctac tggcgtgacg agatattgaa    6720
caagtacttt ggtgcattac tttacagtga gtatggcttg ttcaatgccc attcttccgt    6780
gggaagggat tgcttatcag acacgattag acagacggcc gtatttgctg ccttggacaa    6840
ggtggataac gcccagatga tacaaatgga acgtcttttt atcgctaagt tagtgccagg    6900
tttgacgct agtactgacg tgccaaaaaa aatatggacc actgatccca tctattcagg    6960
tgctcgtgcc actgtgcaag aaatatggca gggcgtacag gattggaatg aaatcctttg    7020
ggccggacat gcagtcatga tagctacatt tggccagttc gcaagaaggg aattctttca    7080
aagactggcc actgtgtatg gtgatacttt aacaccattt ttcacggccc aaagtcagac    7140
```

```
ctactttcaa caacgagag gcgctattga tgatttatt gtctactgct tggccaatga      7200
ttctgagttt ggtgcccaca atcgtacttt ccttaatgct tggacggagc actatttagc      7260
cagttctgta gcagcattaa aagacttcgt tggactgtat gccaaggtcg aaaaatctag      7320
ggccgacaga tcccgtagga gacttcgtgg tgctgctgct tcatcagcta ttggtcgttc      7380
tattacgccc gacaagatag gcttccgtgt ggacgtggac caaaaagttg acgccgtcct      7440
agctggttac aagaacggat ccggcaagcc tatcccaaac cccttgttag gtctggactc      7500
caccgctacg aattttccc tacttaaaca ggccggagat gtcgaggaga tcctggacc      7560 tgcaaaacgt gagcctatac acgataactc aatcaggacc gagtgggaag ccaagatagc      7620
taaactgaca tcagttgacc aagcaaccaa attcatccaa gactttagac ttgcatatac      7680
ctctcctttc agaaagtctt atgacataga cgttgattat cagtacattg aaaggaagat      7740
cgaggagaaa ctgtctgtac taagacaga gaaactgcct gtcgctgatc taattaccaa      7800
agctacaact ggagaggacc gtgccgcagt tgaggccacc tggatagcta aaattaaggc      7860
tgctaagtct aagtacgaag ccgacggaat acatattgaa ttccgtcagc tatataagcc      7920
tccagtcctg cctgtgaacg tcttccttag gacagacgct gctctgggta cagtattgat      7980
ggaaattagg aatacggact actatggaac tccactagag ggattgagga aggaacctgg      8040
tgtaaaagtt ctgcatttac aggctggatc cggcaagcca atccctaacc ccttattggg      8100
tctggattcc accggatcct aactcgagag cttttgatta agccttctag tccaaaaaac      8160
acgttttttt gtcatttatt tcattttctt agaatagttt agtttattca ttttatagtc      8220
acgaatgttt tatgattcta tagggttgca caaacaagca tttttcattt tatgttaaaa      8280
caatttcagg tttacctttt attctgcttg tggtgacgcg tgtatccgcc cgctcttttg      8340
gtcacccatg tatgctg                                                   8357

<210> SEQ ID NO 44
<211> LENGTH: 4502
<212> TYPE: DNA
<213> ORGANISM: Artificial sequence
<220> FEATURE:
<223> OTHER INFORMATION: Synthetic plasmid pPTK097

<400> SEQUENCE: 44
gatgtgagac gataaatcgc agccaagtga gtgaatagat gacgcaccac ggtcagacac        60
ggccacatcg tatctcacag gagcaagcgc gataggagca ctcacacata gtacggtgat       120
ccgctgactc ctttgcccaa ataagacgtg agccactagt gcactgcagt acagcggccg       180
cgattatcaa aaaggatctt cacctagatc cttttaaatt aaaaatgaag ttttaaatca       240
atctaaagta tatatgagta aacttggtct gacagttacc aatgcttaat cagtgaggca       300
cctatctcag cgatctgtct atttcgttca tccatagttg cctgactccc cgtcgtgtag       360
ataactacga tacgggaggg cttaccatct ggccccagtg ctgcaatgat accgcgggac       420
ccacgctcac cggctccaga tttatcagca ataaccagc cagccggaag ggccgagcgc       480
agaagtggtc ctgcaacttt atccgcctcc atccagtcta ttaattgttg ccgggaagct       540
agagtaagta gttcgccagt taatagtttg cgcaacgttg ttgccattgc tacaggcatc       600
gtggtgtcac gctcgtcgtt tggtatggct tcattcagct ccggttccca acgatcaagg       660
cgagttacat gatcccccat gttgtgcaaa aaagcggtta gctccttcgg tcctccgatc       720
gttgtcagaa gtaagttggc cgcagtgtta tcactcatgg ttatggcagc actgcataat       780
tctcttactg tcatgccatc cgtaagatgc ttttctgtga ctggtgagta ctcaaccaag       840
```

```
tcattctgag aatagtgtat gcggcgaccg agttgctctt gcccggcgtc aatacgggat      900
aataccgcgc cacatagcag aactttaaaa gtgctcatca ttggaaaacg ttcttcgggg      960
cgaaaactct caaggatctt accgctgttg agatccagtt cgatgtaacc cactcgtgca     1020
cccaactgat cttcagcatc ttttactttc accagcgttt ctgggtgagc aaaaacagga     1080
aggcaaaatg ccgcaaaaaa gggaataagg gcgacacgga aatgttgaat actcatactc     1140
ttcctttttc aatattattg aagcatttat cagggttatt gtctcatgag cggatacata     1200
tttgaatgta tttagaaaaa taaacaaata ggggttccgc gcacatttcc ccgaaaagtg     1260
ccacctgtca tgaccaaaat cccttaacgt gagttttcgt tccactgagc gtcagacccc     1320
gtagaaaaga tcaaaggatc ttcttgagat ccttttttc tgcgcgtaat ctgctgcttg     1380
caaacaaaaa aaccaccgct accagcggtg gtttgtttgc cggatcaaga gctaccaact     1440
cttttccga aggtaactgg cttcagcaga gcgcagatac caaatactgt tcttctagtg     1500
tagccgtagt taggccacca cttcaagaac tctgtagcac cgcctacata cctcgctctg     1560
ctaatcctgt taccagtggc tgctgccagt ggcgataagt cgtgtcttac cgggttggac     1620
tcaagacgat agttaccgga taaggcgcag cggtcgggct gaacggggggg ttcgtgcaca     1680
cagcccagct tggagcgaac gacctacacc gaactgagat acctacagcg tgagctatga     1740
gaaagcgcca cgcttcccga agggagaaag gcggacaggt atccggtaag cggcagggtc     1800
ggaacaggag agcgcacgag ggagcttcca gggggaaacg cctggtatct ttatagtcct     1860
gtcgggtttc gccacctctg acttgagcgt cgatttttgt gatgctcgtc aggggggcgg     1920
agcctatgga aaaacgccag caacgcggcc tttttacggt tcctggcctt ttgctggcct     1980
tttgctcaca tgttctttcc tgcgttatcc cctgattctg tggataaccg tcggccgcc      2040
cctgaattcg catctagaac ggggtcatca cggctcatca tgcgccaaac aaatgtgtgc     2100
aatacacgct cggatgactg catgatgacc gcactgactg gggacagcag atccacctaa     2160
gcctgtgaga gaagcagaca cccgacagat caaggcagtt acgtctcacc aaaccagatg     2220
tcaacacagc tacaacgatc attttttcaaa agtatccagg aaccaggtga agaccatcg     2280
acagaacaga ttattcgtat cgcccgtcgt ttcaagaatg accaagtgct agacaatctt     2340
tcccgaccac aattgatggc aatggcccgt tacatgaatt tacgtccgtt tggaactgac     2400
gagattttac gttatcagat cagatataag ttattgcaaa tcatcaagga tgatcgagcc     2460
attgattacg aaggagttga atctctgtca attcaggagc tccagagtgc ttgtgcttca     2520
cgtggtatca aaaccgttgg tgcttctcct gcaagactga gggatgattt gaagatttgg     2580
ctggacttga ggttgcgtca gaagattcct tcgacacttt tgattttgag tagcacgttc     2640
acttatggag atcacgctga tgacctggac aattactacg atgccctgtt ggcagtactt     2700
tcttcgattc ctgatgaggt ttacaatgtt gctaagttag agctggccga ccaggacaat     2760
aagttgaagc tgaatgtctt gaaggaacaa gatgagctga taaaggaaga gagacaacag     2820
agtaaatcac aacgccgttc cactccaatc aaagacgata tcaaactaga cgaatacgag     2880
gaggtgaaag aagatgaagt gaaggatgac gttactaaag acaccgtgga ggagaagagg     2940
gaagatacga acgaacatgt caaagaagaa ccaaggttg atgcaagcga ggaggtcaaa     3000
gacgaaactc cagcgcaatc tgaagaggag gtgaaagaac ccagtaagga tggcaccgta     3060
atcgagtcca aggaccaacc tcaaaccacc gacaaaaagg agtaggaaaa taccagcaaa     3120
taaaacagct cagcgtctgt ttcaattaaa tatctacaat caatttatca cgccgaaatt     3180
```

-continued

```
aaattcaatc ccacgactag tgtatatagt atatgaatat agtaaaaaga gatccgttat    3240
gtatcaaata gtgatagaga ctgaagatgg cgagacttgc aggaggatga ggccatctga    3300
agattggatc tcaagagctg aggctgaaag aaacttgttg gcctcctgtc gtgctggttg    3360
tgccacctgc aaagcagact gcacggacgg cgactacgaa cttattgacg tgaaggtcca    3420
agctgtgcca ccagacgagg aagaagatgg aaaagtgttg ttgtgcagga ccttccccag    3480
atcagactta catcttctag taccttacac ctacgatagg atcagttttg aagccattca    3540
aacaaattgg ttagctgaaa ttttagcatg cgacagagtt tctagtaacg tcgtacgttt    3600
ggtactacag agatctcgtc ccatggctgc ccgtatatca ctaaatttcg ttcccggcca    3660
attcgtggac atcgagatcc caggaacgca cacacgtaga agttactcaa tggcctctgt    3720
agctgaggat ggacaactag aatttatcat acgttactta ccagatggtg cttttttctaa   3780 atttcttcag acagaggcaa aagtgggaat gagagtggac ttgagaggcc cagctggttc    3840
tttttttttg cacgatcatg gaggccgttc tcgtgtgttt gtcgcaggcg gtacaggatt    3900
atcccccgtg ttaagtatga tcaggcagct gggcaaggca tctgacccat ctcccgccac    3960
acttctgttt ggagtaacaa accgtgaaga acttttctat gtagacgaat taaaaacgct    4020
tgcacagagt atgccaaccc tgggagtgag gatcgccgtt gtaaatgacg acggtggaaa    4080
cggagttgat aaaggtactg tcatagatct tctgagagca gagctagaga atccgatgc    4140 caaacccgac atctatctat gcggcccacc aggaatgatc gaggctgcct tgccgccgc    4200 agctacagct ggtgtaccaa agaacaagt atacttagag aagttttag ccagtggcgg    4260 atcctaactc gagagctttt gattaagcct tctagtccaa aaaacacgtt tttttgtcat    4320
ttatttcatt ttcttagaat agtttagttt attcatttta tagtcacgaa tgttttatga    4380
ttctatatag ggttgcaaac aagcattttt cattttatgt taaaacaatt tcaggtttac    4440
cttttattct gcttgtggtg acgcgtgtat ccgcccgctc ttttggtcac ccatgtatgc    4500
tg                                                                   4502
```

<210> SEQ ID NO 45
<211> LENGTH: 3915
<212> TYPE: DNA
<213> ORGANISM: Artificial sequence
<220> FEATURE:
<223> OTHER INFORMATION: Synthetic plasmid pPTK098

<400> SEQUENCE: 45

```
ccaatgagac gacggggtca tcacggctca tcatgcgcca aacaaatgtg tgcaatacac     60
gctcggatga ctgcatgatg accgcactga ctggggacag cagatccacc taagcctgtg    120
agagaagcag acacccgaca gatcaaggca gttaactagt gcactgcagt acagcggccg    180
cgattatcaa aaaggatctt cacctagatc cttttaaatt aaaaatgaag ttttaaatca    240
atctaaagta tatatgagta aacttggtct gacagttacc aatgcttaat cagtgaggca    300
cctatctcag cgatctgtct atttcgttca tccatagttg cctgactccc cgtcgtgtag    360
ataactacga tacgggaggg cttaccatct ggccccagtg ctgcaatgat accgcgggac    420
ccacgctcac cggctccaga tttatcagca ataaaccagc cagccggaag ggccgagcgc    480
agaagtggtc ctgcaacttt atccgcctcc atccagtcta ttaattgttg ccgggaagct    540
agagtaagta gttcgccagt taatagtttg cgcaacgttg ttgccattgc tacaggcatc    600
gtggtgtcac gctcgtcgtt tggtatggct tcattcagct ccggttccca acgatcaagg    660
cgagttacat gatcccccat gttgtgcaaa aaagcggtta gctccttcgg tcctccgatc    720
```

-continued

```
gttgtcagaa gtaagttggc cgcagtgtta tcactcatgg ttatggcagc actgcataat      780
tctcttactg tcatgccatc cgtaagatgc ttttctgtga ctggtgagta ctcaaccaag      840
tcattctgag aatagtgtat gcggcgaccg agttgctctt gcccggcgtc aatacgggat      900
aataccgcgc cacatagcag aactttaaaa gtgctcatca ttggaaaacg ttcttcgggg      960
cgaaaactct caaggatctt accgctgttg agatccagtt cgatgtaacc cactcgtgca     1020
cccaactgat cttcagcatc ttttactttc accagcgttt ctgggtgagc aaaaacagga     1080
aggcaaaatg ccgcaaaaaa gggaataagg gcgacacgga aatgttgaat actcatactc     1140
ttcctttttc aatattattg aagcatttat cagggttatt gtctcatgag cggatacata     1200
tttgaatgta tttagaaaaa taaacaaata ggggttccgc gcacatttcc ccgaaaagtg     1260
ccacctgtca tgaccaaaat cccttaacgt gagttttcgt tccactgagc gtcagacccc     1320
gtagaaaaga tcaaaggatc ttcttgagat cctttttttc tgcgcgtaat ctgctgcttg     1380
caaacaaaaa aaccaccgct accagcggtg gtttgtttgc cggatcaaga gctaccaact     1440
ctttttccga aggtaactgg cttcagcaga gcgcagatac caaatactgt tcttctagtg     1500
tagccgtagt taggccacca cttcaagaac tctgtagcac cgcctacata cctcgctctg     1560
ctaatcctgt taccagtggc tgctgccagt ggcgataagt cgtgtcttac cgggttggac     1620
tcaagacgat agttaccgga taaggcgcag cggtcgggct gaacggggggg ttcgtgcaca     1680
cagcccagct tggagcgaac gacctacacc gaactgagat acctacagcg tgagctatga     1740
gaaagcgcca cgcttcccga agggagaaag gcggacaggt atccggtaag cggcagggtc     1800
ggaacaggag agcgcacgag ggagcttcca gggggaaacg cctggtatct ttatagtcct     1860
gtcgggtttc gccacctctg acttgagcgt cgatttttgt gatgctcgtc aggggggcgg     1920
agcctatgga aaaacgccag caacgcggcc tttttacggt tcctggcctt ttgctggcct     1980
tttgctcaca tgttctttcc tgcgttatcc cctgattctg tggataaccg tcggccgcc      2040
cctgaattcg catctagatg gtagagccac aaacagccgg tacaagcaac gatctccagg     2100
accatctgaa tcatgcgcgg atgacacgaa ctcacgacgg cgatcacaga cattaaccca     2160
cagtacagac actgcgacaa cgtggcaatt cgtcgcaata ccgtctcact gaactggccg     2220
ataattgcag acgaacgaca cgacatcaat gcaatcaata gtcaacgcaa tgcaattact     2280
aaactttatt actttcatta ttatgtatct tagccagaaa ttgggacaac ttcttttgctg    2340
gtaaagcaac tcctaaagtg tctctgccac atataataca atttggtttt cttcttgacc     2400
gttgcaggaa acattgttcg caaaaataat gattgcaaga agttttcacg ggtgatttgt     2460
aatctccttt gcatataatg catttaaacg ggatatcttt gagctcatct tcattaaaca     2520
tttggatctc cttaacccct tgagagtat tatgcttctt cttttggaca ttttcccact      2580
ccctatctaa tttccatccc tgtttgaaat catccctcag gtgcaaaaac ttacaagtgt     2640
caccatatcc gcagtaacct gtctgtttgt agtccttgca aacatctggt tgaaaatcga     2700
tagttgttgt actattaatg ttagtagccg actttgacat tggcttatta gcgcttgggg     2760
ttatgaattt ggcaaagttg ttcactgaat gctcttctcg tggtgcatcc cctcctattt     2820
ctgttactgt gtttctctgt ggcaatgtaa ttggagcttt atcatcagcc tcaacaggtg     2880
ctcttttctt gtgcacttta actaccgcta ttgatccttc attatcttgt atgctagcta     2940
actctccctc gcctatatgc cttttctttc ctttcactac ccttttcttg aacatataga     3000
atgatgccta cggagcaaga aagatgacct aatcgctttg atagtagtgc agcggataat     3060
```

```
atgaatacct tatcaactgt ggtccttgcc cctcgctgaa acgatcacgt ggttgttttt    3120
agggctactg ccgctcctac ctcctacttt cctccatgaa ccttcttcct cgcgaggaga    3180
ttaccgattt ttttcagtc tgaccaaatt aattttgcac accaacacac acaccaatat    3240
gtcatctgcc cataatgcat ataatgccgg tatcatgcag aaaacaggca aggcttttgc    3300
agatgagttt tttgcagaag aaaaccaggt cgtccatgaa agtaatgccg ttgttctggt    3360
attaatgaag agtgacgaga ttgatgctat aattgaggac atagttctaa aaggcggaaa    3420
agcaaaaaac ccatcaattg tggtagagga taaagctgga ttttggtgga taaaggccga    3480
tggcgcaatt gaaatagatg ccgccgaggc tggagaactt ttgggtaagc ccttctctgt    3540
gtacgattta ctaataaacg tgtcctctac agtaggaaga gcctatacgc taggcactaa    3600
gttcactatt acgtcagagc ttatgggttt agacagggct ctaacggaca tcggatccta    3660
aattcggata gtgtaattta atcaataact tgaaaaaaat atcatttaat ttactataca    3720
cacggacata aactgaaagg gcaaggaagg ggaaatgggg aaaaataatg aggatatgca    3780
agatgagaga tgagagatga gagatgtcca ctttagtcag ttttggcttt acttttatct    3840
ttttctatgg catctttcgt ttcttcaacg tttacctgct ccttttcttg ctctggttct    3900
atatcgatct cgctg                                                     3915
```

<210> SEQ ID NO 46
<211> LENGTH: 5244
<212> TYPE: DNA
<213> ORGANISM: Artificial sequence
<220> FEATURE:
<223> OTHER INFORMATION: Synthetic plasmid pPTK099

<400> SEQUENCE: 46

```
agcatgagac ggaaatctgc tcgtcagtgg tgctcacact gacgaatcat gtacagatca      60
taccgatgac tgcctggcga ctcacaacta agcaagacag ccggaaccag cgccggcgaa     120
caccactgca tatatggcat atcacaacag tccaactagt gcactgcagt acagcggccg     180
cgattatcaa aaaggatctt cacctagatc cttttaaatt aaaaatgaag ttttaaatca     240
atctaaagta tatatgagta aacttggtct gacagttacc aatgcttaat cagtgaggca     300
cctatctcag cgatctgtct atttcgttca tccatagttg cctgactccc cgtcgtgtag     360
ataactacga tacgggaggg cttaccatct ggccccagtg ctgcaatgat accgcgggac     420
ccacgctcac cggctccaga tttatcagca ataaaccagc cagccggaag ggccgagcgc     480
agaagtggtc ctgcaacttt atccgcctcc atccagtcta ttaattgttg ccgggaagct     540
agagtaagta gttcgccagt taatagtttg cgcaacgttg ttgccattgc tacaggcatc     600
gtggtgtcac gctcgtcgtt tggtatggct tcattcagct ccggttccca acgatcaagg     660
cgagttacat gatccccat gttgtgcaaa aaagcggtta gctccttcgg tcctccgatc     720
gttgtcagaa gtaagttggc cgcagtgtta tcactcatgg ttatggcagc actgcataat     780
tctcttactg tcatgccatc cgtaagatgc ttttctgtga ctggtgagta ctcaaccaag     840
tcattctgag aatagtgtat gcggcgaccg agttgctctt gcccggcgtc aatacgggat     900
aataccgcgc cacatagcag aactttaaaa gtgctcatca ttggaaaacg ttcttcgggg     960
cgaaaactct caaggatctt accgctgttg agatccagtt cgatgtaacc cactcgtgca    1020
cccaactgat cttcagcatc ttttactttc accagcgttt ctgggtgagc aaaaacagga    1080
aggcaaaatg ccgcaaaaaa gggaataagg gcgacacgga aatgttgaat actcatactc    1140
ttcctttttc aatattattg aagcatttat cagggttatt gtctcatgag cggatacata    1200
```

```
tttgaatgta tttagaaaaa taaacaaata ggggttccgc gcacatttcc ccgaaaagtg    1260
ccacctgtca tgaccaaaat cccttaacgt gagttttcgt tccactgagc gtcagacccc    1320
gtagaaaaga tcaaaggatc ttcttgagat cctttttttc tgcgcgtaat ctgctgcttg    1380
caaacaaaaa aaccaccgct accagcggtg gtttgtttgc cggatcaaga gctaccaact    1440
ctttttccga aggtaactgg cttcagcaga gcgcagatac caaatactgt tcttctagtg    1500
tagccgtagt taggccacca cttcaagaac tctgtagcac cgcctacata cctcgctctg    1560
ctaatcctgt taccagtggc tgctgccagt ggcgataagt cgtgtcttac cgggttggac    1620
tcaagacgat agttaccgga taaggcgcag cggtcgggct gaacggggg ttcgtgcaca     1680 cagcccagct tggagcgaac gacctacacc gaactgagat acctacagcg tgagctatga    1740
gaaagcgcca cgcttcccga agggagaaag gcggacaggt atccggtaag cggcagggtc    1800
ggaacaggag agcgcacgag ggagcttcca gggggaaacg cctggtatct ttatagtcct    1860
gtcgggtttc gccacctctg acttgagcgt cgatttttgt gatgctcgtc aggggggcgg    1920
agcctatgga aaaacgccag caacgcggcc ttttacggt tcctggcctt ttgctggcct     1980
tttgctcaca tgttctttcc tgcgttatcc cctgattctg tggataaccg tgcggccgcc    2040
cctgaattcg catctagaat aaatcgcagc caagtgagtg aatagatgac gcaccacggt    2100
cagacacggc cacatcgtat ctcacaggag caagcgcgat aggagcactc acacatagta    2160
cggtgatccg ctgactcctt tgcccaaata agacgtgagc ccgtctcaga tgcacacact    2220
ggcttaagat gacaacgccg ttcgtttcct tctttagaac ctcacactgt attgcctata    2280
tcaacagaat ttttgaacag tccacttagg agggatttgc tatggaaagc agtagtgatg    2340
gaatttgaca acatacgtgt aggtgcttcg aatccacctg gtaggggtga acataagttc    2400
tccaggagaa aattacgccc ccaaaaaggg tctggaaggg ctcgtgtagg agatgccaac    2460
tctccgacga gacacaatgg agctagagcg ctagctagaa atgcgcctaa tgatttctct    2520
actgatttac cgtttaaagt ttatgctagg gcttacagaa tagctttaag cagttttac     2580 atcaaggggc atttacatat cattggaggt tgttcatcac tcatcccttt caatcgaggt    2640
gatcaaaata tactcgagct ctctaccgac aaaaaagagg ccctggaaat tttccaggca    2700
attcacaatc taaaaggact gaatattctg ttcatctctg atagcttaaa taactcacag    2760
aatctgaaca aagccattca ggcttaaaac gatgaccaga tcagcctgtt ggataaagaa    2820
aatgttgagg ttaggcattt attgaaagct aatagagtgt tcattgatca ggcatcactg    2880 cagttttttcg cgaaggagtt tgctggctga tgcatttttg tatatagtta cgctatgtaa    2940
atagtcaaaa tagattcgct ccactgttta agggtcaaaa attacctctc caaatagaag    3000
gaggctagaa tttaaactac cgataaccat gttcgaagaa acgttggaag gctcagccag    3060
attcttgaca agctcgacaa attgtttctt aagactaaaa actcactcat acattctagg    3120
gctcaaccct aatgtacaat aattgcacgt gcacagagaa tttacaccct cacataatct    3180
cactgttttt cgaatacgaa aaaaattcgt tttctaactt ctcttcacta cagcaactat    3240
gaccaaccca cgtaaaaggg agcgtaggcg tcccgccttc gacgtcacga gagaaaagtt    3300
cgtggcacgt aatatccgtt tcggtgatgt agttagaagg gatctactag ccggagtgga    3360
cgccttggct gacgcagtcg ctgtaacact tggccctcgt ggtcgtaacg tggttataga    3420
acatagggcc gctggactgc ctcctgttgc cactaaagac ggcgtgacag tggcccaggc    3480
tgtcgagtta gcaggccgta cccagtccgt cggtgtctcc ttagtccgtc agatggccac    3540
```

```
cgcagtggca aaggaagctg gtgacggaac tacaacttcc gtagttctgg ccaggagact   3600
agctgcagaa acacgtaaag ccttagctgc tggcatgaac cctagagaca tagttttagg   3660
catggaaaag gctgcaagga ttgtggatag ggacctagca gccagagctc gtcgttgcga   3720
cgacacgagg gccttggctc acgtggccac cttggccgcc ggaggtgacg aaagtatagg   3780
agcaatagtt gccgatgctc tgacacgtgc tggagaagga ggcgttgtag acgttgaact   3840
gggtgccgct ctatgcgacg aaatggatat tgtagaggga atgaggtggg agcaaggtta   3900
ccgttcccca tacttcatga ctgactccgc cagaaagatc gctgaattag agaacccta    3960 tatcttaatt tacgataggg tgataaatca attttcagag ttggttcctg ctctggagct   4020
agtcaggagg cagagaggca gtcttttgat cgtggccgaa acatcgttg aagaggcttt    4080 gccaggtctg ttgcttaatc atatcaggaa aaactatgt agtattgcag tcaagggacc    4140
tggctacggc gacagtcgtt acgaattctt gcatgacctg gcagcattaa ctggcggacg   4200
tgcaattatg gaagcttgtg gtgaagaact gagtaatgtc acaatggcac atttgggtag   4260
ggccaaaaga gtagtcgtgc gtgaagatga cacagtggta ataggcggag aaggagatgg   4320
agctgcaatt acggaaaggt tagctgcagc aagacaacag gccgattgga ttacggatgg   4380 cgaccctcc aagggttctc cctccggcaa acgtcacgac ctagagaatc ttcaaacacg    4440
tattaaagcc ttgagtggaa aggtcgtaac gatcaaagcc ggaggattat ccgacatctt   4500
gataaaagaa agaatgcaaa gaatcgagaa cgccctagct tccgccagag ctgctcgttc   4560
agatggagtg gttgctggcg gaggtgtcgg attgtatcgt gcccgtgctg ctcttacaga   4620
ggctacagga gataccccttg atcagactta cggcattgct attgttcgtg ccgctctaga   4680
cgagccaatt cgtagaatag ctgcaaatgc tggcagggac gcacatgagt ttttgttcga   4740
gcttaaaaga tctaacgatg acttctgggg tatggatatg aggagtggtg aatgcggtga   4800
cttgtatgct gcaggagtta tcgatcctgc ccgtgtcacc agattagctc taagaaacgc   4860
tgttgcaacc gcctccagtt tgatgacggt cgaatgtgca gttacacaca ttcctccctc   4920
tgatcctact tatggatttg accctcacct agctgctgca acgcgtgaag atcctcgttc   4980
aggatcctaa gccaattagt ttgaagtgag attttatttc attcctgtta atattatata   5040
ctagagtata ttttaaatta attgttcatg aacttgccaa attatgttag ttttgtgtaa   5100
acaatcttag gctatccaat ttagttctac ttttggtaga tttcctgttt tggtaaatta   5160
caaacaacaa tgatttgact tatattctat tcggaatttt acttatcacc ttgtacagtt   5220
tgtggggatt tccggacatg gctg                                         5244
```

<210> SEQ ID NO 47
<211> LENGTH: 11257
<212> TYPE: DNA
<213> ORGANISM: Artificial sequence
<220> FEATURE:
<223> OTHER INFORMATION: plasmid

<400> SEQUENCE: 47

```
gctggaaatc tgctcgtcag tggtgctcac actgacgaat catgtacaga tcataccgat     60
gactgcctgg cgactcacaa ctaagcaaga cagccggaac cagcgccggc gaacaccact    120
gcatatatgg catatcacaa cagtccacgt ctcaagcagt tacagagatg ttacgaacca    180
ctagtgcact gcagtacagt ttagcttgcc tcgtccccgc cgggtcaccc ggccagcgac    240
atggaggccc agaataccct ccttgacagt cttgacgtgc gcagctcagg gcatgatgt    300 gactgtcgcc cgtacattta gcccatacat ccccatgtat aatcatttgc atccatacat    360
```

```
tttgatggcc gcacggcgcg aagcaaaaat tacggctcct cgctccagac ctgcgagcag    420
ggaaacgctc ccctcacaga cgcgttgaat tgtccccacg ccgcgcccct gtagagaaat    480
ataaaaggtt aggatttgcc actgaggttc ttctttcata tacttccttt taaaatcttg    540
ctaggataca gttctcacat cacatccgaa cataaacaaa aatgggtaaa aagcctgaac    600
tcaccgcgac gtctgtcgag aagtttctga tcgaaaagtt cgacagcgtg tccgacctga    660
tgcagctctc ggagggcgaa gaatctcgtg ctttcagctt cgatgtagga gggcgtggat    720
atgtcctgcg ggtaaatagc tgcgccgatg gtttctacaa agatcgttat gtttatcggc    780
actttgcatc ggccgcgctc ccgattccgg aagtgcttga cattggggaa tttagcgaga    840
gcctgaccta ttgcatctcc cgccgtgcac agggtgtcac gttgcaagac ctgcctgaaa    900
ccgaactgcc cgctgttctg caaccggtcg cggaggccat ggatgcgatc gctgcggccg    960
atcttagcca gacgagcggg ttcggcccat tcggaccgca aggaatcggt caatacacta   1020
catgcgtga tttcatatgc gcgattgctg atccccatgt gtatcactgg caaactgtga    1080
tggacgacac cgtcagtgcg tccgtcgcgc aggctctcga tgagctgatg ctttgggccg   1140
aggactgccc cgaagtccgg cacctcgtgc acgcggattt cggctccaac aatgtcctga   1200
cggacaatgg ccgcataaca gcggtcattg actggagcga ggcgatgttc ggggattccc   1260
aatacgaggt cgccaacatc ttcttctgga ggccgtggtt ggcttgtatg gagcagcaga   1320
cgcgctactt cgagcggagg catccggagc ttgcaggatc gccgcggctc cgggcgtata   1380
tgctccgcat tggtcttgac caactctatc agagcttggt tgacggcaat ttcgatgatg   1440
cagcttgggc gcagggtcga tgcgacgcaa tcgtccgatc cggagccggg actgtcgggc   1500
gtacacaaat cgcccgcaga agcgcggccg tctggaccga tggctgtgta gaagtactcg   1560
ccgatagtgg aaaccgacgc cccagcactc gtccgagggc aaaggaataa agtaactgac   1620
aataaaaga ttcttgtttt caagaacttg tcatttgtat agttttttta tattgtagtt    1680
gttctatttt aatcaaatgt tagcgtgatt tatattttt ttcgcctcga catcatctgc    1740
ccagatgcga agttaagtgc gcagaaagta atatcatgcg tcaatcgtat gtgaatgctg    1800
gtcgctatac tggagttcaa catctttgga taatatcaga atgagaaaga acagatacgc    1860
agtacgtttt ttggtgagct ctttgcactt ctttagttct ttccatcaat atcagttgct    1920
tatgcactta tgactaatat tgatgtttaa cttcaatatc tttaaacttt tgttcttccc    1980
gacgttcatt aagaatacta atacacttta ataattagtt taatatttgt ttctatataa    2040
tgacatttaa ttaaaaaaga taaaatataa aaacatcata ataactcacc agaggttaag    2100
aacaaaaaaa caaattagat atctgctaat ccaatatagt taaatcaatc tttccttggt    2160
ataatgggta tattacatat atttcaagga ccgacactcc taccaaatat ctaaaattta    2220
ccatattaac ataacatgta tataaacgtc aaatcataat cagcactacc gagcggccgc    2280
gtgttacaac caattaacca attctgatta gaaaaactca tcgagcatca aatgaaactg    2340
caatttattc atatcaggat tatcaatacc atattttga aaaagccgtt tctgtaatga    2400
aggagaaaac tcaccgaggc agttccatag gatggcaaga tcctggtatc ggtctgcgat    2460
tccgactcgt ccaacatcaa tacaacctat taatttcccc tcgtcaaaaa taaggttatc    2520
aagtgagaaa tcaccatgag tgacgactga atccggtgag aatggcaaaa gcttatgcat    2580
ttctttccag acttgttcaa caggccagcc attacgctcg tcatcaaaat cactcgcatc    2640
aaccaaaccg ttattcattc gtgattgcgc ctgagcgagg cgaaatacgc gatcgctgtt    2700
```

```
aaaaggacaa ttacaaacag gaatcgaatg caaccggcgc aggaacactg ccagcgcatc      2760
aacaatattt tcacctgaat caggatattc ttctaatacc tggaatgctg ttttcccggg      2820
gatcgcagtg gtgagtaacc atgcatcatc aggagtacgg ataaaatgct tgatggtcgg      2880
aagaggcata aattccgtca gccagtttag tctgaccatc tcatctgtaa catcattggc      2940
aacgctacct ttgccatgtt tcagaaacaa ctctggcgca tcgggcttcc catacaatcg      3000
atagattgtc gcacctgatt gcccgacatt atcgcgagcc catttatacc catataaatc      3060
agcatccatg ttggaattta atcgcggcct ggagcaagac gtttcccgtt gaatatggct      3120
cataacaccc cttgtattac tgtttatgta agcagacagt tttattgttc atgatgatat      3180
atttttatct tgtgcaatgt aacatcagag attttgagac acaacgtggc tttgttgaat      3240
aaatcgaact tttgctgagt tgaaggatca gtcatgacca aaatccctta acgtgagttt      3300
tcgttccact gagcgtcaga ccccgtagaa aagatcaaag gatcttcttg agatcctttt      3360
tttctgcgcg taatctgctg cttgcaaaca aaaaaaccac cgctaccagc ggtggtttgt      3420
ttgccggatc aagagctacc aactcttttt ccgaaggtaa ctggcttcag cagagcgcag      3480
ataccaaata tgttcttct agtgtagccg tagttaggcc accacttcaa gaactctgta      3540
gcaccgccta catacctcgc tctgctaatc ctgttaccag tggctgctgc cagtggcgat      3600
aagtcgtgtc ttaccgggtt ggactcaaga cgatagttac cggataaggc gcagcggtcg      3660
ggctgaacgg ggggttcgtg cacacagccc agcttggagc gaacgaccta caccgaactg      3720
agatacctac agcgtgagct atgagaaagc gccacgcttc ccgaagggag aaaggcggac      3780
aggtatccgg taagcggcag ggtcggaaca ggagagcgca cgagggagct tccaggggga      3840
aacgcctggt atctttatag tcctgtcggg tttcgccacc tctgacttga gcgtcgattt      3900
ttgtgatgct cgtcaggggg gcggagccta tggaaaaacg ccagcaacgc ggccttttta      3960
cggttcctgg ccttttgctg gccttttgct cacatgttct ttcctgcgtt atcccctgat      4020
tctgtggata accgtgcggc cgcccctgaa ttcgcatcta gactgatgag acgtggtaga      4080
gccacaaaca gccggtacaa gcaacgatct ccaggaccat ctgaatcatg cgcggatgac      4140
acgaactcac gacggcgatc acagacatta acccacagta cagacactgc gacaacgtgg      4200
caattcgtcg caatacaacg ctgaactggc cgataattgc agacgaacga cacgacatca      4260
atgcaatcaa tagtcaacgc aatgcaatta ctaaacttta ttactttcat tattatgtat      4320
cttagccaga aattgggaca acttctttgc tggtaaagca actcctaaag tgtctctgcc      4380
acatataata caatttggtt ttcttcttga ccgttgcagg aaacattgtt cgcaaaaata      4440
atgattgcaa gaagttttca cgggtgattt gtaatctcct ttgcatataa tgcatttaaa      4500
cgggatatct ttgagctcat cttcattaaa catttggatc tccttaaccc ctttgagagt      4560
attatgcttc ttcttttgga catttttccca ctccctatct aatttccatc cctgtttgaa      4620
atcatccctc aggtgcaaaa acttacaagt gtcaccatat ccgcagtaac ctgtctgttt      4680
gtagtccttg caaacatctg gttgaaaatc gatagttgtt gtactattaa tgttagtagc      4740
cgactttgac attggcttat tagcgcttgg ggttatgaat ttggcaaagt tgttcactga      4800
atgctcttct cgtggtgcat cccctcctat ttctgttact gtgtttctct gtggcaatgt      4860
aattggagct ttatcatcag cctcaacagg tgctcttttc ttgtgcactt taactaccgc      4920
tattgatcct tcattatctt gtatgctagc taactctccc tcgcctatat gccttttctt      4980
tcctttcact acccttttct tgaacatata gaatgatgcc tacggagcaa gaaagatgac      5040
ctaatcgctt tgatagtagt gcagcggata atatgaatac cttatcaact gtggtccttg      5100
```

```
cccctcgctg aaacgatcac gtggttgttt ttagggctac tgccgctcct acctcctact    5160
ttcctccatg aaccttcttc ctcgcgagga gattaccgat tttttttcag tctgaccaaa    5220
ttaattttgc acaccaacac acacaccaat atgtcatctg cccataatgc atataatgcc    5280
ggtatcatgc agaaaacagg caaggctttt gcagatgagt tttttgcaga agaaaaccag    5340
gtcgtccatg aaagtaatgc cgttgttctg gtattaatga agagtgacga gattgatgct    5400
ataattgagg acatagttct aaaaggcgga aaagcaaaaa acccatcaat tgtggtagag    5460
gataaagctg gattttggtg gataaaggcc gatggcgcaa ttgaaataga tgccgccgag    5520
gctggagaac ttttgggtaa gcccttctct gtgtacgatt tactaataaa cgtgtcctct    5580
acagtaggaa gagcctatac gctaggcact aagttcacta ttacgtcaga gcttatgggt    5640
ttagacaggg ctctaacgga catcggatcc taaattcgga tagtgtaatt taatcaataa    5700
cttgaaaaaa atatcattta atttactata cacacggaca taaactgaaa gggcaaggaa    5760
ggggaaaatg ggaaaaataa tgaggatatg caagatgaga gatgagagat gagagatgtc    5820
cactttagtc agttttggct ttacttttat ctttttctat ggcatctttc gtttcttcaa    5880
cgtttacctg ctcctttttct tgctctggtt ctatatcgat ctcgctgcca aaccagatgt    5940
caacacagct acaacgatca tttttcaaaa gtatccagga accaggtgaa agaccatcga    6000
cagaacagat tattcgtatc gcccgtcgtt tcaagaatga ccaagtgcta gacaatcttt    6060
cccgaccaca attgatggca atggcccgtt acatgaattt acgtccgttt ggaactgacg    6120
agattttacg ttatcagatc agatataagt tattgcaaat catcaaggat gatcgagcca    6180
ttgattacga aggagttgaa tctctgtcaa ttcaggagct ccagagtgct tgtgcttcac    6240
gtggtatcaa aaccgttggt gcttctcctg caagactgag ggatgatttg aagatttggc    6300
tggacttgag gttgcgtcag aagattcctt cgacactttt gattttgagt agcacgttca    6360
cttatggaga tcacgctgat gacctggaca attactacga tgccctgttg gcagtacttt    6420
cttcgattcc tgatgaggtt tacaatgttg ctaagttaga gctggccgac caggacaata    6480
agttgaagct gaatgtcttg aaggaacaag atgagctgat aaaggaagag agacaacaga    6540
gtaaatcaca acgccgttcc actccaatca aagacgatat caaactagac gaatacgagg    6600
aggtgaaaga agatgaagtg aaggatgacg ttactaaaga caccgtggag gagaagaggg    6660
aagatacgaa cgaacatgtc aaagaagaac caaaggttga tgcaagcgag gaggtcaaag    6720
acgaaactcc agcgcaatct gaagaggagg tgaaagaacc cagtaaggat ggcaccgtaa    6780
tcgagtccaa ggaccaacct caaaccaccg acaaaaagga gtaggaaaat accagcaaat    6840
aaaacagctc agcgtctgtt tcaattaaat atctacaatc aatttatcac gccgaaatta    6900
aattcaatcc cacgactagt gtatatagta tatgaatata gtaaaaagag atccgttatg    6960
tatcaaatag tgatagagac tgaagatggc gagacttgca ggaggatgag gccatctgaa    7020
gattggatct caagagctga ggctgaaaga aacttgttgg cctcctgtcg tgctggttgt    7080
gccacctgca aagcagactg cacggacggc gactacgaac ttattgacgt gaaggtccaa    7140
gctgtgccac cagacgagga agaagatgga aaagtgttgt tgtgcaggac cttccccaga    7200
tcagacttac atcttctagt accttacacc tacgatagga tcagttttga agccattcaa    7260
acaaattggt tagctgaaat tttagcatgc gacagagttt ctagtaacgt cgtacgtttg    7320
gtactacaga gatctcgtcc catggctgcc cgtatatcac taaatttcgt tcccggccaa    7380
ttcgtggaca tcgagatccc aggaacgcac acacgtagaa gttactcaat ggcctctgta    7440
```

```
gctgaggatg gacaactaga atttatcata cgtttactac cagatggtgc tttttctaaa    7500
tttcttcaga cagaggcaaa agtgggaatg agagtggact tgagaggccc agctggttct    7560
ttttttttgc acgatcatgg aggccgttct cgtgtgtttg tcgcaggcgg tacaggatta    7620
tcccccgtgt taagtatgat caggcagctg ggcaaggcat ctgacccatc tcccgccaca    7680
cttctgtttg gagtaacaaa ccgtgaagaa cttttctatg tagacgaatt aaaaacgctt    7740
gcacagagta tgccaaccct gggagtgagg atcgccgttg taaatgacga cggtggaaac    7800
ggagttgata aaggtactgt catagatctt ctgagagcag agctagagaa atccgatgcc    7860
aaacccgaca tctatctatg cggcccacca ggaatgatcg aggctgcctt tgccgccgca    7920
gctacagctg gtgtaccaaa agaacaagta tacttagaga agttttagc cagtggcgga     7980 tcctaactcg agagcttttg attaagcctt ctagtccaaa aaacacgttt ttttgtcatt    8040
tatttcattt tcttagaata gtttagttta ttcattttat agtcacgaat gttttatgat    8100
tctatatagg gttgcaaaca agcattttc attttatgtt aaaacaattt caggtttacc     8160
ttttattctg cttgtggtga cgcgtgtatc cgcccgctct tttggtcacc catgtatgct    8220
ggatgcacac actggcttaa gatgacaacg ccgttcgttt ccttctttag aacctcacac    8280
tgtattgcct atatcaacag aattttttgaa cagtccactt aggagggatt tgctatggaa    8340
agcagtagtg atggaatttg acaacatacg tgtaggtgct tcgaatccac ctggtagggg    8400
tgaacataag ttctccagga gaaaattacg ccccccaaaaa gggtctggaa gggctcgtgt    8460
aggagatgcc aactctccga cgagacacaa tggagctaga gcgctagcta gaaatgcgcc    8520
taatgatttc tctactgatt taccgtttaa agtttatgct agggcttaca gaatagcttt    8580 aagcagttt tacatcaagg ggcatttaca tatcattgga ggttgttcat cactcatccc     8640
tttcaatcga ggtgatcaaa atatactcga gctctctacc gacaaaaaag aggccctgga    8700
aattttccag gcaattcaca atctaaaagg actgaatatt ctgttcatct ctgatagctt    8760
aaataactca cagaatctga acaaagccat tcaggcttta acgatgacc agatcagcct     8820 gttggataaa gaaaatgttg aggttaggca tttattgaaa gctaatagag tgttcattga    8880
tcaggcatca ctgcagtttt tcgcgaagga gtttgctggc tgatgcattt ttgtatatag    8940
ttacgctatg taaatagtca aaatagattc gctccactgt ttaagggtca aaaattaccct   9000 ctccaaatag aaggaggcta gaatttaaac taccgataac catgttcgaa gaaacgttgg    9060
aaggctcagc cagattcttg acaagctcga caaattgttt cttaagacta aaaactcact    9120
catacattct agggctcaac cctaatgtac aataattgca cgtgcacaga gaatttacac    9180
cctcacataa tctcactgtt tttcgaatac gaaaaaaatt cgttttctaa cttctcttca    9240
ctacagcaac tatgaccaac ccacgtaaaa gggagcgtag gcgtcccgcc ttcgacgtca    9300
cgagagaaaa gttcgtggca cgtaatatcc gtttcggtga tgtagttaga agggatctac    9360
tagccggagt ggacgccttg gctgacgcag tcgctgtaac acttggccct cgtggtcgta    9420
acgtggttat agaacatagg gccgctggac tgcctcctgt tgccactaaa gacggcgtga    9480
cagtggccca ggctgtcgag ttagcaggcc gtacccagtc cgtcggtgtc tccttagtcc    9540
gtcagatggc caccgcagtg gcaaggaag ctggtgacgg aactacaact tccgtagttc     9600
tggccaggag actagctgca gaaacacgta agccttagc tgctggcatg aaccctagag     9660 acatagttt aggcatggaa aaggctgcaa ggattgtgga tagggaccta gcagccagag     9720
ctcgtcgttg cgacgacacg agggccttgg ctcacgtggc caccttggcc gccggaggtg    9780
acgaaagtat aggagcaata gttgccgatg ctctgacacg tgctggagaa ggaggcgttg    9840
```

```
tagacgttga actgggtgcc gctctatgcg acgaaatgga tattgtagag ggaatgaggt    9900
gggagcaagg ttaccgttcc ccatacttca tgactgactc cgccagaaag atcgctgaat    9960
tagagaaccc ctatatctta atttacgata gggtgataaa tcaatttcca gagttggttc   10020
ctgctctgga gctagtcagg aggcagagag gcagtctttt gatcgtggcc gaaaacatcg   10080
ttgaagaggc tttgccaggt ctgttgctta atcatatcag gaaaaactta tgtagtattg   10140
cagtcaaggg acctggctac ggcgacagtc gttacgaatt cttgcatgac ctggcagcat   10200
taactggcgg acgtgcaatt atggaagctt gtggtgaaga actgagtaat gtcacaatgg   10260
cacatttggg tagggccaaa agagtagtcg tgcgtgaaga tgacacagtg gtaataggcg   10320
gagaaggaga tggagctgca attacggaaa ggttagctgc agcaagacaa caggccgatt   10380
ggattacgga tggcgacccc tccaagggtt ctccctccgg caaacgtcac gacctagaga   10440
atcttcaaac acgtattaaa gccttgagtg gaaaggtcgt aacgatcaaa gccggaggat   10500
tatccgacat cttgataaaa gaaagaatgc aaagaatcga gaacgcccta gcttccgcca   10560
gagctgctcg ttcagatgga gtggttgctg gcggaggtgt cggattgtat cgtgcccgtg   10620
ctgctcttac agaggctaca ggagataccc ttgatcagac ttacggcatt gctattgttc   10680
gtgccgctct agacgagcca attcgtagaa tagctgcaaa tgctggcagg gacgcacatg   10740 agttttttgtt cgagcttaaa agatctaacg atgacttctg gggtatggat atgaggagtg   10800
gtgaatgcgg tgacttgtat gctgcaggag ttatcgatcc tgcccgtgtc accagattag   10860
ctctaagaaa cgctgttgca accgcctcca gtttgatgac ggtcgaatgt gcagttacac   10920
acattcctcc ctctgatcct acttatggat ttgaccctca cctagctgct gcaacgcgtg   10980
aagatcctcg ttcaggatcc taagccaatt agtttgaagt gagatttat ttcattcctg   11040 ttaatattat atactagagt atattttaaa ttaattgttc atgaacttgc caaattatgt   11100
tagttttgtg taaacaatct taggctatcc aatttagttc tacttttggt agatttcctg   11160
ttttggtaaa ttacaaacaa caatgatttg acttatattc tattcggaat tttacttatc   11220
accttgtaca gtttgtgggg atttccggac atggctg                           11257
```

<210> SEQ ID NO 48
<211> LENGTH: 4502
<212> TYPE: DNA
<213> ORGANISM: Artificial sequence
<220> FEATURE:
<223> OTHER INFORMATION: plasmid

<400> SEQUENCE: 48

```
agcatgagac ggaaatctgc tcgtcagtgg tgctcacact gacgaatcat gtacagatca     60
taccgatgac tgcctggcga ctcacaacta agcaagacag ccggaaccag cgccggcgaa    120
caccactgca tatatggcat atcacaacag tccaactagt gcactgcagt acagcggccg    180
cgattatcaa aaaggatctt cacctagatc cttttaaatt aaaaatgaag ttttaaatca    240
atctaaagta tatatgagta aacttggtct gacagttacc aatgcttaat cagtgaggca    300
cctatctcag cgatctgtct atttcgttca tccatagttg cctgactccc cgtcgtgtag    360
ataactacga tacgggaggg cttaccatct ggccccagtg ctgcaatgat accgcgggac    420
ccacgctcac cggctccaga tttatcagca ataaaccagc cagccggaag ggccgagcgc    480
agaagtggtc ctgcaacttt atccgcctcc atccagtcta ttaattgttg ccgggaagct    540
agagtaagta gttcgccagt taatagtttg cgcaacgttg ttgccattgc tacaggcatc    600
```

```
gtggtgtcac gctcgtcgtt tggtatggct tcattcagct ccggttccca acgatcaagg      660
cgagttacat gatcccccat gttgtgcaaa aaagcggtta gctccttcgg tcctccgatc      720
gttgtcagaa gtaagttggc cgcagtgtta tcactcatgg ttatggcagc actgcataat      780
tctcttactg tcatgccatc cgtaagatgc ttttctgtga ctggtgagta ctcaaccaag      840
tcattctgag aatagtgtat gcggcgaccg agttgctctt gcccggcgtc aatacgggat      900
aataccgcgc cacatagcag aactttaaaa gtgctcatca ttggaaaacg ttcttcgggg      960
cgaaaactct caaggatctt accgctgttg agatccagtt cgatgtaacc cactcgtgca     1020
cccaactgat cttcagcatc ttttactttc accagcgttt ctgggtgagc aaaaacagga     1080
aggcaaaatg ccgcaaaaaa gggaataagg gcgacacgga aatgttgaat actcatactc     1140
ttcctttttc aatattattg aagcatttat cagggttatt gtctcatgag cggatacata     1200
tttgaatgta tttagaaaaa taaacaaata ggggttccgc gcacatttcc ccgaaaagtg     1260
ccacctgtca tgaccaaaat cccttaacgt gagttttcgt tccactgagc gtcagacccc     1320
gtagaaaaga tcaaaggatc ttcttgagat ccttttttc tgcgcgtaat ctgctgcttg     1380
caaacaaaaa aaccaccgct accagcggtg gtttgtttgc cggatcaaga gctaccaact     1440
ctttttccga aggtaactgg cttcagcaga gcgcagatac caaatactgt tcttctagtg     1500
tagccgtagt taggccacca cttcaagaac tctgtagcac cgcctacata cctcgctctg     1560
ctaatcctgt taccagtggc tgctgccagt ggcgataagt cgtgtcttac cgggttggac     1620
tcaagacgat agttaccgga taaggcgcag cggtcgggct gaacggggg ttcgtgcaca     1680 cagcccagct tggagcgaac gacctacacc gaactgagat acctacagcg tgagctatga     1740
gaaagcgcca cgcttcccga agggagaaag gcggacaggt atccggtaag cggcagggtc     1800
ggaacaggag agcgcacgag ggagcttcca gggggaaacg cctggtatct ttatagtcct     1860
gtcgggtttc gccacctctg acttgagcgt cgatttttgt gatgctcgtc aggggggcgg     1920
agcctatgga aaaacgccag caacgcggcc ttttacggt tcctggcctt ttgctggcct     1980
tttgctcaca tgttctttcc tgcgttatcc cctgattctg tggataaccg tgcggccgcc     2040
cctgaattcg catctagaac ggggtcatca cggctcatca tgcgccaaac aaatgtgtgc     2100
aatacacgct cggatgactg catgatgacc gcactgactg gggacagcag atccacctaa     2160
gcctgtgaga gaagcagaca cccgacagat caaggcagtt acgtctcacc aaaccagatg     2220
tcaacacagc tacaacgatc attttttcaaa agtatccagg aaccaggtga agaccatcg     2280 acagaacaga ttattcgtat cgcccgtcgt ttcaagaatg accaagtgct agacaatctt     2340
tcccgaccac aattgatggc aatggcccgt tacatgaatt tacgtccgtt tggaactgac     2400
gagattttac gttatcagat cagatataag ttattgcaaa tcatcaagga tgatcgagcc     2460
attgattacg aaggagttga atctctgtca attcaggagc tccagagtgc ttgtgcttca     2520
cgtggtatca aaaccgttgg tgcttctcct gcaagactga gggatgattt gaagatttgg     2580
ctggacttga ggttgcgtca gaagattcct tcgacacttt tgattttgag tagcacgttc     2640
acttatggag atcacgctga tgacctggac aattactacg atgccctgtt ggcagtactt     2700
tcttcgattc ctgatgaggt ttacaatgtt gctaagttag agctggccga ccaggacaat     2760
aagttgaagc tgaatgtctt gaaggaacaa gatgagctga taaaggaaga gagacaacag     2820
agtaaatcac aacgccgttc cactccaatc aaagacgata tcaaactaga cgaatacgag     2880
gaggtgaaag aagatgaagt gaaggatgac gttactaaag acaccgtgga ggagaagagg     2940
gaagatacga acgaacatgt caaagaagaa ccaaaggttg atgcaagcga ggaggtcaaa     3000
```

```
gacgaaactc cagcgcaatc tgaagaggag gtgaaagaac ccagtaagga tggcaccgta    3060
atcgagtcca aggaccaacc tcaaaccacc gacaaaaagg agtaggaaaa taccagcaaa    3120
taaaacagct cagcgtctgt ttcaattaaa tatctacaat caatttatca cgccgaaatt    3180
aaattcaatc ccacgactag tgtatatagt atatgaatat agtaaaaaga gatccgttat    3240
gtatcaaata gtgatagaga ctgaagatgg cgagacttgc aggaggatga ggccatctga    3300
agattggatc tcaagagctg aggctgaaag aaacttgttg gcctcctgtc gtgctggttg    3360
tgccacctgc aaagcagact gcacggacgg cgactacgaa cttattgacg tgaaggtcca    3420
agctgtgcca ccgacgagg aagaagatgg aaaagtgttg ttgtgcagga ccttccccag    3480
atcagactta catcttctag taccttacac ctacgatagg atcagttttg aagccattca    3540
aacaaattgg ttagctgaaa ttttagcatg cgacagagtt tctagtaacg tcgtacgttt    3600
ggtactacag agatctcgtc ccatggctgc ccgtatatca ctaaatttcg ttcccggcca    3660
attcgtggac atcgagatcc caggaacgca cacacgtaga agttactcaa tggcctctgt    3720
agctgaggat ggacaactag aatttatcat acgtttacta ccagatggtg ctttttctaa    3780
atttcttcag acagaggcaa aagtgggaat gagagtggac ttgagaggcc cagctggttc    3840
tttttttttg cacgatcatg gaggccgttc tcgtgtgttt gtcgcaggcg gtacaggatt    3900 atccccgtg ttaagtatga tcaggcagct gggcaaggca tctgacccat ctcccgccac    3960
acttctgttt ggagtaacaa accgtgaaga acttttctat gtagacgaat aaaaacgct    4020 tgcacagagt atgccaaccc tgggagtgag gatcgccgtt gtaaatgacg acggtggaaa    4080
cggagttgat aaaggtactg tcatagatct tctgagagca gagctagaga aatccgatgc    4140
caaacccgac atctatctat gcggcccacc aggaatgatc gaggctgcct ttgccgccgc    4200
agctacagct ggtgtaccaa agaacaagt atacttagag aagttttag ccagtggcgg    4260 atcctaactc gagagctttt gattaagcct tctagtccaa aaaacacgtt ttttgtcat    4320 ttatttcatt ttcttagaat agtttagttt attcatttta tagtcacgaa tgttttatga    4380
ttctatatag ggttgcaaac aagcattttt cattttatgt taaaacaatt tcaggtttac    4440
cttttattct gcttgtggtg acgcgtgtat ccgcccgctc ttttggtcac ccatgtatgc    4500
tg                                                                   4502

<210> SEQ ID NO 49
<211> LENGTH: 20
<212> TYPE: PRT
<213> ORGANISM: Artificial sequence
<220> FEATURE:
<223> OTHER INFORMATION: synthetic self-cleaving peptide sequence E2A

<400> SEQUENCE: 49

Gln Cys Thr Asn Tyr Ala Leu Leu Lys Leu Ala Gly Asp Val Glu Ser
1               5                   10                  15

Asn Pro Gly Pro
            20

<210> SEQ ID NO 50
<211> LENGTH: 22
<212> TYPE: PRT
<213> ORGANISM: Artificial sequence
<220> FEATURE:
<223> OTHER INFORMATION: synthetic self-cleaving peptide sequence F2A

<400> SEQUENCE: 50
```

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 51
<211> LENGTH: 19
<212> TYPE: PRT
<213> ORGANISM: Artificial sequence
<220> FEATURE:
<223> OTHER INFORMATION: synthetic self-cleaving peptide sequence P2A

<400> SEQUENCE: 51

Ala Thr Asn Phe Ser Leu Leu Lys Gln Ala Gly Asp Val Glu Glu Asn
1               5                   10                  15

Pro Gly Pro

<210> SEQ ID NO 52
<211> LENGTH: 18
<212> TYPE: PRT
<213> ORGANISM: Artificial sequence
<220> FEATURE:
<223> OTHER INFORMATION: synthetic self-cleaving peptide sequence T2A

<400> SEQUENCE: 52

Glu Gly Arg Gly Ser Leu Leu Thr Cys Gly Asp Val Glu Glu Asn Pro
1               5                   10                  15

Gly Pro

<210> SEQ ID NO 53
<211> LENGTH: 23
<212> TYPE: PRT
<213> ORGANISM: Artificial sequence
<220> FEATURE:
<223> OTHER INFORMATION: synthetic self-cleaving peptide sequence GE2A

<400> SEQUENCE: 53

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 54
<211> LENGTH: 25
<212> TYPE: PRT
<213> ORGANISM: Artificial sequence
<220> FEATURE:
<223> OTHER INFORMATION: synthetic self-cleaving peptide sequence GF2A

<400> SEQUENCE: 54

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 55
<211> LENGTH: 22
<212> TYPE: PRT
<213> ORGANISM: Artificial sequence
<220> FEATURE:
<223> OTHER INFORMATION: synthetic self-cleaving peptide sequence GP2A

<400> SEQUENCE: 55

Gly Ser Gly Ala Thr Asn Phe Ser Leu Leu Lys Gln Ala Gly Asp Val

```
1               5                   10                  15
Glu Glu Asn Pro Gly Pro
            20

<210> SEQ ID NO 56
<211> LENGTH: 21
<212> TYPE: PRT
<213> ORGANISM: Artificial sequence
<220> FEATURE:
<223> OTHER INFORMATION: synthetic self-cleaving peptide sequence GT2A

<400> SEQUENCE: 56

Gly Ser Gly Glu Gly Arg Gly Ser Leu Leu Thr Cys Gly Asp Val Glu
1               5                   10                  15
Glu Asn Pro Gly Pro
            20

<210> SEQ ID NO 57
<211> LENGTH: 8
<212> TYPE: PRT
<213> ORGANISM: Artificial sequence
<220> FEATURE:
<223> OTHER INFORMATION: protease recognition site for HRV 3 C Protease

<400> SEQUENCE: 57

Leu Glu Val Leu Phe Gln Gln Pro
1               5

<210> SEQ ID NO 58
<211> LENGTH: 5
<212> TYPE: PRT
<213> ORGANISM: Artificial sequence
<220> FEATURE:
<223> OTHER INFORMATION: protease recognition site Enterokinase

<400> SEQUENCE: 58

Asp Asp Asp Asp Lys
1               5

<210> SEQ ID NO 59
<211> LENGTH: 4
<212> TYPE: PRT
<213> ORGANISM: Artificial sequence
<220> FEATURE:
<223> OTHER INFORMATION: protease recognition site Factor Xa

<400> SEQUENCE: 59

Ile Glu Gly Arg
1

<210> SEQ ID NO 60
<211> LENGTH: 7
<212> TYPE: PRT
<213> ORGANISM: Artificial sequence
<220> FEATURE:
<223> OTHER INFORMATION: protease recognition site Tobacco etch virs
      protease

<400> SEQUENCE: 60

Glu Asn Leu Tyr Phe Gln Gly
1               5

<210> SEQ ID NO 61
<211> LENGTH: 6
<212> TYPE: PRT
<213> ORGANISM: Artificial sequence
```

```
<220> FEATURE:
<223> OTHER INFORMATION: protease recognition site thrombin

<400> SEQUENCE: 61

Leu Val Pro Arg Gly Ser
1               5

<210> SEQ ID NO 62
<211> LENGTH: 8
<212> TYPE: PRT
<213> ORGANISM: Artificial sequence
<220> FEATURE:
<223> OTHER INFORMATION: TVMV protease recognition site

<400> SEQUENCE: 62

Glu Thr Val Arg Phe Gln Gly Ser
1               5

<210> SEQ ID NO 63
<211> LENGTH: 6
<212> TYPE: PRT
<213> ORGANISM: Artificial sequence
<220> FEATURE:
<223> OTHER INFORMATION: Plum pox virus protease recog site

<400> SEQUENCE: 63

Asn Val Val Val His Ala
1               5

<210> SEQ ID NO 64
<211> LENGTH: 5
<212> TYPE: PRT
<213> ORGANISM: Artificial  sequence
<220> FEATURE:
<223> OTHER INFORMATION: synthetic flexible linker monomer GGSGG

<400> SEQUENCE: 64

Gly Gly Ser Gly Gly
1               5

<210> SEQ ID NO 65
<211> LENGTH: 5
<212> TYPE: PRT
<213> ORGANISM: Artificial sequence
<220> FEATURE:
<223> OTHER INFORMATION: synthetic flexible linker monomer GGSGG

<400> SEQUENCE: 65

Gly Gly Gly Gly Ser
1               5

<210> SEQ ID NO 66
<211> LENGTH: 4
<212> TYPE: PRT
<213> ORGANISM: Artificial sequence
<220> FEATURE:
<223> OTHER INFORMATION: Flexible linker sequence 3 (GGGG)

<400> SEQUENCE: 66

Gly Gly Gly Gly
1

<210> SEQ ID NO 67
<211> LENGTH: 18
<212> TYPE: PRT
<213> ORGANISM: Artificial sequence
<220> FEATURE:
```

-continued

<223> OTHER INFORMATION: Flexible Linker Sequence 4

<400> SEQUENCE: 67

Lys Glu Ser Gly Ser Val Ser Glu Gln Leu Ala Gln Phe Arg Ser
1               5                   10                  15

Leu Asp

<210> SEQ ID NO 68
<211> LENGTH: 12
<212> TYPE: PRT
<213> ORGANISM: Artificial Sequence
<220> FEATURE:
<223> OTHER INFORMATION: Flexible linker sequence 5

<400> SEQUENCE: 68

Gly Ser Ala Gly Ser Ala Ala Gly Ser Asp Glu Phe
1               5                   10

<210> SEQ ID NO 69
<211> LENGTH: 526
<212> TYPE: PRT
<213> ORGANISM: Methylosinus tricosporium

<400> SEQUENCE: 69

Met Ala Ile Ser Leu Ala Thr Lys Ala Ala Thr Asp Ala Leu Lys Val
1               5                   10                  15

Asn Arg Ala Pro Val Gly Val Glu Pro Gln Glu Val His Lys Trp Leu
                20                  25                  30

Gln Ser Phe Asn Trp Asp Phe Lys Glu Asn Arg Thr Lys Tyr Pro Thr
            35                  40                  45

Lys Tyr His Met Ala Asn Glu Thr Lys Glu Gln Phe Lys Val Ile Ala
        50                  55                  60

Lys Glu Tyr Ala Arg Met Glu Ala Ala Lys Asp Glu Arg Gln Phe Gly
65                  70                  75                  80

Thr Leu Leu Asp Gly Leu Thr Arg Leu Gly Ala Gly Asn Lys Val His
                85                  90                  95

Pro Arg Trp Gly Glu Thr Met Lys Val Ile Ser Asn Phe Leu Glu Val
            100                 105                 110

Gly Glu Tyr Asn Ala Ile Ala Ala Ser Ala Met Leu Trp Asp Ser Ala
        115                 120                 125

Thr Ala Ala Glu Gln Lys Asn Gly Tyr Leu Ala Gln Val Leu Asp Glu
130                 135                 140

Ile Arg His Thr His Gln Cys Ala Phe Ile Asn His Tyr Tyr Ser Lys
145                 150                 155                 160

His Tyr His Asp Pro Ala Gly His Asn Asp Ala Arg Arg Thr Arg Ala
                165                 170                 175

Ile Gly Pro Leu Trp Lys Gly Met Lys Arg Val Phe Ala Asp Gly Phe
            180                 185                 190

Ile Ser Gly Asp Ala Val Glu Cys Ser Val Asn Leu Gln Leu Val Gly
        195                 200                 205

Glu Ala Cys Phe Thr Asn Pro Leu Ile Val Ala Val Thr Glu Trp Ala
210                 215                 220

Ser Ala Asn Gly Asp Glu Ile Thr Pro Thr Val Phe Leu Ser Val Glu
225                 230                 235                 240

Thr Asp Glu Leu Arg His Met Ala Asn Gly Tyr Gln Thr Val Val Ser
                245                 250                 255

Ile Ala Asn Asp Pro Ala Ser Ala Lys Phe Leu Asn Thr Asp Leu Asn

```
            260                 265                 270
Asn Ala Phe Trp Thr Gln Gln Lys Tyr Phe Thr Pro Val Leu Gly Tyr
        275                 280                 285

Leu Phe Glu Tyr Gly Ser Lys Phe Lys Val Glu Pro Trp Val Lys Thr
    290                 295                 300

Trp Asn Arg Trp Val Tyr Glu Asp Trp Gly Ile Trp Ile Gly Arg
305                 310                 315                 320

Leu Gly Lys Tyr Gly Val Glu Ser Pro Ala Ser Leu Arg Asp Ala Lys
                325                 330                 335

Arg Asp Ala Tyr Trp Ala His His Asp Leu Ala Leu Ala Ala Tyr Ala
            340                 345                 350

Met Trp Pro Leu Gly Phe Ala Arg Leu Ala Leu Pro Asp Glu Glu Asp
        355                 360                 365

Gln Ala Trp Phe Glu Ala Asn Tyr Pro Gly Trp Ala Asp His Tyr Gly
    370                 375                 380

Lys Ile Phe Asn Glu Trp Lys Lys Leu Gly Tyr Glu Asp Pro Lys Ser
385                 390                 395                 400

Gly Phe Ile Pro Tyr Lys Trp Leu Leu Glu Asn Gly His Asp Val Tyr
                405                 410                 415

Ile Asp Arg Val Ser Gln Val Pro Phe Ile Pro Ser Leu Ala Lys Gly
            420                 425                 430

Ser Gly Ser Leu Arg Val His Glu Phe Asn Gly Lys Lys His Ser Leu
        435                 440                 445

Thr Asp Asp Trp Gly Glu Arg Gln Trp Leu Ile Glu Pro Glu Arg Tyr
    450                 455                 460

Glu Cys His Asn Val Phe Glu Gln Tyr Glu Gly Arg Glu Leu Ser Glu
465                 470                 475                 480

Val Ile Ala Glu Gly His Gly Val Arg Ser Asp Gly Lys Thr Leu Ile
                485                 490                 495

Ala Gln Pro His Thr Arg Gly Asp Asn Leu Trp Thr Leu Glu Asp Ile
            500                 505                 510

Lys Arg Ala Gly Cys Val Phe Pro Asp Pro Leu Ala Lys Phe
        515                 520                 525

<210> SEQ ID NO 70
<211> LENGTH: 527
<212> TYPE: PRT
<213> ORGANISM: Methylococcus capsulatus

<400> SEQUENCE: 70

Met Ala Leu Ser Thr Ala Thr Lys Ala Ala Thr Asp Ala Leu Ala
1               5                   10                  15

Asn Arg Ala Pro Thr Ser Val Asn Ala Gln Glu Val His Arg Trp Leu
            20                  25                  30

Gln Ser Phe Asn Trp Asp Phe Lys Asn Arg Thr Lys Tyr Ala Thr
        35                  40                  45

Lys Tyr Lys Met Ala Asn Glu Thr Lys Glu Gln Phe Lys Leu Ile Ala
    50                  55                  60

Lys Glu Tyr Ala Arg Met Glu Ala Val Lys Asp Glu Arg Gln Phe Gly
65                  70                  75                  80

Ser Leu Gln Asp Ala Leu Thr Arg Leu Asn Ala Gly Val Arg Val His
                85                  90                  95

Pro Lys Trp Asn Glu Thr Met Lys Val Val Ser Asn Phe Leu Glu Val
            100                 105                 110
```

```
Gly Glu Tyr Asn Ala Ile Ala Ala Thr Gly Met Leu Trp Asp Ser Ala
            115                 120                 125
Gln Ala Ala Glu Gln Lys Asn Gly Tyr Leu Ala Gln Val Leu Asp Glu
        130                 135                 140
Ile Arg His Thr His Gln Cys Ala Tyr Val Asn Tyr Tyr Phe Ala Lys
145                 150                 155                 160
Asn Gly Gln Asp Pro Ala Gly His Asn Asp Ala Arg Arg Thr Arg Thr
                165                 170                 175
Ile Gly Pro Leu Trp Lys Gly Met Lys Arg Val Phe Ser Asp Gly Phe
            180                 185                 190
Ile Ser Gly Asp Ala Val Glu Cys Ser Leu Asn Leu Gln Leu Val Gly
        195                 200                 205
Glu Ala Cys Phe Thr Asn Pro Leu Ile Val Ala Val Thr Glu Trp Ala
210                 215                 220
Ala Ala Asn Gly Asp Glu Ile Thr Pro Thr Val Phe Leu Ser Ile Glu
225                 230                 235                 240
Thr Asp Glu Leu Arg His Met Ala Asn Gly Tyr Gln Thr Val Val Ser
                245                 250                 255
Ile Ala Asn Asp Pro Ala Ser Ala Lys Tyr Leu Asn Thr Asp Leu Asn
            260                 265                 270
Asn Ala Phe Trp Thr Gln Gln Lys Tyr Phe Thr Pro Val Leu Gly Met
        275                 280                 285
Leu Phe Glu Tyr Gly Ser Lys Phe Lys Val Glu Pro Trp Val Lys Thr
    290                 295                 300
Trp Asn Arg Trp Val Tyr Glu Asp Trp Gly Ile Trp Ile Gly Arg
305                 310                 315                 320
Leu Gly Lys Tyr Gly Val Glu Ser Pro Arg Ser Leu Lys Asp Ala Lys
                325                 330                 335
Gln Asp Ala Tyr Trp Ala His His Asp Leu Tyr Leu Leu Ala Tyr Ala
            340                 345                 350
Leu Trp Pro Thr Gly Phe Phe Arg Leu Ala Leu Pro Asp Gln Glu Glu
        355                 360                 365
Met Glu Trp Phe Glu Ala Asn Tyr Pro Gly Trp Tyr Asp His Tyr Gly
    370                 375                 380
Lys Ile Tyr Glu Glu Trp Arg Ala Arg Gly Cys Glu Asp Pro Ser Ser
385                 390                 395                 400
Gly Phe Ile Pro Leu Met Trp Phe Ile Glu Asn His Pro Ile Tyr
                405                 410                 415
Ile Asp Arg Val Ser Gln Val Pro Phe Cys Pro Ser Leu Ala Lys Gly
            420                 425                 430
Ala Ser Thr Leu Arg Val His Glu Tyr Asn Gly Gln Met His Thr Phe
        435                 440                 445
Ser Asp Gln Trp Gly Glu Arg Met Trp Leu Ala Glu Pro Glu Arg Tyr
    450                 455                 460
Glu Cys Gln Asn Ile Phe Glu Gly Tyr Glu Gly Arg Glu Leu Ser Glu
465                 470                 475                 480
Val Ile Ala Glu Leu His Gly Leu Arg Ser Asp Gly Lys Thr Leu Ile
                485                 490                 495
Ala Gln Pro His Val Arg Gly Asp Lys Leu Trp Thr Leu Asp Asp Ile
            500                 505                 510
Lys Arg Leu Asn Cys Val Phe Lys Asn Pro Val Lys Ala Phe Asn
        515                 520                 525
```

<210> SEQ ID NO 71
<211> LENGTH: 395
<212> TYPE: PRT
<213> ORGANISM: Methylosinus trichosporium

<400> SEQUENCE: 71

| Met | Ser | Gln | Pro | Gln | Ser | Ser | Gln | Val | Thr | Lys | Arg | Gly | Leu | Thr | Asp |
|---|---|---|---|---|---|---|---|---|---|---|---|---|---|---|---|
| 1 | | | | 5 | | | | | 10 | | | | | 15 | |

| Pro | Glu | Arg | Ala | Ala | Ile | Ile | Ala | Ala | Val | Pro | Asp | His | Ala | Leu |
|---|---|---|---|---|---|---|---|---|---|---|---|---|---|---|
| | | | 20 | | | | | 25 | | | | | 30 | |

| Asp | Thr | Gln | Arg | Lys | Tyr | His | Tyr | Phe | Ile | Gln | Pro | Arg | Trp | Lys | Arg |
|---|---|---|---|---|---|---|---|---|---|---|---|---|---|---|---|
| | | 35 | | | | | 40 | | | | | 45 | | | |

| Leu | Ser | Glu | Tyr | Glu | Gln | Leu | Ser | Cys | Tyr | Ala | Gln | Pro | Asn | Pro | Asp |
|---|---|---|---|---|---|---|---|---|---|---|---|---|---|---|---|
| | 50 | | | | | 55 | | | | | 60 | | | | |

| Trp | Ile | Ala | Gly | Gly | Leu | Asp | Trp | Gly | Asp | Trp | Thr | Gln | Lys | Phe | His |
|---|---|---|---|---|---|---|---|---|---|---|---|---|---|---|---|
| 65 | | | | | 70 | | | | | 75 | | | | | 80 |

| Gly | Gly | Arg | Pro | Ser | Trp | Gly | Asn | Glu | Ser | Thr | Glu | Leu | Arg | Thr | Thr |
|---|---|---|---|---|---|---|---|---|---|---|---|---|---|---|---|
| | | | | 85 | | | | | 90 | | | | | 95 | |

| Asp | Trp | Phe | Arg | His | Arg | Asp | Pro | Ala | Arg | Arg | Trp | His | His | Pro | Tyr |
|---|---|---|---|---|---|---|---|---|---|---|---|---|---|---|---|
| | | | 100 | | | | | 105 | | | | | 110 | | |

| Val | Lys | Asp | Lys | Ser | Glu | Glu | Ala | Arg | Tyr | Thr | Gln | Arg | Phe | Leu | Ala |
|---|---|---|---|---|---|---|---|---|---|---|---|---|---|---|---|
| | | 115 | | | | | 120 | | | | | 125 | | | |

| Gly | Tyr | Ala | Ser | Glu | Gly | Ser | Ile | Arg | Thr | Ile | Asp | Pro | Tyr | Trp | Arg |
|---|---|---|---|---|---|---|---|---|---|---|---|---|---|---|---|
| | 130 | | | | | 135 | | | | | 140 | | | | |

| Asp | Glu | Ile | Leu | Asn | Lys | Tyr | Tyr | Gly | Ala | Leu | Ile | Tyr | Ser | Glu | Tyr |
|---|---|---|---|---|---|---|---|---|---|---|---|---|---|---|---|
| 145 | | | | | 150 | | | | | 155 | | | | | 160 |

| Gly | Leu | Phe | Asn | Ser | His | Ser | Ser | Val | Gly | Arg | Asp | Cys | Leu | Ser | Asp |
|---|---|---|---|---|---|---|---|---|---|---|---|---|---|---|---|
| | | | | 165 | | | | | 170 | | | | | 175 | |

| Thr | Ile | Arg | Gln | Ser | Ala | Val | Phe | Ala | Ala | Leu | Asp | Lys | Val | Asp | Asn |
|---|---|---|---|---|---|---|---|---|---|---|---|---|---|---|---|
| | | | 180 | | | | | 185 | | | | | 190 | | |

| Ala | Gln | Met | Ile | Gln | Met | Glu | Arg | Leu | Phe | Ile | Ala | Lys | Leu | Val | Pro |
|---|---|---|---|---|---|---|---|---|---|---|---|---|---|---|---|
| | | 195 | | | | | 200 | | | | | 205 | | | |

| Gly | Phe | Asp | Ala | Ser | Thr | Asp | Val | Pro | Lys | Lys | Val | Trp | Thr | Thr | Asp |
|---|---|---|---|---|---|---|---|---|---|---|---|---|---|---|---|
| | 210 | | | | | 215 | | | | | 220 | | | | |

| Pro | Ile | Tyr | Ala | Gly | Ala | Arg | Gly | Thr | Val | Gln | Ala | Ile | Trp | Gln | Gly |
|---|---|---|---|---|---|---|---|---|---|---|---|---|---|---|---|
| 225 | | | | | 230 | | | | | 235 | | | | | 240 |

| Ile | Gln | Asp | Trp | Asn | Glu | Ile | Leu | Trp | Ala | Gly | His | Ala | Val | Tyr | Asp |
|---|---|---|---|---|---|---|---|---|---|---|---|---|---|---|---|
| | | | | 245 | | | | | 250 | | | | | 255 | |

| Ala | Thr | Phe | Gly | Gln | Phe | Ala | Arg | Arg | Glu | Phe | Phe | Gln | Arg | Leu | Ala |
|---|---|---|---|---|---|---|---|---|---|---|---|---|---|---|---|
| | | | 260 | | | | | 265 | | | | | 270 | | |

| Thr | Val | Tyr | Gly | Asp | Thr | Leu | Thr | Pro | Phe | Phe | Thr | Ala | Gln | Ser | Gln |
|---|---|---|---|---|---|---|---|---|---|---|---|---|---|---|---|
| | | 275 | | | | | 280 | | | | | 285 | | | |

| Thr | Tyr | Phe | Gln | Thr | Thr | Arg | Gly | Ala | Ile | Asp | Asp | Leu | Phe | Val | Tyr |
|---|---|---|---|---|---|---|---|---|---|---|---|---|---|---|---|
| | 290 | | | | | 295 | | | | | 300 | | | | |

| Cys | Leu | Ala | Asn | Asp | Ser | Glu | Phe | Gly | Ala | His | Asn | Arg | Thr | Phe | Leu |
|---|---|---|---|---|---|---|---|---|---|---|---|---|---|---|---|
| 305 | | | | | 310 | | | | | 315 | | | | | 320 |

| Asn | Ala | Trp | Thr | Glu | His | Tyr | Leu | Ala | Ser | Ser | Val | Ala | Ala | Leu | Lys |
|---|---|---|---|---|---|---|---|---|---|---|---|---|---|---|---|
| | | | | 325 | | | | | 330 | | | | | 335 | |

| Asp | Phe | Val | Gly | Leu | Tyr | Ala | Lys | Val | Glu | Lys | Val | Ala | Gly | Ala | Thr |
|---|---|---|---|---|---|---|---|---|---|---|---|---|---|---|---|
| | | | 340 | | | | | 345 | | | | | 350 | | |

| Asp | Arg | Ala | Gly | Val | Ser | Glu | Ala | Leu | Gln | Arg | Val | Phe | Gly | Asp | Trp |
|---|---|---|---|---|---|---|---|---|---|---|---|---|---|---|---|
| | | 355 | | | | | 360 | | | | | 365 | | | |

| Lys | Val | Asp | Tyr | Ala | Asp | Lys | Ile | Gly | Phe | Lys | Val | Asp | Val | Asp | Gln |
|---|---|---|---|---|---|---|---|---|---|---|---|---|---|---|---|
| | 370 | | | | | 375 | | | | | 380 | | | | |

```
Lys Val Asp Ala Val Leu Ala Gly Tyr Lys Asn
385                 390                 395

<210> SEQ ID NO 72
<211> LENGTH: 389
<212> TYPE: PRT
<213> ORGANISM: Methylococcus capsulatus

<400> SEQUENCE: 72

Met Ser Met Leu Gly Glu Arg Arg Gly Leu Thr Asp Pro Glu Met
1               5                   10                  15

Ala Ala Val Ile Leu Lys Ala Leu Pro Glu Ala Pro Leu Asp Gly Asn
                20                  25                  30

Asn Lys Met Gly Tyr Phe Val Thr Pro Arg Trp Lys Arg Leu Thr Glu
        35                  40                  45

Tyr Glu Ala Leu Thr Val Tyr Ala Gln Pro Asn Ala Asp Trp Ile Ala
    50                  55                  60

Gly Gly Leu Asp Trp Gly Asp Trp Thr Gln Lys Phe His Gly Arg
65                  70                  75                  80

Pro Ser Trp Gly Asn Glu Thr Thr Glu Leu Arg Thr Val Asp Trp Phe
                85                  90                  95

Lys His Arg Asp Pro Leu Arg Arg Trp His Ala Pro Tyr Val Lys Asp
            100                 105                 110

Lys Ala Glu Glu Trp Arg Tyr Thr Asp Arg Phe Leu Gln Gly Tyr Ser
        115                 120                 125

Ala Asp Gly Gln Ile Arg Ala Met Asn Pro Thr Trp Arg Asp Glu Phe
    130                 135                 140

Ile Asn Arg Tyr Trp Gly Ala Phe Leu Phe Asn Glu Tyr Gly Leu Phe
145                 150                 155                 160

Asn Ala His Ser Gln Gly Ala Arg Glu Ala Leu Ser Asp Val Thr Arg
                165                 170                 175

Val Ser Leu Ala Phe Trp Gly Phe Asp Lys Ile Asp Ile Ala Gln Met
            180                 185                 190

Ile Gln Leu Glu Arg Gly Phe Leu Ala Lys Ile Val Pro Gly Phe Asp
        195                 200                 205

Glu Ser Thr Ala Val Pro Lys Ala Glu Trp Thr Asn Gly Glu Val Tyr
    210                 215                 220

Lys Ser Ala Arg Leu Ala Val Glu Gly Leu Trp Gln Glu Val Phe Asp
225                 230                 235                 240

Trp Asn Glu Ser Ala Phe Ser Val His Ala Val Tyr Asp Ala Leu Phe
                245                 250                 255

Gly Gln Phe Val Arg Arg Glu Phe Phe Gln Arg Leu Ala Pro Arg Phe
            260                 265                 270

Gly Asp Asn Leu Thr Pro Phe Phe Ile Asn Gln Ala Gln Thr Tyr Phe
        275                 280                 285

Gln Ile Ala Lys Gln Gly Val Gln Asp Leu Tyr Tyr Asn Cys Leu Gly
    290                 295                 300

Asp Asp Pro Glu Phe Ser Asp Tyr Asn Arg Thr Val Met Arg Asn Trp
305                 310                 315                 320

Thr Gly Lys Trp Leu Glu Pro Thr Ile Ala Ala Leu Arg Asp Phe Met
                325                 330                 335

Gly Leu Phe Ala Lys Leu Pro Ala Gly Thr Thr Asp Lys Glu Glu Ile
            340                 345                 350

Thr Ala Ser Leu Tyr Arg Val Val Asp Asp Trp Ile Glu Asp Tyr Ala
        355                 360                 365
```

Ser Arg Ile Asp Phe Lys Ala Asp Arg Asp Gln Ile Val Lys Ala Val
    370                 375                 380

Leu Ala Gly Leu Lys
385

<210> SEQ ID NO 73
<211> LENGTH: 169
<212> TYPE: PRT
<213> ORGANISM: Methylosinus trichosporium

<400> SEQUENCE: 73

Met Ala Lys Arg Glu Pro Ile His Asp Asn Ser Thr Arg Thr Glu Trp
1               5                   10                  15

Glu Ala Lys Ile Ala Lys Leu Thr Ser Val Asp Gln Ala Thr Lys Phe
            20                  25                  30

Ile Gln Asp Phe Arg Val Ala Tyr Thr Ser Pro Phe Arg Lys Ser Tyr
        35                  40                  45

Asp Ile Asp Val Asp Tyr Gln Tyr Ile Glu Arg Lys Ile Glu Glu Lys
    50                  55                  60

Leu Ser Val Leu Lys Thr Glu Lys Leu Pro Val Ala Asp Leu Ile Thr
65                  70                  75                  80

Lys Ala Ser Thr Gly Glu Asp Ala Ala Val Glu Ala Ala Trp Ile
                85                  90                  95

Ala Lys Ile Lys Ala Ala Lys Thr Lys Tyr Glu Ala Glu Arg Val His
            100                 105                 110

Ile Glu Phe Arg Gln Leu Tyr Lys Pro Pro Val Leu Pro Val Asn Val
        115                 120                 125

Phe Leu Arg Thr Asp Ala Ala Leu Gly Thr Val Leu Met Glu Ile Arg
    130                 135                 140

Asn Thr Asp Tyr Tyr Ala Thr Pro Leu Glu Gly Leu Arg Lys Glu Arg
145                 150                 155                 160

Gly Val Lys Val Leu His Leu Gln Ala
                165

<210> SEQ ID NO 74
<211> LENGTH: 170
<212> TYPE: PRT
<213> ORGANISM: Methylococcus capsulatus

<400> SEQUENCE: 74

Met Ala Lys Leu Gly Ile His Ser Asn Asp Thr Arg Asp Ala Trp Val
1               5                   10                  15

Asn Lys Ile Ala Gln Leu Asn Thr Leu Glu Lys Ala Ala Glu Met Leu
            20                  25                  30

Lys Gln Phe Arg Met Asp His Thr Thr Pro Phe Arg Asn Ser Tyr Glu
        35                  40                  45

Leu Asp Asn Asp Tyr Leu Trp Ile Glu Ala Lys Leu Glu Glu Lys Val
    50                  55                  60

Ala Val Leu Lys Ala Arg Ala Phe Asn Glu Val Asp Phe Arg His Lys
65                  70                  75                  80

Thr Ala Phe Gly Glu Asp Ala Lys Ser Val Leu Asp Gly Thr Val Ala
                85                  90                  95

Lys Met Asn Ala Ala Lys Asp Lys Trp Glu Ala Glu Lys Ile His Ile
            100                 105                 110

Gly Phe Arg Gln Ala Tyr Lys Pro Pro Ile Met Pro Val Asn Tyr Phe
        115                 120                 125

Leu Asp Gly Glu Arg Gln Leu Gly Thr Arg Leu Met Glu Leu Arg Asn
130                 135                 140

Leu Asn Tyr Tyr Asp Thr Pro Leu Glu Glu Leu Arg Lys Gln Arg Gly
145                 150                 155                 160

Val Arg Val Val His Leu Gln Ser Pro His
                165                 170

<210> SEQ ID NO 75
<211> LENGTH: 343
<212> TYPE: PRT
<213> ORGANISM: Methylosinus trichosporium

<400> SEQUENCE: 75

Met Tyr Gln Ile Val Ile Glu Thr Glu Asp Gly Glu Thr Cys Ser Phe
1               5                   10                  15

Glu Cys Gly Pro Ser Glu Asp Val Ile Ser Ala Gly Leu Arg Gln Ser
            20                  25                  30

Val Ile Leu Leu Ala Ser Cys Arg Ala Gly Gly Cys Ala Thr Cys Lys
        35                  40                  45

Gly Asp Cys Thr Asp Gly Asp Tyr Glu Leu Ile Asp Val Lys Val Gln
50                  55                  60

Ala Leu Pro Pro Asp Glu Glu Asn Gly Lys Val Leu Leu Cys Arg
65                  70                  75                  80

Thr Phe Pro Arg Ser Asp Leu His Ile Leu Val Pro Tyr Thr Phe Asp
                85                  90                  95

Arg Ile Ser Phe Gln Ala Ile Gln Thr Asn Trp Leu Ala Glu Ile Val
            100                 105                 110

Ala Cys Asp Lys Val Ser Ser Asn Val Ala Arg Leu Val Leu Gln Cys
        115                 120                 125

Leu Thr Ala Asp Gly Ser Thr Pro Ile Ala Leu Asp Phe Val Pro Gly
130                 135                 140

Gln Phe Val Asp Ile Glu Ile Pro Gly Thr His Thr Arg Arg Ser Tyr
145                 150                 155                 160

Ser Met Ala Ser Val Ala Glu Asp Gly Arg Leu Glu Phe Phe Ile Arg
                165                 170                 175

Leu Leu Pro Asp Gly Ala Phe Ser Asn Tyr Leu Gln Thr Gly Ala Lys
            180                 185                 190

Val Gly Gln Arg Val Ala Leu Arg Gly Pro Ala Gly Ser Phe Ser Leu
        195                 200                 205

His Lys Ser Glu Arg Ala Arg Phe Phe Val Ala Gly Thr Gly Leu
210                 215                 220

Ser Pro Val Leu Ser Met Ile Arg Gln Leu Lys Lys Glu Ser Ala Ser
225                 230                 235                 240

Gln Pro Ala Thr Leu Phe Phe Gly Val Thr Asn His Glu Glu Leu Phe
                245                 250                 255

Tyr Val Asp Glu Leu Lys Ala Leu Gln Glu Ala Met Pro Ser Leu Asp
            260                 265                 270

Val Arg Val Ala Val Val Asn Ala Ala Glu Gly Asn Gly Val Ala Lys
        275                 280                 285

Gly Thr Val Ile Asp Leu Met Arg Ala Glu Leu Ala Lys Ser Gly Glu
290                 295                 300

Lys Pro Asp Ile Tyr Leu Cys Gly Pro Pro Gly Met Ile Glu Ala Ala
305                 310                 315                 320

Phe Ala Ala Ala Ala Thr Ala Gly Val Pro Lys Glu Gln Val Tyr Leu

-continued

```
                           325                 330                 335
Glu Lys Phe Leu Ala Ser Gly
                340

<210> SEQ ID NO 76
<211> LENGTH: 348
<212> TYPE: PRT
<213> ORGANISM: Methylococcus capsulatus

<400> SEQUENCE: 76

Met Gln Arg Val His Thr Ile Thr Ala Val Thr Asp Gly Glu Ser
1               5                   10                  15

Leu Arg Phe Glu Cys Arg Ser Asp Glu Asp Val Ile Thr Ala Ala Leu
                20                  25                  30

Arg Gln Asn Ile Phe Leu Met Ser Ser Cys Arg Glu Gly Gly Cys Ala
                35                  40                  45

Thr Cys Lys Ala Leu Cys Ser Glu Gly Asp Tyr Asp Leu Lys Gly Cys
                50                  55                  60

Ser Val Gln Ala Leu Pro Pro Glu Glu Glu Gly Leu Val Leu
65                  70                  75                  80

Leu Cys Arg Thr Tyr Pro Lys Thr Asp Leu Glu Ile Glu Leu Pro Tyr
                85                  90                  95

Thr His Cys Arg Ile Ser Phe Gly Glu Val Gly Ser Phe Glu Ala Glu
                100                 105                 110

Val Val Gly Leu Asn Trp Val Ser Ser Asn Thr Val Gln Phe Leu Leu
                115                 120                 125

Gln Lys Arg Pro Asp Glu Cys Gly Asn Arg Gly Val Lys Phe Glu Pro
130                 135                 140

Gly Gln Phe Met Asp Leu Thr Ile Pro Gly Thr Asp Val Ser Arg Ser
145                 150                 155                 160

Tyr Ser Pro Ala Asn Leu Pro Asn Pro Glu Gly Arg Leu Glu Phe Leu
                165                 170                 175

Ile Arg Val Leu Pro Glu Gly Arg Phe Ser Asp Tyr Leu Arg Asn Asp
                180                 185                 190

Ala Arg Val Gly Gln Val Leu Ser Val Lys Gly Pro Leu Gly Val Phe
                195                 200                 205

Gly Leu Lys Glu Arg Gly Met Ala Pro Arg Tyr Phe Val Ala Gly Gly
                210                 215                 220

Thr Gly Leu Ala Pro Val Val Ser Met Val Arg Gln Met Gln Glu Trp
225                 230                 235                 240

Thr Ala Pro Asn Glu Thr Arg Ile Tyr Phe Gly Val Asn Thr Glu Pro
                245                 250                 255

Glu Leu Phe Tyr Ile Asp Glu Leu Lys Ser Leu Glu Arg Ser Met Arg
                260                 265                 270

Asn Leu Thr Val Lys Ala Cys Val Trp His Pro Ser Gly Asp Trp Glu
                275                 280                 285

Gly Glu Gln Gly Ser Pro Ile Asp Ala Leu Arg Glu Asp Leu Glu Ser
                290                 295                 300

Ser Asp Ala Asn Pro Asp Ile Tyr Leu Cys Gly Pro Pro Gly Met Ile
305                 310                 315                 320

Asp Ala Ala Cys Glu Leu Val Arg Ser Arg Gly Ile Pro Gly Glu Gln
                325                 330                 335

Val Phe Phe Glu Lys Phe Leu Pro Ser Gly Ala Ala
                340                 345
```

<210> SEQ ID NO 77
<211> LENGTH: 138
<212> TYPE: PRT
<213> ORGANISM: Methylosinus trichosporium

<400> SEQUENCE: 77

Met Thr Ser Ala His Asn Ala Tyr Asn Ala Gly Ile Met Gln Lys Thr
1               5                   10                  15

Gly Lys Ala Phe Ala Asp Glu Phe Ala Glu Glu Asn Gln Val Val
            20                  25                  30

His Glu Ser Asn Ala Val Val Leu Val Leu Met Lys Ser Asp Glu Ile
        35                  40                  45

Asp Ala Ile Ile Glu Asp Ile Val Leu Lys Gly Gly Lys Ala Lys Asn
    50                  55                  60

Pro Ser Ile Val Val Glu Asp Lys Ala Gly Phe Trp Trp Ile Lys Ala
65                  70                  75                  80

Asp Gly Ala Ile Glu Ile Asp Ala Ala Glu Ala Gly Glu Leu Leu Gly
                85                  90                  95

Lys Pro Phe Ser Val Tyr Asp Leu Leu Ile Asn Val Ser Ser Thr Val
            100                 105                 110

Gly Arg Ala Tyr Thr Leu Gly Thr Lys Phe Thr Ile Thr Ser Glu Leu
        115                 120                 125

Met Gly Leu Asp Arg Ala Leu Thr Asp Ile
    130                 135

<210> SEQ ID NO 78
<211> LENGTH: 141
<212> TYPE: PRT
<213> ORGANISM: Methylococcus capsulatus

<400> SEQUENCE: 78

Met Ser Val Asn Ser Asn Ala Tyr Asp Ala Gly Ile Met Gly Leu Lys
1               5                   10                  15

Gly Lys Asp Phe Ala Asp Gln Phe Phe Ala Asp Glu Asn Gln Val Val
            20                  25                  30

His Glu Ser Asp Thr Val Val Leu Val Leu Lys Lys Ser Asp Glu Ile
        35                  40                  45

Asn Thr Phe Ile Glu Glu Ile Leu Leu Thr Asp Tyr Lys Lys Asn Val
    50                  55                  60

Asn Pro Thr Val Asn Val Glu Asp Arg Ala Gly Tyr Trp Trp Ile Lys
65                  70                  75                  80

Ala Asn Gly Lys Ile Glu Val Asp Cys Asp Glu Ile Ser Glu Leu Leu
                85                  90                  95

Gly Arg Gln Phe Asn Val Tyr Asp Phe Leu Val Asp Val Ser Ser Thr
            100                 105                 110

Ile Gly Arg Ala Tyr Thr Leu Gly Asn Lys Phe Thr Ile Thr Ser Glu
        115                 120                 125

Leu Met Gly Leu Asp Arg Lys Leu Glu Asp Tyr His Ala
    130                 135                 140

<210> SEQ ID NO 79
<211> LENGTH: 581
<212> TYPE: PRT
<213> ORGANISM: Methylosinus trichosporium

<400> SEQUENCE: 79

Met Thr Asn Pro Arg Lys Arg Glu Arg Arg Pro Ala Phe Asp Val

```
1               5                   10                  15
Thr Arg Glu Lys Phe Val Ala Arg Asn Ile Arg Phe Gly Asp Val Val
            20                  25                  30
Arg Arg Asp Leu Leu Ala Gly Val Asp Ala Leu Ala Asp Ala Val Ala
            35                  40                  45
Val Thr Leu Gly Pro Arg Gly Arg Asn Val Val Ile Glu His Arg Ala
50                  55                  60
Ala Gly Leu Pro Pro Val Ala Thr Lys Asp Gly Val Thr Val Ala Gln
65                  70                  75                  80
Ala Val Glu Leu Ala Gly Arg Thr Gln Ser Val Gly Val Ser Leu Val
                85                  90                  95
Arg Gln Met Ala Thr Ala Val Ala Lys Glu Ala Gly Asp Gly Thr Thr
            100                 105                 110
Thr Ser Val Val Leu Ala Arg Arg Leu Ala Ala Glu Thr Arg Lys Ala
            115                 120                 125
Leu Ala Ala Gly Met Asn Pro Arg Asp Ile Val Leu Gly Met Glu Lys
130                 135                 140
Ala Ala Arg Ile Val Asp Arg Asp Leu Ala Ala Arg Ala Arg Arg Cys
145                 150                 155                 160
Asp Asp Thr Arg Ala Leu Ala His Val Ala Thr Leu Ala Ala Gly Gly
                165                 170                 175
Asp Glu Ser Ile Gly Ala Ile Val Ala Asp Ala Leu Thr Arg Ala Gly
            180                 185                 190
Glu Gly Gly Val Val Asp Val Glu Leu Gly Ala Ala Leu Cys Asp Glu
            195                 200                 205
Met Asp Ile Val Glu Gly Met Arg Trp Glu Gln Gly Tyr Arg Ser Pro
210                 215                 220
Tyr Phe Met Thr Asp Ser Ala Arg Lys Ile Ala Glu Leu Glu Asn Pro
225                 230                 235                 240
Tyr Ile Leu Ile Tyr Asp Arg Val Ile Asn Gln Phe Ser Glu Leu Val
                245                 250                 255
Pro Ala Leu Glu Leu Val Arg Arg Gln Arg Gly Ser Leu Leu Ile Val
            260                 265                 270
Ala Glu Asn Ile Val Glu Glu Ala Leu Pro Gly Leu Leu Leu Asn His
            275                 280                 285
Ile Arg Lys Asn Leu Cys Ser Ile Ala Val Lys Gly Pro Gly Tyr Gly
290                 295                 300
Asp Ser Arg Tyr Glu Phe Leu His Asp Leu Ala Ala Leu Thr Gly Gly
305                 310                 315                 320
Arg Ala Ile Met Glu Ala Cys Gly Glu Glu Leu Ser Asn Val Thr Met
                325                 330                 335
Ala His Leu Gly Arg Ala Lys Arg Val Val Arg Glu Asp Asp Thr
            340                 345                 350
Val Val Ile Gly Gly Glu Gly Asp Gly Ala Ala Ile Thr Glu Arg Leu
            355                 360                 365
Ala Ala Ala Arg Gln Gln Ala Asp Trp Ile Thr Asp Gly Asp Pro Ser
370                 375                 380
Lys Gly Ser Pro Ser Gly Lys Arg His Asp Leu Glu Asn Leu Gln Thr
385                 390                 395                 400
Arg Ile Lys Ala Leu Ser Gly Lys Val Val Thr Ile Lys Ala Gly Gly
                405                 410                 415
Leu Ser Asp Ile Leu Ile Lys Glu Arg Met Gln Arg Ile Glu Asn Ala
            420                 425                 430
```

```
Leu Ala Ser Ala Arg Ala Ala Arg Ser Asp Gly Val Ala Gly Gly
            435                 440                 445

Gly Val Gly Leu Tyr Arg Ala Arg Ala Ala Leu Thr Glu Ala Thr Gly
    450                 455                 460

Asp Thr Leu Asp Gln Thr Tyr Gly Ile Ala Ile Val Arg Ala Ala Leu
465                 470                 475                 480

Asp Glu Pro Ile Arg Arg Ile Ala Ala Asn Ala Gly Arg Asp Ala His
                485                 490                 495

Glu Phe Leu Phe Glu Leu Lys Arg Ser Asn Asp Asp Phe Trp Gly Met
            500                 505                 510

Asp Met Arg Ser Gly Glu Cys Gly Asp Leu Tyr Ala Ala Gly Val Ile
            515                 520                 525

Asp Pro Ala Arg Val Thr Arg Leu Ala Leu Arg Asn Ala Val Ala Thr
            530                 535                 540

Ala Ser Ser Leu Met Thr Val Glu Cys Ala Val Thr His Ile Pro Pro
545                 550                 555                 560

Ser Asp Pro Thr Tyr Gly Phe Asp Pro His Leu Ala Ala Ala Thr Arg
                565                 570                 575

Glu Asp Pro Arg Ser
            580

<210> SEQ ID NO 80
<211> LENGTH: 559
<212> TYPE: PRT
<213> ORGANISM: Methylococcus capsulatus

<400> SEQUENCE: 80

Met Ala Lys Glu Val Val Tyr Arg Gly Ser Ala Arg Gln Arg Met Met
1               5                   10                  15

Gln Gly Ile Glu Ile Leu Ala Arg Ala Ala Ile Pro Thr Leu Gly Ala
            20                  25                  30

Thr Gly Pro Ser Val Met Ile Gln His Arg Ala Asp Gly Leu Pro Pro
        35                  40                  45

Ile Ser Thr Arg Asp Gly Val Thr Val Ala Asn Ser Ile Val Leu Lys
    50                  55                  60

Asp Arg Val Ala Asn Leu Gly Ala Arg Leu Leu Arg Asp Val Ala Gly
65                  70                  75                  80

Thr Met Ser Arg Glu Ala Gly Asp Gly Thr Thr Ala Ile Val Leu
                85                  90                  95

Ala Arg His Ile Ala Arg Glu Met Phe Lys Ser Leu Ala Val Gly Ala
            100                 105                 110

Asp Pro Ile Ala Leu Lys Arg Gly Ile Asp Arg Ala Val Ala Arg Val
        115                 120                 125

Ser Glu Asp Ile Gly Ala Arg Ala Trp Arg Gly Asp Lys Glu Ser Val
    130                 135                 140

Ile Leu Gly Val Ala Ala Val Ala Thr Lys Gly Glu Pro Gly Val Gly
145                 150                 155                 160

Arg Leu Leu Leu Glu Ala Leu Asp Ala Val Gly Val His Gly Ala Val
                165                 170                 175

Ser Ile Glu Leu Gly Gln Arg Arg Glu Asp Leu Leu Asp Val Val Asp
            180                 185                 190

Gly Tyr Arg Trp Glu Lys Gly Tyr Leu Ser Pro Tyr Phe Val Thr Asp
        195                 200                 205

Arg Ala Arg Glu Leu Ala Glu Leu Glu Asp Val Tyr Leu Leu Met Thr
```

```
                    210                 215                 220
Asp Arg Glu Val Val Asp Phe Ile Asp Leu Val Pro Leu Leu Glu Ala
225                 230                 235                 240

Val Thr Glu Ala Gly Gly Ser Leu Leu Ile Ala Ala Asp Arg Val His
                    245                 250                 255

Glu Lys Ala Leu Ala Gly Leu Leu Leu Asn His Val Arg Gly Val Phe
                    260                 265                 270

Lys Ala Val Ala Val Thr Ala Pro Gly Phe Gly Asp Lys Arg Pro Asn
                275                 280                 285

Arg Leu Leu Asp Leu Ala Ala Leu Thr Gly Gly Arg Ala Val Leu Glu
                290                 295                 300

Ala Gln Gly Asp Arg Leu Asp Arg Val Thr Leu Ala Asp Leu Gly Arg
305                 310                 315                 320

Val Arg Arg Ala Val Val Ser Ala Asp Asp Thr Ala Leu Leu Gly Ile
                    325                 330                 335

Pro Gly Thr Glu Ala Ser Arg Ala Arg Leu Glu Gly Leu Arg Leu Glu
                340                 345                 350

Ala Glu Gln Tyr Arg Ala Leu Lys Pro Gly Gln Gly Ser Ala Thr Gly
                355                 360                 365

Arg Leu His Glu Leu Glu Glu Ile Glu Ala Arg Ile Val Gly Leu Ser
                370                 375                 380

Gly Lys Ser Ala Val Tyr Arg Val Gly Gly Val Thr Asp Val Glu Met
385                 390                 395                 400

Lys Glu Arg Met Val Arg Ile Glu Asn Ala Tyr Arg Ser Val Val Ser
                    405                 410                 415

Ala Leu Glu Glu Gly Val Leu Pro Gly Gly Val Gly Phe Leu Gly
                420                 425                 430

Ser Met Pro Val Leu Ala Glu Leu Glu Ala Arg Asp Ala Asp Glu Ala
                435                 440                 445

Arg Gly Ile Gly Ile Val Arg Ser Ala Leu Thr Glu Pro Leu Arg Ile
                450                 455                 460

Ile Gly Glu Asn Ser Gly Leu Ser Gly Glu Ala Val Val Ala Lys Val
465                 470                 475                 480

Met Asp His Ala Asn Pro Gly Trp Gly Tyr Asp Gln Glu Ser Gly Ser
                    485                 490                 495

Phe Cys Asp Leu His Ala Arg Gly Ile Trp Asp Ala Ala Lys Val Leu
                500                 505                 510

Arg Leu Ala Leu Glu Lys Ala Ala Ser Val Ala Gly Thr Phe Leu Thr
                515                 520                 525

Thr Glu Ala Val Val Leu Glu Ile Pro Asp Thr Asp Ala Phe Ala Gly
                530                 535                 540

Phe Ser Ala Glu Trp Ala Ala Thr Arg Glu Asp Pro Arg Val
545                 550                 555
```